United States Patent
Allen et al.

(10) Patent No.: US 11,512,097 B2
(45) Date of Patent: Nov. 29, 2022

(54) HETEROCYCLIC COMPOUNDS AS DELTA-5 DESATURASE INHIBITORS AND METHODS OF USE

(71) Applicant: Amgen Inc., Thousand Oaks, CA (US)

(72) Inventors: Jennifer R. Allen, Newbury Park, CA (US); Michela Beltrani, Verona (IT); Matthew P. Bourbeau, Woodland Hills, CA (US); Teodora P. Damyanova, Verona (IT); Iain Lingard, Verona (IT); Ana E. Minatti, Los Angeles, CA (US); Paolo Vincetti, Verona (IT)

(73) Assignee: AMGEN INC., Thousand Oaks, CA (US)

(*) Notice: Subject to any disclaimer, the term of this patent is extended or adjusted under 35 U.S.C. 154(b) by 121 days.

(21) Appl. No.: 17/103,389

(22) Filed: Nov. 24, 2020

(65) Prior Publication Data

US 2021/0188874 A1 Jun. 24, 2021

Related U.S. Application Data

(60) Provisional application No. 62/939,821, filed on Nov. 25, 2019.

(51) Int. Cl.
| | |
|---|---|
| *C07D 513/04* | (2006.01) |
| *A61P 3/04* | (2006.01) |
| *C07D 487/04* | (2006.01) |
| *C07D 498/04* | (2006.01) |

(52) U.S. Cl.
CPC .............. *C07D 513/04* (2013.01); *A61P 3/04* (2018.01); *C07D 487/04* (2013.01); *C07D 498/04* (2013.01)

(58) Field of Classification Search
CPC .. C07D 513/04; C07D 487/04; C07D 498/04; A61P 3/04
USPC ..................................................... 514/255.05
See application file for complete search history.

(56) References Cited

U.S. PATENT DOCUMENTS

| | | | |
|---|---|---|---|
| 4,567,263 | A | 1/1986 | Eicken |
| 6,096,753 | A | 8/2000 | Spohr |
| 8,211,828 | B2 | 7/2012 | Dietz et al. |
| 8,952,012 | B2 | 2/2015 | Chicco |
| 9,108,984 | B2 | 8/2015 | Combs |
| 10,065,972 | B2 | 9/2018 | Okuyama |
| 2003/0073704 | A1 | 4/2003 | Spohr |
| 2005/0222171 | A1 | 10/2005 | Bold |
| 2007/0082900 | A1 | 4/2007 | Guzi |
| 2008/0200480 | A1 | 8/2008 | Dietz |
| 2008/0214395 | A1 | 9/2008 | Dietz |
| 2008/0312078 | A1 | 12/2008 | Dietz |
| 2009/0163545 | A1 | 6/2009 | Goldfarb |
| 2009/0253704 | A1 | 10/2009 | Koltun |
| 2009/0286811 | A1 | 11/2009 | Lingham |
| 2010/0029636 | A1 | 2/2010 | Buehlmayer |
| 2010/0105557 | A1 | 4/2010 | Habicher |
| 2010/0150913 | A1 | 6/2010 | Blue |
| 2010/0190747 | A1 | 7/2010 | Suzuki |
| 2011/0015212 | A1 | 1/2011 | Li |
| 2014/0066448 | A1 | 3/2014 | Combs |
| 2014/0275092 | A1 | 9/2014 | Albrecht |
| 2015/0065522 | A1 | 3/2015 | Albrecht |
| 2016/0362425 | A1 | 12/2016 | Li |
| 2016/0376289 | A1 | 12/2016 | Okuyama |
| 2018/0079753 | A1 | 3/2018 | Konteatis |
| 2021/0221824 | A1 | 7/2021 | Allen |

FOREIGN PATENT DOCUMENTS

| | | |
|---|---|---|
| CN | 106749271 B | 4/2019 |
| EP | 242690 A | 10/1987 |
| JP | 2004107228 A | 4/2004 |
| JP | 67917172 A | 5/2017 |
| JP | 2017081908 A | 5/2017 |
| WO | 9824780 | 6/1998 |
| WO | 9824780 W | 6/1998 |
| WO | 2001029044 A1 | 4/2001 |
| WO | 20010290441 | 4/2001 |

(Continued)

OTHER PUBLICATIONS

Baugh, SD. et al., Design, synthesis, and in vivo activity of novel inhibitors of delta-5 desaturase for the treatment of metabolic syndrome, Bioorg. Med. Chem. Lett. 25(18):3836-3839 (2015).

Chopra, M. et al., A global response to a global problem: the epidemic of overnutrition, Bull. World Health Organ. 80:952-958 (2002).

Di Marzo V and Matias I, Endocannabinoid control of food intake and energy balance, Nat. Neurosci. 8(5):585-589 (2005).

Djerrari, et al., L'acide déhydracétique, précurseur de nouvelles pyridopyrimidines, thiazolopyrimidines et pyridones; vol. 5, No. 3., p. 177-183, 2002.

Dupuis, J., New genetic loci implicated in fasting glucose homeostasis and their impact on type 2 diabetes risk, Nat. Genet. 42(2):105-116 (2010).

(Continued)

*Primary Examiner* — Kahsay Habte

(57) ABSTRACT

The present disclosure provides compounds useful for the inhibition of Delta-5 Desaturase ("D5D"). The compounds have a general Formula I

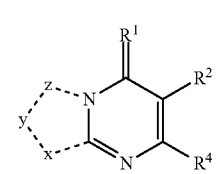

wherein the variables of Formula I are defined herein. This disclosure also provides pharmaceutical compositions comprising the compounds, uses of the compounds, and compositions for treatment of, for example, a metabolic or cardiovascular disorder. Further, the disclosure provides intermediates useful in the synthesis of compounds of Formula I.

38 Claims, No Drawings

(56) References Cited

FOREIGN PATENT DOCUMENTS

| WO | 20010290441 W | 4/2001 |
|---|---|---|
| WO | 2003106435 A1 | 12/2003 |
| WO | 20031064351 | 12/2003 |
| WO | 20031064351 W | 12/2003 |
| WO | 2005070431 A1 | 8/2005 |
| WO | 20050704311 | 8/2005 |
| WO | 20050704311 W | 8/2005 |
| WO | 2007002701 A2 | 1/2007 |
| WO | 20070027012 | 1/2007 |
| WO | 20070027012 W | 1/2007 |
| WO | 2008089307 A2 | 7/2008 |
| WO | 2008089310 A2 | 7/2008 |
| WO | 20080893072 | 7/2008 |
| WO | 20080893072 W | 7/2008 |
| WO | 2008092836 A2 | 8/2008 |
| WO | 2011114148 W | 9/2011 |
| WO | 2012011592 A1 | 1/2012 |
| WO | 2015064714 W | 5/2015 |
| WO | 20150647141 | 5/2015 |
| WO | 20150647141 W | 5/2015 |
| WO | 2015135094 A1 | 9/2015 |
| WO | 20151350941 | 9/2015 |
| WO | 20151350941 W | 9/2015 |
| WO | 2017112678 A1 | 6/2017 |
| WO | 20171126781 | 6/2017 |
| WO | 20171126781 W | 6/2017 |
| WO | 2018045071 A1 | 3/2018 |
| WO | 20180450711 | 3/2018 |
| WO | 20180450711 W | 3/2018 |
| WO | 2018213365 A1 | 11/2018 |
| WO | 2018229683 A1 | 12/2018 |
| WO | 20182296831 | 12/2018 |
| WO | 20182296831 W | 12/2018 |
| WO | 2019055750 A1 | 3/2019 |
| WO | 20190557501 | 3/2019 |
| WO | 20190557501 W | 3/2019 |
| WO | 2021108408 W | 6/2021 |

OTHER PUBLICATIONS

Eliel, Stereochemistry of Carbon 5 Compounds (McGraw-Hill, NY, 1962).
Fumagalli, M. et al., Greenlandic Inuit show genetic signatures of diet and climate adaptation, Science 349(6254):1343-1347 (2015).
Haidar, Y.M. and Cosman B.C., Obesity epidemiology, Clin. Colon Rectal Surg. 24:205-210 (2011).
Harizi, H. et al., Arachidonic-acid-derived eicosanoids: roles in biology and immunopathology, Trends Mol. Med. 14(10):461-469 (2008).
International Search Report for PCT/2020/062020 dated Mar. 4, 2021.
Jacques et al., Enantiomers, Racemates and Resolutions (Wiley-Interscience, New York, 1981).
Kibbe, Arthur H., Handbook of Pharmaceutical Excipients (3rd Ed.), American Pharmaceutical Association, 20 Washington, 2000.
Kroger J. and Schulze M.B., Recent insights into the relation of delta5 desaturase and delta6 desaturase activity to the development of type 2 diabetes, Curr. Opin. Lipidol. 23(1):4-10 (2012).
Liberman et al., Eds., Pharmaceutical Dosage Forms (vol. 1-3), Marcel Dekker, New York, NY, 1992.
Mendis S. et al., World Health Organization (WHO) and International Society of Hypertension (ISH) risk prediction charts: assessment of cardiovascular risk for prevention and control of cardiovascular disease in low and middle-income countries, J. Hypertens. 25:1578-1582 (2007).
Merino, D.M. et al., Genetic variation in lipid desaturases and its impact on the development of human disease, Lipids Health Dis. 9:63 (2010).
Merino, D.M. et al., Polymorphisms in FADS1 and FADS2 alter desaturase activity in young Caucasian and Asian adults, Mol. Genet. Metab. 103(2):171-178 (2011).
Miyahisa, I. et al., T-3364366 Targets the Desaturase Domain of Delta-5 Desaturase with Nanomolar Potency and a Multihour Residence Time, ACS Med. Chem. Lett. 7(9):868-872 (2016).
Monteiro, C.A. et al., Socioeconomic status and obesity in adult populations of developing countries: a review. Bull. World Health Organ. 82:940-946 (2004).
Obukowicz, M.G. et al., Novel, selective delta6 or delta5 fatty acid desaturase inhibitors as antiinflammatory agents in mice, J. Pharmacol. Exp. Ther. 287(1):157-166 (1998).
Powell, D.R. et al., Fatty acid desaturase 1 knockout mice are lean with improved glycemic control and decreased development of atheromatous plaque, Diabetes Metab. Syndr. Obes. 9:185-199 (2016).
Remington: The Science and Practice of Pharmacy, vol. I and vol. II, twenty-second edition, edited by Loyd V. Allen Jr., Philadelphia, PA, Pharmaceutical Press, 2012.
Tosi, F. et al., Delta-5 and delta-6 desaturases: crucial enzymes in polyunsaturated fatty acid-related pathways with pleiotropic influences in health and disease, Adv. Exp. Med. Biol. 824:61-81 (2014).
Tovey, Pharmaceutical Formulation: The Science and Technology of Dosage Forms (Drug Discovery), first edition, Royal Society of Chemistry, 2018.
Wilen, et al., Strategies in optical resolutions, Tetrahedron 33:2725-2769, 1977.
Wilen, Tables of Resolving Agents and Optical Resolutions, p. 268 (Eliel, Ed., Univ. of Notre Dame Press, Notre Dame, IN, 1972).
Willer, C.J. et al., Discovery and refinement of loci associated with lipid levels, Nat. Genet. 45(11):1274-1283 (2013).
Yashiro, H. et al., A Novel Selective Inhibitor of Delta-5 Desaturase Lowers Insulin Resistance and Reduces Body Weight in Diet-Induced Obese C57BL/6J Mice, PLoS One 11(11):e0166198 (2016).
Aretz, et al., Allosteric Inhibition of a Mammalian Lectin, J. Am. Chem. Soc., 2018, 140, 14915-14925.
Jadhav, Sunil B., et al., Antitubercular Activity and Synergistic Study of Novel Pyrazole Derivatives, Journal of Heterocyclic Chemistry, 2018, 55(7), 1634-1644.
Nagender, P., et al., Synthesis of Novel Imidazo[1,2-a]pyrimidin-5(1H)-one Derivatives by Intramolecular Cycloisomerisation of 2-Amino-3-N-alkyl Pyrimidine-4_3H-one in Presence of Aqueous Base, Chemistry Letters, 2013, 42(9), 1018-1019.
Alnajjar, Abdulaziz et al., Synthesis of New [1,2,4]Triazolo[1,5-a]pyrimidine Derivatives: Reactivity of 3-Amino [1,2,4]triazole towards Enaminonitriles and Enaminones, Journal of Heterocyclic Chemistry, 2018, 55 (7) 1804-1808.
Aretz, et al., Allosteric Inhibition of Mammalian Lectin, J. Am. Chem. Soc., 2018, 140, 14915-14925.
Badawey, E. Synthesis of Some New Imidazo[1,2-a]pyrimidin-5_1H-ones as Potential Antineoplastic Agents, J. Heterocyclic Chem. 32:1003-1006 (1995).
Bellec, C. et al. Deaminative electrochemical reduction of pyrazolo[1,5-a]pyrimidine-7-amines Canadian journal of chemistry, 1981, 59(19), 2826-2832.
Berge et al., "Pharmaceutical Salts", Journal of Pharmaceutical Sciences, vol. 86 (1), pp. 1-19 (Jan. 1977).
Bueno, J. et al. The molecular and supramolecular structures of the isomeric compounds 5,7-dimethoxyimidazo[1,2-c]pyrimidine and 7-methoxy-1-methylimidazo[1,2-a]pyrimidin-5(1H)-one, Crystal Structure Communications, 2003, 59 (Pt 7), o363-6.
Frey, R. 7-Aminopyrazolo[1,5-a]pyrimidines as Potent Multitargeted Receptor Tyrosine Kinase Inhibitors, J. Med. Chem. 2008, 51, 13, 3777-3787.
Gommerman, N., et al., New pyrazolo[1,5a]pyrimidines as orally active inhibitors of Lck Bioorganic, Medicinal Chemistry Letters, 2010, 20(12), 3628-3631.
Jadhav, Sunil B., et al., Antitubercular Activity and Synergisitc Study of Novel Pyrazole Derivatives, Journal of Heterocyclic Chemistry, 2018, 55(7), 1634-1644.
Jafari, B. et al. Synthesis and anticancer activity of novel water soluble benzimidazole carbamates, European Journal of Medicinal Chemistry, 2018, 144, 372-385.
Khalymbadzha, Igor, et al., Synthesis of acyclic nucleoside analogs based on 1,2,4-triazolo[1,5-a]pyrimidin-7-ones by one-step Vorbrueggen glycosylation, Tetrahedron, 2014, 70(6), 1298-1305.

(56) References Cited

OTHER PUBLICATIONS

Nagender, P., et al., Synthesis of Novel Imidazo[1,2-a]pyrimiding-5(1H)-one Derivatives by Intramolecular Cycloisomerisation of 2-Amino-3-N-alkyl Pyrimidine-4_3H-one in Presence of Aqueous Base, Chemistry Letters, 2013, 42(9)), 1018-1019.

Shukurov, S., et al., Interaction of 2-bromo-7-methyl-5-oxo-5H-1,3,4-thiadiazolo[3,2-α]pyrimidine with methylene-active compounds and acid hydrolysis of its products, Russian Chemical Bulletin, 1993, 42, 1874-1878.

HETEROCYCLIC COMPOUNDS AS DELTA-5 DESATURASE INHIBITORS AND METHODS OF USE

CROSS-REFERENCE TO RELATED APPLICATION

This application claims benefit of U.S. Provisional Patent Application No. 62/939,821, filed Nov. 25, 2019, which is incorporated by reference in its entirety.

FIELD

The present disclosure provides compounds useful for the inhibition of Delta-5 Desaturase ("D5D"). This disclosure also provides pharmaceutical compositions comprising the compounds, uses of the compounds, and compositions for treatment of, for example, a metabolic or cardiovascular disorder. Further, the disclosure provides intermediates useful in the synthesis of compounds of Formula I.

BACKGROUND

Polyunsaturated fatty acids ("PUFAs") exert important physiological functions in the human body. Kroeger J and Schulze M B, 2012, page 4. PUFAs serve as sources of energy and structural components of cell membranes. Id. PUFAs also regulate genes and are biosynthetic precursors of other physiologically relevant biomolecules, such as eicosanoids and endocannabinoids. Id. Di Marzo V and Matias I, 2005, page 585.

Eicosanoids are signaling molecules that have multiple functions and regulate, among other things, the human inflammatory response. Harizi H et al., 2008. Endocannabinoids (N-arachidonoyl ethanolamine (anandamide) and 2-arachidonoyl glycerol (2-AG) are endogenous ligands for the cannabinoid receptors which have been established to have a role in food intake and energy balance. Di Marzo V and Matias I, 2005, page 585.

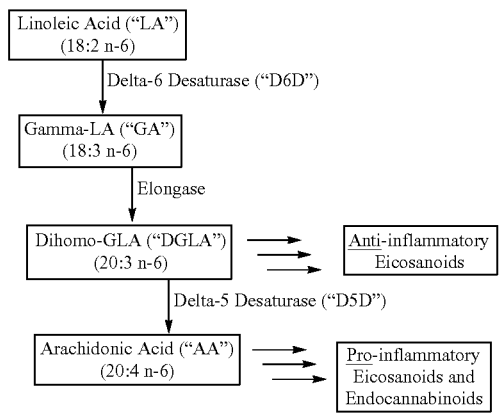

Yashiro H et al., 2016, page 2/18. Obukowicz M G et al., 1998, page 158. Di Marzo V and Matias I, 2005, page 585.

The pertinent part of the metabolic pathway of a certain PUFA, linoleic acid ("LA"), which leads, among other things, to the formation of anti- and pro-inflammatory eicosanoids and endocannabinoids, is shown in the scheme above.

The desaturase enzymes, which catalyze certain steps in the conversion of LA in AA are delta-6-desaturase ("D6D;" encoded by the gene Fatty Acid Desaturase 2 ("FADS2")) and delta-5-desaturase ("D5D;" encoded by the gene Fatty Acid Desaturase 1 ("FADS1")). Yashiro H et al., 2016, page 2/18. Selectively inhibiting D5D activity reduces the amount of AA generated, while increasing the amount of DGLA. Such a pharmacological intervention reduces downstream generation of, for example, pro-inflammatory eicosanoids and endocannabinoids and leads to build-up of anti-inflammatory eicosanoids, both of which may overall ameliorate inflammation-related conditions and may improve energy balance. Yashiro H et al., 2016, page 3/18. Di Marzo V and Matias I, 2005, page 585. This is especially relevant in subjects with high intake of LA, for example, humans exposed to Western-style diets. Yashiro H et al., 2016, page 3/18.

The FADS1-3 locus has been associated with many metabolic traits in human genome-wide association studies including fasting glucose, plasma lipids, and body weight. Fumagalli M et al., 2015. Willer C J et al., 2013. Dupuis J et al., 2010. An increase or elevation of each metabolic trait is associated with the FADS1-3 locus is also associated with an increase in the activity of D5D as estimated by AA:DGLA ratios. Fumagalli M et al., 2015. Merino D M et al., 2011.

In addition to human genetic evidence supporting a role of FADS1/D5D in metabolic disorders, FADS1 knock out ("KO") mice also show a phenotype with protection from diet-induced obesity including low body fat content, improved glycemic control, and decreased circulating lipid levels. Powell D R et al., 2016, page 197. In addition, the FADS1 KO mice are resistant to the development of arterial atheromatous plaque. Id.

Desaturase enzyme activity has been linked to a variety of diseases, in particular metabolic and cardiovascular diseases, such as obesity, diabetes, nonalcoholic steatohepatitis ("NASH"), dyslipidemia, and coronary artery disease. Tosi F et al., 2014; Kroeger J and Schulze M B, 2012; and Merino D M et al., 2010. Therefore, the pharmacological inhibition of D5D is a target of interest for treating metabolic, cardiovascular and other diseases. Powell D R et al., 2016, page 197.

Despite some progress in the area of small molecule therapeutics (for example, Miyahisa I et al., 2016; Yashiro H et al., 2016; and Baugh S D et al., 2015), a need for inhibitors of D5D, which may be suitable for use as therapeutic agents, remains in view of the significant continuing societal burden caused by, for example, metabolic and cardiovascular diseases (for example, Haidar Y M and Cosman B C, 2011; Mendis S et al., 2007; Chopra M et al., 2002; and Monteiro C A et al., 2004).

SUMMARY

First, provided herein is a compound of Formula I

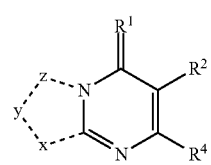

I or a tautomer thereof, or a pharmaceutically acceptable salt of said compound or said tautomer, wherein the

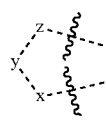

group together with the N atom and the C atom to which it is attached forms a 5 membered ring, wherein the ring is aromatic, unsaturated, partially saturated, or saturated;

x, y, and z are independently selected from CR, CRR', N, NR", O, S(O)$_n$, C=O, C=S, and C=NH;

each R and R' are independently selected from H, halogen, —OH, —CN, —CO(C$_{1-4}$alkyl), —S(O)$_n$(C$_{1-4}$alkyl), —COOH, —COO(C$_{1-4}$alkyl), —CONH$_2$, —CONH(C$_{1-4}$alkyl), —CO(diC$_{1-4}$alkylamino), —NH$_2$, C$_{1-4}$alkylamino, diC$_{1-4}$alkylamino, —NH(COC$_{1-4}$alkyl), —N(C$_{1-4}$alkyl)C(=O)F, C$_{1-4}$alkyl, —(CH$_2$)$_m$(C$_{3-5}$cycloalkyl), —CH$_2$(C$_{3-5}$heterocycloalkyl), C$_{1-4}$deuteroalkyl, C$_{3-5}$cycloalkyl, C$_{3-4}$heterocycloalkyl, C$_{2-4}$alkenyl, C$_{2-4}$alkynyl, C$_{1-4}$alkoxy, C$_{1-4}$deuteroalkoxy, phenyl, 5-membered heteroaryl, and 6-membered heteroaryl;

wherein the C$_{1-4}$alkyl group is optionally substituted with 1 to 4 F or optionally substituted with a substituent selected from —OH, —CN, C$_{1-4}$alkoxy, —NH$_2$, C$_{1-4}$alkylamino, diC$_{1-4}$alkylamino, and —S(O)$_n$(C$_{1-4}$alkyl);

wherein the C$_{1-4}$alkoxy group is optionally substituted with 1 to 4 independently selected halogens or optionally substituted with a substituent selected from —OH, —CN, C$_{1-4}$alkoxy, —NH$_2$, C$_{1-4}$alkylamino, diC$_{1-4}$alkylamino, and —S(O)$_n$(C$_{1-4}$alkyl);

wherein the —CH$_2$(C$_{3-5}$cycloalkyl), C$_{3-4}$heterocycloalkyl, phenyl, 5-membered heteroaryl, and 6-membered heteroaryl groups are optionally substituted with 1 to 4 substituents independently selected from halogen, —OH, —CN, C$_{1-4}$alkoxy, C$_{1-4}$alkyl, —NH$_2$, C$_{1-4}$alkylamino, diC$_{1-4}$alkylamino, and —S(O)$_n$(C$_{1-4}$alkyl); and wherein R of a first CR or CRR' group and R of a second CR or CRR' group, if present, together with the atoms to which they are attached, form a C$_{3-8}$carbocycle;

each R" is independently selected from H, —OH, —CO(C$_{1-4}$alkyl), —S(O)$_n$(C$_{1-4}$alkyl), —COO(C$_{1-4}$alkyl), —CONH$_2$, —CONH(C$_{1-4}$alkyl), —CO(diC$_{1-4}$alkylamino), C$_{1-4}$alkyl, —(CH$_2$)$_m$(C$_{3-8}$cycloalkyl), —CH$_2$(C$_{3-8}$heterocycloalkyl), C$_{1-4}$deuteroalkyl, C$_{3-5}$cycloalkyl, C$_{3-4}$heterocycloalkyl, C$_{2-4}$alkenyl, C$_{2-4}$alkynyl, phenyl, 5-membered heteroaryl, and 6-membered heteroaryl;

wherein the C$_{1-4}$alkyl group is optionally substituted with 1 to 4 F or optionally substituted with a substituent selected from —OH, —CN, C$_{1-4}$alkoxy, —NH$_2$, C$_{1-4}$alkylamino, diC$_{1-4}$alkylamino, and —S(O)$_n$(C$_{1-4}$alkyl); and wherein the —(CH$_2$)$_m$(C$_{3-5}$cycloalkyl), C$_{3-4}$heterocycloalkyl, phenyl, 5-membered heteroaryl, and 6-membered heteroaryl groups are optionally substituted with 1 to 4 substituents independently selected from halogen, —OH, —CN, C$_{1-4}$alkoxy, C$_{1-4}$alkyl, —NH$_2$, C$_{1-4}$alkylamino, diC$_{1-4}$alkylamino, and —S(O)$_n$(C$_{1-4}$alkyl);

R$^1$ is O, S, or NH;

R$^2$ is

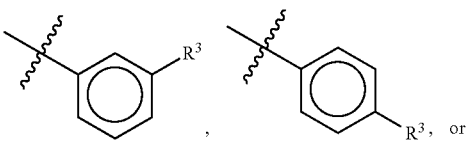

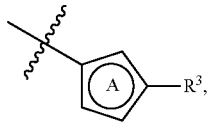

wherein

Ring A is a 5-membered heteroaryl containing one heteroatom selected from N, S, and O and optionally one or two further N atoms with the remaining ring atoms of the 5-membered heteroaryl being carbon, wherein i) Ring A is attached via a C atom to the bicyclic core and R$^3$ is attached via an N atom; or ii) Ring A is attached via an N atom to the bicyclic core and R$^3$ is attached via a C atom; or iii) Ring A is attached via a C atom to the bicyclic core and R$^3$ is attached via a C atom;

and wherein the

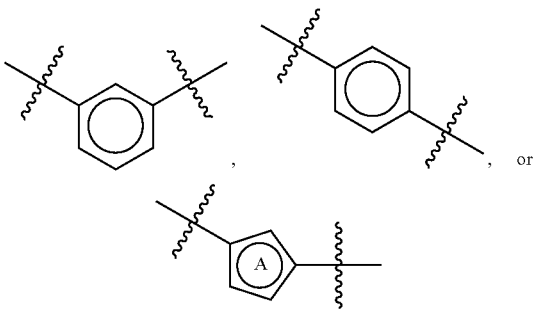

portion of R$^2$ is further optionally substituted with one or two independently selected substituents R$^{3'}$;

R$^3$ is C$_{1-6}$alkyl, C$_{3-5}$cycloalkyl, C$_{2-6}$alkoxy, C$_{1-6}$alkylamino, diC$_{1-6}$alkylamino, —S(O)$_n$(C$_{1-6}$alkyl), —CH$_2$(C$_{3-5}$cycloalkyl), —OCH$_2$(C$_{3-5}$cycloalkyl), —NHCH$_2$(C$_{3-5}$cycloalkyl), —S(O)$_n$CH$_2$(C$_{3-5}$cycloalkyl), —CH$_2$(C$_{3-5}$heterocycloalkyl), or phenyl; wherein the C$_{1-6}$alkyl, C$_{3-5}$ cycloalkyl, C$_{2-6}$alkoxy, C$_{1-6}$alkylamino, diC$_{1-6}$alkylamino, —S(O)$_n$(C$_{1-6}$alkyl), —CH$_2$(C$_{3-5}$cycloalkyl), —OCH$_2$(C$_{3-5}$cycloalkyl), —NHCH$_2$(C$_{3-5}$cycloalkyl), and —S(O)$_n$CH$_2$(C$_{3-5}$cycloalkyl) groups are optionally substituted with 1-9 halogen atoms and are optionally substituted with —CN and wherein the phenyl is optionally substituted with 1-3 substituents selected from halogen, C$_{1-4}$alkyl, C$_{1-4}$haloalkyl, C$_{1-4}$alkoxy, and C$_{1-4}$haloalkoxy;

R$^{3'}$ is independently halogen, C$_{1-4}$alkyl, C$_{1-4}$haloalkyl, C$_{1-4}$alkoxy, or C$_{1-4}$haloalkoxy;-

$R^4$ is $C_{1-3}$alkyl, $C_{1-4}$haloalkyl, $C_{1-4}$alkoxy, $C_{1-4}$haloalkoxy, $C_{3-5}$cycloalkyl, or $C_{3-5}$cyclohaloalkyl;

n is 0, 1, or 2; and m is 1 or 2; provided that (1) if

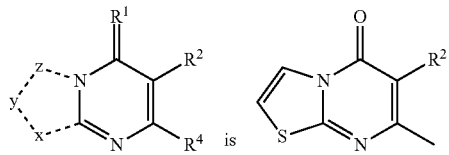

then $R^2$ is not

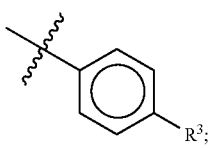

(2) if

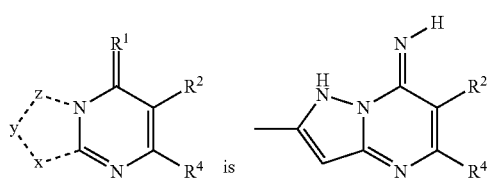

then $R^2$ is not

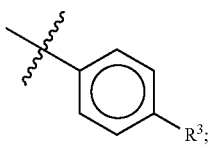

(3) if

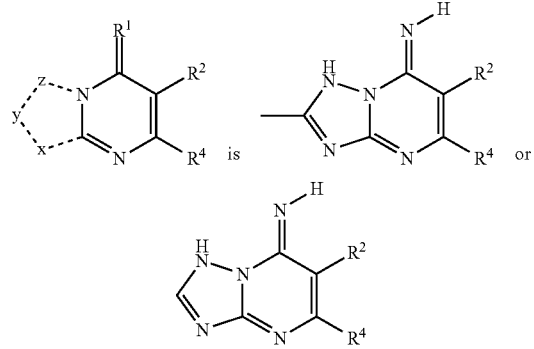

then $R^2$ is not

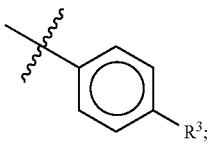

and (4) if any of R, R' or R" is phenyl then $R^3$ is not an unsubstituted $C_{1-6}$alkyl and $R^3$ is not $C_{1-2}$alkoxy.

Second, provided herein is a pharmaceutical composition comprising a compound of Formula I, or a tautomer thereof, or a pharmaceutically acceptable salt of said compound or said tautomer, and a pharmaceutically acceptable excipient.

Third, provided herein is a compound of Formula I, or a tautomer thereof, or a pharmaceutically acceptable salt of said compound or said tautomer, or the pharmaceutical composition as described hereinabove for use in reducing the body weight of a subject or for use in reducing the body-mass-index of a subject.

Fourth, provided herein is a compound of Formula I, or a tautomer thereof, or a pharmaceutically acceptable salt of said compound or said tautomer, or the pharmaceutical composition as described hereinabove for use in treating a metabolic disorder or for use in treating a cardiovascular disorder.

Fifth, provided herein is a compound of Formula I, or a tautomer thereof, or a pharmaceutically acceptable salt of said compound or said tautomer, or the pharmaceutical composition as described hereinabove for use in treating a metabolic disorder or for use in treating diabetes, obesity, dyslipidemia, or non-alcoholic steatohepatitis (NASH).

Reference will now be made in detail to embodiments of the present disclosure. While certain embodiments of the present disclosure will be described, it will be understood that it is not intended to limit the embodiments of the present disclosure to those described embodiments. To the contrary, reference to embodiments of the present disclosure is intended to cover alternatives, modifications, and equivalents as may be included within the spirit and scope of the embodiments of the present disclosure as defined by the appended claims.

DETAILED DESCRIPTION

Provided herein as Embodiment 1 is a compound of Formula I

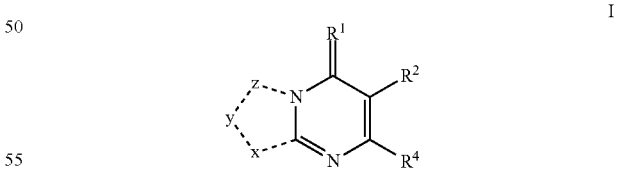

I or a tautomer thereof, or a pharmaceutically acceptable salt of said compound or said tautomer, wherein the

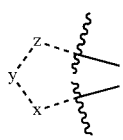

group together with the N atom and the C atom to which it is attached forms a 5 membered ring, wherein the ring is aromatic, unsaturated, partially saturated, or saturated;

x, y, and z are independently selected from CR, CRR', N, NR", O, S(O)$_n$, C=O, C=S, and C=NH;

each R and R' are independently selected from H, halogen, —OH, —CN, —CO(C$_{1-4}$alkyl), —S(O)$_n$(C$_{1-4}$alkyl), —COOH, —COO(C$_{1-4}$alkyl), —CONH$_2$, —CONH(C$_{1-4}$alkyl), —CO(diC$_{1-4}$alkylamino), —NH$_2$, C$_{1-4}$alkylamino, diC$_{1-4}$alkylamino, —NH(COC$_{1-4}$alkyl), —N(C$_{1-4}$alkyl)C(=O)F, C$_{1-4}$alkyl, —(CH$_2$)$_m$(C$_{3-5}$cycloalkyl), —CH$_2$(C$_{3-5}$heterocycloalkyl), C$_{1-4}$deuteroalkyl, C$_{3-5}$cycloalkyl, C$_{3-4}$heterocycloalkyl, C$_{2-4}$alkenyl, C$_{2-4}$alkynyl, C$_{1-4}$alkoxy, C$_{1-4}$deuteroalkoxy, phenyl, 5-membered heteroaryl, and 6-membered heteroaryl;

wherein the C$_{1-4}$alkyl group is optionally substituted with 1 to 4 F or optionally substituted with a substituent selected from —OH, —CN, C$_{1-4}$alkoxy, —NH$_2$, C$_{1-4}$alkylamino, diC$_{1-4}$alkylamino, and —S(O)$_n$(C$_{1-4}$alkyl);

wherein the C$_{1-4}$alkoxy group is optionally substituted with 1 to 4 independently selected halogens or optionally substituted with a substituent selected from —OH, —CN, C$_{1-4}$alkoxy, —NH$_2$, C$_{1-4}$alkylamino, diC$_{1-4}$alkylamino, and —S(O)$_n$(C$_{1-4}$alkyl);

wherein the —CH$_2$(C$_{3-5}$cycloalkyl), C$_{3-4}$heterocycloalkyl, phenyl, 5-membered heteroaryl, and 6-membered heteroaryl groups are optionally substituted with 1 to 4 substituents independently selected from halogen, —OH, —CN, C$_{1-4}$alkoxy, C$_{1-4}$alkyl, —NH$_2$, C$_{1-4}$alkylamino, diC$_{1-4}$alkylamino, and —S(O)$_n$(C$_{1-4}$alkyl); and wherein R of a first CR or CRR' group and R of a second CR or CRR' group, if present, together with the atoms to which they are attached, form a C$_{3-5}$carbocycle;

each R" is independently selected from H, —OH, —CO(C$_{1-4}$alkyl), —S(O)$_n$(C$_{1-4}$alkyl), —COO(C$_{1-4}$alkyl), —CONH$_2$, —CONH(C$_{1-4}$alkyl), —CO(diC$_{1-4}$alkylamino), C$_{1-4}$alkyl, —(CH$_2$)$_m$(C$_{3-5}$cycloalkyl), —CH$_2$(C$_{3-5}$heterocycloalkyl), C$_{1-4}$deuteroalkyl, C$_{3-5}$cycloalkyl, C$_{3-4}$heterocycloalkyl, C$_{2-4}$alkenyl, C$_{2-4}$alkynyl, phenyl, 5-membered heteroaryl, and 6-membered heteroaryl;

wherein the C$_{1-4}$alkyl group is optionally substituted with 1 to 4 F or optionally substituted with a substituent selected from —OH, —CN, C$_{1-4}$alkoxy, —NH$_2$, C$_{1-4}$alkylamino, diC$_{1-4}$alkylamino, and —S(O)$_n$(C$_{1-4}$alkyl); and wherein the —(CH$_2$)$_m$(C$_{3-5}$cycloalkyl), C$_{3-4}$heterocycloalkyl, phenyl, 5-membered heteroaryl, and 6-membered heteroaryl groups are optionally substituted with 1 to 4 substituents independently selected from halogen, —OH, —CN, C$_{1-4}$alkoxy, C$_{1-4}$alkyl, —NH$_2$, C$_{1-4}$alkylamino, diC$_{1-4}$alkylamino, and —S(O)$_n$(C$_{1-4}$alkyl);

R is O, S, or NH;

R$^2$ is

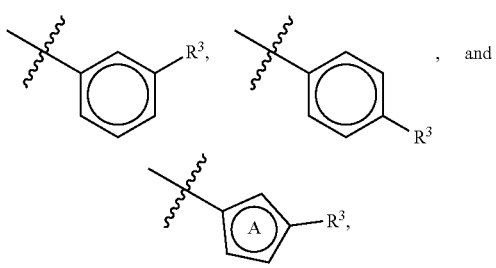

wherein

Ring A is a 5-membered heteroaryl containing one heteroatom selected from N, S, and O and optionally one or two further N atoms with the remaining ring atoms of the 5-membered heteroaryl being carbon, wherein i) Ring A is attached via a C atom to the bicyclic core and R$^3$ is attached via an N atom; or ii) Ring A is attached via an N atom to the bicyclic core and R$^3$ is attached via a C atom; or iii) Ring A is attached via a C atom to the bicyclic core and R$^3$ is attached via a C atom;

and wherein the

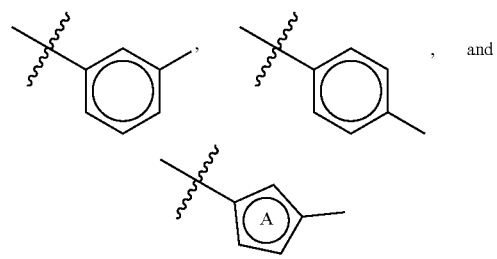

or portion of R$^2$ is further optionally substituted with one or two independently selected substituents R$^{3'}$;

R$^3$ is C$_{1-6}$alkyl, C$_{3-5}$cycloalkyl, C$_{2-6}$alkoxy, C$_{1-6}$alkylamino, diC$_{1-6}$alkylamino, —S(O)$_n$(C$_{1-6}$alkyl), —CH$_2$(C$_{3-5}$cycloalkyl), —OCH$_2$(C$_{3-5}$cycloalkyl), —NHCH$_2$(C$_{3-5}$cycloalkyl), —S(O)$_n$CH$_2$(C$_{3-5}$cycloalkyl), —CH$_2$(C$_{3-5}$heterocycloalkyl), or phenyl; wherein the C$_{1-6}$alkyl, C$_{3-5}$cycloalkyl, C$_{2-6}$alkoxy, C$_{1-6}$alkylamino, diC$_{1-6}$alkylamino, —S(O)$_n$(C$_{1-6}$alkyl), —CH$_2$(C$_{3-5}$cycloalkyl), —OCH$_2$(C$_{3-5}$cycloalkyl), —NHCH$_2$(C$_{3-5}$cycloalkyl), and —S(O)$_n$CH$_2$(C$_{3-5}$cycloalkyl) groups are optionally substituted with 1-9 halogen atoms and are optionally substituted with —CN and wherein the phenyl is optionally substituted with 1-3 substituents selected from halogen, C$_{1-4}$alkyl, C$_{1-4}$haloalkyl, C$_{1-4}$alkoxy, and C$_{1-4}$haloalkoxy;

R$^{3'}$ is independently halogen, C$_{1-4}$alkyl, C$_{1-4}$haloalkyl, C$_{1-4}$alkoxy, or C$_{1-4}$haloalkoxy;

R$^4$ is C$_{1-3}$alkyl, C$_{1-4}$haloalkyl, C$_{1-4}$alkoxy, C$_{1-4}$haloalkoxy, C$_{3-5}$cycloalkyl, or C$_{3-5}$cyclohaloalkyl;

n is 0, 1, or 2; and m is 1 or 2; provided that (1) if

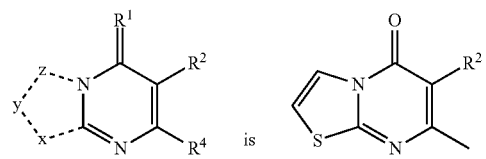

then R$^2$ is not

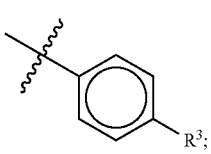

(2) if

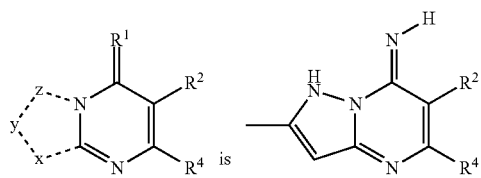 is then R² is not

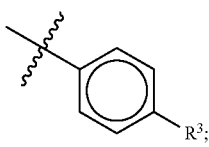;

(3) if

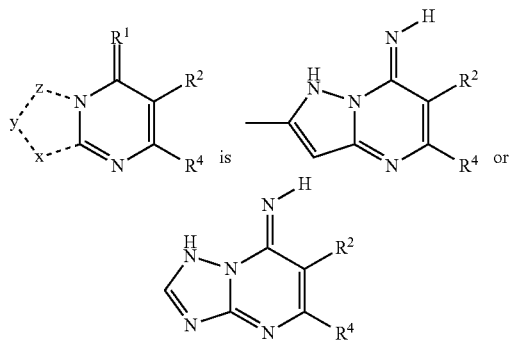 is then R² is not

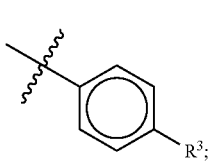;

and
(4) if any of R, R' or R" is phenyl then R³ is not an unsubstituted C₁₋₆alkyl and R³ is not C₁₋₂alkoxy.

Provided herein as Embodiment 2 is the compound according to Embodiment 1, or a tautomer thereof, or a pharmaceutically acceptable salt of said compound or said tautomer, wherein the compound is not
1,3,3-trimethyl-6-[1-(2,2,3,3,3-pentafluoropropyl)-1H-pyrazol-4-yl]-7-(trifluoromethyl)-1H,2H,3H,5H-imidazo[1,2-a]pyrimidine-2,5-dione;
2-methyl-6-[1-(2,2,3,3,3-pentafluoropropyl)-1H-pyrazol-4-yl]-1-(pyrimidin-5-yl)-7-(trifluoromethyl)-1H,5H-imidazo[1,2-a]pyrimidin-5-one; or
2-[(methylamino)methyl]-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one.

Provided herein as Embodiment 3 is the compound according to Embodiment 1 or Embodiment 2, or a tautomer thereof, or a pharmaceutically acceptable salt of said compound or said tautomer, wherein
x, y, and z are independently selected from CR, N, and NR".

Provided herein as Embodiment 4 is the compound according to Embodiment 1 or Embodiment 2, or a tautomer thereof, or a pharmaceutically acceptable salt of said compound or said tautomer, wherein
x, y, and z are independently selected from CR, N, and S.

Provided herein as Embodiment 5 is the compound according to Embodiment 1 or Embodiment 2, or a tautomer thereof, or a pharmaceutically acceptable salt of said compound or said tautomer, wherein

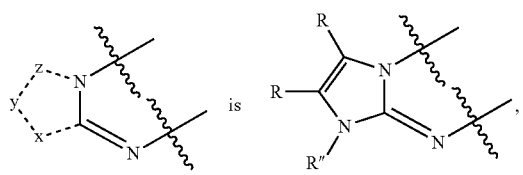 is

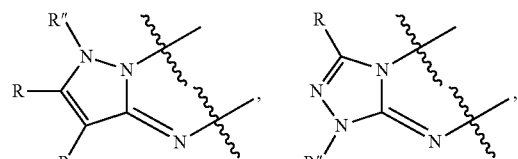

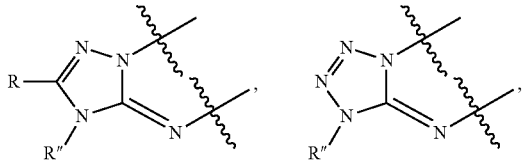

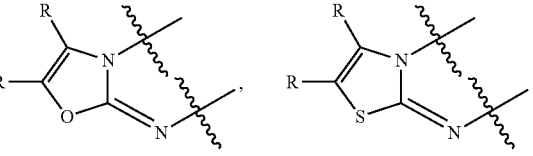

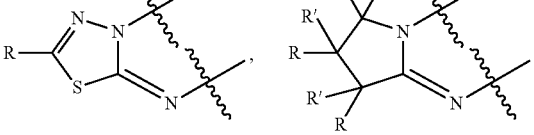

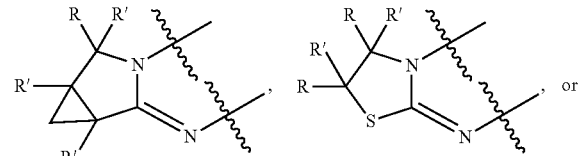

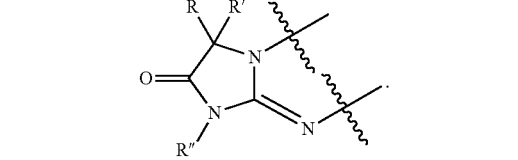

Provided herein as Embodiment 6 is the compound according to Embodiment 1 or Embodiment 2, or a tautomer thereof, or a pharmaceutically acceptable salt of said compound or said tautomer, wherein

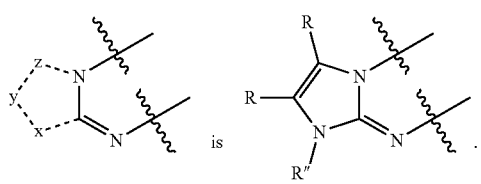
is

Provided herein as Embodiment 7 is the compound according to Embodiment 1 or Embodiment 2, or a tautomer thereof, or a pharmaceutically acceptable salt of said compound or said tautomer, wherein

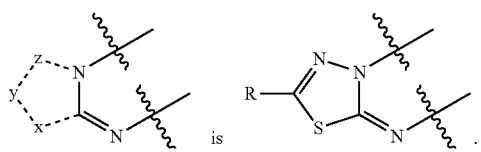
is

Provided herein as Embodiment 8 is the compound according to any one of Embodiments 1-7, or a tautomer thereof, or a pharmaceutically acceptable salt of said compound or said tautomer, wherein each R and R', if present, are independently selected from H, halogen, —COO($C_{1-4}$alkyl), $C_{1-4}$alkyl, —(CH$_2$)$_m$($C_{3-5}$cycloalkyl), —CH$_2$($C_{3-8}$heterocycloalkyl), $C_{1-4}$deuteroalkyl, $C_{3-5}$cycloalkyl, $C_{3-4}$heterocycloalkyl, $C_{2-4}$alkynyl, $C_{1-4}$alkoxy, phenyl, 5-membered heteroaryl, and 6-membered heteroaryl;
  wherein the $C_{1-4}$alkyl group is optionally substituted with 1 to 4 F or optionally substituted with a substituent selected from —OH, —CN, $C_{1-4}$alkoxy, $C_{1-4}$alkylamino, and di$C_{1-4}$alkylamino; and
  wherein the —(CH$_2$)$_m$($C_{3-5}$cycloalkyl), 5-membered heteroaryl, and 6-membered heteroaryl groups are optionally substituted with 1 to 4 substituents independently selected from halogen, —OH, and $C_{1-4}$alkyl.

Provided herein as Embodiment 9 is the compound according to any one of Embodiments 1-7, or a tautomer thereof, or a pharmaceutically acceptable salt of said compound or said tautomer, wherein
  each R and R', if present, are independently selected from H, halogen, $C_{1-4}$alkyl, $C_{1-4}$deuteroalkyl, and $C_{1-4}$alkoxy; wherein the $C_{1-4}$alkyl group is optionally substituted with a substituent selected from —OH and —CN.

Provided herein as Embodiment 10 is the compound according to any one of Embodiments 1-7, or a tautomer thereof, or a pharmaceutically acceptable salt of said compound or said tautomer, wherein
  each R and R', if present, are independently selected from H and $C_{1-4}$alkyl.

Provided herein as Embodiment 11 is the compound according to any one of Embodiments 1-7, or a tautomer thereof, or a pharmaceutically acceptable salt of said compound or said tautomer, wherein
  each R and R', if present, are independently selected from H, F, Cl, —COOMe, methyl, ethyl, isopropyl, fluoromethyl, trifluoromethyl, —CH$_2$OH, 2-hydroxyethyl, 2-hydroxy-2-methylpropyl, —CH$_2$CN, 2-hydroxypropyl, —CH$_2$OCH$_3$, —CH$_2$CH$_2$OCH$_3$, methylaminomethyl, dimethylaminomethyl, 2-(dimethylamino)ethyl, cyclopropylmethyl, (2,2-difluorocyclopropyl)methyl, (3,3-difluorocyclobutyl)methyl, (1-hydroxycyclopropyl)ethyl, —CD$_3$, cyclopropyl, (oxetan-3-yl)methyl, oxetan-3-yl, prop-2-yn-1-yl, methoxy, phenyl, pyrazolyl, 1-methyl-pyrazol-4-yl, pyridinyl, pyrazinyl, pyrimidinyl, 6-methylpyridin-2-yl, and 6-chloropyridin-2-yl.

Provided herein as Embodiment 12 is the compound according to any one of Embodiments 1-7, or a tautomer thereof, or a pharmaceutically acceptable salt of said compound or said tautomer, wherein
  each R and R', if present, are independently selected from H, Cl, methyl, —CH$_2$OH, 2-hydroxyethyl, —CH$_2$CN, —CD$_3$, and methoxy.

Provided herein as Embodiment 13 is the compound according to any one of Embodiments 1-7, or a tautomer thereof, or a pharmaceutically acceptable salt of said compound or said tautomer, wherein
  each R and R', if present, are independently selected from H and methyl.

Provided herein as Embodiment 14 is the compound according to any one of Embodiments 1-13, or a tautomer thereof, or a pharmaceutically acceptable salt of said compound or said tautomer, wherein
  each R", if present, is independently selected from H, —COO($C_{1-4}$alkyl), $C_{1-4}$alkyl, —(CH$_2$)$_m$($C_{3-5}$cycloalkyl), —CH$_2$($C_{3-8}$heterocycloalkyl), $C_{1-4}$deuteroalkyl, $C_{3-5}$cycloalkyl, $C_{3-4}$heterocycloalkyl, $C_{2-4}$alkynyl, phenyl, 5-membered heteroaryl, and 6-membered heteroaryl;
    wherein the $C_{1-4}$alkyl group is optionally substituted with 1 to 4 F or optionally substituted with a substituent selected from —OH, —CN, $C_{1-4}$alkoxy, $C_{1-4}$alkylamino, and di$C_{1-4}$alkylamino; and
    wherein the —(CH$_2$)$_m$($C_{3-5}$cycloalkyl), 5-membered heteroaryl, and 6-membered heteroaryl groups are optionally substituted with 1 to 4 substituents independently selected from halogen, —OH, and $C_{1-4}$alkyl.

Provided herein as Embodiment 15 is the compound according to any one of Embodiments 1-13, or a tautomer thereof, or a pharmaceutically acceptable salt of said compound or said tautomer, wherein
  each R", if present, is independently selected from H, $C_{1-4}$alkyl, and $C_{1-4}$deuteroalkyl; wherein the $C_{1-4}$alkyl group is optionally substituted with a substituent selected from —OH and —CN.

Provided herein as Embodiment 16 is the compound according to any one of Embodiments 1-13, or a tautomer thereof, or a pharmaceutically acceptable salt of said compound or said tautomer, wherein
  each R", if present, is independently selected from H and $C_{1-4}$alkyl.

Provided herein as Embodiment 17 is the compound according to any one of Embodiments 1-13, or a tautomer thereof, or a pharmaceutically acceptable salt of said compound or said tautomer, wherein
  each R", if present, is independently selected from H, —COOMe, methyl, ethyl, isopropyl, fluoromethyl, trifluoromethyl, 2-hydroxyethyl, 2-hydroxy-2-methylpropyl, —CH$_2$CN, 2-hydroxypropyl, —CH$_2$OCH$_3$, —CH$_2$CH$_2$OCH$_3$, dimethylaminomethyl, 2-(dimethylamino)ethyl, cyclopropylmethyl, (2,2-difluorocyclopropyl)methyl, (3,3-difluorocyclobutyl)methyl, (1-hydroxycyclopropyl)ethyl, —CD$_3$, cyclopropyl, (oxetan-3-yl)methyl, oxetan-3-yl, prop-2-yn-1-yl, phenyl, pyrazolyl, 1-methyl-pyrazol-4-yl, pyridinyl, pyrazinyl, pyrimidinyl, 6-methylpyridin-2-yl, and 6-chloropyridin-2-yl.

Provided herein as Embodiment 18 is the compound according to any one of Embodiments 1-13, or a tautomer thereof, or a pharmaceutically acceptable salt of said compound or said tautomer, wherein each R", if present, is independently selected from H, methyl, 2-hydroxyethyl, —CH$_2$CN, and —CD$_3$.

Provided herein as Embodiment 19 is the compound according to any one of Embodiments 1-13, or a tautomer thereof, or a pharmaceutically acceptable salt of said compound or said tautomer, wherein each R", if present, is independently selected from H and methyl.

Provided herein as Embodiment 20 is the compound according to any one of Embodiments 1-19, or a tautomer thereof, or a pharmaceutically acceptable salt of said compound or said tautomer, wherein R of a first CR or CRR' group and R of a second CR or CRR' group, if present, together with the atoms to which they are attached, form a cyclopropyl.

Provided herein as Embodiment 21 is the compound according to any one of Embodiments 1-20, or a tautomer thereof, or a pharmaceutically acceptable salt of said compound or said tautomer, wherein R$^1$ is O or S.

Provided herein as Embodiment 22 is the compound according to any one of Embodiments 1-20, or a tautomer thereof, or a pharmaceutically acceptable salt of said compound or said tautomer, wherein R$^1$ is O.

Provided herein as Embodiment 23 is the compound according to any one of Embodiments 1-22, or a tautomer thereof, or a pharmaceutically acceptable salt of said compound or said tautomer, wherein R$^2$ is

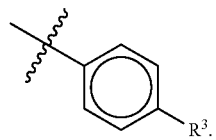

Provided herein as Embodiment 24 is the compound according to any one of Embodiments 1-22, or a tautomer thereof, or a pharmaceutically acceptable salt of said compound or said tautomer, wherein R$^2$ is

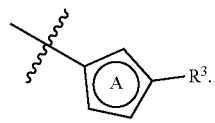

Provided herein as Embodiment 25 is the compound according to any one of Embodiments 1-22, or a tautomer thereof, or a pharmaceutically acceptable salt of said compound or said tautomer, wherein R$^2$ is

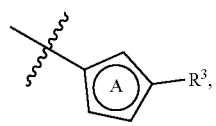

wherein A is a 5-membered heteroaryl containing two N atoms.

Provided herein as Embodiment 26 is the compound according to any one of Embodiments 1-22, 24, and 25, or a tautomer thereof, or a pharmaceutically acceptable salt of said compound or said tautomer, wherein A is attached via a C atom to the bicyclic core and R$^3$ is attached via an N atom.

Provided herein as Embodiment 27 is the compound according to any one of Embodiments 1-22, 24, and 25, or a tautomer thereof, or a pharmaceutically acceptable salt of said compound or said tautomer, wherein A is attached via an N atom to the bicyclic core and R$^3$ is attached via an C atom.

Provided herein as Embodiment 28 is the compound according to any one of Embodiments 1-22, 24, and 25, or a tautomer thereof, or a pharmaceutically acceptable salt of said compound or said tautomer, wherein A is attached via a C atom to the bicyclic core and R$^3$ is attached via a C atom.

Provided herein as Embodiment 29 is the compound according to any one of Embodiments 1-22, or a tautomer thereof, or a pharmaceutically acceptable salt of said compound or said tautomer, wherein R$^2$ is

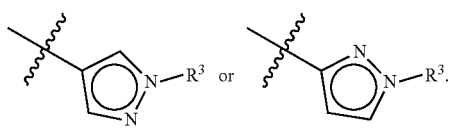

Provided herein as Embodiment 30 is the compound according to any one of Embodiments 1-22, or a tautomer thereof, or a pharmaceutically acceptable salt of said compound or said tautomer, wherein R$^2$ is

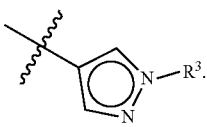

Provided herein as Embodiment 31 is the compound according to any one of Embodiments 1-30, or a tautomer thereof, or a pharmaceutically acceptable salt of said compound or said tautomer, wherein the

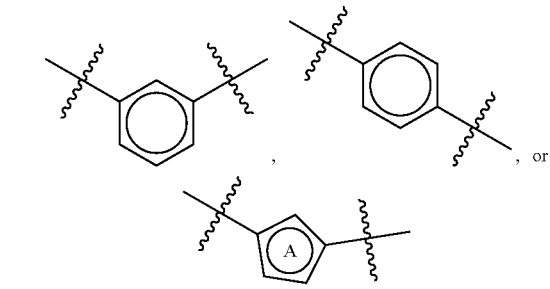

portion of R$^2$ is not further optionally substituted with one or two independently selected substituents R$^{3'}$.

Provided herein as Embodiment 32 is the compound according to any one of Embodiments 1-30, or a tautomer thereof, or a pharmaceutically acceptable salt of said compound or said tautomer, wherein the

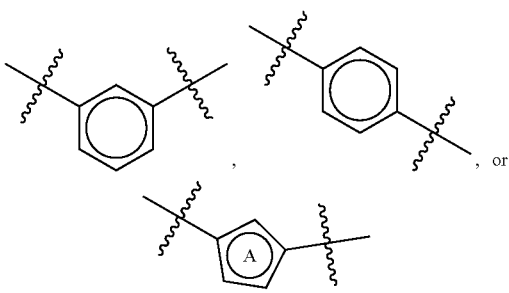

, or or portion of R² is substituted with one or two independently selected substituents R³'.

Provided herein as Embodiment 33 is the compound according to any one of Embodiments 1-30, or a tautomer thereof, or a pharmaceutically acceptable salt of said compound or said tautomer, wherein the

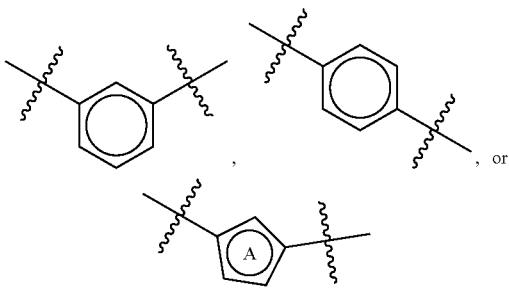

, or portion of R² is substituted with one substituent R³'.

Provided herein as Embodiment 34 is the compound according to any one of Embodiments 1-33, or a tautomer thereof, or a pharmaceutically acceptable salt of said compound or said tautomer, wherein R³ is $C_{1-6}$alkyl, $C_{2-6}$alkoxy, —$CH_2(C_{3-5}$cycloalkyl), —$OCH_2(C_{3-5}$cycloalkyl), —$CH_2(C_{3-5}$heterocycloalkyl), or phenyl; wherein the $C_{1-6}$alkyl, $C_{2-6}$alkoxy, —$CH_2(C_{3-5}$cycloalkyl), and —$OCH_2(C_{3-5}$cycloalkyl) groups are optionally substituted with 1-9 halogen atoms and are optionally substituted with —CN and wherein the phenyl is optionally substituted with one halogen substituent.

Provided herein as Embodiment 35 is the compound according to any one of Embodiments 1-33, or a tautomer thereof, or a pharmaceutically acceptable salt of said compound or said tautomer, wherein R³ is $C_{1-6}$alkyl, $C_{2-6}$alkoxy, —$CH_2(C_{3-5}$cycloalkyl), or —$CH_2(C_{3-8}$heterocycloalkyl); wherein the $C_{1-6}$alkyl, $C_{2-6}$alkoxy, and —$CH_2(C_{3-5}$cycloalkyl) groups are optionally substituted with 1-9 halogen atoms.

Provided herein as Embodiment 36 is the compound according to any one of Embodiments 1-33, or a tautomer thereof, or a pharmaceutically acceptable salt of said compound or said tautomer, wherein R³ is $C_{1-6}$alkyl, $C_{2-6}$alkoxy, —$CH_2(C_{3-5}$cycloalkyl), or —$CH_2(C_{3-8}$heterocycloalkyl); wherein the $C_{1-6}$alkyl, $C_{2-6}$alkoxy, and —$CH_2(C_{3-5}$cycloalkyl) groups are substituted with 2-5 halogen atoms.

Provided herein as Embodiment 37 is the compound according to any one of Embodiments 1-33, or a tautomer thereof, or a pharmaceutically acceptable salt of said compound or said tautomer, wherein R³ is 2,2,2-trifluoroethyl, propyl, 2,2-difluoropropyl, 3,3,3-trifluoropropyl, 4,4,4-trifluorobutyl, 2,2,3,3,3-pentafluoropropyl, —$OCH_2CN$, —$OC(CH_3)_2CN$, difluoromethoxy, trifluoromethoxy, —$OCH(CN)CH_3$, 2-fluoroethoxy, 2,2,-difluoroethoxy, 2,2,2-trifluoroethoxy, 2,2-difluoropropoxy, 2,2,3,3-tetrafluoropropoxy, 2,2,3,3,3-pentafluoropropoxy, cyclopropylmethyl, (2,2-difluorocyclopropyl)methyl, (3,3-difluorocyclobutyl)methyl, cyclopropylmethoxy, (2,2-difluorocyclopropyl)methoxy, (oxetan-3-yl)methyl, phenyl, 3-fluorophenyl, or 4-fluorophenyl.

Provided herein as Embodiment 38 is the compound according to any one of Embodiments 1-33, or a tautomer thereof, or a pharmaceutically acceptable salt of said compound or said tautomer, wherein R³ is 3,3,3-trifluoropropyl, 2,2,3,3,3-pentafluoropropyl, 2,2,2-trifluoroethoxy, or (2,2-difluorocyclopropyl)methyl.

Provided herein as Embodiment 39 is the compound according to any one of Embodiments 1-30 and 32-38, or a tautomer thereof, or a pharmaceutically acceptable salt of said compound or said tautomer, wherein R³' is independently halogen or $C_{1-4}$alkyl.

Provided herein as Embodiment 40 is the compound according to any one of Embodiments 1-30 and 32-38, or a tautomer thereof, or a pharmaceutically acceptable salt of said compound or said tautomer, wherein R³' is independently F or methyl.

Provided herein as Embodiment 41 is the compound according to any one of Embodiments 1-40, or a tautomer thereof, or a pharmaceutically acceptable salt of said compound or said tautomer, wherein R⁴ is $C_{1-3}$alkyl, $C_{1-4}$haloalkyl, $C_{1-4}$alkoxy, or $C_{3-5}$cycloalkyl.

Provided herein as Embodiment 42 is the compound according to any one of Embodiments 1-40, or a tautomer thereof, or a pharmaceutically acceptable salt of said compound or said tautomer, wherein R⁴ is $C_{1-4}$haloalkyl.

Provided herein as Embodiment 43 is the compound according to any one of Embodiments 1-40, or a tautomer thereof, or a pharmaceutically acceptable salt of said compound or said tautomer, wherein R⁴ is methyl, ethyl, fluoromethyl, difluoromethyl, trifluoromethyl, methoxy, ethoxy, or cyclopropyl.

Provided herein as Embodiment 44 is the compound according to any one of Embodiments 1-40, or a tautomer thereof, or a pharmaceutically acceptable salt of said compound or said tautomer, wherein R⁴ is trifluoromethyl.

Provided herein as Embodiment 45 is the compound according to any one of Embodiments 1-44, or a tautomer thereof, or a pharmaceutically acceptable salt of said compound or said tautomer, wherein n is 0.

Provided herein as Embodiment 46 is the compound according to any one of Embodiments 1-44, or a tautomer thereof, or a pharmaceutically acceptable salt of said compound or said tautomer, wherein n is 1.

Provided herein as Embodiment 47 is the compound according to any one of Embodiments 1-44, or a tautomer thereof, or a pharmaceutically acceptable salt of said compound or said tautomer, wherein n is 2.

Provided herein as Embodiment 48 is the compound according to any one of Embodiments 1-47, or a tautomer thereof, or a pharmaceutically acceptable salt of said compound or said tautomer, wherein m is 1.

Provided herein as Embodiment 49 is the compound according to any one of Embodiments 1-47, or a tautomer thereof, or a pharmaceutically acceptable salt of said compound or said tautomer, wherein
m is 2.

Provided herein as Embodiment 50 is the compound according to Embodiment 1, or a tautomer thereof, or a pharmaceutically acceptable salt of said compound or said tautomer, wherein the compound is 6-[1-(2,2,3,3,3-pentafluoropropyl)-1H-pyrazol-4-yl]-7-(trifluoromethyl)-5H-[1,3]thiazolo[3,2-a]pyrimidin-5-one;

2-methyl-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one;

1-methyl-6-[1-(2,2,3,3,3-pentafluoropropyl)-1H-pyrazol-4-yl]-7-(trifluoromethyl)-1H,2H,3H,5H-imidazo[1,2-a]pyrimidine-2,5-dione;

2-methyl-6-[1-(2,2,3,3,3-pentafluoropropyl)-1H-pyrazol-4-yl]-7-(trifluoromethyl)-5H-[1,3]thiazolo[3,2-a]pyrimidin-5-one;

3-methyl-6-[1-(2,2,3,3,3-pentafluoropropyl)-1H-pyrazol-4-yl]-7-(trifluoromethyl)-5H-[1,3]thiazolo[3,2-a]pyrimidin-5-one;

6-[1-(2,2,3,3,3-pentafluoropropyl)-1H-pyrazol-4-yl]-3,7-bis(trifluoromethyl)-5H-[1,3]thiazolo[3,2-a]pyrimidin-5-one;

2-fluoro-6-[1-(2,2,3,3,3-pentafluoropropyl)-1H-pyrazol-4-yl]-7-(trifluoromethyl)-5H-[1,3]thiazolo[3,2-a]pyrimidin-5-one;

7-(trifluoromethyl)-6-[1-(3,3,3-trifluoropropyl)-1H-pyrazol-4-yl]-5H-[1,3]thiazolo[3,2-a]pyrimidin-5-one;

2-chloro-6-[1-(2,2,3,3,3-pentafluoropropyl)-1H-pyrazol-4-yl]-7-(trifluoromethyl)-5H-[1,3]thiazolo[3,2-a]pyrimidin-5-one;

2-(methoxymethyl)-7-(trifluoromethyl)-6-[1-(3,3,3-trifluoropropyl)-1H-pyrazol-4-yl]-5H-[1,3,4]thiadiazolo[3,2-a]pyrimidin-5-one;

2-cyclopropyl-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one;

2-cyclopropyl-7-(trifluoromethyl)-6-[1-(3,3,3-trifluoropropyl)-1H-pyrazol-4-yl]-5H-[1,3,4]thiadiazolo[3,2-a]pyrimidin-5-one;

2,3-dimethyl-6-[1-(2,2,3,3,3-pentafluoropropyl)-1H-pyrazol-4-yl]-5-(trifluoromethyl)-3H,7H-[1,2,4]triazolo[1,5-a]pyrimidin-7-one;

2,3-dimethyl-5-(trifluoromethyl)-6-[1-(3,3,3-trifluoropropyl)-1H-pyrazol-4-yl]-3H,7H-[1,2,4]triazolo[1,5-a]pyrimidin-7-one;

7-ethyl-2-methyl-6-[1-(2,2,3,3,3-pentafluoropropyl)-1H-pyrazol-4-yl]-5H-[1,3,4]thiadiazolo[3,2-a]pyrimidin-5-one;

1,2-dimethyl-6-[1-(2,2,3,3,3-pentafluoropropyl)-1H-pyrazol-4-yl]-5-(trifluoromethyl)-1H,7H-pyrazolo[1,5-a]pyrimidin-7-one;

1-methyl-6-[1-(2,2,3,3,3-pentafluoropropyl)-1H-pyrazol-4-yl]-5-(trifluoromethyl)-1H,7H-pyrazolo[1,5-a]pyrimidin-7-one;

1,3-dimethyl-6-[1-(2,2,3,3,3-pentafluoropropyl)-1H-pyrazol-4-yl]-5-(trifluoromethyl)-1H,7H-pyrazolo[1,5-a]pyrimidin-7-one;

3-[1-(2,2,3,3,3-pentafluoropropyl)-1H-pyrazol-4-yl]-2-(trifluoromethyl)-4H,6H,7H,8H-pyrrolo[1,2-a]pyrimidin-4-one;

2-methyl-7-(trifluoromethyl)-6-[1-(3,3,3-trifluoropropyl)-1H-pyrazol-4-yl]-5H-[1,3,4]thiadiazolo[3,2-a]pyrimidin-5-one;

2-(trifluoromethyl)-3-[1-(3,3,3-trifluoropropyl)-1H-pyrazol-4-yl]-4H,6H,7H,8H-pyrrolo[1,2-a]pyrimidin-4-one;

6-[1-(2,2,3,3,3-pentafluoropropyl)-1H-pyrazol-4-yl]-7-(trifluoromethyl)-2H,3H,5H-[1,3]thiazolo[3,2-a]pyrimidin-5-one;

6-{1-[(2,2-difluorocyclopropyl)methyl]-1H-pyrazol-4-yl}-2-methyl-7-(trifluoromethyl)-5H-[1,3,4]thiadiazolo[3,2-a]pyrimidin-5-one;

2-methyl-6-[1-(2,2,3,3,3-pentafluoropropyl)-1H-pyrazol-4-yl]-7-(trifluoromethyl)-2H,3H,5H-[1,3]thiazolo[3,2-a]pyrimidin-5-one;

8-[1-(2,2,3,3,3-pentafluoropropyl)-1H-pyrazol-4-yl]-9-(trifluoromethyl)-6,10-diazatricyclo[4.4.0.0$^{2,4}$]deca-1(10),8-dien-7-one;

6-{1-[(3,3-difluorocyclobutyl)methyl]-1H-pyrazol-4-yl}-2-methyl-7-(trifluoromethyl)-5H-[1,3,4]thiadiazolo[3,2-a]pyrimidin-5-one;

1-methyl-6-[1-(2,2,3,3,3-pentafluoropropyl)-1H-pyrazol-4-yl]-7-(trifluoromethyl)-1H,5H-[1,2,4]triazolo[4,3-a]pyrimidin-5-one;

3-methyl-6-[1-(2,2,3,3,3-pentafluoropropyl)-1H-pyrazol-4-yl]-5-(trifluoromethyl)-3H,7H-[1,2,3,4]tetrazolo[1,5-a]pyrimidin-7-one;

2-methyl-6-{1-[(oxetan-3-yl)methyl]-1H-pyrazol-4-yl}-7-(trifluoromethyl)-5H-[1,3,4]thiadiazolo[3,2-a]pyrimidin-5-one;

2-methyl-6-[1-(2,2,3,3,3-pentafluoropropyl)-1H-pyrazol-3-yl]-7-(trifluoromethyl)-5H-[1,3,4]thiadiazolo[3,2-a]pyrimidin-5-one;

6-[4-(2,2,2-trifluoroethoxy)phenyl]-7-(trifluoromethyl)-5H-[1,3]thiazolo[3,2-a]pyrimidin-5-one;

2-(hydroxymethyl)-6-[1-(2,2,3,3,3-pentafluoropropyl)-1H-pyrazol-4-yl]-7-(trifluoromethyl)-5H-[1,3]thiazolo[3,2-a]pyrimidin-5-one;

2-(hydroxymethyl)-6-[4-(2,2,2-trifluoroethoxy)phenyl]-7-(trifluoromethyl)-5H-[1,3]thiazolo[3,2-a]pyrimidin-5-one;

2-chloro-6-[4-(2,2,2-trifluoroethoxy)phenyl]-7-(trifluoromethyl)-5H-[1,3]thiazolo[3,2-a]pyrimidin-5-one;

6-[1-(2,2,3,3,3-pentafluoropropyl)-1H-pyrazol-4-yl]-1-(propan-2-yl)-7-(trifluoromethyl)-1H,2H,3H,5H-imidazo[1,2-a]pyrimidine-2,5-dione;

1-methyl-6-[1-(2,2,3,3,3-pentafluoropropyl)-1H-pyrazol-4-yl]-7-(trifluoromethyl)-1H,5H-imidazo[1,2-a]pyrimidin-5-one;

3-methyl-6-[1-(2,2,3,3,3-pentafluoropropyl)-1H-pyrazol-4-yl]-5-(trifluoromethyl)-3H,7H-[1,2,4]triazolo[1,5-a]pyrimidin-7-one;

2-methyl-6-[1-(2,2,3,3,3-pentafluoropropyl)-1H-pyrazol-4-yl]-7-(trifluoromethyl)-5H-[1,3]oxazolo[3,2-a]pyrimidin-5-one;

2-methyl-6-[4-(2,2,2-trifluoroethoxy)phenyl]-7-(trifluoromethyl)-5H-[1,3,4]thiadiazolo[3,2-a]pyrimidin-5-one;

7-ethoxy-2-methyl-6-[1-(2,2,3,3,3-pentafluoropropyl)-1H-pyrazol-4-yl]-5H-[1,3,4]thiadiazolo[3,2-a]pyrimidin-5-one;

2-(methoxymethyl)-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one;

2-methoxy-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one;

3-chloro-1-methyl-6-[1-(2,2,3,3,3-pentafluoropropyl)-1H-pyrazol-4-yl]-7-(trifluoromethyl)-1H,5H-imidazo[1,2-a]pyrimidin-5-one;

2-(hydroxymethyl)-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one;

2-(hydroxymethyl)-7-(trifluoromethyl)-6-[1-(3,3,3-trifluoropropyl)-1H-pyrazol-4-yl]-5H-[1,3,4]thiadiazolo[3,2-a]pyrimidin-5-one;

6-[1-(2,2,3,3,3-pentafluoropropyl)-1H-pyrazol-4-yl]-7-(trifluoromethyl)-1H,2H,3H,5H-imidazo[1,2-a]pyrimidine-2,5-dione;

2-chloro-1-methyl-6-[1-(2,2,3,3,3-pentafluoropropyl)-1H-pyrazol-4-yl]-7-(trifluoromethyl)-1H,5H-imidazo[1,2-a]pyrimidin-5-one;

2-chloro-6-[1-(2,2,3,3,3-pentafluoropropyl)-1H-pyrazol-4-yl]-7-(trifluoromethyl)-1H,5H-imidazo[1,2-a]pyrimidin-5-one;

2-cyclopropyl-1-methyl-6-[1-(2,2,3,3,3-pentafluoropropyl)-1H-pyrazol-4-yl]-7-(trifluoromethyl)-1H,5H-imidazo[1,2-a]pyrimidin-5-one;

2-chloro-1-methyl-7-(trifluoromethyl)-6-[1-(3,3,3-trifluoropropyl)-1H-pyrazol-4-yl]-1H,5H-imidazo[1,2-a]pyrimidin-5-one;

1,2-dimethyl-6-[1-(2,2,3,3,3-pentafluoropropyl)-1H-pyrazol-4-yl]-7-(trifluoromethyl)-1H,5H-imidazo[1,2-a]pyrimidin-5-one;

1,2-dimethyl-7-(trifluoromethyl)-6-[1-(3,3,3-trifluoropropyl)-1H-pyrazol-4-yl]-1H,5H-imidazo[1,2-a]pyrimidin-5-one;

1,2-dimethyl-6-[4-(2,2,2-trifluoroethoxy)phenyl]-7-(trifluoromethyl)-1H,5H-imidazo[1,2-a]pyrimidin-5-one;

2-(methoxymethyl)-1-methyl-6-[1-(2,2,3,3,3-pentafluoropropyl)-1H-pyrazol-4-yl]-7-(trifluoromethyl)-1H,5H-imidazo[1,2-a]pyrimidin-5-one;

1-ethyl-2-methyl-6-[1-(2,2,3,3,3-pentafluoropropyl)-1H-pyrazol-4-yl]-7-(trifluoromethyl)-1H,5H-imidazo[1,2-a]pyrimidin-5-one;

1-(2-methoxyethyl)-2-methyl-6-[1-(2,2,3,3,3-pentafluoropropyl)-1H-pyrazol-4-yl]-7-(trifluoromethyl)-1H,5H-imidazo[1,2-a]pyrimidin-5-one;

2-methyl-6-[1-(2,2,3,3,3-pentafluoropropyl)-1H-pyrazol-4-yl]-1-(propan-2-yl)-7-(trifluoromethyl)-1H,5H-imidazo[1,2-a]pyrimidin-5-one;

6-{1-[(2,2-difluorocyclopropyl)methyl]-1H-pyrazol-4-yl}-1,2-dimethyl-7-(trifluoromethyl)-1H,5H-imidazo[1,2-a]pyrimidin-5-one;

6-{1-[(3,3-difluorocyclobutyl)methyl]-1H-pyrazol-4-yl}-1,2-dimethyl-7-(trifluoromethyl)-1H,5H-imidazo[1,2-a]pyrimidin-5-one;

6-[1-(cyclopropylmethyl)-1H-pyrazol-4-yl]-1,2-dimethyl-7-(trifluoromethyl)-1H,5H-imidazo[1,2-a]pyrimidin-5-one;

1-(cyclopropylmethyl)-2-methyl-6-[1-(2,2,3,3,3-pentafluoropropyl)-1H-pyrazol-4-yl]-7-(trifluoromethyl)-1H,5H-imidazo[1,2-a]pyrimidin-5-one;

2-(methoxymethyl)-1-methyl-7-(trifluoromethyl)-6-[1-(3,3,3-trifluoropropyl)-1H-pyrazol-4-yl]-1H,5H-imidazo[1,2-a]pyrimidin-5-one;

1-(2-hydroxypropyl)-2-methyl-6-[1-(2,2,3,3,3-pentafluoropropyl)-1H-pyrazol-4-yl]-7-(trifluoromethyl)-1H,5H-imidazo[1,2-a]pyrimidin-5-one;

1,2-dimethyl-6-{1-[(oxetan-3-yl)methyl]-1H-pyrazol-4-yl}-7-(trifluoromethyl)-1H,5H-imidazo[1,2-a]pyrimidin-5-one;

1-(cyclopropylmethyl)-2-methyl-7-(trifluoromethyl)-6-[1-(3,3,3-trifluoropropyl)-1H-pyrazol-4-yl]-1H,5H-imidazo[1,2-a]pyrimidin-5-one;

1-[2-(dimethylamino)ethyl]-2-methyl-7-(trifluoromethyl)-6-[1-(3,3,3-trifluoropropyl)-1H-pyrazol-4-yl]-1H,5H-imidazo[1,2-a]pyrimidin-5-one;

1-(cyclopropylmethyl)-2-methyl-6-[4-(2,2,2-trifluoroethoxy)phenyl]-7-(trifluoromethyl)-1H,5H-imidazo[1,2-a]pyrimidin-5-one;

1-[2-(dimethylamino)ethyl]-2-methyl-6-[4-(2,2,2-trifluoroethoxy)phenyl]-7-(trifluoromethyl)-1H,5H-imidazo[1,2-a]pyrimidin-5-one;

1,2-dimethyl-6-[1-(2,2,3,3,3-pentafluoropropyl)-1H-pyrazol-3-yl]-7-(trifluoromethyl)-1H,5H-imidazo[1,2-a]pyrimidin-5-one;

2-methoxy-1-methyl-6-[1-(2,2,3,3,3-pentafluoropropyl)-1H-pyrazol-4-yl]-7-(trifluoromethyl)-1H,5H-imidazo[1,2-a]pyrimidin-5-one;

2-methoxy-1-methyl-7-(trifluoromethyl)-6-[1-(3,3,3-trifluoropropyl)-1H-pyrazol-4-yl]-1H,5H-imidazo[1,2-a]pyrimidin-5-one;

2-methyl-6-[1-(2,2,3,3,3-pentafluoropropyl)-1H-pyrazol-4-yl]-7-(trifluoromethyl)-1H,5H-imidazo[1,2-a]pyrimidin-5-one;

2-methyl-7-(trifluoromethyl)-6-[1-(3,3,3-trifluoropropyl)-1H-pyrazol-4-yl]-1H,5H-imidazo[1,2-a]pyrimidin-5-one;

2-methyl-6-[4-(2,2,2-trifluoroethoxy)phenyl]-7-(trifluoromethyl)-1H,5H-imidazo[1,2-a]pyrimidin-5-one;

6-{1-[(2,2-difluorocyclopropyl)methyl]-1H-pyrazol-4-yl}-2-methyl-7-(trifluoromethyl)-1H,5H-imidazo[1,2-a]pyrimidin-5-one;

1-($^2$H$_3$)methyl-2-methyl-6-[1-(2,2,3,3,3-pentafluoropropyl)-1H-pyrazol-4-yl]-7-(trifluoromethyl)-1H,5H-imidazo[1,2-a]pyrimidin-5-one;

1-(2H$_3$)methyl-2-methyl-7-(trifluoromethyl)-6-[1-(3,3,3-trifluoropropyl)-1H-pyrazol-4-yl]-1H,5H-imidazo[1,2-a]pyrimidin-5-one;

1-(2-hydroxyethyl)-2-methyl-6-[1-(2,2,3,3,3-pentafluoropropyl)-1H-pyrazol-4-yl]-7-(trifluoromethyl)-1H,5H-imidazo[1,2-a]pyrimidin-5-one;

methyl 2-methyl-5-oxo-6-[1-(2,2,3,3,3-pentafluoropropyl)-1H-pyrazol-4-yl]-7-(trifluoromethyl)-1H,5H-imidazo[1,2-a]pyrimidine-1-carboxylate;

1-[(2,2-difluorocyclopropyl)methyl]-2-methyl-7-(trifluoromethyl)-6-[1-(3,3,3-trifluoropropyl)-1H-pyrazol-4-yl]-1H,5H-imidazo[1,2-a]pyrimidin-5-one;

1-[(3,3-difluorocyclobutyl)methyl]-2-methyl-7-(trifluoromethyl)-6-[1-(3,3,3-trifluoropropyl)-1H-pyrazol-4-yl]-1H,5H-imidazo[1,2-a]pyrimidin-5-one;

1-(2-hydroxyethyl)-2-methyl-7-(trifluoromethyl)-6-[1-(3,3,3-trifluoropropyl)-1H-pyrazol-4-yl]-1H,5H-imidazo[1,2-a]pyrimidin-5-one;

1-[2-(dimethylamino)ethyl]-2-methyl-6-[1-(2,2,3,3,3-pentafluoropropyl)-1H-pyrazol-4-yl]-7-(trifluoromethyl)-1H,5H-imidazo[1,2-a]pyrimidin-5-one;

2-methyl-6-[1-(2,2,3,3,3-pentafluoropropyl)-1H-pyrazol-4-yl]-1-(prop-2-yn-1-yl)-7-(trifluoromethyl)-1H,5H-imidazo[1,2-a]pyrimidin-5-one;

2-{2-methyl-5-oxo-6-[1-(2,2,3,3,3-pentafluoropropyl)-1H-pyrazol-4-yl]-7-(trifluoromethyl)-1H,5H-imidazo[1,2-a]pyrimidin-1-yl}acetonitrile;

2-[2-methyl-5-oxo-7-(trifluoromethyl)-6-[1-(3,3,3-trifluoropropyl)-1H-pyrazol-4-yl]-1H,5H-imidazo[1,2-a]pyrimidin-1-yl]acetonitrile;

1-(2-hydroxy-2-methylpropyl)-2-methyl-6-[1-(2,2,3,3,3-pentafluoropropyl)-1H-pyrazol-4-yl]-7-(trifluoromethyl)-1H,5H-imidazo[1,2-a]pyrimidin-5-one;

1-[2-(1-hydroxycyclopropyl)ethyl]-2-methyl-6-[1-(2,2,3,3,3-pentafluoropropyl)-1H-pyrazol-4-yl]-7-(trifluoromethyl)-1H,5H-imidazo[1,2-a]pyrimidin-5-one;

2-methyl-1-[(oxetan-3-yl)methyl]-6-[1-(2,2,3,3,3-pentafluoropropyl)-1H-pyrazol-4-yl]-7-(trifluoromethyl)-1H,5H-imidazo[1,2-a]pyrimidin-5-one;

2-methyl-1-(oxetan-3-yl)-6-[1-(2,2,3,3,3-pentafluoropropyl)-1H-pyrazol-4-yl]-7-(trifluoromethyl)-1H,5H-imidazo[1,2-a]pyrimidin-5-one;

1,2-dimethyl-6-[1-(2,2,3,3,3-pentafluoropropyl)-1H-pyrazol-4-yl]-7-(trifluoromethyl)-1H,5H-imidazo[1,2-a]pyrimidine-5-thione;

2-methyl-6-[1-(2,2,3,3,3-pentafluoropropyl)-1H-pyrazol-4-yl]-1-(pyridin-2-yl)-7-(trifluoromethyl)-1H,5H-imidazo[1,2-a]pyrimidin-5-one;

2-methyl-1-(pyridin-2-yl)-7-(trifluoromethyl)-6-[1-(3,3,3-trifluoropropyl)-1H-pyrazol-4-yl]-1H,5H-imidazo[1,2-a]pyrimidin-5-one;

2-methyl-6-[1-(2,2,3,3,3-pentafluoropropyl)-1H-pyrazol-4-yl]-1-(pyrazin-2-yl)-7-(trifluoromethyl)-1H,5H-imidazo[1,2-a]pyrimidin-5-one;

2-methyl-1-(6-methylpyridin-2-yl)-6-[1-(2,2,3,3,3-pentafluoropropyl)-1H-pyrazol-4-yl]-7-(trifluoromethyl)-1H,5H-imidazo[1,2-a]pyrimidin-5-one;

2-methyl-1-(1-methyl-1H-pyrazol-4-yl)-6-[1-(2,2,3,3,3-pentafluoropropyl)-1H-pyrazol-4-yl]-7-(trifluoromethyl)-1H,5H-imidazo[1,2-a]pyrimidin-5-one;

2-methyl-6-[1-(2,2,3,3,3-pentafluoropropyl)-1H-pyrazol-4-yl]-1-(pyridin-3-yl)-7-(trifluoromethyl)-1H,5H-imidazo[1,2-a]pyrimidin-5-one;

2-methyl-6-[1-(2,2,3,3,3-pentafluoropropyl)-1H-pyrazol-4-yl]-1-phenyl-7-(trifluoromethyl)-1H,5H-imidazo[1,2-a]pyrimidin-5-one;

1-(6-chloropyridin-2-yl)-2-methyl-6-[1-(2,2,3,3,3-pentafluoropropyl)-1H-pyrazol-4-yl]-7-(trifluoromethyl)-1H,5H-imidazo[1,2-a]pyrimidin-5-one;

2-methyl-6-[1-(2,2,3,3,3-pentafluoropropyl)-1H-pyrazol-4-yl]-1-(pyridin-4-yl)-7-(trifluoromethyl)-1H,5H-imidazo[1,2-a]pyrimidin-5-one;

2-methyl-6-[1-(2,2,3,3,3-pentafluoropropyl)-1H-pyrazol-4-yl]-1-(1H-pyrazol-4-yl)-7-(trifluoromethyl)-1H,5H-imidazo[1,2-a]pyrimidin-5-one;

2-(fluoromethyl)-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one;

2-[(dimethylamino)methyl]-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one;

6-(1-{[(1R)-2,2-difluorocyclopropyl]methyl}-1H-pyrazol-4-yl)-2-methyl-7-(trifluoromethyl)-1H,5H-imidazo[1,2-a]pyrimidin-5-one;

6-(1-{[(1S)-2,2-difluorocyclopropyl]methyl}-1H-pyrazol-4-yl)-2-methyl-7-(trifluoromethyl)-1H,5H-imidazo[1,2-a]pyrimidin-5-one;

6-(1-{[(1R)-2,2-difluorocyclopropyl]methyl}-1H-pyrazol-4-yl)-1,2-dimethyl-7-(trifluoromethyl)-1H,5H-imidazo[1,2-a]pyrimidin-5-one;

6-(1-{[(1S)-2,2-difluorocyclopropyl]methyl}-1H-pyrazol-4-yl)-1,2-dimethyl-7-(trifluoromethyl)-1H,5H-imidazo[1,2-a]pyrimidin-5-one;

6-(1-{[(1R)-2,2-difluorocyclopropyl]methyl}-1H-pyrazol-4-yl)-2-methyl-7-(trifluoromethyl)-5H-[1,3,4]thiadiazolo[3,2-a]pyrimidin-5-one;

6-(1-{[(1S)-2,2-difluorocyclopropyl]methyl}-1H-pyrazol-4-yl)-2-methyl-7-(trifluoromethyl)-5H-[1,3,4]thiadiazolo[3,2-a]pyrimidin-5-one;

(2R)-2-methyl-6-[1-(2,2,3,3,3-pentafluoropropyl)-1H-pyrazol-4-yl]-7-(trifluoromethyl)-2H,3H,5H-[1,3]thiazolo[3,2-a]pyrimidin-5-one;

(2S)-2-methyl-6-[1-(2,2,3,3,3-pentafluoropropyl)-1H-pyrazol-4-yl]-7-(trifluoromethyl)-2H,3H,5H,6H,7H-[1,3]thiazolo[3,2-a]pyrimidin-5-one;

1-{[(1R)-2,2-difluorocyclopropyl]methyl}-2-methyl-7-(trifluoromethyl)-6-[1-(3,3,3-trifluoropropyl)-1H-pyrazol-4-yl]-1H,5H-imidazo[1,2-a]pyrimidin-5-one; or 1-{[(1S)-2,2-difluorocyclopropyl]methyl}-2-methyl-7-(trifluoromethyl)-6-[1-(3,3,3-trifluoropropyl)-1H-pyrazol-4-yl]-1H,5H-imidazo[1,2-a]pyrimidin-5-one.

Provided herein as Embodiment 51 is the compound according to Embodiment 1, or a tautomer thereof, or a pharmaceutically acceptable salt of said compound or said tautomer, wherein the compound is 2-methyl-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one;

2-methoxy-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one;

2-(hydroxymethyl)-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one;

2-chloro-1-methyl-6-[1-(2,2,3,3,3-pentafluoropropyl)-1H-pyrazol-4-yl]-7-(trifluoromethyl)-1H,5H-imidazo[1,2-a]pyrimidin-5-one;

1,2-dimethyl-6-[1-(2,2,3,3,3-pentafluoropropyl)-1H-pyrazol-4-yl]-7-(trifluoromethyl)-1H,5H-imidazo[1,2-a]pyrimidin-5-one;

1,2-dimethyl-7-(trifluoromethyl)-6-[1-(3,3,3-trifluoropropyl)-1H-pyrazol-4-yl]-1H,5H-imidazo[1,2-a]pyrimidin-5-one;

1,2-dimethyl-6-[4-(2,2,2-trifluoroethoxy)phenyl]-7-(trifluoromethyl)-1H,5H-imidazo[1,2-a]pyrimidin-5-one;

2-methyl-6-[1-(2,2,3,3,3-pentafluoropropyl)-1H-pyrazol-4-yl]-7-(trifluoromethyl)-1H,5H-imidazo[1,2-a]pyrimidin-5-one;

2-methyl-7-(trifluoromethyl)-6-[1-(3,3,3-trifluoropropyl)-1H-pyrazol-4-yl]-1H,5H-imidazo[1,2-a]pyrimidin-5-one;

2-methyl-6-[4-(2,2,2-trifluoroethoxy)phenyl]-7-(trifluoromethyl)-1H,5H-imidazo[1,2-a]pyrimidin-5-one;

1-($2H_3$)methyl-2-methyl-6-[1-(2,2,3,3,3-pentafluoropropyl)-1H-pyrazol-4-yl]-7-(trifluoromethyl)-1H,5H-imidazo[1,2-a]pyrimidin-5-one;

1-(2-hydroxyethyl)-2-methyl-6-[1-(2,2,3,3,3-pentafluoropropyl)-1H-pyrazol-4-yl]-7-(trifluoromethyl)-1H,5H-imidazo[1,2-a]pyrimidin-5-one;

2-{2-methyl-5-oxo-6-[1-(2,2,3,3,3-pentafluoropropyl)-1H-pyrazol-4-yl]-7-(trifluoromethyl)-1H,5H-imidazo[1,2-a]pyrimidin-1-yl}acetonitrile;

2-[2-methyl-5-oxo-7-(trifluoromethyl)-6-[1-(3,3,3-trifluoropropyl)-1H-pyrazol-4-yl]-1H,5H-imidazo[1,2-a]pyrimidin-1-yl]acetonitrile;

6-(1-{[(1R)-2,2-difluorocyclopropyl]methyl}-1H-pyrazol-4-yl)-2-methyl-7-(trifluoromethyl)-1H,5H-imidazo[1,2-a]pyrimidin-5-one; or 6-(1-{[(1S)-2,2-difluorocyclopropyl]methyl}-1H-pyrazol-4-yl)-2-methyl-7-(trifluoromethyl)-1H,5H-imidazo[1,2-a]pyrimidin-5-one.

Provided herein as Embodiment 52 is the compound according to Embodiment 1, or a pharmaceutically acceptable salt thereof, wherein the compound is

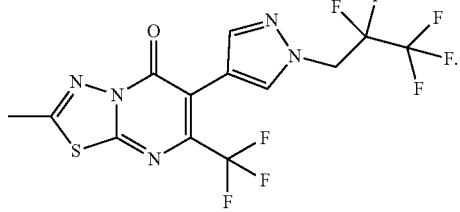

Provided herein as Embodiment 53 is the compound according to Embodiment 1, or a pharmaceutically acceptable salt thereof, wherein the compound is

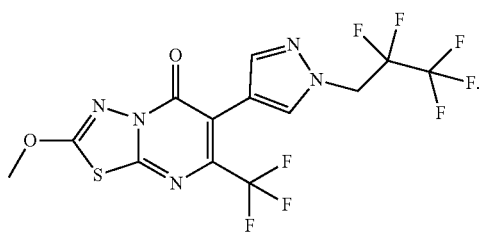 [SMILES: COc1nn2c(=O)c(-c3cnn(CC(F)(F)C(F)(F)F)c3)c(C(F)(F)F)nc2s1]

Provided herein as Embodiment 54 is the compound according to Embodiment 1, or a pharmaceutically acceptable salt thereof, wherein the compound is

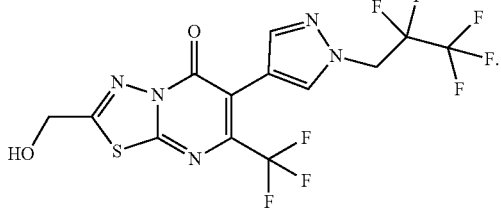

Provided herein as Embodiment 55 is the compound according to Embodiment 1, or a pharmaceutically acceptable salt thereof, wherein the compound is

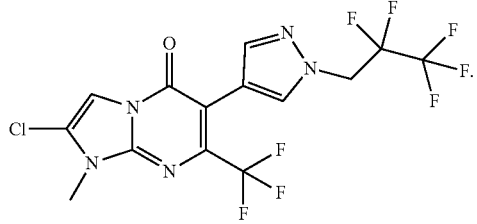 [SMILES: Cn1c(Cl)cn2c(=O)c(-c3cnn(CC(F)(F)C(F)(F)F)c3)c(C(F)(F)F)nc12]

Provided herein as Embodiment 56 is the compound according to Embodiment 1, or a pharmaceutically acceptable salt thereof, wherein the compound is

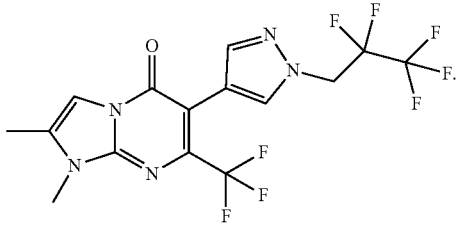 [SMILES: Cc1cn2c(=O)c(-c3cnn(CC(F)(F)C(F)(F)F)c3)c(C(F)(F)F)nc2n1C]

Provided herein as Embodiment 57 is the compound according to Embodiment 1, or a pharmaceutically acceptable salt thereof, wherein the compound is

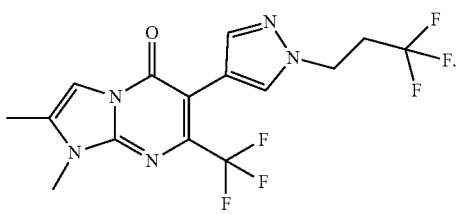 [SMILES: Cc1cn2c(=O)c(-c3cnn(CCC(F)(F)F)c3)c(C(F)(F)F)nc2n1C]

Provided herein as Embodiment 58 is the compound according to Embodiment 1, or a pharmaceutically acceptable salt thereof, wherein the compound is

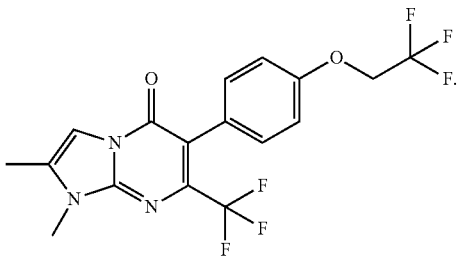 [SMILES: Cc1cn2c(=O)c(-c3ccc(OCC(F)(F)F)cc3)c(C(F)(F)F)nc2n1C]

Provided herein as Embodiment 59 is the compound according to Embodiment 1, or a tautomer thereof, or a pharmaceutically acceptable salt of said compound or said tautomer, wherein the compound is

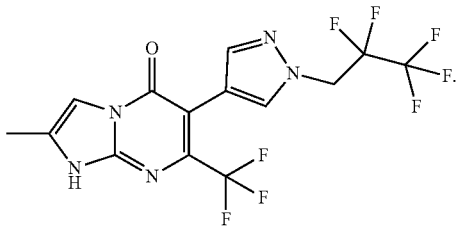 [SMILES: Cc1cn2c(=O)c(-c3cnn(CC(F)(F)C(F)(F)F)c3)c(C(F)(F)F)nc2[nH]1]

Provided herein as Embodiment 60 is the compound according to Embodiment 1, or a tautomer thereof, or a pharmaceutically acceptable salt of said compound or said tautomer, wherein the compound is

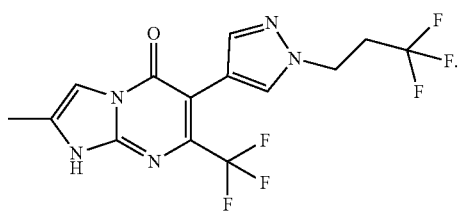 [SMILES: Cc1cn2c(=O)c(-c3cnn(CCC(F)(F)F)c3)c(C(F)(F)F)nc2[nH]1]

Provided herein as Embodiment 61 is the compound according to Embodiment 1, or a tautomer thereof, or a pharmaceutically acceptable salt of said compound or said tautomer, wherein the compound is

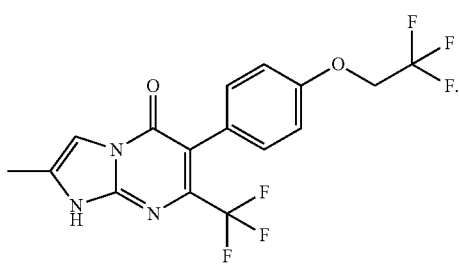 [SMILES: Cc1cn2c(=O)c(-c3ccc(OCC(F)(F)F)cc3)c(C(F)(F)F)nc2[nH]1]

Provided herein as Embodiment 62 is the compound according to Embodiment 1, or a pharmaceutically acceptable salt thereof, wherein the compound is

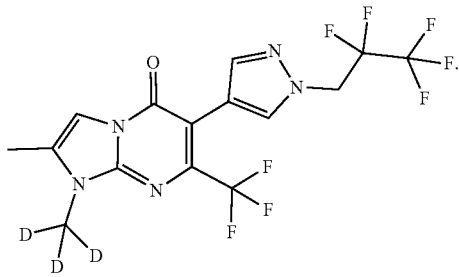 [SMILES: [2H]C([2H])([2H])n1c(C)cn2c(=O)c(-c3cnn(CC(F)(F)C(F)(F)F)c3)c(C(F)(F)F)nc12]

Provided herein as Embodiment 63 is the compound according to Embodiment 1, or a pharmaceutically acceptable salt thereof, wherein the compound is

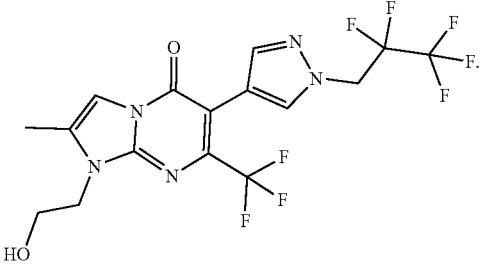

Provided herein as Embodiment 64 is the compound according to Embodiment 1, or a pharmaceutically acceptable salt thereof, wherein the compound is

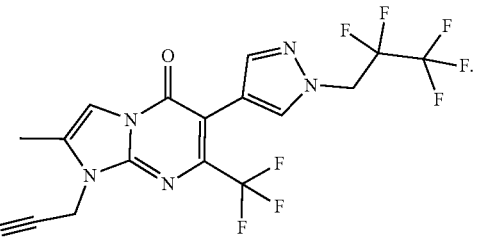

Provided herein as Embodiment 65 is the compound according to Embodiment 1, or a pharmaceutically acceptable salt thereof, wherein the compound is

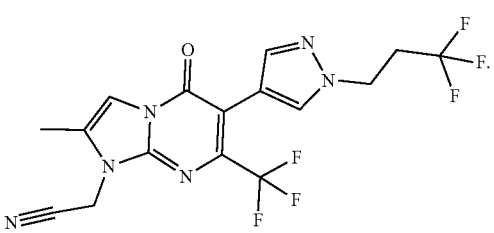 [SMILES: Cc1cn2c(=O)c(-c3cnn(CCC(F)(F)F)c3)c(C(F)(F)F)nc2n1CC#N]

Provided herein as Embodiment 66 is the compound according to Embodiment 1, or a tautomer thereof, or a pharmaceutically acceptable salt of said compound or said tautomer, wherein the compound is

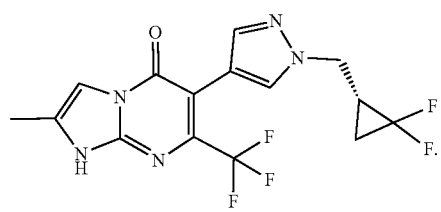 [SMILES: Cc1cn2c(=O)c(-c3cnn(C[C@H]4CC4(F)F)c3)c(C(F)(F)F)nc2[nH]1]

Provided herein as Embodiment 67 is the compound according to Embodiment 1, or a tautomer thereof, or a pharmaceutically acceptable salt of said compound or said tautomer, wherein the compound is

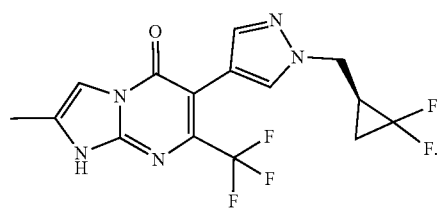 [SMILES: Cc1cn2c(=O)c(-c3cnn(C[C@@H]4CC4(F)F)c3)c(C(F)(F)F)nc2[nH]1]

The foregoing merely summarizes certain aspects of this disclosure and is not intended, nor should it be construed, as limiting the disclosure in any way.

Formulation, and Route of Administration

While it may be possible to administer a compound disclosed herein alone in the uses described, the compound administered normally will be present as an active ingredient in a pharmaceutical composition. Thus, in one embodiment, provided herein is a pharmaceutical composition comprising a compound disclosed herein in combination with one or more pharmaceutically acceptable excipients, such as diluents, carriers, adjuvants and the like, and, if desired, other active ingredients. See, e.g., Remington: The Science and Practice of Pharmacy, Volume I and Volume II, twenty-second edition, edited by Loyd V. Allen Jr., Philadelphia, Pa., Pharmaceutical Press, 2012; Pharmaceutical Dosage Forms (Vol. 1-3), Liberman et al., Eds., Marcel Dekker, New York, N.Y., 1992; Handbook of Pharmaceutical Excipients (3rd Ed.), edited by Arthur H. Kibbe, American Pharmaceutical Association, Washington, 2000; Pharmaceutical Formulation: The Science and Technology of Dosage Forms (Drug Discovery), first edition, edited by G D Tovey, Royal Society of Chemistry, 2018. In one embodiment, a pharmaceutical composition comprises a therapeutically effective amount of a compound disclosed herein.

The compound(s) disclosed herein may be administered by any suitable route in the form of a pharmaceutical composition adapted to such a route and in a dose effective for the treatment intended. The compounds and compositions presented herein may, for example, be administered orally, mucosally, topically, transdermally, rectally, pulmonarily, parentally, intranasally, intravascularly, intravenously, intraarterial, intraperitoneally, intrathecally, subcutaneously, sublingually, intramuscularly, intrasternally, vaginally or by infusion techniques, in dosage unit formulations containing conventional pharmaceutically acceptable excipients.

The pharmaceutical composition may be in the form of, for example, a tablet, chewable tablet, minitablet, caplet, pill, bead, hard capsule, soft capsule, gelatin capsule, granule, powder, lozenge, patch, cream, gel, sachet, microneedle array, syrup, flavored syrup, juice, drop, injectable solution, emulsion, microemulsion, ointment, aerosol, aqueous suspension, or oily suspension. The pharmaceutical composition is typically made in the form of a dosage unit containing a particular amount of the active ingredient.

Provided herein as Embodiment 68 is a pharmaceutical composition comprising the compound according to any one of Embodiments 1-67, or a tautomer thereof, or a pharmaceutically acceptable salt of said compound or said tautomer, and a pharmaceutically acceptable excipient.

Provided herein as Embodiment 69 is a compound according to any one of Embodiments 1-67, or a tautomer thereof, or a pharmaceutically acceptable salt of said compound or said tautomer, or the pharmaceutical composition according to Embodiment 68 for use as a medicament.

Further, this disclosure encompasses pharmaceutical compositions comprising mixtures of any of the compounds disclosed herein and one or more other active agents disclosed herein.

Methods of Use

As discussed herein (see, section entitled "Definitions"), the compounds described herein are to be understood to include all stereoisomers, tautomers, or pharmaceutically acceptable salts of any of the foregoing or solvates of any of the foregoing. Accordingly, the scope of the methods and uses provided in the instant disclosure is to be understood to encompass also methods and uses employing all such forms.

Besides being useful for human treatment, the compounds provided herein may be useful for veterinary treatment of companion animals, exotic animals and farm animals, including mammals, rodents, and the like. For example, animals including horses, dogs, and cats may be treated with compounds provided herein.

Provided herein as Embodiment 70 is a compound according to any one of Embodiments 1-67, or a tautomer thereof, or a pharmaceutically acceptable salt of said compound or said tautomer, or the pharmaceutical composition according to Embodiment 68 for use in reducing the body weight of a subject.

Provided herein as Embodiment 71 is a compound according to any one of Embodiments 1-67, or a tautomer thereof, or a pharmaceutically acceptable salt of said compound or said tautomer, or the pharmaceutical composition according to Embodiment 68 for use in reducing the body-mass-index of a subject.

Provided herein as Embodiment 72 is a compound according to any one of Embodiments 1-67, or a tautomer thereof, or a pharmaceutically acceptable salt of said compound or said tautomer, or the pharmaceutical composition according to Embodiment 68 for use in treating a metabolic disorder.

Provided herein as Embodiment 73 is a compound according to any one of Embodiments 1-67, or a tautomer thereof, or a pharmaceutically acceptable salt of said compound or said tautomer, or the pharmaceutical composition according to Embodiment 68 for use in treating a cardiovascular disorder.

Provided herein as Embodiment 74 is a compound according to any one of Embodiments 1-67, or a tautomer thereof, or a pharmaceutically acceptable salt of said compound or said tautomer, or the pharmaceutical composition according to Embodiment 68 for use in treating diabetes.

Provided herein as Embodiment 75 is a compound according to any one of Embodiments 1-67, or a tautomer thereof, or a pharmaceutically acceptable salt of said compound or said tautomer, or the pharmaceutical composition according to Embodiment 68 for use in treating obesity.

Provided herein as Embodiment 76 is a compound according to any one of Embodiments 1-67, or a tautomer thereof, or a pharmaceutically acceptable salt of said compound or said tautomer, or the pharmaceutical composition according to Embodiment 68 for use in treating dyslipidemia.

Provided herein as Embodiment 77 is a compound according to any one of Embodiments 1-67, or a tautomer thereof, or a pharmaceutically acceptable salt of said compound or said tautomer, or the pharmaceutical composition according to Embodiment 68 for use in treating non-alcoholic steatohepatitis (NASH).

Provided herein as Embodiment 79 is use of the compound according to any one of Embodiments 1-67, or a tautomer thereof, or a pharmaceutically acceptable salt of said compound or said tautomer, or the pharmaceutical composition according to Embodiment 68 in the preparation of a medicament for reducing the body weight or the body-mass-index of a subject.

Provided herein as Embodiment 80 is use of the compound according to any one of Embodiments 1-67, or a tautomer thereof, or a pharmaceutically acceptable salt of said compound or said tautomer, or the pharmaceutical composition according to Embodiment 68 in the preparation of a medicament for treating a metabolic or a cardiovascular disorder.

Provided herein as Embodiment 81 is use of the compound according to any one of Embodiments 1-67, or a tautomer thereof, or a pharmaceutically acceptable salt of said compound or said tautomer, or the pharmaceutical composition according to Embodiment 68 in the preparation of a medicament for treating diabetes, obesity, dyslipidemia, or non-alcoholic steatohepatitis (NASH).

Provided herein as Embodiment 82 is a method of reducing the body weight or the body-mass-index of a subject in need thereof, the method comprising administering to the subject a therapeutically effective amount of the compound according to any one of Embodiments 1-67, or a tautomer thereof, or a pharmaceutically acceptable salt of said compound or said tautomer.

Provided herein as Embodiment 83 is a method of treating a metabolic or a cardiovascular disorder in a subject in need thereof, the method comprising administering to the subject a therapeutically effective amount of the compound according to any one of Embodiments 1-67, or a tautomer thereof, or a pharmaceutically acceptable salt of said compound or said tautomer.

Provided herein as Embodiment 84 is a method of treating diabetes, obesity, dyslipidemia, or non-alcoholic steatohepatitis (NASH) in a subject in need thereof, the method comprising administering to the subject a therapeutically effective amount of the compound according to any one of Embodiments 1-67, or a tautomer thereof, or a pharmaceutically acceptable salt of said compound or said tautomer.

Provided herein as a further embodiment is a method of reducing the waist-to-hip ratio (WHR) of a subject in need thereof, the method comprising administering to the subject a therapeutically effective amount of the compound according to any one of Embodiments 1-67, or a tautomer thereof, or a pharmaceutically acceptable salt of said compound or said tautomer. Provided herein as a further embodiment is use of the compound according to any one of Embodiments 1-67, or a tautomer thereof, or a pharmaceutically acceptable salt of said compound or said tautomer, or the pharmaceutical composition according to Embodiment 68 in the preparation of a medicament for reducing the waist-to-hip ratio (WHR) of a subject. Provided herein as a further embodiment is a compound according to any one of Embodiments 1-67, or a tautomer thereof, or a pharmaceutically acceptable salt of said compound or said tautomer, or the pharmaceutical composition according to Embodiment 68 for use in reducing the waist-to-hip ratio (WHR) of a subject.

Provided herein as a further embodiment is a method of lowering blood glucose in a subject in need thereof, the method comprising administering a therapeutically effective amount of the compound according to any one of Embodiments 1-67, or a tautomer thereof, or a pharmaceutically acceptable salt of said compound or said tautomer, or the pharmaceutical composition according to embodiment 68. In some embodiments, the method lowers blood glucose 10% or greater. In some embodiments, the method lowers blood glucose 15% or greater. In some embodiments, the method lowers blood glucose 20% or greater. In some embodiments, the method lowers blood glucose 25% or greater. In some embodiments, the method lowers blood glucose while having minimal effect on food intake/appetite. In some embodiments, the method lowers blood glucose while having no effect on food intake/appetite.

Provided herein as a further embodiment is a method of lowering insulin in a subject in need thereof, the method comprising administering a therapeutically effective amount of the compound according to any one of Embodiments 1-67, or a tautomer thereof, or a pharmaceutically acceptable salt of said compound or said tautomer, or the pharmaceutical composition according to embodiment 68. In some embodiments, the method lowers insulin 50% or greater. In some embodiments, the method lowers insulin 60% or greater. In some embodiments, the method lowers insulin 70% or greater. In some embodiments, the method lowers insulin 80% or greater. In some embodiments, the method lowers blood insulin 85% or greater. In some embodiments, the method lowers insulin 86% or greater. In some embodiments, the method lowers insulin 87% or greater. In some embodiments, the method lowers insulin 88% or greater. In some embodiments, the method lowers insulin 89% or greater. In some embodiments, the method lowers insulin 90% or greater. In some embodiments, the method lowers insulin 91% or greater. In some embodiments, the method lowers insulin while having minimal effect on food intake/appetite. In some embodiments, the method lowers insulin while having no effect on food intake/appetite.

Provided herein as a further embodiment is a method of lowering cholesterol in a subject in need thereof, the method comprising administering a therapeutically effective amount of the compound according to any one of Embodiments 1-67, or a tautomer thereof, or a pharmaceutically acceptable salt of said compound or said tautomer, or the pharmaceutical composition according to embodiment 68. In some embodiments, the method lowers cholesterol 10% or greater. In some embodiments, the method lowers cholesterol 15% or greater. In some embodiments, the method lowers cholesterol 20% or greater. In some embodiments, the method lowers cholesterol 30% or greater. In some embodiments, the method lowers cholesterol 31% or greater. In some embodiments, the method lowers cholesterol 32% or greater. In some embodiments, the method lowers cholesterol 33% or greater. In some embodiments, the method lowers cholesterol 34% or greater. In some embodiments, the method lowers cholesterol 35% or greater. In some embodiments, the method lowers blood cholesterol 36% or greater. In some embodiments, the method lowers cholesterol 37% or greater. In some embodiments, the method lowers cholesterol 38% or greater. In some embodiments, the method lowers cholesterol 39% or greater. In some embodiments, the method lowers cholesterol while having minimal effect on food intake/appetite. In some embodiments, the method lowers cholesterol while having no effect on food intake/appetite.

Provided herein as a further embodiment is a method of lowering LDL in a subject in need thereof, the method comprising administering a therapeutically effective amount of the compound according to any one of Embodiments 1-67, or a tautomer thereof, or a pharmaceutically acceptable salt of said compound or said tautomer, or the pharmaceutical composition according to embodiment 68. In some embodiments, the method lowers low-density lipoproteins (LDL) 10% or greater. In some embodiments, the method lowers LDL 20% or greater. In some embodiments, the method lowers LDL 21% or greater. In some embodiments, the method lowers LDL 22% or greater. In some embodiments, the method lowers LDL 23% or greater. In some embodiments, the method lowers LDL 24% or greater. In some embodiments, the method lowers LDL 25% or greater. In some embodiments, the method lowers LDL 26% or greater. In some embodiments, the method lowers blood LDL 27% or greater. In some embodiments, the method lowers LDL while having minimal effect on food intake/appetite. In some embodiments, the method lowers LDL while having no effect on food intake/appetite.

Provided herein as a further embodiment is a method of lowering triglycerides in a subject in need thereof, the method comprising administering a therapeutically effective amount of the compound according to any one of Embodiments 1-67, or a tautomer thereof, or a pharmaceutically acceptable salt of said compound or said tautomer, or the pharmaceutical composition according to embodiment 68. In some embodiments, the method lowers triglycerides 30% or greater. In some embodiments, the method lowers triglycerides 40% or greater. In some embodiments, the method lowers triglycerides 50% or greater. In some embodiments, the method lowers triglycerides 51% or greater. In some embodiments, the method lowers triglycerides 52% or greater. In some embodiments, the method lowers triglycerides 53% or greater. In some embodiments, the method lowers triglycerides 54% or greater. In some embodiments, the method lowers triglycerides 55% or greater. In some embodiments, the method lowers blood triglycerides 56% or greater. In some embodiments, the method lowers triglycerides 57% or greater. In some embodiments, the method lowers triglycerides while having minimal effect on food intake/appetite. In some embodiments, the method lowers triglycerides while having no effect on food intake/appetite Provided herein as a further embodiment is a method of lowering fat mass in a subject in need thereof, the method comprising administering a therapeutically effective amount of the compound according to any one of Embodiments 1-67, or a tautomer thereof, or a pharmaceutically acceptable salt of said compound or said tautomer, or the pharmaceutical composition according to embodiment 68. In some embodiments, the method lowers fat mass of a subject 30% or greater. In some embodiments, the method lowers fat mass of a subject 40% or greater. In some embodiments, the method lowers fat mass of a subject 45% or greater. In some embodiments, the method lowers fat mass of a subject 50% or greater. In some embodiments, the method lowers fat mass of a subject 55% or greater. In some embodiments, the method lowers blood fat mass of a subject 60% or greater. In some embodiments, the method lowers fat mass of a subject 65% or greater. In some embodiments, the method lowers fat mass of a subject 70% or greater. In some embodiments, the method lowers fat mass of a subject 75% or greater. In some embodiments, the method lowers fat mass of a subject while having minimal effect on food intake/appetite. In some embodiments, the method lowers fat mass of a subject while having no effect on food intake/appetite.

Provided herein as a further embodiment is a method of raising adiponectin in a subject in need thereof, the method comprising administering a therapeutically effective amount of the compound according to any one of Embodiments 1-67, or a tautomer thereof, or a pharmaceutically acceptable salt of said compound or said tautomer, or the pharmaceutical composition according to embodiment 68.

Provided herein as a further embodiment is a method of lowering leptin in a subject in need thereof, the method comprising administering a therapeutically effective amount of the compound according to any one of Embodiments 1-67, or a tautomer thereof, or a pharmaceutically acceptable salt of said compound or said tautomer, or the pharmaceutical composition according to embodiment 68.

Provided herein as a further embodiment is a method of lowering resisten in a subject in need thereof, the method comprising administering a therapeutically effective amount of the compound according to any one of Embodiments 1-67, or a tautomer thereof, or a pharmaceutically acceptable salt of said compound or said tautomer, or the pharmaceutical composition according to embodiment 68.

Combinations

Provided herein is a further embodiment is a pharmaceutical composition comprising a compound according to any one of Embodiments 1-67 and one or more other active agents. In some embodiments, the one or more active agents include but are not limited to a source of omega-3 fatty acids. In some embodiments, the one or more active agents include but are not limited to omega-3 fatty acid supplements. In some embodiments, the one or more active agents include but are not limited to omega-3-carboxylic acids (e.g., Epanova®), omega-3-acid ethyl esters (e.g., Lovaza® or Omtryg©) or icosapent ethyl (e.g., Vascepa®).

Provided herein as a further embodiment is a method of treating diabetes, obesity, dyslipidemia, or non-alcoholic steatohepatitis (NASH) in a subject in need thereof, the method comprising administering a combination of a therapeutically effective amount of the compound according to any one of Embodiments 1-67, or a tautomer thereof, or a pharmaceutically acceptable salt of said compound or said tautomer in combination with one or more other active agents. In some embodiments, the one or more active agents include but are not limited to a source of omega-3 fatty acids. In some embodiments, the one or more active agents include but are not limited to omega-3 fatty acid supplements. In some embodiments, the one or more active agents include but are not limited to omega-3-carboxylic acids (e.g., Epanova©), omega-3-acid ethyl esters (e.g., Lovaza© or Omtryg©) or icosapent ethyl (e.g., Vascepa©).

Provided herein as a further embodiment is a method of reducing body weight or the body-mass-index of a subject in need thereof, the method comprising administering a combination of a therapeutically effective amount of the compound according to any one of Embodiments 1-67, or a tautomer thereof, or a pharmaceutically acceptable salt of said compound or said tautomer in combination with one or more other active agents. In some embodiments, the one or more active agents include but are not limited to a source of omega-3 fatty acids. In some embodiments, the one or more active agents include but are not limited to omega-3 fatty acid supplements. In some embodiments, the one or more active agents include but are not limited to omega-3-carboxylic acids (e.g., Epanova©), omega-3-acid ethyl esters (e.g., Lovaza® or Omtryg®) or icosapent ethyl (e.g., Vascepa®).

Provided herein as a further embodiment is a method of treating a metabolic or cardiovascular disorder in a subject in need thereof, the method comprising administering a combination of a therapeutically effective amount of the compound according to any one of Embodiments 1-67, or a tautomer thereof, or a pharmaceutically acceptable salt of said compound or said tautomer in combination with one or more other active agents. In some embodiments, the one or more active agents include but are not limited to a source of omega-3 fatty acids. In some embodiments, the one or more active agents include but are not limited to omega-3 fatty acid supplements. In some embodiments, the one or more active agents include but are not limited to omega-3-carboxylic acids (e.g., Epanova®), omega-3-acid ethyl esters (e.g., Lovaza® or Omtryg®) or icosapent ethyl (e.g., Vascepa®).

Provided herein as a further embodiment is a method of reducing the waist-to-hip ratio (WHR) of a subject in need thereof, the method comprising administering a combination of a therapeutically effective amount of the compound according to any one of Embodiments 1-67, or a tautomer thereof, or a pharmaceutically acceptable salt of said compound or said tautomer in combination with one or more other active agents.

Provided herein as a further embodiment is a method of lowering blood glucose in a subject in need thereof, the method comprising administering a combination of a therapeutically effective amount of the compound according to any one of Embodiments 1-67, or a tautomer thereof, or a pharmaceutically acceptable salt of said compound or said tautomer in combination with one or more other active agents.

Provided herein as a further embodiment is a method of lowering insulin in a subject in need thereof, the method comprising administering a combination of a therapeutically effective amount of the compound according to any one of Embodiments 1-67, or a tautomer thereof, or a pharmaceutically acceptable salt of said compound or said tautomer in combination with one or more other active agents.

Provided herein as a further embodiment is a method of lowering cholesterol in a subject in need thereof, the method comprising administering a combination of a therapeutically effective amount of the compound according to any one of Embodiments 1-67, or a tautomer thereof, or a pharmaceutically acceptable salt of said compound or said tautomer in combination with one or more other active agents.

Provided herein as a further embodiment is a method of lowering LDL in a subject in need thereof, the method comprising administering a combination of a therapeutically effective amount of the compound according to any one of Embodiments 1-67, or a tautomer thereof, or a pharmaceutically acceptable salt of said compound or said tautomer in combination with one or more other active agents.

Provided herein as a further embodiment is a method of lowering triglycerides in a subject in need thereof, the method comprising administering a combination of a therapeutically effective amount of the compound according to any one of Embodiments 1-67, or a tautomer thereof, or a pharmaceutically acceptable salt of said compound or said tautomer in combination with one or more other active agents.

Provided herein as a further embodiment is a method of lowering fat mass in a subject in need thereof, the method comprising administering a combination of a therapeutically effective amount of the compound according to any one of Embodiments 1-67, or a tautomer thereof, or a pharmaceutically acceptable salt of said compound or said tautomer in combination with one or more other active agents.

Provided herein as a further embodiment is a method of raising adiponectin in a subject in need thereof, the method comprising administering a combination of a therapeutically effective amount of the compound according to any one of Embodiments 1-67, or a tautomer thereof, or a pharmaceutically acceptable salt of said compound or said tautomer in combination with one or more other active agents.

Provided herein as a further embodiment is a method of lowering leptin in a subject in need thereof, the method comprising administering a combination of a therapeutically effective amount of the compound according to any one of Embodiments 1-67, or a tautomer thereof, or a pharmaceutically acceptable salt of said compound or said tautomer in combination with one or more other active agents.

Provided herein as a further embodiment is a method of lowering resisten in a subject in need thereof, the method comprising administering a combination of a therapeutically effective amount of the compound according to any one of Embodiments 1-67, or a tautomer thereof, or a pharmaceutically acceptable salt of said compound or said tautomer in combination with one or more other active agents.

In some embodiments, the one or more active agents of the combinations described herein or methods utilizing these combinations described herein include but are not limited to omega-3-carboxylic acids (e.g., Epanova®), omega-3-acid ethyl esters (e.g., Lovaza® or Omtryg©) or icosapent ethyl (e.g., Vascepa®).

Definitions

The following definitions are provided to assist in understanding the scope of this disclosure.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the standard deviation found in their respective testing measurements.

As used herein, if any variable occurs more than one time in a chemical formula, its definition on each occurrence is independent of its definition at every other occurrence. If the chemical structure and chemical name conflict, the chemical structure is determinative of the identity of the compound.

Stereoisomers

The compounds of the present disclosure may contain, for example, double bonds, one or more asymmetric carbon atoms, and bonds with a hindered rotation, and therefore, may exist as stereoisomers, such as double-bond isomers (i.e., geometric isomers (E/Z)), enantiomers, diastereomers, and atropoisomers. Accordingly, the scope of the instant disclosure is to be understood to encompass all possible stereoisomers of the illustrated compounds, including the stereoisomerically pure form (for example, geometrically pure, enantiomerically pure, diastereomerically pure, and atropoisomerically pure) and stereoisomeric mixtures (for example, mixtures of geometric isomers, enantiomers, diastereomers, and atropoisomers, or mixture of any of the foregoing) of any chemical structures disclosed herein (in whole or in part), unless the stereochemistry is specifically identified.

If the stereochemistry of a structure or a portion of a structure is not indicated with, for example, bold or dashed lines, the structure or portion of the structure is to be interpreted as encompassing all stereoisomers of it. If the stereochemistry of a structure or a portion of a structure is indicated with, for example, bold or dashed lines, the structure or portion of the structure is to be interpreted as encompassing only the stereoisomer indicated. A bond drawn with a wavy line indicates that both stereoisomers are encompassed. This is not to be confused with a wavy line drawn perpendicular to a bond which indicates the point of attachment of a group to the rest of the molecule.

The term "stereoisomer" or "stereoisomerically pure" compound as used herein refers to one stereoisomer (for example, geometric isomer, enantiomer, diastereomer and atropoisomer) of a compound that is substantially free of other stereoisomers of that compound. For example, a stereoisomerically pure compound having one chiral center will be substantially free of the mirror image enantiomer of the compound and a stereoisomerically pure compound having two chiral centers will be substantially free of other enantiomers or diastereomers of the compound. A typical stereoisomerically pure compound comprises greater than about 80% by weight of one stereoisomer of the compound and equal or less than about 20% by weight of other stereoisomers of the compound, greater than about 90% by weight of one stereoisomer of the compound and equal or less than about 10% by weight of the other stereoisomers of the compound, greater than about 95% by weight of one stereoisomer of the compound and equal or less than about 5% by weight of the other stereoisomers of the compound, or greater than about 97% by weight of one stereoisomer of the compound and equal or less than about 3% by weight of the other stereoisomers of the compound.

This disclosure also encompasses the pharmaceutical compositions comprising stereoisomerically pure forms and the use of stereoisomerically pure forms of any compounds disclosed herein. Further, this disclosure also encompasses pharmaceutical compositions comprising mixtures of stereoisomers of any compounds disclosed herein and the use of said pharmaceutical compositions or mixtures of stereoisomers. These stereoisomers or mixtures thereof may be synthesized in accordance with methods well known in the art and methods disclosed herein. Mixtures of stereoisomers may be resolved using standard techniques, such as chiral columns or chiral resolving agents. See, for example, Jacques et al., Enantiomers, Racemates and Resolutions (Wiley-Interscience, New York, 1981); Wilen et al., *Tetrahedron* 33:2725; Eliel, Stereochemistry of Carbon Compounds (McGraw-Hill, N Y, 1962); and Wilen, Tables of Resolving Agents and Optical Resolutions, page 268 (Eliel, Ed., Univ. of Notre Dame Press, Notre Dame, Ind., 1972).

Tautomers

As known by those skilled in the art, certain compounds disclosed herein may exist in one or more tautomeric forms. Because one chemical structure may only be used to represent one tautomeric form, it will be understood that for convenience, referral to a compound of a given structural formula includes other tautomers of said structural formula. For example, the following is illustrative of tautomers of the compounds of Formula I, wherein x, y, and z are N, C, and C, respectively:

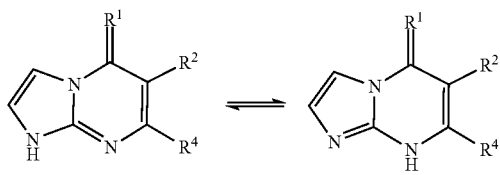

Accordingly, the scope of the instant disclosure is to be understood to encompass all tautomeric forms of the compounds disclosed herein.

Isotopically-Labelled Compounds

Further, the scope of the present disclosure includes all pharmaceutically acceptable isotopically-labelled compounds of the compounds disclosed herein, such as the compounds of Formula I, wherein one or more atoms are replaced by atoms having the same atomic number, but an atomic mass or mass number different from the atomic mass or mass number usually found in nature. Examples of isotopes suitable for inclusion in the compounds disclosed herein include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S. Certain isotopically-labelled compounds of Formula I, for example, those incorporating a radioactive isotope, are useful in drug and/or substrate tissue distribution studies. The radioactive isotopes tritium ($^3$H) and carbon-14 ($^{14}$C) are particularly useful for this purpose in view of their ease of incorporation and ready means of detection. Substitution with isotopes such as deuterium ($^2$H or D) may afford certain therapeutic advantages resulting from greater metabolic stability, for example, increased in vivo half-life or reduced dosage requirements, and hence may be advantageous in some circumstances. Substitution with positron emitting isotopes, such as $^{11}$C, $^{18}$F, $^{15}$O and $^{13}$N, can be useful in Positron Emission Topography (PET) studies, for example, for examining target occupancy. Isotopically-labelled compounds of the compounds disclosed herein can generally be prepared by conventional techniques known to those skilled in the art or by processes analogous to those described in the accompanying General Synthetic Schemes and Examples using an appropriate isotopically-labelled reagent in place of the non-labelled reagent previously employed.

Solvates

As discussed above, the compounds disclosed herein and the stereoisomers, tautomers, and isotopically-labelled forms thereof or a pharmaceutically acceptable salt of any of the foregoing may exist in solvated or unsolvated forms.

The term "solvate" as used herein refers to a molecular complex comprising a compound or a pharmaceutically acceptable salt thereof as described herein and a stoichiometric or non-stoichiometric amount of one or more pharmaceutically acceptable solvent molecules. If the solvent is water, the solvate is referred to as a "hydrate."

Accordingly, the scope of the instant disclosure is to be understood to encompass all solvents of the compounds disclosed herein and the stereoisomers, tautomers and isotopically-labelled forms thereof or a pharmaceutically acceptable salt of any of the foregoing.

Miscellaneous Definitions

This section will define additional terms used to describe the scope of the compounds, compositions and uses disclosed herein.

The terms "$C_{1-3}$alkyl," "$C_{1-4}$alkyl," "$C_{2-6}$alkyl," and "$C_{1-6}$alkyl" as used herein refer to a straight or branched chain hydrocarbon containing from 1 to 3, 1 to 4, 2 to 6, and 1 to 6 carbon atoms, respectively. Representative examples of $C_{1-3}$alkyl, $C_{1-4}$alkyl, $C_{2-6}$alkyl, or $C_{1-6}$alkyl include, but are not limited to, methyl, ethyl, n-propyl, iso-propyl, n-butyl, sec-butyl, iso-butyl, tert-butyl, pentyl and hexyl.

The term "$C_{2-4}$alkenyl" as used herein refers to a saturated hydrocarbon containing 2 to 4 carbon atoms having at least one carbon-carbon double bond. Alkenyl groups include both straight and branched moieties. Representative examples of $C_{2-4}$alkenyl include, but are not limited to, 1-propenyl, 2-propenyl, 2-methyl-2-propenyl, and butenyl.

The term "$C_{2-4}$alkynyl" as used herein refers to a saturated hydrocarbon containing 2 to 4 carbon atoms having at least one carbon-carbon triple bond. The term includes both straight and branched moieties. Representative examples of $C_{3-6}$alkynyl include, but are not limited to, ethynyl, 1-propynyl, 2-propynyl, 2-butynyl and 3-butynyl.

The terms "$C_{1-4}$alkylamino" or "$C_{1-6}$alkylamino" as used herein refer to —NHR*, wherein R* represents a $C_{1-4}$alkyl and $C_{1-6}$alkyl, respectively, as defined herein. Representative examples of $C_{1-4}$alkylamino or $C_{1-6}$alkylamino include, but are not limited to, —NHCH$_3$, —NHCH$_2$CH$_3$, —NHCH$_2$CH$_2$CH$_3$, and —NHCH(CH$_3$)$_2$.

The term "$C_{3-5}$cycloalkyl" as used herein refers to a saturated carbocyclic molecule wherein the cyclic framework has 3 to 5 carbons. Representative examples of $C_{3-5}$cycloalkyl include, but are not limited to, cyclopropyl and cyclobutyl.

The term "deutero" as used herein as a prefix to another term for a chemical group refers to a modification of the chemical group, wherein one or more hydrogen atoms are substituted with deuterium ("D" or "$^2$H"). For example, the term "$C_{1-4}$deuteroalkyl" refers to a $C_{1-4}$alkyl as defined herein, wherein one or more hydrogen atoms are substituted with D. Representative examples of $C_{1-4}$deuteroalkyl include, but are not limited to, —CH$_2$D, —CHD$_2$, —CD$_3$, —CH$_2$CD$_3$, —CDHCD$_3$, —CD$_2$CD$_3$, —CH(CD$_3$)$_2$, —CD(CHD$_2$)$_2$, and —CH(CH$_2$D)(CD$_3$).

The terms "diC$_{1-4}$alkylamino" or "diC$_{1-6}$alkylamino" as used herein refer to —NR*R**, wherein R* and R** independently represent a C$_{1-4}$alkyl and C$_{1-6}$alkyl, respectively, as defined herein. Representative examples of diC$_{1-4}$alkylamino or diC$_{1-6}$alkylamino include, but are not limited to, —N(CH$_3$)$_2$, —N(CH$_2$CH$_3$)$_2$, —N(CH$_3$)(CH$_2$CH$_3$), —N(CH$_2$CH$_2$CH$_3$)$_2$, and —N(CH(CH$_3$)$_2$)$_2$.

The term "C$_{1-4}$alkoxy" or "C$_{2-6}$alkoxy" as used herein refers to —OR$^4$, wherein R$^\#$ represents a C$_{1-4}$alkyl group or C$_{2-6}$alkyl group, respectively, as defined herein. Representative examples of C$_{1-4}$alkoxy include, but are not limited to, methoxy, ethoxy, propoxy, iso-propoxy, and butoxy. Representative examples of C$_{2-6}$alkoxy include, but are not limited to, ethoxy, propoxy, iso-propoxy, and butoxy.

The term "halogen" as used herein refers to —F, —Cl, —Br, or —I.

The term "halo" as used herein as a prefix to another term for a chemical group refers to a modification of the chemical group, wherein one or more hydrogen atoms are substituted with a halogen as defined herein. The halogen is independently selected at each occurrence. For example, the term "C$_{1-4}$haloalkyl" refers to a C$_{1-4}$alkyl as defined herein, wherein one or more hydrogen atoms are substituted with a halogen. Representative examples of C$_{1-4}$haloalkyl include, but are not limited to, —CH$_2$F, —CHF$_2$, —CF$_3$, —CHFCl, —CH$_2$CF$_3$, —CFHCF$_3$, —CF$_2$CF$_3$, —CH(CF$_3$)$_2$, —CF(CHF$_2$)$_2$, and —CH(CH$_2$F)(CF$_3$).

The term "5-membered heteroaryl" or "6-membered heteroaryl" as used herein refers to a 5 or 6-membered carbon ring with two or three double bonds containing one ring heteroatom selected from N, S, and O and optionally one or two further ring N atoms instead of the one or more ring carbon atom(s). Representative examples of a 5-membered heteroaryl include, but are not limited to, furyl, imidazolyl, pyrazolyl, isoxazolyl, isothiazolyl, oxadiazolyl, and oxazolyl. Representative examples of a 6-membered heteroaryl include, but are not limited to, pyridyl, pyrimidyl, pyrazyl, and pyridazyl.

The term "C$_{3-8}$heterocycloalkyl" or "C$_{3-4}$heterocycloalkyl" as used herein refers to a saturated carbocyclic molecule wherein the cyclic framework has 3 to 5 carbons or 3 to 4 carbons and wherein one carbon atom is substituted with a heteroatom selected from N, O, and S. Representative examples of C$_{3-8}$heterocycloalkyl include, but are not limited to, aziridinyl, azetidinyl, oxetanyl, and pyrrolidinyl. Representative examples of C$_{3-4}$heterocycloalkyl include, but are not limited to, aziridinyl, azetidinyl, and oxetanyl.

The phrase "5 membered ring, wherein the ring is aromatic, unsaturated, partially saturated, or saturated" as used herein refers in the context of Formula I to structures including, but not limited to,

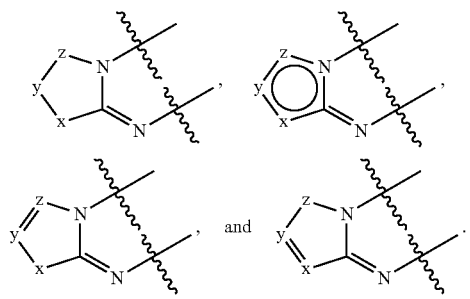

The term "pharmaceutically acceptable" as used herein refers to generally recognized for use in subjects, particularly in humans.

The term "pharmaceutically acceptable salt" as used herein refers to a salt of a compound that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, and the like; or (2) salts formed when an acidic proton present in the parent compound either is replaced by a metal ion, for example, an alkali metal ion, an alkaline earth ion, or an aluminum ion; or coordinates with an organic base such as ethanolamine, diethanolamine, triethanolamine, N-methylglucamine, dicyclohexylamine, and the like. Additional examples of such salts can be found in Berge et al., *J. Pharm. Sci.* 66(1):1-19 (1977). See also Stahl et al., Pharmaceutical Salts: Properties, Selection, and Use, 2$^{nd}$ Revised Edition (2011).

The term "pharmaceutically acceptable excipient" as used herein refers to a broad range of ingredients that may be combined with a compound or salt disclosed herein to prepare a pharmaceutical composition or formulation. Typically, excipients include, but are not limited to, diluents, colorants, vehicles, anti-adherants, glidants, disintegrants, flavoring agents, coatings, binders, sweeteners, lubricants, sorbents, preservatives, and the like.

The term "subject" as used herein refers to humans and mammals, including, but not limited to, primates, cows, sheep, goats, horses, dogs, cats, rabbits, rats, and mice. In one embodiment the subject is a human.

The term "therapeutically effective amount" as used herein refers to that amount of a compound disclosed herein that will elicit the biological or medical response of a tissue, a system, or subject that is being sought by a researcher, veterinarian, medical doctor or other clinician.

The term "body-mass-index" ("BMI") as used herein may be calculated, for example, by determining a subject's weight in kilograms and dividing it by the square of height in meters. See, e.g., https://www.cdc.gov/healthyweight/assessing/bmi/index.html (last accessed Nov. 4, 2019). The BMI is an indicator of the amount of body fat in a subject, such as a human. The BMI is used as a screening tool to identify whether a subject is at a healthy weight or responds to weight loss treatment.

General Synthetic Procedures

The compounds provided herein can be synthesized according to the procedures described in this and the following sections. The synthetic methods described herein are merely exemplary, and the compounds disclosed herein may also be synthesized by alternate routes utilizing alternative synthetic strategies, as appreciated by persons of ordinary skill in the art. It should be appreciated that the general synthetic procedures and specific examples provided herein are illustrative only and should not be construed as limiting the scope of the present disclosure in any manner.

Generally, the compounds of Formula I can be synthesized according to the following schemes. Any variables used in the following schemes are the variables as defined for Formula I, unless otherwise noted. All starting materials are either commercially available, for example, from Merck Sigma-Aldrich Inc., Fluorochem Ltd, and Enamine Ltd. or known in the art and may be synthesized by employing known procedures using ordinary skill. Starting material may also be synthesized via the procedures disclosed herein. Suitable reaction conditions, such as, solvent, reaction temperature, and reagents, for the Schemes discussed in this section, may be found in the examples provided herein.

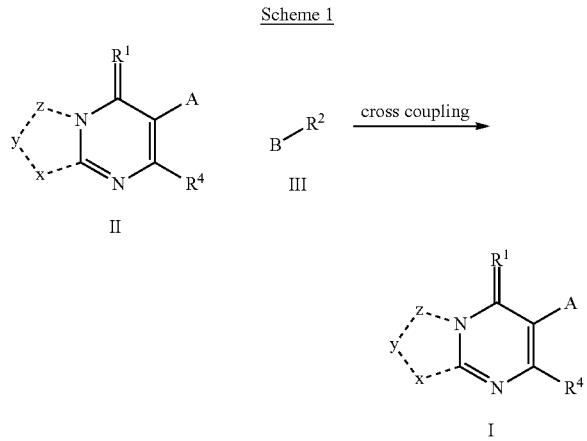

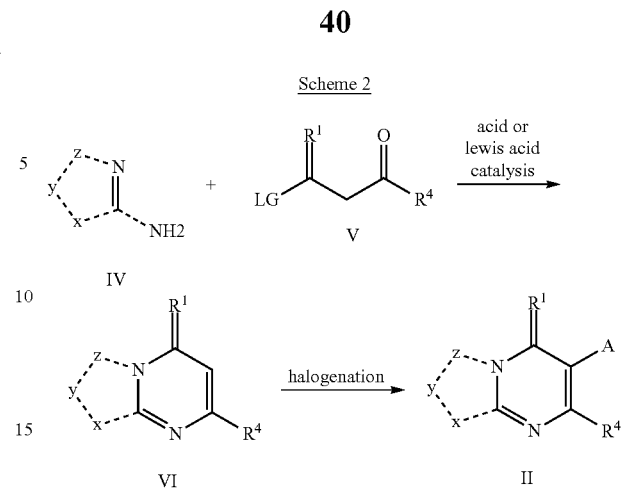

For some compounds disclosed herein, as illustrated in Scheme 2, intermediates of Formula II can be prepared by the treatment of an intermediate of Formula VI with a suitable halogenating reagent, such as N-bromosuccinimide in a suitable solvent. Intermediates of Formula VI in turn can be prepared by the reaction of an intermediate of Formula IV or a salt thereof with a reagent of Formula V in which LG represents a suitable leaving group, such as an alkoxy group, in a condensation reaction, which may be assisted, if required, by heating and/or the presence of an acid or lewis acid.

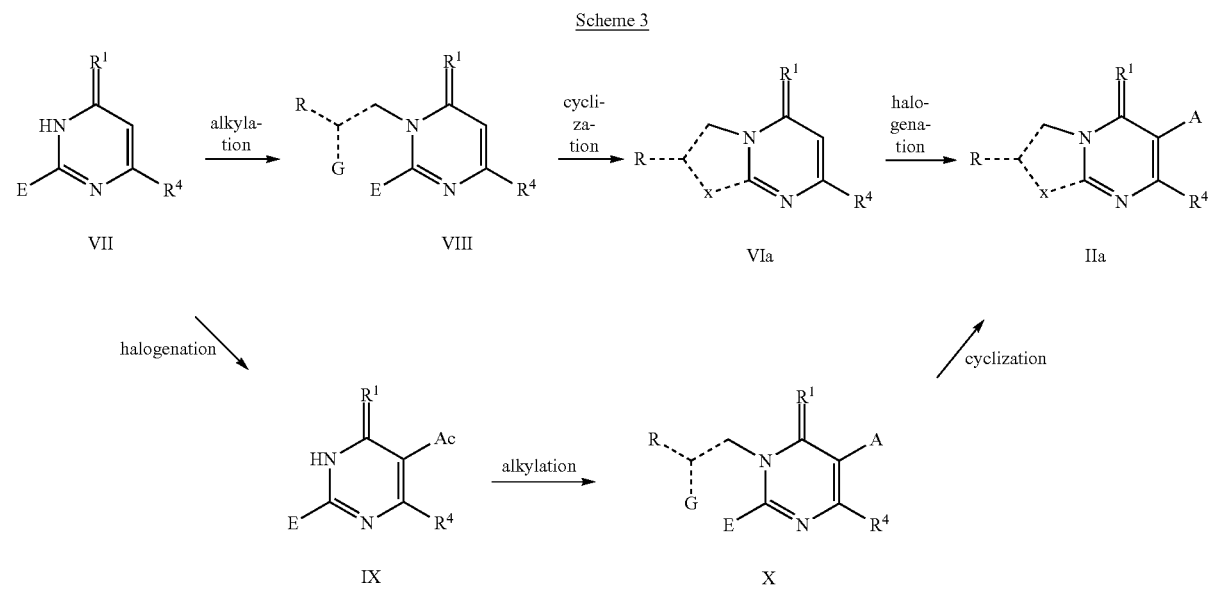

As illustrated in Scheme 1, compounds of Formula I can be prepared by the reaction of an intermediate of Formula II, in which A represents a suitable halogen atom (e.g., Br) or a similar reactive group with an intermediate of Formula III in which B represents a suitable reactive moiety, such as a boronic acid ester in a cross-coupling reaction (e.g., Suzuki) using a palladium or similar transition metal catalyst together with appropriate ligands according to methods described in the literature and known to those skilled in the art.

For some compounds disclosed herein, as illustrated in Scheme 3, intermediates of Formula IIa, in which x is N, O or S and y and z are C, can be prepared as follows. A compound of Formula VII, in which E represents OH, NH$_2$, SH, or a tautomer and/or salt thereof, can be alkylated with a suitable bifunctional reagent followed by a cyclisation in which E reacts with the second reactive group G to form a bicyclic intermediate of Formula VIa. For some compounds of Formula VIa the cyclisation step may occur spontaneously without isolation of the intermediate of Formula VIII. Halogenation as previously described herein will give an intermediate of Formula IIa (see, e.g., Scheme 2). Alternatively, a compound of Formula VII can be halogenated to give an intermediate of Formula IX followed by alkylation to give an intermediate of Formula X followed by cyclization. As above, for some compounds of Formula IIa, the cyclisation step may occur spontaneously.

Scheme 4

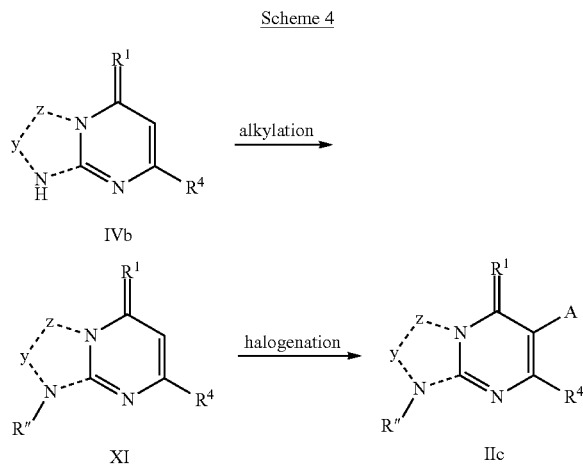

For some compounds disclosed herein, as illustrated in Scheme 4, intermediates of Formula IIc, in which x is N—R" can be prepared as follows. A compound of Formula IVb, prepared as described in Scheme 2 or Scheme 3 above is reacted with a suitable alkylating agent in the presence of a base and a suitable solvent to give an intermediate of Formula XI, which can then be halogenated as previously described herein to give the desired intermediate of Formula IIc.

Scheme 5

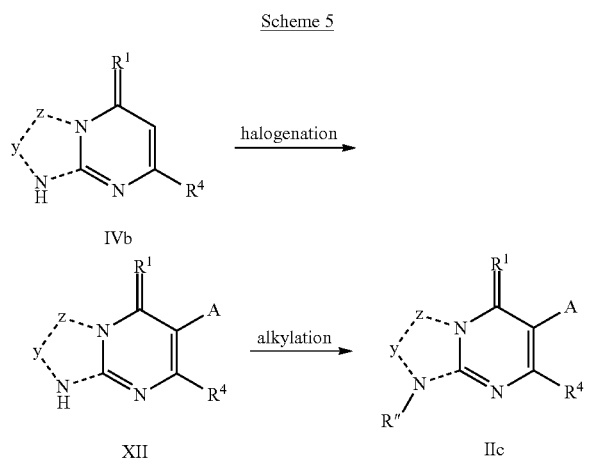

For some compounds disclosed herein, as illustrated in Scheme 5, intermediates of Formula IIc, in which x is N—R" can be prepared as follows. A compound of Formula IVb, prepared as described in Scheme 2 or Scheme 3 above is halogenated as previously described to give an intermediate of Formula XII, which in turn can be reacted with a suitable alkylating agent in the presence of a base and a suitable solvent to give the desired intermediate of Formula IIc.

Scheme 6

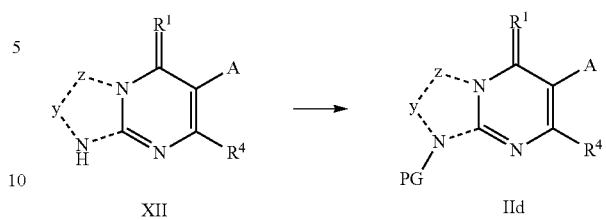

For some compounds disclosed herein, as illustrated in Scheme 6, intermediates of Formula IId, wherein x is N and the N atom is protected with a suitable protecting group PG, can be prepared by the treatment of an intermediate of Formula XII, prepared as described in Scheme 5 above, with a suitable reagent using methods described in the literature and known to those skilled in the art to give the desired intermediate. Suitable protecting groups may include tert-butyloxycarbonyl (Boc), benzyloxycarbonyl (Cbz), triphenylmethyl (Trityl), 2-(trimethylsilyl)ethoxymethyl (SEM), fluorenylmethoxycarbonyl (Fmoc) amongst others known to those skilled in the art.

Scheme 7

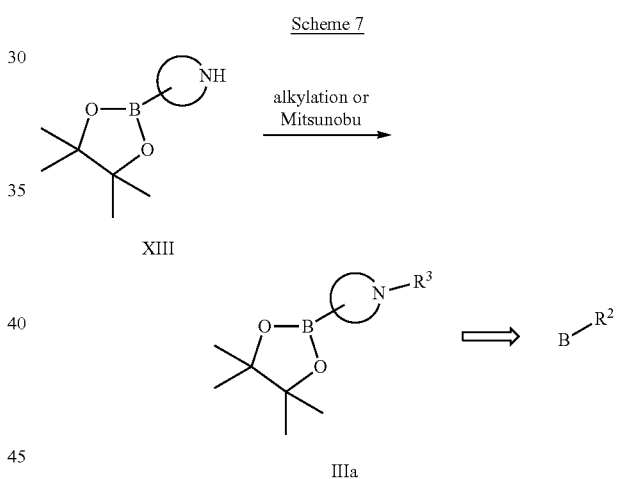

For some compounds disclosed herein, as illustrated in Scheme 7, intermediates of Formula IIIa, wherein the nitrogen-containing ring system is

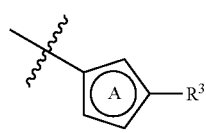

as defined herein, substituted on a nitrogen atom with $R^3$, can be prepared by reacting a boronic ester of Formula XIII with a suitable alkylating agent in the presence of a suitable base or with a suitable alcohol in the presence of activating reagents described in the literature and known to those skilled in the art in a Mitsunobu-type reaction to give an intermediate of Formula IIIa.

Scheme 8

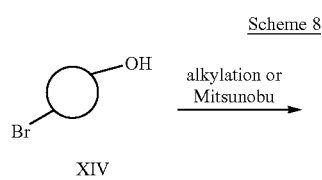

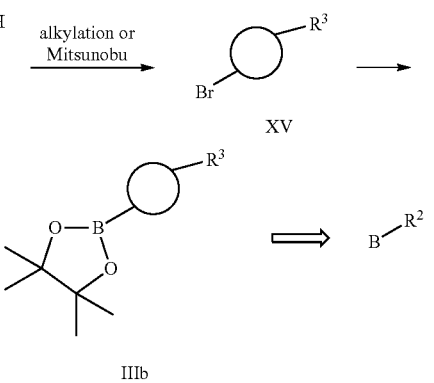

For some compounds disclosed herein, as illustrated in Scheme 8, intermediates of Formula IIIb, wherein the ring system is

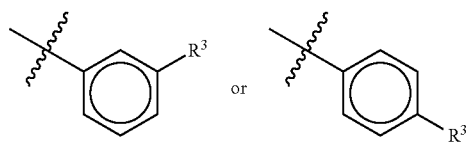

or $R^3$ as defined herein, can be prepared by reacting a hydroxy substituted bromobenzene of Formula XIV with a suitable alkylating agent in the presence of a suitable base or with a suitable alcohol in the presence of activating reagents described in the literature and known to those skilled in the art in a Mitsunobu-type reaction to give an intermediate of Formula XV. Treatment with bis(pinacolato)diboron together with a suitable palladium catalyst in a Miyaura-type borylation reaction using conditions and reagents described in the literature and known to those skilled in the art will give an intermediate of Formula IIIb.

Scheme 9

For some compounds disclosed herein, in which x is N—H or N—R" as illustrated in Scheme 9, intermediates of Formula IId, synthesized as described in Scheme 6 above, in which PG is a suitable protecting group can be reacted with intermediates of Formula III (see, e.g., Schemes 7 and 8) in a cross-coupling reaction as described in Scheme 1 to give an intermediate of formula XVI. The protecting group can then be removed under suitable conditions to give a product of Formula Ia. This can optionally be further substituted by alkylation with a suitable alkylating reagent in the presence of a base or with a suitable (hetero)aromatic boronic acid or ester, bromide, halide or similar in a transition metal catalyzed cross coupling reaction, such as a Buckwald-Hartwig, Chan-Lam, or similar reaction using conditions and reagents described in the literature and known to those skilled in the art to give a product of Formula Ib.

As can be appreciated by the skilled artisan, the above synthetic schemes and representative examples are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

Purification methods for the compounds described herein are known in the art and include, for example, crystallization, chromatography (for example, liquid and gas phase), extraction, distillation, trituration, and reverse phase HPLC.

The disclosure further encompasses "intermediate" compounds, including structures produced from the synthetic procedures described, whether isolated or generated in-situ and not isolated, prior to obtaining the finally desired compound. These intermediates are included in the scope of this disclosure. Exemplary embodiments of such intermediate compounds are set forth below.

Provided herein as Embodiment 84 is a compound of Formula I-1

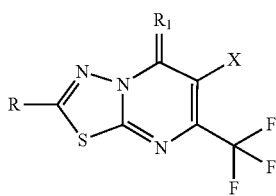

I-1 wherein
X is H or Br;
R$^1$ is O, S, or NH; and
R is H, F, Cl, —OH, —CN, —CO(C$_{1-4}$alkyl), —S(O)$_n$(C$_{1-4}$alkyl), —COOH, —COO(C$_{1-4}$alkyl), —CONH$_2$, —CONH(C$_{1-4}$alkyl), —CO(diC$_{1-4}$alkylamino), —NH(COC$_{1-4}$alkyl), —N(C$_{1-4}$alkyl)C(=O)F, C$_{1-4}$alkyl, —(CH$_2$)$_m$(C$_{3-5}$cycloalkyl), —CH$_2$(C$_{3-8}$heterocycloalkyl), C$_{1-4}$deuteroalkyl, C$_{3-5}$cycloalkyl, C$_{3-4}$heterocycloalkyl, C$_{2-4}$alkenyl, C$_{2-4}$alkynyl, C$_{1-4}$alkoxy, C$_{1-4}$deuteroalkoxy, 5-membered heteroaryl, or 6-membered heteroaryl;
  wherein the C$_{1-4}$alkyl group is optionally substituted with 1 to 4 F or optionally substituted with a substituent selected from —OH, —CN, C$_{1-4}$alkoxy, —NH$_2$, C$_{1-4}$alkylamino, diC$_{1-4}$alkylamino, and —S(O)$_n$(C$_{1-4}$alkyl);
  wherein the C$_{1-4}$alkoxy group is optionally substituted with 1 to 4 independently selected halogens or optionally substituted with a substituent selected from —OH, —CN, C$_{1-4}$alkoxy, —NH$_2$, C$_{1-4}$alkylamino, diC$_{1-4}$alkylamino, and —S(O)$_n$(C$_{1-4}$alkyl); and
  wherein the —CH$_2$(C$_{3-5}$cycloalkyl), C$_{3-4}$heterocycloalkyl, 5-membered heteroaryl, and 6-membered heteroaryl groups are optionally substituted with 1 to 4 substituents independently selected from halogen, —OH, —CN, C$_{1-4}$alkoxy, C$_{1-4}$alkyl, —NH$_2$, C$_{1-4}$alkylamino, diC$_{1-4}$alkylamino, and —S(O)$_n$(C$_{1-4}$alkyl).

Provided herein as Embodiment 85 is the compound of Embodiment 84, wherein X is H.

Provided herein as Embodiment 86 is the compound of Embodiment 84, wherein X is Br.

Provided herein as Embodiment 87 is the compound of any one of Embodiments 84-86, wherein R$^1$ is O.

Provided herein as Embodiment 88 is the compound of any one of Embodiments 84-87, wherein R is methyl.

Provided herein as Embodiment 89 is the compound of any one of Embodiments 84-87, wherein R is methoxy.

Provided herein as Embodiment 90 is the compound of any one of Embodiments 84-87, wherein R is hydroxymethyl.

Provided herein as Embodiment 91 is a compound of Formula I-2

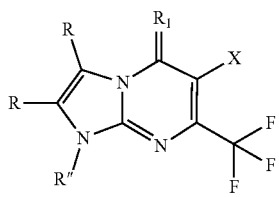

or a tautomer thereof, wherein
X is H or Br;
R$^1$ is O, S, or NH;
R is H, halogen, —OH, —CN, —CO(C$_{1-4}$alkyl), —S(O)$_n$(C$_{1-4}$alkyl), —COOH, —COO(C$_{1-4}$alkyl), —CONH$_2$, —CONH(C$_{1-4}$alkyl), —CO(diC$_{1-4}$alkylamino), —NH$_2$, C$_{1-4}$alkylamino, diC$_{1-4}$alkylamino, —NH(COC$_{1-4}$alkyl), —N(C$_{1-4}$alkyl)C(=O)F, C$_{1-4}$alkyl, —(CH$_2$)$_m$(C$_{3-5}$cycloalkyl), —CH$_2$(C$_{3-5}$heterocycloalkyl), C$_{1-4}$deuteroalkyl, C$_{3-5}$cycloalkyl, C$_{3-4}$heterocycloalkyl, C$_{2-4}$alkenyl, C$_{2-4}$alkynyl, C$_{1-4}$alkoxy, C$_{1-4}$deuteroalkoxy, phenyl, 5-membered heteroaryl, and 6-membered heteroaryl;
  wherein the C$_{1-4}$alkyl group is optionally substituted with 1 to 4 F or optionally substituted with a substituent selected from —OH, —CN, C$_{1-4}$alkoxy, —NH$_2$, C$_{1-4}$alkylamino, diC$_{1-4}$alkylamino, and —S(O)$_n$(C$_{1-4}$alkyl);
  wherein the C$_{1-4}$alkoxy group is optionally substituted with 1 to 4 independently selected halogens or optionally substituted with a substituent selected from —OH, —CN, C$_{1-4}$alkoxy, —NH$_2$, C$_{1-4}$alkylamino, diC$_{1-4}$alkylamino, and —S(O)$_n$(C$_{1-4}$alkyl); and
  wherein the —CH$_2$(C$_{3-5}$cycloalkyl), C$_{3-4}$heterocycloalkyl, phenyl, 5-membered heteroaryl, and 6-membered heteroaryl groups are optionally substituted with 1 to 4 substituents independently selected from halogen, —OH, —CN, C$_{1-4}$alkoxy, C$_{1-4}$alkyl, —NH$_2$, C$_{1-4}$alkylamino, diC$_{1-4}$alkylamino, and —S(O)$_n$(C$_{1-4}$alkyl); and
R" is H, 2-trimethylsilylethoxymethyl, —OH, —CO(C$_{1-4}$alkyl), —S(O)$_n$(C$_{1-4}$alkyl), —COO(C$_{1-4}$alkyl), —CONH$_2$, —CONH(C$_{1-4}$alkyl), —CO(diC$_{1-4}$alkylamino), C$_{1-4}$alkyl, —(CH$_2$)$_m$(C$_{3-8}$cycloalkyl), —CH$_2$(C$_{3-5}$heterocycloalkyl), C$_{1-4}$deuteroalkyl, C$_{3-5}$cycloalkyl, C$_{3-4}$heterocycloalkyl, C$_{2-4}$alkenyl, C$_{2-4}$alkynyl, phenyl, 5-membered heteroaryl, or 6-membered heteroaryl;
  wherein the C$_{1-4}$alkyl group is optionally substituted with 1 to 4 F or optionally substituted with a substituent selected from —OH, —CN, C$_{1-4}$alkoxy, —NH$_2$, C$_{1-4}$alkylamino, diC$_{1-4}$alkylamino, and —S(O)$_n$(C$_{1-4}$alkyl); and
  wherein the —(CH$_2$)$_m$(C$_{3-5}$cycloalkyl), C$_{3-4}$heterocycloalkyl, phenyl, 5-membered heteroaryl, and 6-membered heteroaryl groups are optionally substituted with 1 to 4 substituents independently selected from halogen, —OH, —CN, C$_{1-4}$alkoxy, C$_{1-4}$alkyl, —NH$_2$, C$_{1-4}$alkylamino, diC$_{1-4}$alkylamino, and —S(O)$_n$(C$_{1-4}$alkyl);
with the proviso that if X is H and R" is not 2-trimethylsilylethoxymethyl, then R is not H, C$_{1-4}$alkyl, or phenyl.

Provided herein as Embodiment 92 is the compound of Embodiment 91, or a tautomer thereof, wherein X is H.

Provided herein as Embodiment 93 is the compound of Embodiment 91, or a tautomer thereof, wherein X is Br.

Provided herein as Embodiment 94 is the compound of any one of Embodiments 91-93, or a tautomer thereof, wherein R$^1$ is O.

Provided herein as Embodiment 95 is the compound of any one of Embodiments 93-94, or a tautomer thereof, wherein R is H.

Provided herein as Embodiment 96 is the compound of any one of Embodiments 93-94, or a tautomer thereof, wherein R is Cl.

Provided herein as Embodiment 97 is the compound of any one of Embodiments 93-94, or a tautomer thereof, wherein R is hydroxymethyl.

Provided herein as Embodiment 98 is the compound of any one of Embodiments 93-94, or a tautomer thereof, wherein R is methyl.

Provided herein as Embodiment 99 is the compound of any one of Embodiments 91-98, or a tautomer thereof, wherein R" is H.

Provided herein as Embodiment 100 is the compound of any one of Embodiments 91-98, or a tautomer thereof, wherein R" is methyl.

Provided herein as Embodiment 101 is the compound of any one of Embodiments 91-98, or a tautomer thereof, wherein R" is CD$_3$.

Provided herein as Embodiment 102 is the compound of any one of Embodiments 91-98, or a tautomer thereof, wherein R" is —CH₂CH₂OH.

Provided herein as Embodiment 103 is the compound of any one of Embodiments 91-98, or a tautomer thereof, wherein R" is —CH₂CN.

Provided herein as Embodiment 104 is a compound, wherein the compound is 1-(2,2,3,3,3-pentafluoropropyl)-4-(4,4,5,5-tetramethyl-1,3,2-dioxaborolan-2-yl)pyrazole.

EXAMPLES

This section provides specific examples of compounds of Formula I and methods of making the same.

List of Abbreviations

TABLE 1

| | |
|---|---|
| AcOH | acetic acid |
| aq or aq. | aqueous |
| BOC or Boc | tert-butyloxycarbonyl |
| Cu(OTf)₂ | Copper trifluoromethanesulfonate |
| Cy | Cyclohexane |
| DCE | 1,2-dichloroethane |
| DCM | dichloromethane |
| DIAD | Diisopropyl azodiformate |
| DME | 1,2-dimethoxyethane |
| DMF | N,N-dimethylformamide |
| DMSO | dimethyl sulfoxide |
| Dppf, DPPF or dppf | 1,1'-bis(diphenylphosphino)ferrocene |
| ESI or ES | electrospray ionization |
| Et | ethyl |
| Et₂O | diethyl ether |
| EtOAc | ethyl acetate |
| g | gram(s) |
| h | hour(s) |
| HPLC | high pressure liquid chromatography |
| iPr | isopropyl |
| iPr₂NEt or DIPEA | N-ethyl diisopropylamine (Hunig's base) |
| KOAc | potassium acetate |
| LCMS, LCMS, LC-MS or LC/MS | liquid chromatography mass spectroscopy |
| m/z | mass divided by charge |
| Me | methyl |
| MeCN | acetonitrile |
| MeOH | methanol |
| μL | microliter |
| mg | milligrams |
| min | minutes |
| mL or ml | milliliters |
| MS | mass spectra |
| Ms | methane sulfonyl |
| MsCl | methanesulfonyl chloride |
| NBS | N-bromosuccinimide |
| NCS | N-chlorosuccinimide |
| NIS | N-iodosuccinimide |
| NMP | N-Methyl-2-pyrrolidone |
| NMR | nuclear magnetic resonance |
| Pd(amphos)Cl₂ | bis(di-tert-butyl(4-dimethylaminophenyl)phosphine)dichloropalladium(II) |
| Pd₂(dba)₃ | tris(dibenzylideneacetone)dipalladium(0) |
| Pd(dppf)Cl₂ | [1,1'-bis(diphenylphosphino)ferrocene]dichloropalladium(II) |
| Pd(dtbpf)Cl₂ | 1,1'-Bis(di-tert-butylphosphino)ferrocene-palladium dichloride |
| Pd(PPh₃)₄ | tetrakis(triphenylphosphine)palladium(0) |
| Ph | phenyl |
| PPh₃ | triphenylphosphine |
| PPSE | trimethylsilyl polyphosphate |
| RuPhos Pd G2 | Chloro(2-dicyclohexylphosphino-2',6'-diisopropoxy-1,1'-biphenyl)[2-(2'-amino-1,1'-biphenyl)]palladium(II), |
| p-TsOH | p-Toluenesulfonic acid |
| RP | reverse phase |
| RT or rt or r.t. | room temperature |
| sat. or satd | saturated |

TABLE 1-continued

| | |
|---|---|
| SEMCl | 2-(chloromethoxy)ethyl-trimethylsilane |
| SFC | supercritical fluid chromatography |
| SPhos | 2-dicyclohexylphosphino-2',6'-dimethoxybiphenyl |
| TBAF | tetra-n-butylammonium fluoride |
| TBAI | tetra-n-butylammonium iodide |
| TBDMSCl | tert-butyl-chloro-dimethylsilane |
| TEA or Et3N | trimethylamine |
| TFA | trifluoroacetic acid |
| THF | tetrahydrofuran |
| TTIP | Titanium(IV) isopropoxide |
| XPhos Pd G1 | (2-dicyclohexylphosphino-2',4',6'-triisopropyl-1,1'-biphenyl)[2-(2-aminoethyl)phenyl)]palladium(II) chloride |

General Analytical and Purification Methods Provided in this section are descriptions of the general analytical and purification methods used to prepare the specific compounds provided herein.

Chromatography:

Unless otherwise indicated, crude product-containing residues were purified by passing the crude material or concentrate through either a Biotage brand silica gel column pre-packed with flash silica (SiO₂) or reverse phase flash silica (C18) and eluting the product off the column with a solvent gradient as indicated. For example, a description of (330 g SiO₂, 0-40% EtOAc/hexane) means the product was obtained by elution from the column packed with 330 grams of silica, with a solvent gradient of 0% to 40% EtOAc in hexanes.

Preparative HPLC Method:

Where so indicated, the compounds described herein were purified via reverse phase HPLC using Waters Fractionlynx semi-preparative HPLC-MS system utilizing one of the following two HPLC columns: (a) Phenominex Gemini column (5 micron, C18, 150×30 mm) or (b) Waters X-select CSH column (5 micron, C18, 100×30 mm).

A typical run through the instrument included: eluting at 45 mL/min with a linear gradient of 10% (v/v) to 100% MeCN (0.1% v/v formic acid) in water (0.1% formic acid) over 10 minutes; conditions can be varied to achieve optimal separations.

Proton NMR Spectra:

Unless otherwise indicated, all ¹H NMR spectra were collected on a Bruker NMR Instrument at 300, 400 or 500 Mhz. Where so characterized, all observed protons are reported as parts-per-million (ppm) downfield from tetramethylsilane (TMS) using the internal solvent peak as reference.

Mass Spectra (MS)

Unless otherwise indicated, all mass spectral data for starting materials, intermediates and/or exemplary compounds are reported as mass/charge (m/z), having an [M+H]⁺ molecular ion. The molecular ion reported was obtained by electrospray detection method (commonly referred to as an ESI MS) utilizing a Waters Acquity UPLC/MS system.

Compounds having an isotopic atom, such as bromine and the like, are generally reported according to the detected isotopic pattern, as appreciated by those skilled in the art.

Compound Names

The compounds disclosed and described herein have been named using the IUPAC naming function provided with JChem for Excel 18.22.1.7 from ChemAxon Ltd.

Specific Examples

Provided in this section are the procedures to synthesize specific examples of the compounds provided herein. All starting materials are either commercially available from Merck Sigma-Aldrich Inc., Fluorochem Ltd or Enamine Ltd, unless otherwise noted, or known in the art and may be synthesized by employing known procedures using ordinary skill.

Synthesis of Intermediates

Intermediate 1A 6-bromo-7-(trifluoromethyl)-[1,3]thiazolo[3,2-a]pyrimidin-5-one

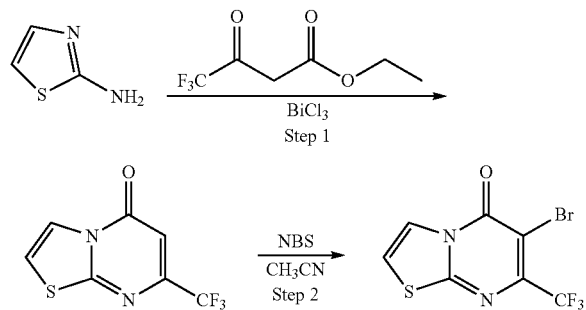

Step 1: 7-(trifluoromethyl)-[1,3]thiazolo[3,2-a]pyrimidin-5-one

A reaction mixture of 2-thiazolamine (1.0 g, 9.99 mmol), ethyl 4,4,4-trifluoroacetoacetate (7.3 ml, 49.93 mmol), and bismuth(III) trichloride (0.31 g, 1.0 mmol) was heated at 120° C. for 14 h. The reaction mixture was cooled to rt, diluted with water and extracted with EtOAc. The organic layer was washed with brine, dried over $Na_2SO_4$, filtered and concentrated under reduced pressure. The crude material was purified by flash chromatography (C18, 20-80% acetonitrile/0.1% formic acid in water) to afford 7-(trifluoromethyl)-[1,3]thiazolo[3,2-a]pyrimidin-5-one (0.53 g, 2.4 mmol, 24% yield) as off white solid. LC/MS (ESI+) m/z=221.0 [M+H]+.

Step 2: 6-bromo-7-(trifluoromethyl)-[1,3]thiazolo[3,2-a]pyrimidin-5-one

N-Bromosuccinimide (420 mg, 2.36 mmol) was added to a stirred solution of 7-(trifluoromethyl)-[1,3]thiazolo[3,2-a]pyrimidin-5-one (520 mg, 2.36 mmol) in $CH_3CN$ (16.3 mL). The reaction mixture was stirred at rt for 20 h, then concentrated under reduced pressure. The residue was diluted with EtOAc and washed with satd. aq. $NaHCO_3$ solution and brine. The organic layer was dried over $Na_2SO_4$, filtered and concentrated under reduced pressure to afford 6-bromo-7-(trifluoromethyl)-[1,3]thiazolo[3,2-a]pyrimidin-5-one (654 mg, 2.19 mmol, 93% yield) as pale-yellow solid. LC/MS (ESI) m/z=299.0/301.0 [M+H]+.

Intermediates 1B-1M listed in Table 2 below were prepared following the procedure described for Intermediate 1A, Steps 1 and 2, above as follows

TABLE 2

| Int. # | Chemical Structure | Name | LC/MS (ESI+) m/z | Conditions | Reagent |
|---|---|---|---|---|---|
| 1B | 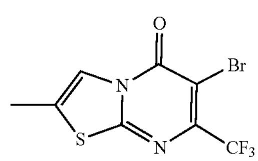 | 6-bromo-2-methyl-7-(trifluoromethyl)-[1,3]thiazolo[3,2-a]pyrimidin-5-one | Step 1: 235.0 Step 2: 312.9/314.9 | Step 1: 100° C., 15 h Step 2: 50° C., 3 h | Step 1: 5-methyl-2-thiazolamine and 4,4,4-trifluoro-3-oxobutanoic acid ethyl ester |
| 1C | 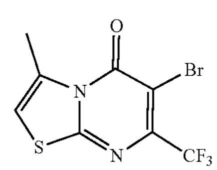 [SMILES: Cc1csc2nc(C(F)(F)F)c(Br)c(=O)n12] | 6-bromo-3-methyl-7-(trifluoromethyl)-[1,3]thiazolo[3,2-a]pyrimidin-5-one | Step 1: 235.3 Step 2: 313.1/315.2 | Step 1: 120° C., 6 h Step 2: 50° C., 3 h | Step 1: 4-methyl-2-thiazolamine and 4,4,4-trifluoro-3-oxobutanoic acid ethyl ester |
| 1D | 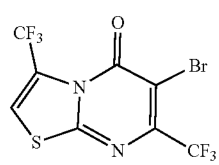 [SMILES: O=c1c(Br)c(C(F)(F)F)nc2scc(C(F)(F)F)n12] | 6-bromo-3,7-bis(trifluoromethyl)-[1,3]thiazolo[3,2-a]pyrimidin-5-one | Step 1: 289.0 Step 2: 367.0/369.0 | Step 1: 120° C., 72 h Step 2: 90° C., 16 h | Step 1: 4-(trifluoromethyl)-2-thiazolamine and 4,4,4-trifluoro-3-oxobutanoic acid ethyl ester |
| 1E | 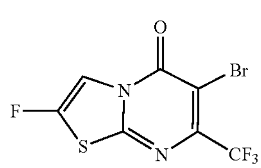 | 6-bromo-2-fluoro-7-(trifluoromethyl)-[1,3]thiazolo[3,2-a]pyrimidin-5-one | Step 1: 239.0 Step 2: 317.0/319.0 | Step 1: 120° C., 6 h Step 2: 80° C., 6 h | Step 1: 5-fluoro-1,3-thiazol-2-amine and 4,4,4-trifluoro-3-oxobutanoic acid ethyl ester |

TABLE 2-continued

| Int. # | Chemical Structure | Name | LC/MS (ESI+) m/z | Conditions | Reagent |
|---|---|---|---|---|---|
| 1F | 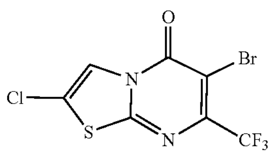 | 6-bromo-2-chloro-7-(trifluoromethyl)-[1,3]thiazolo[3,2-a]pyrimidin-5-one | Step 1: 255.1 Step 2: 333.0/335.0/337.0 | Step 1: 100° C., 2 h Step 2: 50° C., 5 h | Step 1: 5-chloro-1,3-thiazol-2-amine (Enamine) and 4,4,4-trifluoro-3-oxobutanoic acid ethyl ester |
| 1G | 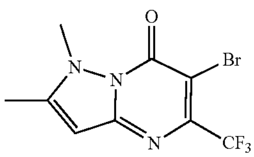 [SMILES: Cc1cc2nc(C(F)(F)F)c(Br)c(=O)n2n1C] | 6-bromo-1,2-dimethyl-5-(trifluoromethyl)-pyrazolo[1,5-a]pyrimidin-7-one | Step 1: 232.0 Step 2: 310.0/312.0 | Step 1: 120° C., 24 h Step 2: rt, 6 h | Step 1: 1,5-dimethyl-1H-pyrazol-3-amine and 4,4,4-trifluoro-3-oxobutanoic acid ethyl ester |
| 1H | 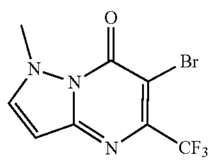 | 6-bromo-1-methyl-5-(trifluoromethyl)-pyrazolo[1,5-a]pyrimidin-7-one | Step 1: 218.0 Step 2: 296.0/298.0 | Step 1: 120° C., 24 h Step 2: rt, 4 h | Step 1: 3-amino-1-methyl-1H-pyrazole and 4,4,4-trifluoro-3-oxobutanoic acid ethyl ester |
| 1I | 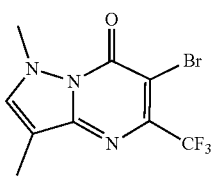 [SMILES: Cc1cn(C)n2c(=O)c(Br)c(C(F)(F)F)nc12] | 6-bromo-1,3-dimethyl-5-(trifluoromethyl)-pyrazolo[1,5-a]pyrimidin-7-one | Step 1: 232.1 Step 2: 310.2/312.2 | Step 1: 120° C., 24 h Step 2: rt, 2 h | Step 1: 1,4-dimethylpyrazol-3-amine (Enamine) and 4,4,4-trifluoro-3-oxobutanoic acid ethyl ester |
| 1J | 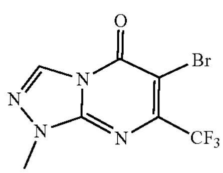 | 6-bromo-1-methyl-7-(trifluoromethyl)-[1,2,4]-triazolo-[4,3-a]pyrimidin-5-one | Step 1: 219.1 Step 2: 296.9/298.9 | Step 1: 100° C. Step 2: rt, 48 h | Step 1: 2-methyl-1,2,4-triazol-3-amine (Enamine) and 4,4,4-trifluoro-3-oxobutanoic acid ethyl ester |
| 1K | 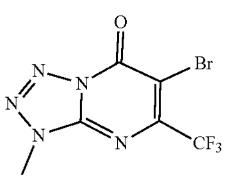 [SMILES: Cn1nnn2c(=O)c(Br)c(C(F)(F)F)nc12] | 6-bromo-3-methyl-5-(trifluoromethyl)-tetrazolo[1,5-a]pyrimidin-7-one | Step 1: 220.0 Step 2: 297.9/299.9 | Step 1: 100° C., 48 h Step 2: rt, 96 h | Step 1: 1-methyltetrazol-5-amine and 4,4,4-trifluoro-3-oxobutanoic acid ethyl ester |
| 1L | 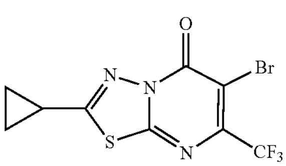 [SMILES: O=c1c(Br)c(C(F)(F)F)nc2sc(C3CC3)nn12] | 6-bromo-2-cyclopropyl-7-(trifluoromethyl)-[1,3,4]thiadiazolo-[3,2-a]pyrimidin-5-one | Step 1: 262.1 Step 2: 340.0/342.0 | Step 1: MW, 120° C., 14 h Step 2: 80° C., 20 h | Step 1: 5-cyclopropyl-1,3,4-thiadiazol-2-amine (Enamine) and 4,4,4-trifluoro-3-oxobutanoic acid ethyl ester |
| 1M | 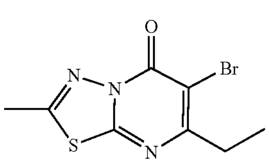 | 6-bromo-7-ethyl-2-methyl-[1,3,4]thiadiazolo-[3,2-a]pyrimidin-5-one | Step 1: 196.0 Step 2: 274.0/276.0 | Step 1: MW, 120° C., 10 h Step 2: rt, 2 h | Step 1: 5-methyl-1,3,4-thiadiazol-2-amine (Enamine) and 3-oxopentanoic acid ethyl ester |

Intermediate 2A 6-bromo-2-(methoxymethyl)-7-(trifluoromethyl)-[1,3,4]thiadiazolo[3,2-a]pyrimidin-5-one

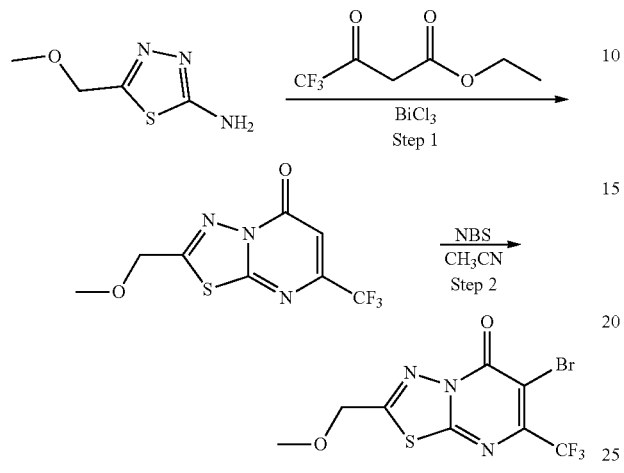

Step 1: 2-(methoxymethyl)-7-(trifluoromethyl)-[1,3,4]thiadiazolo[3,2-a]pyrimidin-5-one A mixture 5-(methoxymethyl)-1,3,4-thiadiazol-2-amine (1.50 g, 10.33 mmol, Enamine), 4,4,4-trifluoro-3-oxobutanoic acid ethyl ester (8.47 mL, 51.66 mmol) and bismuth (III) trichloride (190 mg, 1.03 mmol) was heated at 120° C. for 18 h. The reaction mixture was cooled to rt, diluted with water and extracted with EtOAc. The organic phase was washed with brine, dried over $Na_2SO_4$, filtered and concentrated under reduced pressure. The crude material was purified by flash chromatography ($SiO_2$, 10-50% EtOAc/cyclohexane) to afford 2-(methoxymethyl)-7-(trifluoromethyl)-[1,3,4]thiadiazolo[3,2-a]pyrimidin-5-one (1.04 g, 3.92 mmol, 38% yield) as yellow solid. LC/MS (ESI$^+$) m/z=266.1 [M+H]$^+$.

Step 2: 6-bromo-2-(methoxymethyl)-7-(trifluoromethyl)-[1,3,4]thiadiazolo[3,2-a]pyrimidin-5-one A solution of 2-(methoxymethyl)-7-(trifluoromethyl)-[1,3,4]thiadiazolo[3,2-a]pyrimidin-5-one (600 mg, 2.24 mmol) and N-bromosuccinimide (598 mg, 3.36 mmol) in MeCN (7.2 mL) was heated at 80° C. for 16 h. More N-bromosuccinimide (100 mg, 0.56 mmol) was added and heating was continued for 6 h. The reaction mixture was concentrated, dissolved in EtOAc and washed subsequently with satd. aq. $Na_2S_2O_3$, $NaHCO_3$ solutions and brine. The organic phase was dried over $Na_2SO_4$, filtered and concentrated under reduced pressure. The crude material was purified by flash chromatography ($SiO_2$, 30-60% EtOAc/cyclohexane) to give 6-bromo-2-(methoxymethyl)-7-(trifluoromethyl)-[1,3,4]thiadiazolo[3,2-a]pyrimidin-5-one (350 mg, 1.02 mmol, 45% yield) as a yellow solid. LC/MS (ESI$^+$) m/z=344.0/346.0 [M+H]$^+$.

Intermediate 3A 6-bromo-2-methyl-7-(trifluoromethyl)-[1,3,4]thiadiazolo[3,2-a]pyrimidin-5-one

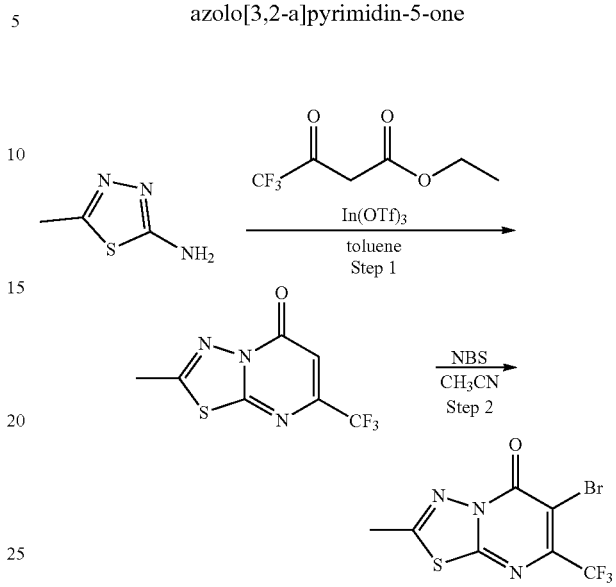

Step 1: 2-methyl-7-(trifluoromethyl)-[1,3,4]thiadiazolo[3,2-a]pyrimidin-5-one 4,4,4-Trifluoro-3-oxobutanoic acid ethyl ester (33.14 mL, 225.36 mmol) and indium(III) trifluoromethanesulfonate (5.31 g, 9.39 mmol) were added to a suspension of 5-methyl-1,3,4-thiadiazol-2-amine (21.63 g, 187.8 mmol, Enamine) in toluene (210 mL). The reaction mixture was heated at 95° C. for 24 h, then cooled to rt and filtered under vacuum. The solid was discarded and the solution was concentrated under reduced pressure. The residue was partitioned between EtOAc (600 mL) and water (600 mL) and the two phases were separated. The organic layer was washed with water (600 mL) and concentrated under reduced pressure. Cyclohexane (100 mL) was added to the residue and the resulting precipitate was filtered, washed with cyclohexane and dried under vacuum to afford 2-methyl-7-(trifluoromethyl)-[1,3,4]thiadiazolo[3,2-a]pyrimidin-5-one (24.1 g, 102.47 mmol, 55% yield) as off white solid. LC/MS (ESI$^+$) m/z=236.0 [M+H]$^+$.

Step 2: 6-bromo-2-methyl-7-(trifluoromethyl)-[1,3,4]thiadiazolo[3,2-a]pyrimidin-5-one N-Bromosuccinimide (20.06 g, 112.72 mmol) was added to a stirred suspension of 2-methyl-7-(trifluoromethyl)-[1,3,4]thiadiazolo[3,2-a]pyrimidin-5-one (24.1 g, 102.47 mmol) in MeCN (206.6 mL). The mixture was heated at 70° C. overnight. After cooling to rt, saturated aqueous $NaHCO_3$ solution (200 mL) and water (800 mL) were slowly added to the reaction mixture. The suspension was stirred at rt for 1 h, then the solid obtained was filtered under vacuum, washed with water (50 mL) and dried under high vacuum to afford 6-bromo-2-methyl-7-(trifluoromethyl)-[1,3,4]thiadiazolo[3,2-a]pyrimidin-5-one (25.47 g, 81.09 mmol, 79% yield). LC/MS (ESI$^+$) m/z=313.9/316.0 [M+H]$^+$.

Intermediate 4A 6-bromo-2-methoxy-7-(trifluoromethyl)-[1,3,4]thiadiazolo[3,2-a]pyrimidin-5-one

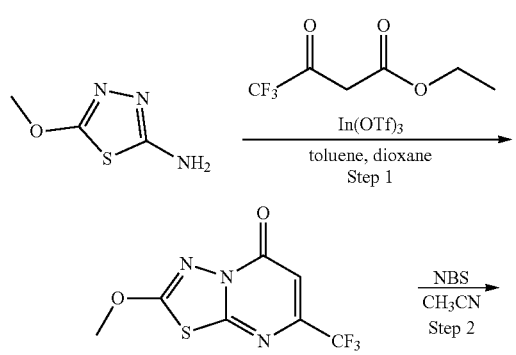

Step 1: 2-methoxy-7-(trifluoromethyl)-[1,3,4]thiadiazolo[3,2-a]pyrimidin-5-one A mixture of 5-methoxy-1,3,4-thiadiazol-2-amine (1.7 g, 12.96 mmol, Enamine), 4,4,4-trifluoro-3-oxobutanoic acid ethyl ester (9.47 mL, 64.81 mmol) and Indium(III) trifluoromethanesulfonate (728.5 mg, 1.3 mmol) in toluene (50 mL) and 1,4-dioxane (5 mL) was heated at 80° C. for 16 h. The reaction mixture was cooled to rt and concentrated under reduced pressure. The obtained crude material was purified by flash chromatography (C18, 3-100% acetonitrile/ 0.1% formic acid in water) to afford 2-methoxy-7-(trifluoromethyl)-[1,3,4]thiadiazolo[3,2-a]pyrimidin-5-one (548 mg, 2.18 mmol, 17% yield) as a white solid. LC/MS (ESI) m/z=252.0 [M+H]$^+$.

Step 2: 6-bromo-2-methoxy-7-(trifluoromethyl)-[1,3,4]thiadiazolo[3,2-a]pyrimidin-5-one A mixture of 2-methoxy-7-(trifluoromethyl)-[1,3,4]thiadiazolo[3,2-a]pyrimidin-5-one (548.0 mg, 2.18 mmol) and N-bromosuccinimide (582.43 mg, 3.27 mmol) in MeCN (10 mL) was heated at 80° C. for 48 h. After cooling to rt, the mixture was diluted with EtOAc and washed subsequently with satd. aq. $Na_2S_2O_3$ and $NaHCO_3$ solutions and brine. The organic layer was dried over $Na_2SO_4$, filtered and concentrated under reduced pressure. The obtained crude material was purified by flash chromatography ($SiO_2$, 0-80% EtOAc/cyclohexane) to afford 6-bromo-2-methoxy-7-(trifluoromethyl)-[1,3,4]thiadiazolo[3,2-a]pyrimidin-5-one (577 mg, 1.75 mmol, 80% yield) as a white solid. LC/MS (ESI$^+$) m/z=329.9/332.0 [M+H]$^+$.

Intermediate 4B listed in Table 3 below was prepared following the procedure described for Intermediate 4A, Steps 1 and 2, above as follows.

TABLE 3

| Int. # | Chemical Structure | Name | LC/MS (ESI$^+$) m/z | Method Changes | Reagent |
|---|---|---|---|---|---|
| 4B | 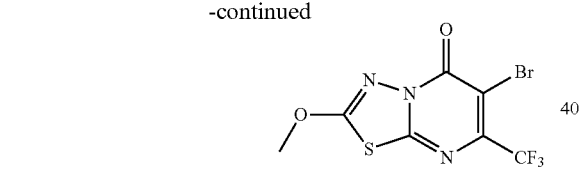 | 6-bromo-2-(hydroxymethyl)-7-(trifluoromethyl)-[1,3]-thiazolo[3,2-a]pyrimidin-5-one | Step 1: 251.1 Step 2: 329.0/331.0 | Step 1: 80° C., 48 h Step 2: 80° C., 48 h | Step 1: (2-amino-1,3-thiazol-5-yl)methanol and 4,4,4-trifluoro-3-oxobutanoic acid ethyl ester |

-continued

Intermediate 5A 6-bromo-3-methyl-5-(trifluoromethyl)-[1,2,4]triazolo[1,5-a]pyrimidin-7-one

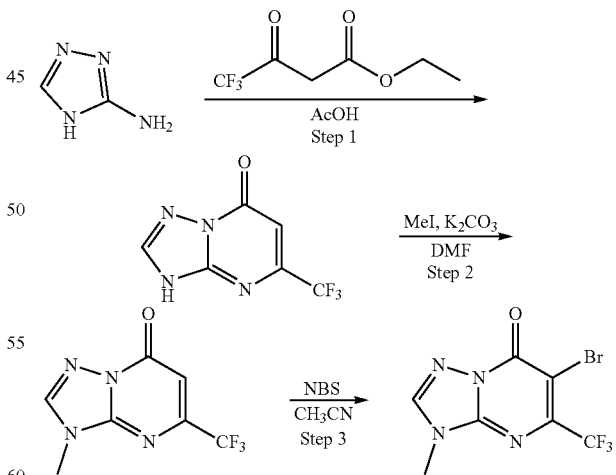

Step 1: 5-(trifluoromethyl)-3H-[1,2,4]triazolo[1,5-a]pyrimidin-7-one 4,4,4-trifluoro-3-oxobutanoic acid ethyl ester (2.09 mL, 14.27 mmol) was added to a solution of 4H-1,2,4-triazol-3- amine (1.0 g, 11.89 mmol) in acetic acid (9 mL). The reaction mixture was heated to reflux for 4 h. After cooling to room temperature, the precipitate was filtered, washed with Et₂O and dried to afford 5-(trifluoromethyl)-3H-[1,2,4]triazolo[1,5-a]pyrimidin-7-one (910 mg, 4.458 mmol, 37% yield) as a white solid. LC/MS (ESI⁺) m/z=205.0 [M+H]⁺.

Step 2: 3-methyl-5-(trifluoromethyl)-[1,2,4]triazolo[1,5-a]pyrimidin-7-one

Potassium carbonate (731 mg, 5.29 mmol) was added to a stirred solution of 5-(trifluoromethyl)-3H-[1,2,4]triazolo[1,5-a]pyrimidin-7-one (900.0 mg, 4.41 mmol) in DMF (30 mL), followed by iodomethane (0.3 mL, 4.85 mmol) after 10 min. The reaction mixture was stirred at rt for 2 h, diluted with water and extracted with EtOAc. The combined organic layers were dried over Na₂SO₄, filtered and concentrated under reduced pressure. The crude material was purified by flash chromatography (SiO₂: 40-100% EtOAc/cyclohexane) to afford 3-methyl-5-(trifluoromethyl)-[1,2,4]triazolo[1,5-a]pyrimidin-7-one (130 mg, 0.6 mmol, 14% yield) as yellow solid. LC/MS (ESI) m/z=219.1 [M+H]⁺.

Step 3: 6-bromo-3-methyl-5-(trifluoromethyl)-[1,2,4]triazolo[1,5-a]pyrimidin-7-one The title compound was prepared using the procedure described for Intermediate 1-A, Step 2 with the following modification: the reaction was performed using 3-methyl-5-(trifluoromethyl)-[1,2,4]triazolo[1,5-a]pyrimidin-7-one and heating the mixture to 80° C. for 2 h. LC/MS (ESI⁺) m/z=297.1/299.1 [M+H]⁺.

Intermediate 5B listed in Table 4 was prepared following the procedure described for Intermediate 5A, Steps 1, 2 and 3, above as follows.

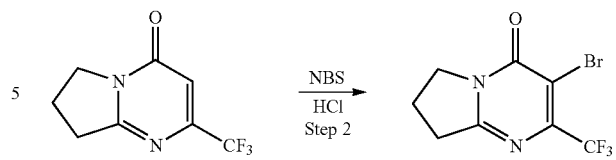

Step 1: 2-(trifluoromethyl)-7,8-dihydro-6H-pyrrolo[1,2-a]pyrimidin-4-one

A reaction mixture of 3,4-dihydro-2H-pyrrol-5-amine hydrochloride (1.0 g, 8.29 mmol), ethyl 4,4,4-trifluoroacetoacetate (6.1 mL, 41.47 mmol), bismuth(III) trichloride (0.26 g, 0.83 mmol) and N,N-diisopropylethylamine (1.44 mL, 8.29 mmol) was heated at 120° C. for 3 h. The reaction mixture was cooled to rt, diluted with water and extracted with EtOAc (2×). The combined organic phases were washed with brine, dried over Na₂SO₄, filtered and concentrated under reduced pressure. The crude was purified by flash chromatography (SiO₂, 0-70% EtOAc/cyclohexane followed by C18, 2-50% acetonitrile/0.1% formic acid in water) to afford 2-(trifluoromethyl)-7,8-dihydro-6H-pyrrolo[1,2-a]pyrimidin-4-one (440 mg, 2.16 mmol, 26% yield) as a white solid. LC/MS (ESI⁺) m/z=205.0 [M+H]⁺.

TABLE 4

| Int. # | Chemical Structure | Name | LC/MS (ESI⁺) m/z | Method Changes | Reagent |
|---|---|---|---|---|---|
| 5B | 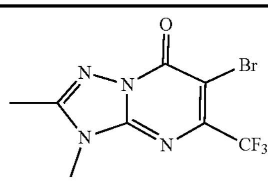 | 6-bromo-2,3-dimethyl-5-(trifluoromethyl)-[1,2,4]triazolo[1,5-a]pyrimidin-7-one | Step 1: 219.1 Step 2: 233.3 Step 3: 311.0/313.0 | Step 2: rt, 22 h Step 3: 80° C., 8 h | Step 1: 5-methyl-4H-1,2,4-triazol-3-amine and 4,4,4-trifluoro-3-oxobutanoic acid ethyl ester |

Intermediate 6A 3-bromo-2-(trifluoromethyl)-7,8-dihydro-6H-pyrrolo[1,2-a]pyrimidin-4-one

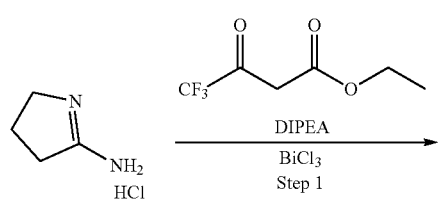

Step 2: 3-bromo-2-(trifluoromethyl)-7,8-dihydro-6H-pyrrolo[1,2-a]pyrimidin-4-one A suspension of 2-(trifluoromethyl)-7,8-dihydro-6H-pyrrolo[1,2-a]pyrimidin-4-one (375 mg, 1.84 mmol) in water (15 mL) and HCl (2N solution in water, 0.92 mL, 1.84 mmol) was stirred at rt for 1 h. N-Bromosuccinimide (409 mg, 2.3 mmol) was added and stirring was continued overnight. Further N-bromosuccinimide (490 mg, 2.75 mmol) was added and stirring was continued for 24 h. The reaction mixture was cooled to 0° C., treated with 1N NaOH aq sol (until pH 8) and extracted with DCM. The organic phase was dried over Na₂SO₄, filtered and concentrated under reduced pressure. The crude material was purified by flash chromatography (SiO₂, 0-70% EtOAc/cyclohexane) to provide 3-bromo-2-(trifluoromethyl)-7,8-dihydro-6H-pyrrolo[1,2-a]pyrimidin-4-one (190 mg, 0.67 mmol, 37% yield) as off-white solid. LC/MS (ESI) m/z=283.0/285.0 [M+H]⁺.

Intermediate 7A

3-bromo-2-(trifluoromethyl)-6,6a,7,7a-tetrahydrocyclopropa[1,2]pyrrolo[4,5-a]pyrimidin-4-one

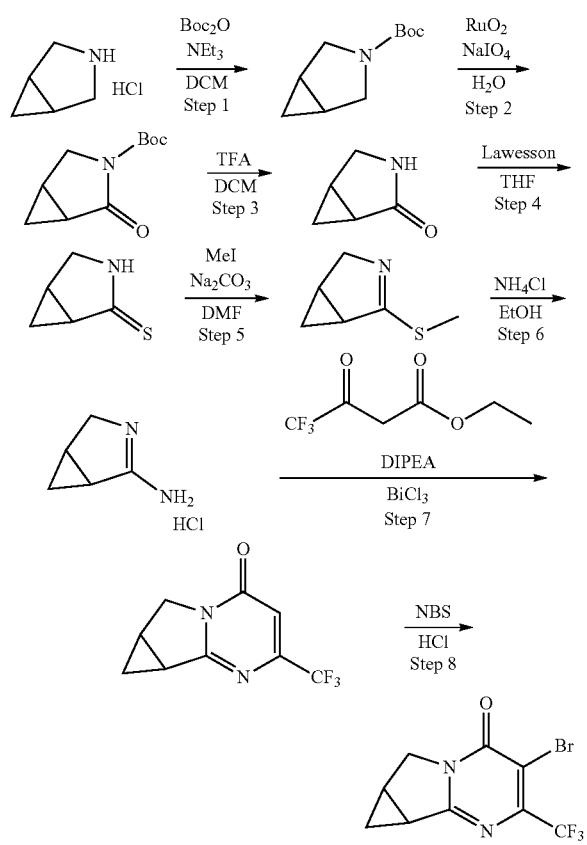

Step 1: tert-butyl 3-azabicyclo[3.1.0]hexane-3-carboxylate

A mixture of 3-azabicyclo[3.1.0]hexane hydrochloride (2.5 g, 20.9 mmol), triethylamine (6.1 mL, 43.9 mmol) and di-tert-butyl dicarbonate (5 g, 23 mmol) in dry DCM (41.7 mL) was stirred at rt for 3 h. Saturated aqueous NH$_4$Cl solution was added, the two phases were separated and the aqueous one was extracted with DCM. The combined organic layers were dried over Na$_2$SO$_4$, filtered and concentrated under reduced pressure to afford tert-butyl 3-azabicyclo[3.1.0]hexane-3-carboxylate (3.83 g, 20.9 mmol, 100% yield) as brown oil. LC/MS (ESI$^+$) m/z=184.0 [M+H]$^+$.

Step 2: tert-butyl 4-oxo-3-azabicyclo[3.1.0]hexane-3-carboxylate

Ruthenium dioxide hydrate (32.2 mg, 0.21 mmol) was added to a 10% solution of sodium periodate (16.8 g, 78.74 mmol) in water (168 ml). After stirring at rt for 20 minutes, a solution of tert-butyl 3-azabicyclo[3.1.0]hexane-3-carboxylate (3.83 g, 20.9 mmol) in EtOAc (56 mL) was added and the resulting reaction mixture was vigorously stirred at rt for 16 h. The mixture was diluted with water and extracted with EtOAc (2×). Isopropyl alcohol (20 mL) was added to the combined organic phases and the mixture was stirred at rt for 3 h, after which the precipitates were filtered off. The filtrate was washed with brine, dried over Na$_2$SO$_4$, filtered and carefully concentrated under reduced pressure to afford tert-butyl 4-oxo-3-azabicyclo[3.1.0]hexane-3-carboxylate (4.1 g, 20.9 mmol, 100% yield) as brown oil. LC/MS (ESI$^+$) m/z=198.3 [M+H]$^+$.

Step 3: 3-azabicyclo[3.1.0]hexan-4-one

A solution of tert-butyl 4-oxo-3-azabicyclo[3.1.0]hexane-3-carboxylate (4.1 g, 20.9 mmol) and trifluoroacetic acid (3.81 ml, 49.74 mmol) in DCM (15 ml), was stirred at rt for 1 h. The reaction mixture was quenched with saturated aq NaHCO$_3$ solution and extracted with DCM (3×). The organic phase was dried over Na$_2$SO$_4$, filtered and carefully concentrated under reduced pressure to afford 3-azabicyclo[3.1.0]hexan-4-one (1.5 g, 15.44 mmol, 74% yield) as yellow oil. $^1$H NMR (400 MHz, DMSO-d$_6$) δ 7.03 (br. s., 1H), 3.37-3.32 (m, 1H), 3.14 (d, J=10.3 Hz, 1H), 1.90 (dq, J=4.4, 5.9 Hz, 1H), 1.62 (tddd, J=1.5, 3.1, 5.8, 8.6 Hz, 1H), 1.01 (dt, J=4.0, 8.0 Hz, 1H), 0.45 (q, J=4.0 Hz, 1H).

Step 4: 3-azabicyclo[3.1.0]hexane-4-thione

A mixture of 3-azabicyclo[3.1.0]hexan-4-one (500 mg, 5.15 mmol) and Lawesson reagent (1.25 g, 3.09 mmol) in THF (5.7 ml) was heated to reflux for 2 h. After cooling to rt, the mixture was concentrated under reduced pressure and the residue material was purified by flash chromatography (SiO$_2$, 0-50% EtOAc/cyclohexane) to give 3-azabicyclo[3.1.0]hexane-4-thione (450 mg, 3.98 mmol, 77% yield). $^1$H NMR (400 MHz, DMSO-d$_6$) δ 0.33-0.46 (m, 1H) 1.10-1.26 (m, 1H) 2.04 (m, 1H) 2.22-2.32 (m, 1H) 3.46 (d, J=12.54 Hz, 1H) 3.65 (dd, J=12.54, 6.16 Hz, 1H) 9.40-9.63 (m, 1H).

Step 5: 4-methylsulfanyl-3-azabicyclo[3.1.0]hex-3-ene

A mixture of 3-azabicyclo[3.1.0]hexane-4-thione (425 mg, 3.76 mmol), sodium carbonate (438 mg, 4.13 mmol) and iodomethane (0.26 ml, 4.13 mmol) in DMF (18.8 ml) was stirred at rt for 5 h. The mixture was partitioned between water and EtOAc and extracted with EtOAc (3×). The combined organic phases were dried over Na$_2$SO$_4$, filtered and carefully concentrated under reduced to provide 4-methylsulfanyl-3-azabicyclo[3.1.0]hex-3-ene (475 mg, 3.76 mmol, 100% yield) as yellowish oil, which was used in the following step without further purification. LC/MS (ESI) m/z=127.9 [M+H]$^+$.

Step 6: 3-azabicyclo[3.1.0]hex-3-en-4-amine Hydrochloride

A mixture of 4-methylsulfanyl-3-azabicyclo[3.1.0]hex-3-ene (475 mg, 3.76 mmol) and ammonium chloride (221 mg, 4.13 mmol) in anhydrous ethanol (9 ml) was heated to reflux for 6 h. After cooling to rt, the reaction mixture was concentrated under vacuum to provide crude 3-azabicyclo[3.1.0]hex-3-en-4-amine hydrochloride (500 mg, 3.76 mmol, 100% yield). $^1$H NMR (400 MHz, DMSO-d$_6$) δ 0.62-0.69 (m, 1H) 1.34 (m, 1H) 2.16-2.26 (m, 1H) 2.34 (m, 1H) 3.47-3.55 (m, 1H) 3.66 (m, 1H) 8.31-9.81 (m, 3H).

Step 7: 2-(trifluoromethyl)-6,6a,7,7a-tetrahydrocyclopropa[1,2]pyrrolo[4,5-a]pyrimidin-4-one The title compound was prepared using the procedure described for Intermediate 6A, Step 1 with the following modification: the reaction was performed with 3-azabicyclo[3.1.0]hex-3-en-4-amine hydrochloride, DIPEA and 4,4,4-trifluoro-3-oxobutanoic acid ethyl ester. LC/MS (ESI⁺) m/z=217.0 [M+H]⁺.

Step 8: 3-bromo-2-(trifluoromethyl)-6,6a,7,7a-tetrahydrocyclopropa[1,2]pyrrolo[4,5-a]pyrimidin-4-one The title compound was prepared using the procedure described for Intermediate 1 6A, Step 2 with the following modification: the reaction was performed with 2-(trifluoromethyl)-6,6a,7,7a-tetrahydrocyclopropa[1,2]pyrrolo[4,5-a]pyrimidin-4-one. LC/MS (ESI⁺) m/z=295.0/297.0 [M+H]⁺.

Intermediate 8A 6-bromo-2-methyl-7-(trifluoromethyl)-2,3-dihydro-[1,3]thiazolo[3,2-a]pyrimidin-5-one

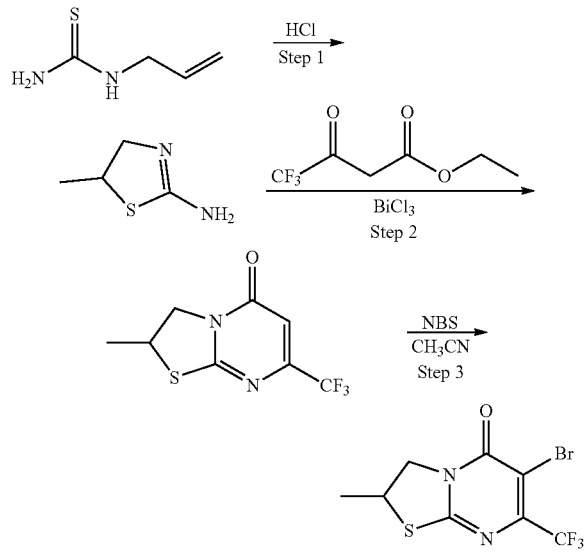

Step 1: 5-methyl-4,5-dihydro-1,3-thiazol-2-amine

A solution of prop-2-enylthiourea (2.0 g, 17.21 mmol) in 3N aq HCl (30.0 mL, 103.5 mmol) was heated at 70° C. for 16 h. After cooling to room temperature, the mixture was evaporated under reduced pressure. The crude material was purified by strong cation exchange chromatography to afford 5-methyl-4,5-dihydro-1,3-thiazol-2-amine (1.67 g, 14.37 mmol, 84% yield) as colourless oil. LC/MS (ESI⁺) m/z=116.9 [M+H]⁺.

Step 2: 2-methyl-7-(trifluoromethyl)-2,3-dihydro-[1,3]thiazolo[3,2-a]pyrimidin-5-one The title compound was prepared using the procedure described for Intermediate 1A, Step 1 with the following modification: the reaction was performed using 5-methyl-4,5-dihydro-1,3-thiazol-2-amine and 4,4,4-trifluoro-3-oxobutanoic acid ethyl ester heating the reaction mixture to 100° C. for 24 h. LC/MS (ESI) m/z=237.0 [M+H]⁺.

Step 3: 6-bromo-2-methyl-7-(trifluoromethyl)-2,3-dihydro-[1,3]thiazolo[3,2-a]pyrimidin-5-one The title compound was prepared using the procedure described for Intermediate 1A, Step 2 with the following modification: the reaction was performed with 2-methyl-7-(trifluoromethyl)-2,3-dihydro-[1,3]thiazolo[3,2-a]pyrimidin-5-one and heating the reaction mixture to 80° C. for 20 h. LC/MS (ESI⁺) m/z=315.1/317.1 [M+H]⁺.

Intermediate 9A 6-bromo-7-ethoxy-2-methyl-[1,3,4]thiadiazolo[3,2-a]pyrimidin-5-one

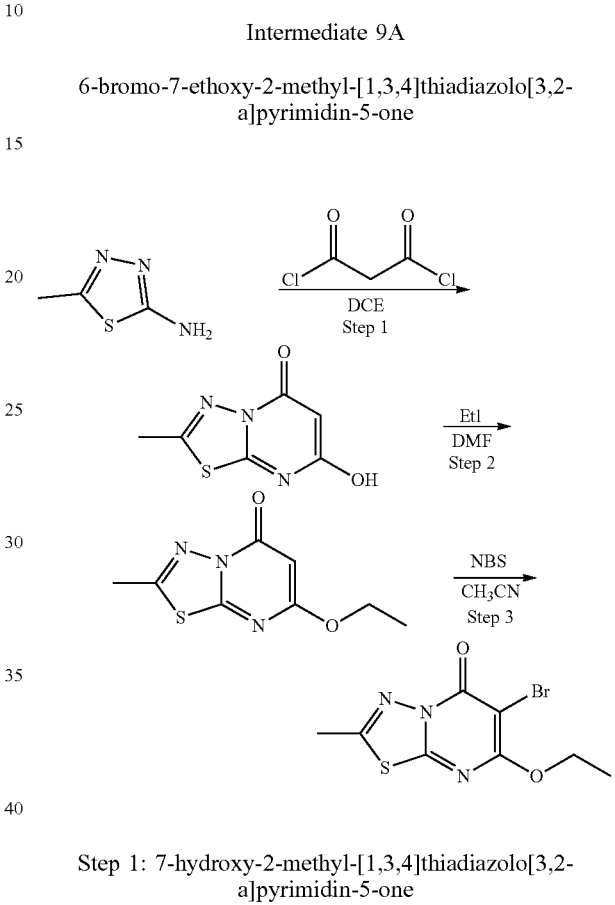

Step 1: 7-hydroxy-2-methyl-[1,3,4]thiadiazolo[3,2-a]pyrimidin-5-one

Malonyl dichloride (0.84 mL, 8.68 mmol) was added dropwise to a solution of 5-methyl-1,3,4-thiadiazol-2-amine (1 g, 8.68 mmol, Enamine) in DCE (8.2 mL) cooled to 0° C. The reaction mixture was allowed to reach room temperature and stirred for 48 h. The suspension was filtered, washed with DCM (3×30 mL) and water (2×20 mL) and dried under vacuum to afford 7-hydroxy-2-methyl-[1,3,4]thiadiazolo[3,2-a]pyrimidin-5-one (950 mg, 5.19 mmol, 60% yield). LC/MS (ESI⁺) m/z=183.9 [M+H]⁺.

Step 2: 7-ethoxy-2-methyl-[1,3,4]thiadiazolo[3,2-a]pyrimidin-5-one

Iodoethane (625.79 mg, 4.01 mmol) was added to a solution of 7-hydroxy-2-methyl-[1,3,4]thiadiazolo[3,2-a]pyrimidin-5-one (700.0 mg, 3.82 mmol) in DMF (18.67 mL). The reaction mixture was heated at 65° C. for 16 h. After cooling to rt, the mixture was concentrated under reduced pressure. The crude material was purified by flash chromatography (SiO₂, 0-10% MeOH/DCM) to afford 7-ethoxy-2-methyl-[1,3,4]thiadiazolo[3,2-a]pyrimidin-5-one (306 mg, 1.45 mmol, 38% yield). LC/MS (ESI⁺) m/z=212.0 [M+H]⁺.

Step 3: 6-bromo-7-ethoxy-2-methyl-[1,3,4]thiadiazolo[3,2-a]pyrimidin-5-one

The title compound was prepared using the procedure described for Intermediate 1A, Step 2 with the following modification: the reaction was performed with 7-ethoxy-2-methyl-[1,3,4]thiadiazolo[3,2-a]pyrimidin-5-one. LC/MS (ESI$^+$) m/z=289.9/291.9 [M+H]$^+$.

Intermediate 10A 6-bromo-1-methyl-7-(trifluoromethyl)imidazo[1,2-a]pyrimidin-5-one

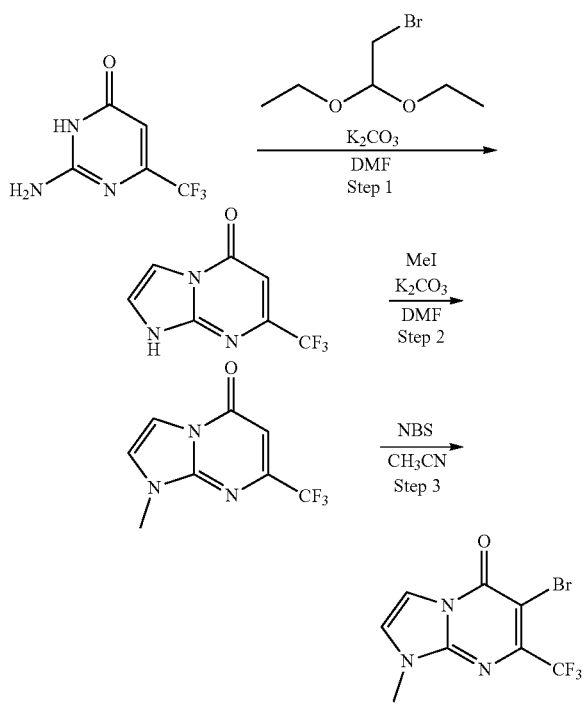

Step 1: 7-(trifluoromethyl)-1H-imidazo[1,2-a]pyrimidin-5-one

2-Bromo-1,1-diethoxyethane (4.4 g, 22.33 mmol) was added to a stirred solution of 2-amino-6-(trifluoromethyl)-1H-pyrimidin-4-one (2.0 g, 11.17 mmol) and potassium carbonate (3.86 g, 27.92 mmol) in DMF (16 mL) at rt. The reaction mixture was heated at 80° C. for 16 h, then cooled to rt and partitioned between water and EtOAc. The organic phase was washed with water and brine, dried over Na$_2$SO$_4$, filtered and concentrated under reduced pressure. The residue was dissolved in acetic acid (10.66 mL, 186.33 mmol) and heated at 120° C. for 1 h. The mixture was cooled to rt, diluted with water and extracted with EtOAc (2×). The organic phase was slowly added to a stirred satd. aq. NaHCO$_3$ solution. The two phases were separated and the organic one washed with brine, dried over Na$_2$SO$_4$, filtered and concentrated under vacuum. The residue was purified by flash chromatography (SiO$_2$, 0-60% EtOAc/Cyclohexane) to afford 7-(trifluoromethyl)-1H-imidazo[1,2-a]pyrimidin-5-one (580 mg, 2.86 mmol, 26% yield). LC/MS (ESI$^+$) m/z=204.2 [M+H]$^+$.

Step 2: 1-methyl-7-(trifluoromethyl)imidazo[1,2-a]pyrimidin-5-one

The title compound was prepared using the procedure described for Intermediate 5A, Step 2 with the following modification: the reaction was performed using 7-(trifluoromethyl)-1H-imidazo[1,2-a]pyrimidin-5-one. LC/MS (ESI$^+$)$_m$/z=218.2 [M+H]$^+$.

Step 3: 6-bromo-1-methyl-7-(trifluoromethyl)imidazo[1,2-a]pyrimidin-5-one

The title compound was prepared using the procedure described for Intermediate 1A, Step 2 with the following modification: the reaction was performed with 1-methyl-7-(trifluoromethyl)imidazo[1,2-a]pyrimidin-5-one. LC/MS (ESI$^+$) m/z=296.2/298.2 [M+H]$^+$.

Intermediate 11A 6-bromo-7-(trifluoromethyl)-2,3-dihydro-[1,3]thiazolo[3,2-a]pyrimidin-5-one

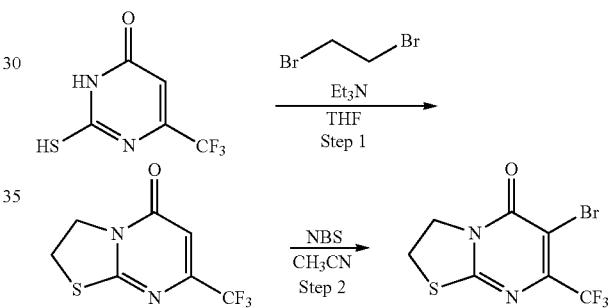

Step 1: 7-(trifluoromethyl)-2,3-dihydro-[1,3]thiazolo[3,2-a]pyrimidin-5-one 1,2-Dibromoethane (105.35 mg, 0.560 mmol) was added to a stirred solution of 2-sulfanyl-4-(trifluoromethyl)-1H-pyrimidin-6-one (100.0 mg, 0.51 mmol) and triethylamine (0.14 mL, 1.02 mmol) in THF (3 mL). After stirring at rt for 24 h, the reaction mixture was heated at 60° C. for 5 h. After cooling to rt, the mixture was concentrated under reduced pressure, the residue was diluted with EtOAc and washed with water. The organic phase was dried over Na$_2$SO$_4$, filtered and concentrated under reduced pressure to afford 7-(trifluoromethyl)-2,3-dihydro-[1,3]thiazolo[3,2-a]pyrimidin-5-one (110 mg, 0.5 mmol, 97% yield) as a pale-yellow oil. LC/MS (ESI$^+$) m/z=223.1 [M+H]$^+$.

Step 2: 6-bromo-7-(trifluoromethyl)-2,3-dihydro-[1,3]thiazolo[3,2-a]pyrimidin-5-one The title compound was prepared using the procedure described for Intermediate 1A, Step 2 with the following modification: the reaction was performed with 7-(trifluoromethyl)-2,3-dihydro-[1,3]thiazolo[3,2-a]pyrimidin-5-one. LC/MS (ESI) m/z=301.1/303.1 [M+H]$^+$.

Intermediate 12A 6-bromo-2-methyl-7-(trifluoromethyl)-[1,3]oxazolo[3,2-a]pyrimidin-5-one

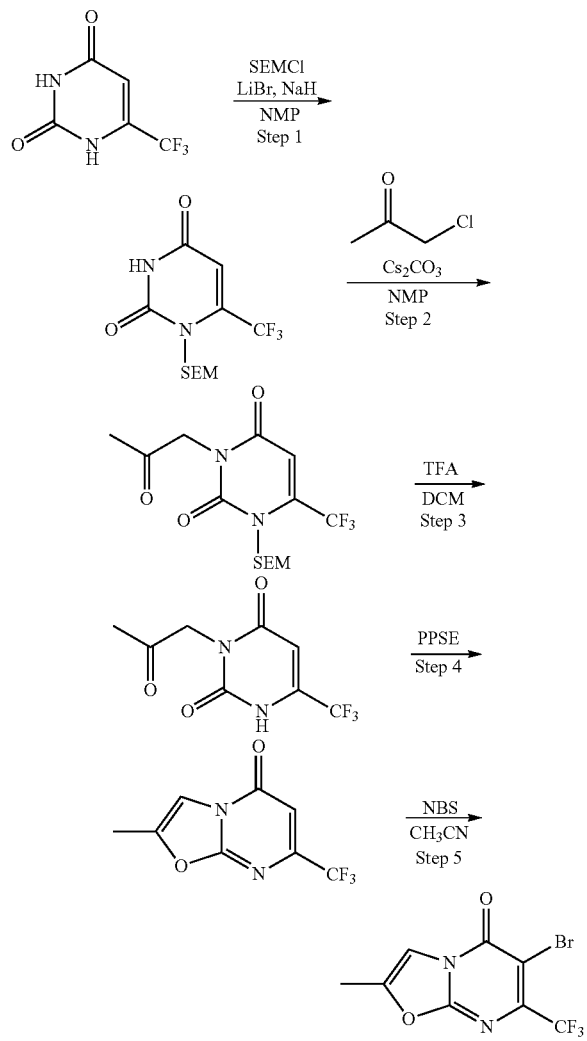

Step 1: 6-(trifluoromethyl)-1-(2-trimethylsilylethoxymethyl)pyrimidine-2,4-dione Sodium hydride (60% in mineral oil, 55.50 mg, 1.39 mmol) was added to a solution of 6-(trifluoromethyl)uracil (250 mg, 1.39 mmol) and lithium bromide (122 mg, 1.39 mmol) in anhydrous NMP (4.8 mL). The mixture was stirred at rt for 30 minutes then 2-(chloromethoxy)ethyl-trimethylsilane (0.25 mL, 1.39 mmol) was added. After stirring for 4 h at rt, the mixture was diluted with 10% $Na_2CO_3$ aq solution and extracted with EtOAc (2×). The organic phase was washed with brine, dried over $Na_2SO_4$, filtered and concentrated under reduced pressure. The crude material was purified by flash chromatography ($SiO_2$, 10-30% EtOAc/Cyclohexane) to afford 6-(trifluoromethyl)-1-(2-trimethylsilylethoxymethyl)pyrimidine-2,4-dione (165 mg, 0.53 mmol, 38% yield) as colorless oil. $^1$H NMR (400 MHz, DMSO-$d_6$) δ −0.02 (s, 9H), 0.89-0.85 (m, 2H), 3.66-3.61 (m, 2H), 5.21 (s, 2H), 6.31 (d, J=2.1 Hz, 1H), 12.00-11.94 (m, 1H).

Step 2: 3-(2-oxopropyl)-6-(trifluoromethyl)-1-(2-trimethylsilylethoxymethyl)pyrimidine-2,4-dione 1-Chloro-2-propanone (0.02 mL, 0.27 mmol) was added to a suspension of 6-(trifluoromethyl)-1-(2-trimethylsilylethoxymethyl)pyrimidine-2,4-dione (70 mg, 0.23 mmol) and cesium carbonate (148 mg, 0.45 mmol) in NMP (1 mL). The reaction mixture was stirred at rt for 16 h, then diluted with EtOAc and washed with brine (3×). The organic phase was dried over $Na_2SO_4$, filtered and concentrated under reduced pressure. The crude material was purified by flash chromatography ($SiO_2$, 10-30% EtOAc/Cyclohexane) to afford 3-(2-oxopropyl)-6-(trifluoromethyl)-1-(2-trimethylsilylethoxymethyl)pyrimidine-2,4-dione (74 mg, 0.2 mmol, 90% yield) as colorless oil. $^1$H NMR (400 MHz, DMSO-$d_6$) δ −0.02 (s, 9H), 0.89-0.84 (m, 2H), 2.22 (s, 3H), 3.64-3.60 (m, 2H), 4.75 (s, 2H), 5.29 (s, 2H), 6.55 (s, 1H).

Step 3: 3-(2-oxopropyl)-6-(trifluoromethyl)-1H-pyrimidine-2,4-dione

A solution of 3-(2-oxopropyl)-6-(trifluoromethyl)-1-(2-trimethylsilylethoxymethyl)pyrimidine-2,4-dione (72 mg, 0.2 mmol) in TFA (0.5 mL) was stirred at rt for 2 h. The reaction mixture was concentrated in vacuo to afford 3-(2-oxopropyl)-6-(trifluoromethyl)-1H-pyrimidine-2,4-dione (45 mg, 0.19 mmol, 97% yield) that was used in the next step without any further purification. LC/MS (ESI$^+$) m/z=237.1 [M+H]$^+$.

Step 4: 2-methyl-7-(trifluoromethyl)-[1,3]oxazolo[3,2-a]pyrimidin-5-one

A mixture of 3-(2-oxopropyl)-6-(trifluoromethyl)-1H-pyrimidine-2,4-dione (45 mg, 0.19 mmol) in trimethylsilyl polyphosphate (2 mL) was heated at 160° C. for 6 h. The reaction mixture was cooled to rt, diluted with water and extracted with DCM (3×). The combined organic phases were washed with brine, dried over $Na_2SO_4$, filtered and concentrated under reduced pressure to afford 2-methyl-7-(trifluoromethyl)-[1,3]oxazolo[3,2-a]pyrimidin-5-one (42 mg, 0.19 mmol, 100% yield) as yellow solid. LC/MS (ESI$^+$) m/z=219.1 [M+H]$^+$.

Step 5: 6-bromo-2-methyl-7-(trifluoromethyl)-[1,3]oxazolo[3,2-a]pyrimidin-5-one

The title compound was prepared using the procedure described for Intermediate 1A, Step 2 with the following modification: the reaction was performed using 2-methyl-7-(trifluoromethyl)-[1,3]oxazolo[3,2-a]pyrimidin-5-one. LC/MS (ESI) m/z=297.0/299.0 [M+H]$^+$.

Intermediate 13A 7-(trifluoromethyl)-1,3-dihydroimidazo[1,2-a]pyrimidine-2,5-dione

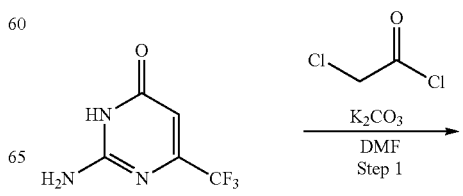

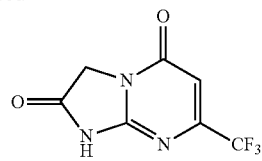

Step 1: 7-(trifluoromethyl)-1,3-dihydroimidazo[1,2-a]pyrimidine-2,5-dione 2-chloroacetyl chloride (1.96 mL, 24.57 mmol) was added dropwise to a stirred solution of 2-amino-6-(trifluoromethyl)-1H-pyrimidin-4-one (2.0 g, 11.17 mmol) in DMF (13 mL) at rt. The resulting mixture was heated at 50° C. for 3 h and stirred at rt overnight. Potassium carbonate (4.63 g, 33.5 mmol) was added and the suspension was stirred at 50° C. for 2 h. After cooling to rt, the mixture was diluted with water, treated with HCl 1M aq solution until pH=4 and extracted with EtOAc. The organic layer was dried over $Na_2SO_4$, filtered and concentrated under reduced pressure. The residue was purified by flash chromatography ($SiO_2$, 0-5% MeOH/DCM) to afford 7-(trifluoromethyl)-1,3-dihydroimidazo[1,2-a]pyrimidine-2,5-dione (1.31 g, 5.98 mmol, 54% yield). LC/MS (ESI$^+$) m/z=220.2 [M+H]$^+$.

Intermediate 14A

7-(trifluoromethyl)-1,3-dihydroimidazo[1,2-a]pyrimidine-2,5-dione

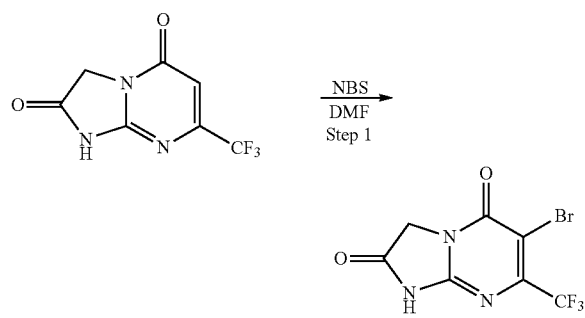

Step 1: 6-bromo-7-(trifluoromethyl)-1,3-dihydroimidazo[1,2-a]pyrimidine-2,5-dione A mixture of 7-(trifluoromethyl)-1,3-dihydroimidazo[1,2-a]pyrimidine-2,5-dione (Intermediate 13A, 700 mg, 3.19 mmol) and N-bromosuccinimide (682 mg, 3.83 mmol) in DMF (13 mL) was stirred at rt for 3 h. The reaction mixture was diluted with water and extracted with EtOAc. The organic layer was dried over $Na_2SO_4$, filtered and concentrated under reduced pressure. The residue was purified by flash chromatography ($SiO_2$, 10% MeOH/DCM) to give 6-bromo-7-(trifluoromethyl)-1,3-dihydroimidazo[1,2-a]pyrimidine-2,5-dione (708 mg, 2.38 mmol, 59% yield). LC/MS (ESI$^+$) m/z=296.1/298.1 [M−H]$^-$.

Intermediate 15A

6-bromo-1-methyl-7-(trifluoromethyl)-3H-imidazo[1,2-a]pyrimidine-2,5-dione

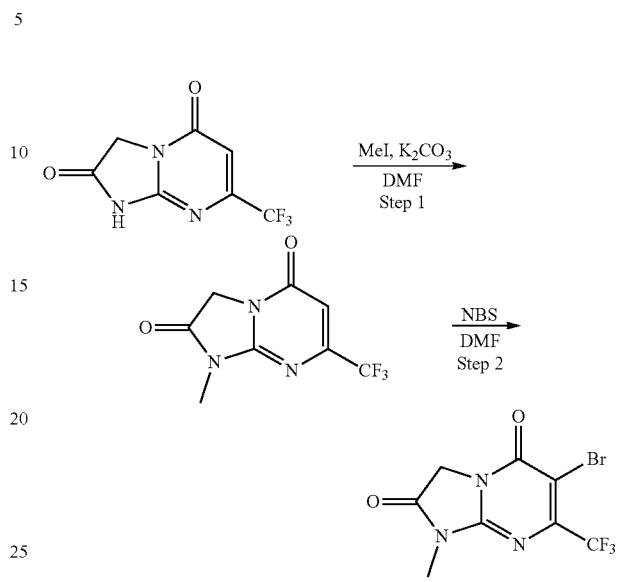

Step 1: 1-methyl-7-(trifluoromethyl)-3H-imidazo[1,2-a]pyrimidine-2,5-dione

Iodomethane (1.79 mL, 28.73 mmol) was added to a stirred suspension of 7-(trifluoromethyl)-1,3-dihydroimidazo[1,2-a]pyrimidine-2,5-dione (Intermediate 13A, 5.3 g, 23.95 mmol) and potassium carbonate (3.97 g, 28.73 mmol) in DMF (100 mL). The mixture was stirred at rt for 1.5 h, then partitioned between water and EtOAc. The organic phase was washed with water and brine, dried over $Na_2SO_4$, filtered and concentrated under reduced pressure. The residue was purified by flash chromatography ($SiO_2$, 0-30% EtOAc/cyclohexane) to give 1-methyl-7-(trifluoromethyl)-3H-imidazo[1,2-a]pyrimidine-2,5-dione (3.18 g, 13.64 mmol, 57% yield). LC/MS (ESI$^+$) m/z=234.2 [M+H]$^+$.

Step 2: 6-bromo-1-methyl-7-(trifluoromethyl)-3H-imidazo[1,2-a]pyrimidine-2,5-dione The title compound was prepared using the procedure described for Intermediate 14A, Step 2 with the following modification: the reaction was performed with 1-methyl-7-(trifluoromethyl)-3H-imidazo[1,2-a]pyrimidine-2,5-dione and heating the mixture to 50° C. for 1 h. LC/MS (ESI$^+$) m/z=310.1/312.2 [M−H]$^-$.

Intermediate 16A

6-bromo-1-propan-2-yl-7-(trifluoromethyl)-3H-imidazo[1,2-a]pyrimidine-2,5-dione

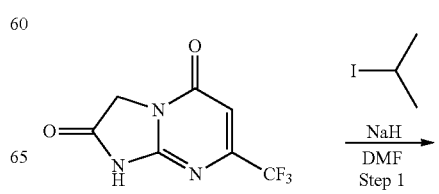

Step 1: 1-propan-2-yl-7-(trifluoromethyl)-3H-imidazo[1,2-a]pyrimidine-2,5-dione Sodium hydride (60% in mineral oil, 54.80 mg, 1.37 mmol) was added to a stirred solution of 7-(trifluoromethyl)-1,3-dihydroimidazo[1,2-a]pyrimidine-2,5-dione (Intermediate 13A, 300.0 mg, 1.37 mmol) in anhydrous DMF (2.7 mL) at 0° C. The mixture stirred at rt for 10 min, then 2-iodopropane (0.15 mL, 1.51 mmol) was added and the mixture was heated at 70° C. for 2 h. The reaction mixture was quenched with satd. aq. NH₄Cl solution and extracted with EtOAc. The organic phase was washed with water and brine, dried over Na₂SO₄, filtered and concentrated under reduced pressure. The residue was purified by flash chromatography (SiO₂, 0-25% EtOAc/cyclohexane) to give 1-propan-2-yl-7-(trifluoromethyl)-3H-imidazo[1,2-a]pyrimidine-2,5-dione (78 mg, 0.30 mmol, 22% yield). LC/MS (ESI⁺) m/z=262.3 [M+H]⁺.

Step 2: 6-bromo-1-propan-2-yl-7-(trifluoromethyl)-3H-imidazo[1,2-a]pyrimidine-2,5-dione The title compound was prepared using the procedure described for Intermediate 14A, Step 2 with the following modification: the reaction was performed with 1-propan-2-yl-7-(trifluoromethyl)-3H-imidazo[1,2-a]pyrimidine-2,5-dione and heating the mixture to 50° C. for 3 h. LC/MS (ESI) m/z=338.2/340.1 [M−H]⁻.

Intermediate 17A 6-bromo-1,3,3-trimethyl-7-(trifluoromethyl)imidazo[1,2-a]pyrimidine-2,5-dione

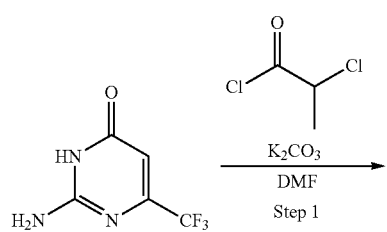

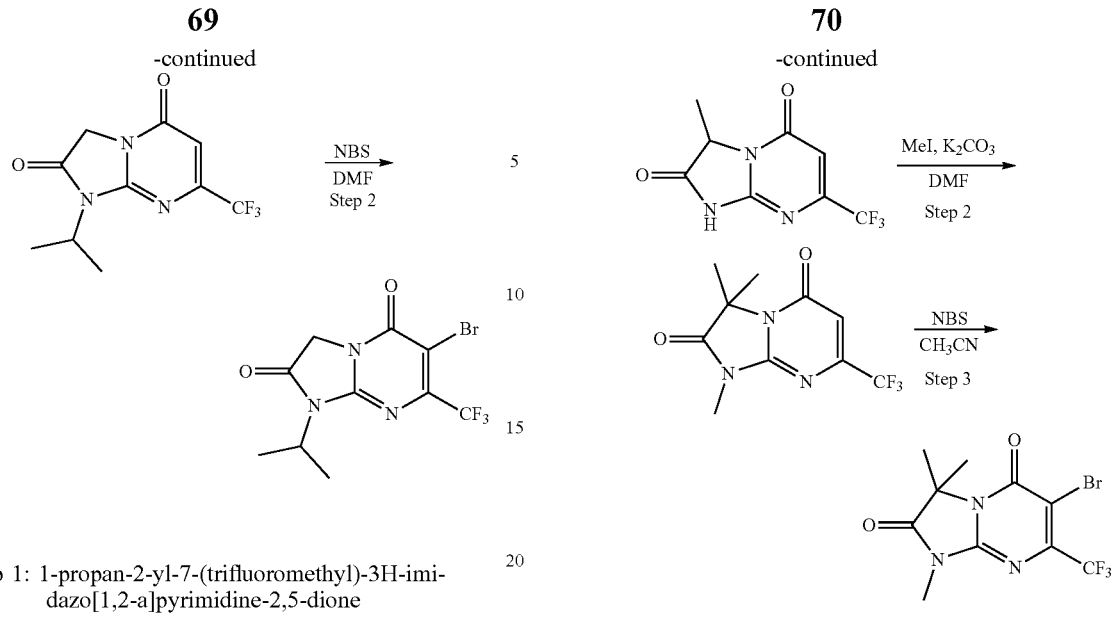

Step 1: 3-methyl-7-(trifluoromethyl)-1,3-dihydroimidazo[1,2-a]pyrimidine-2,5-dione The title compound was prepared using the procedure described for Intermediate 14A, Step 1 with the following modification: the reaction was performed with 2-amino-6-(trifluoromethyl)-1H-pyrimidin-4-one and 2-chloropropanoyl chloride. LC/MS (ESI⁺) m/z=234.2 [M+H]⁺.

Step 2: 1,3,3-trimethyl-7-(trifluoromethyl)imidazo[1,2-a]pyrimidine-2,5-dione Iodomethane (70 μL, 1.16 mmol) was added to a stirred suspension of 3-methyl-7-(trifluoromethyl)-1,3-dihydroimidazo[1,2-a]pyrimidine-2,5-dione (225.0 mg, 0.970 mmol) and potassium carbonate (160 mg, 1.16 mmol) in DMF (4 mL). The mixture was stirred at rt for 1.5 h, then diluted with water and extracted with EtOAc (2×). The combined organic phases were dried over Na₂SO₄, filtered and concentrated under reduced pressure. The residue was purified by flash chromatography (SiO₂, 0-40% EtOAc/cyclohexane) to afford 1,3,3-trimethyl-7-(trifluoromethyl)imidazo[1,2-a]pyrimidine-2,5-dione (90 mg, 0.35 mmol, 36% yield). LC/MS (ESI) m/z=262.2 [M+H]⁺.

Step 3: 6-bromo-1,3,3-trimethyl-7-(trifluoromethyl)imidazo[1,2-a]pyrimidine-2,5-dione A solution of 1,3,3-trimethyl-7-(trifluoromethyl)imidazo[1,2-a]pyrimidine-2,5-dione (90 mg, 0.34 mmol) and N-bromosuccinimide (80 mg, 0.45 mmol) in MeCN (4 mL) was heated at 80° C. for 2 h. More N-bromosuccinimide (80 mg, 0.45 mmol) was added and heating was continued overnight. After cooling to rt, the reaction mixture was concentrated under reduced pressure and purified by flash chromatography (SiO₂, 0-40% EtOAc/cyclohexane) to obtain 6-bromo-1,3,3-trimethyl-7-(trifluoromethyl)imidazo[1,2-a]pyrimidine-2,5-dione (55 mg, 0.16 mmol, 47% yield). LC/MS (ESI⁺) m/z=340.2/342.2 [M+H]⁺.

Intermediate 18A 6-bromo-2-methyl-7-(trifluoromethyl)-1H-imidazo[1,2-a]pyrimidin-5-one

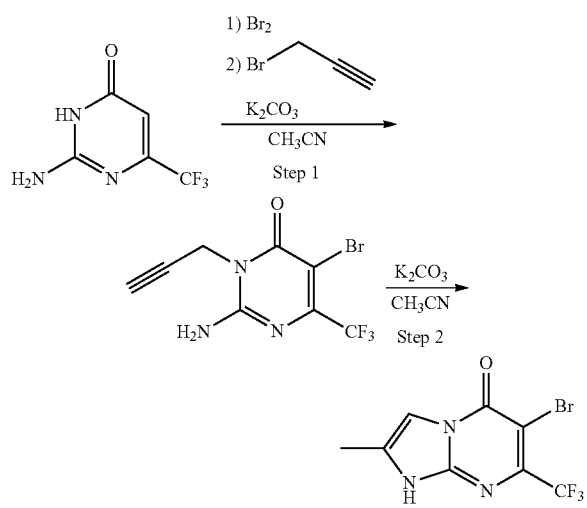

Step 1: 2-amino-5-bromo-3-prop-2-ynyl-6-(trifluoromethyl)pyrimidin-4-one

Molecular bromine (1.76 mL, 34.28 mmol) was added dropwise to a stirred suspension of 2-amino-4-hydroxy-6-(trifluoromethyl)pyrimidine (6.14 g, 34.28 mmol) in MeCN (61.4 mL). After completed addition, potassium carbonate (9.48 g, 68.57 mmol) was added in one portion, followed by 3-bromo-1-propyne (3.05 mL, 27.43 mmol) after 5 min. The reaction mixture was heated at 80° C. for 3 h, then cooled to rt and stirred for 16 h. Further 3-bromo-1-propyne (0.150 mL, 0.35 mmol) was added and the mixture was heated at 80° C. for 5 h. After cooling to rt, DCM (20 mL) was added and the mixture was stirred at rt for 2 min. The resulting precipitate was filtered, washed with DCM (20 mL) and discarded. The filtrate was evaporated under reduced pressure affording 2-amino-5-bromo-3-prop-2-ynyl-6-(trifluoromethyl)pyrimidin-4-one (8.05 g, 27.19 mmol, 79% yield) as slightly orange solid. It was used in the following step without any further purification. LC/MS (ESI) m/z=295.9 [M+H]$^+$.

Step 2: 6-bromo-2-methyl-7-(trifluoromethyl)-1H-imidazo[1,2-a]pyrimidin-5-one Potassium carbonate (4.9 g, 35.47 mmol) was added to a stirred solution of 2-amino-5-bromo-3-prop-2-ynyl-6-(trifluoromethyl)pyrimidin-4-one (7.0 g, 23.65 mmol) in MeCN (70 mL). The mixture was heated at 80° C. for 4 h and stirred at rt overnight. The reaction mixture was evaporated under reduced pressure, DCM (70 mL) was added and the mixture was stirred at rt for 15 min. The resulting precipitate was filtered, washed with DCM (50 mL). The solid obtained was triturated with HCl (1 M aq solution, 90 mL), filtered, washed with H$_2$O (15 mL) and dried under vacuum to afford 6-bromo-2-methyl-7-(trifluoromethyl)-1H-imidazo[1,2-a]pyrimidin-5-one (5.95 g, 20.1 mmol, 85% yield). LC/MS (ESI$^+$) m/z=296.1 [M+H]$^+$.

Intermediate 19A 6-bromo-1,2-dimethyl-7-(trifluoromethyl)imidazo[1,2-a]pyrimidin-5-one

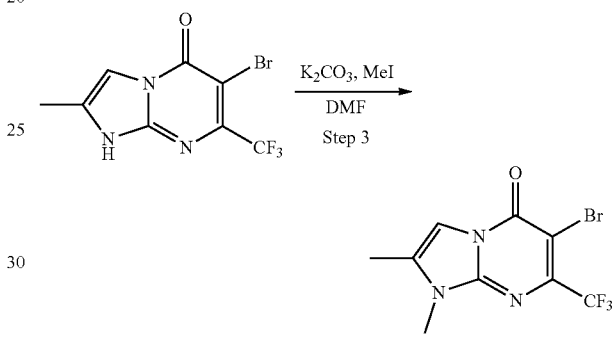

Step 1: 6-bromo-1,2-dimethyl-7-(trifluoromethyl)imidazo[1,2-a]pyrimidin-5-one Potassium carbonate (840.4 mg, 6.08 mmol) was added to a stirred solution of 6-bromo-2-methyl-7-(trifluoromethyl)-1H-imidazo[1,2-a]pyrimidin-5-one (Intermediate 18A, 1.5 g, 5.07 mmol) in DMF (50 mL), followed by iodomethane (0.35 mL, 5.57 mmol) after 10 min. The mixture was stirred at rt for 4 h, then diluted with EtOAc and washed with iced water (×2) and brine. The organic phase was dried over Na$_2$SO$_4$, filtered and concentrated in vacuo. The crude was purified by flash chromatography (SiO$_2$, 0-20% EtOAc/DCM) to give 6-bromo-1,2-dimethyl-7-(trifluoromethyl)imidazo[1,2-a]pyrimidin-5-one (1.38 g, 4.45 mmol, 88% yield). LC/MS (ESI) m/z=310.0/311.9 [M+H]$^+$.

Intermediates 19B-19D listed in Table 5 below were prepared following the procedure described for Intermediate 19A, Step 1, above as follows.

TABLE 5

| Int. # | Chemical Structure | Name | LC/MS (ESI$^+$) m/z | Condition changes | Reagent |
|---|---|---|---|---|---|
| 19B | ![structure] | 6-bromo-1-ethyl-2-methyl-7-(trifluoromethyl)-imidazo[1,2-a]pyrimidin-5-one | 324.0/ 325.9 | rt, 16 h | 6-bromo-2-methyl-7-(trifluoromethyl)-1H-imidazo[1,2-a]pyrimidin-5-one (Intermediate 18A) and iodoethane |

TABLE 5-continued

| Int. # | Chemical Structure | Name | LC/MS (ESI+) m/z | Condition changes | Reagent |
|---|---|---|---|---|---|
| 19C | (structure) | 6-bromo-1-(2-methoxyethyl)-2-(trifluoromethyl)-imidazo[1,2-a]pyrimidin-5-one | 353.9/ 356.0 | 60° C., 24 h | 6-bromo-2-methyl-7-(trifluoromethyl)-1H-imidazo[1,2-a]pyrimidin-5-one (Intermediate 18A) and 1-bromo-2-methoxyethane |
| 19D | (structure) | 6-bromo-2-methyl-1-propan-2-yl-7-(trifluoromethyl)-imidazo[1,2-a]pyrimidin-5-one | 338.0/ 340.0 | 50° C., 6 h | 6-bromo-2-methyl-7-(trifluoromethyl)-1H-imidazo[1,2-a]pyrimidin-5-one (Intermediate 18A) and 2-iodopropane |

Intermediate 20A 6-bromo-2-(methoxymethyl)-1-methyl-7-(trifluoromethyl)imidazo[1,2-a]pyrimidin-5-one

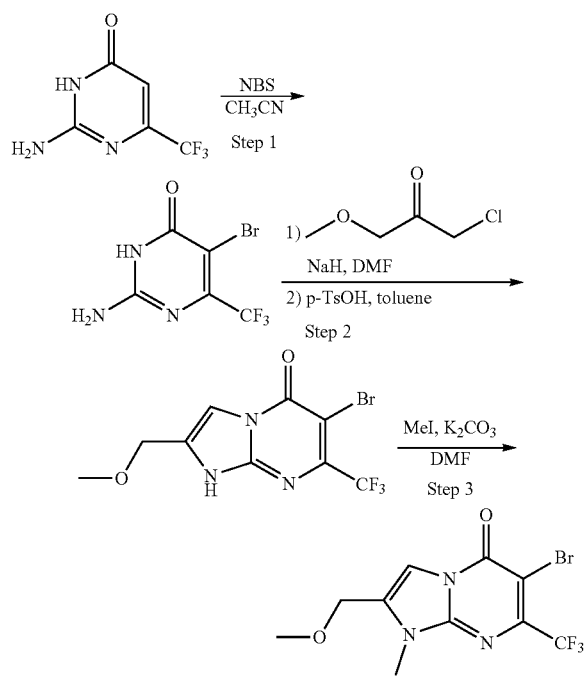

Step 1: 2-amino-5-bromo-4-(trifluoromethyl)-1H-pyrimidin-6-one

A solution of 2-amino-4-(trifluoromethyl)-1H-pyrimidin-6-one (2.5 g, 13.96 mmol) and N-bromosuccinimide (2.61 g, 14.66 mmol) in MeCN (25 mL) was stirred at rt for 2 h. The mixture was concentrated in vacuo, diluted with EtOAc and washed with water, satd. aq. $NaHCO_3$ and satd. aq. $Na_2S_2O_3$ solutions. The organic phase was dried over $Na_2SO_4$, filtered and concentrated under vacuum to afford 2-amino-5-bromo-4-(trifluoromethyl)-1H-pyrimidin-6-one (1.75 g, 6.78 mmol, 49% yield) as a yellow solid. LC/MS (ESI+) m/z=258.0/ 260.0 [M+H]+.

Step 2: 6-bromo-2-(methoxymethyl)-7-(trifluoromethyl)-1H-imidazo[1,2-a]pyrimidin-5-one Sodium hydride (60% in mineral oil, 151 mg, 3.78 mmol) was added to a solution of 2-amino-5-bromo-4-(trifluoromethyl)-1H-pyrimidin-6-one (750 mg, 2.91 mmol) in anhydrous DMF (12 mL), followed by 1-chloro-3-methoxypropan-2-one (463 mg, 3.78 mmol, Enamine) after 15 min. The reaction mixture was stirred at rt for 16 h, then concentrated in vacuo and the residue was dissolved in toluene (10 mL). p-Toluenesulfonic acid hydrate (55 mg, 0.29 mmol) was added and the mixture was heated at 75° C. for 1 h. After cooling to rt, the mixture was treated with satd. aq. $NaHCO_3$ solution and extracted with EtOAc (3×). The combined organic phases were dried over $Na_2SO_4$, filtered and concentrated under reduced pressure. The crude material was purified by flash chromatography (C18, 3-45% MeCN/0.1% formic acid in water). to afford 6-bromo-2-(methoxymethyl)-7-(trifluoromethyl)-1H-imidazo[1,2-a]pyrimidin-5-one (312 mg, 0.96 mmol, 33% yield) as a pale-yellow solid. LC/MS (ESI+) m/z=326.0/328.0 [M+H]+.

Step 3: 6-bromo-2-(methoxymethyl)-1-methyl-7-(trifluoromethyl)imidazo[1,2-a]pyrimidin-5-one The title compound was prepared using the procedure described for Intermediate 19A, Step 3 with the following modification: the reaction was performed with 6-bromo-2-(methoxymethyl)-7-(trifluoromethyl)-1H-imidazo[1,2-a]pyrimidin-5-one. LC/MS (ESI) m/z=340.0/342.0 [M+H]+.

Intermediate 21A 6-bromo-2-methyl-7-(trifluoromethyl)-1-(2-trimethylsilylethoxymethyl)imidazo[1,2-a]pyrimidin-5-one

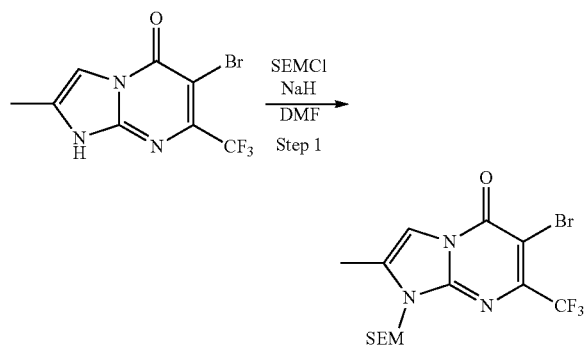

Step 1: 6-bromo-2-methyl-7-(trifluoromethyl)-1-(2-trimethylsilylethoxymethyl)imidazo[1,2-a]pyrimidin-5-one Sodium hydride (60% in mineral oil, 243 mg, 6.08 mmol) was added to a stirred solution of 6-bromo-2-methyl-7-(trifluoromethyl)-1H-imidazo[1,2-a]pyrimidin-5-one (Intermediate 18A, 1.5 g, 5.07 mmol) in anhydrous DMF (50.7 mL) at 0° C. After 15 min at 0° C., 2-(chloromethoxy)ethyl-trimethylsilane (1.17 mL, 6.59 mmol) was added and the mixture was stirred rt for 1 h. The mixture was treated with satd. aq. $NH_4Cl$ solution and extracted with EtOAc. The organic phase was washed with iced water and brine. The organic phase was dried over $Na_2SO_4$, filtered and concentrated under reduced pressure. The crude material was purified by flash chromatography ($SiO_2$, 0-50% EtOAc/cyclohexane) to give 6-bromo-2-methyl-7-(trifluoromethyl)-1-(2-trimethylsilylethoxymethyl)imidazo[1,2-a]pyrimidin-5-one (1.8 g, 4.22 mmol, 83% yield). LC/MS (ESI$^+$) m/z=426.0/428.0 [M+H]$^+$.

Intermediates 21B-21C listed in Table 6 were prepared following the procedure described for Intermediate 21A, Step 1, above as follows.

TABLE 6

| Int. # | Chemical Structure | Name | LC/MS (ESI$^+$) m/z | Conditions | Reagent |
|---|---|---|---|---|---|
| 21B | 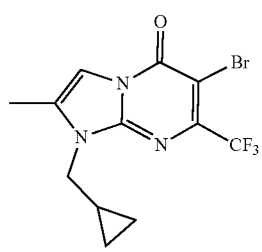 [SMILES: Cc1cn2c(=O)c(Br)c(C(F)(F)F)nc2n1CC1CC1] | 6-bromo-1-(cyclopropylmethyl)-2-methyl-7-(trifluoromethyl)-imidazo[1,2-a]pyrimidin-5-one | 350.0/ 352.0 | 80° C., 5 h | 6-bromo-2-methyl-7-(trifluoromethyl)-1H-imidazo[1,2-a]pyrimidin-5-one (Intermediate 18A) and bromomethyl cyclopropane |
| 21C | 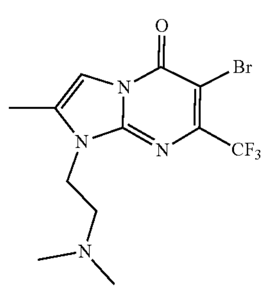 [SMILES: Cc1cn2c(=O)c(Br)c(C(F)(F)F)nc2n1CCN(C)C] | 6-bromo-1-[2-(dimethylamino)ethyl]-2-methyl-7-(trifluoromethyl)-imidazo[1,2-a]pyrimidin-5-one | 367.2/ 369.2 | 80° C., 16 h | 6-bromo-2-methyl-7-(trifluoromethyl)-1H-imidazo[1,2-a]pyrimidin-5-one (Intermediate 18A) and 2-chloro-N,N-dimethylethanamine hydrochloride |

Intermediate 22A 6-bromo-1-(2-hydroxypropyl)-2-methyl-7-(trifluoromethyl)imidazo[1,2-a]pyrimidin-5-one

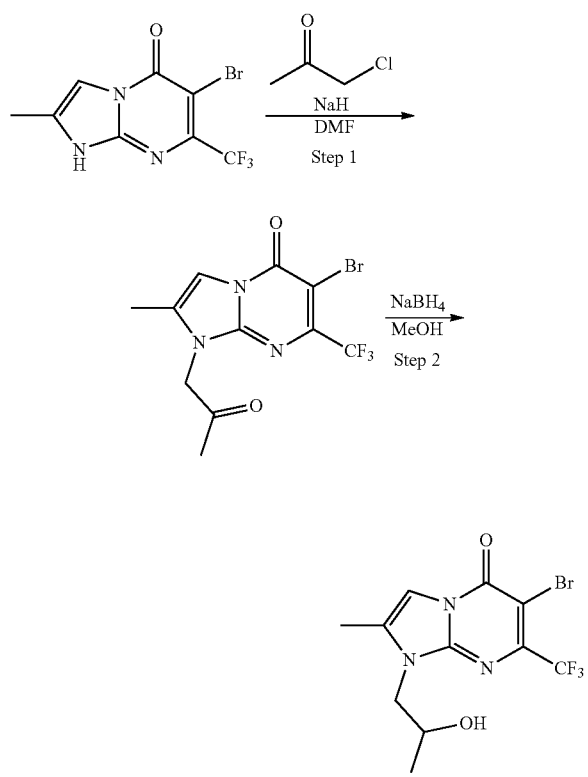

Step 1: 6-bromo-2-methyl-1-(2-oxopropyl)-7-(trifluoromethyl)imidazo[1,2-a]pyrimidin-5-one The title compound was prepared using the procedure described for Intermediate 21A, with the following modification: the reaction was performed with 6-bromo-2-methyl-7-(trifluoromethyl)-1H-imidazo[1,2-a]pyrimidin-5-one (Intermediate 18A) and 1-chloro-2-propanone. LC/MS (ESI$^+$) m/z=352.0/354.0 [M+H]$^+$.

Step 2: 6-bromo-1-(2-hydroxypropyl)-2-methyl-7-(trifluoromethyl)imidazo[1,2-a]pyrimidin-5-one NaBH$_4$ (10.7 mg, 0.28 mmol) was added to a solution of 6-bromo-2-methyl-1-(2-oxopropyl)-7-(trifluoromethyl)imidazo[1,2-a]pyrimidin-5-one (100.0 mg, 0.280 mmol) in methanol (2.8 mL) cooled to 0° C. The mixture was stirred at 0° C. for 1 h, then quenched with satd. aq. NH$_4$Cl solution and extracted with EtOAc (2×). The combined organic phases were dried over Na$_2$SO$_4$, filtered and concentrated in vacuo. The crude was purified by flash chromatography (SiO$_2$, 0-100% EtOAc/cyclohexane) to give 6-bromo-1-(2-hydroxypropyl)-2-methyl-7-(trifluoromethyl)imidazo[1,2-a]pyrimidin-5-one (67 mg, 0.19 mmol, 67% yield). LC/MS (ESI$^+$) m/z=354.0/356.0 [M+H]$^+$.

Intermediate 23A 6-bromo-2-methoxy-1-methyl-7-(trifluoromethyl)imidazo[1,2-a]pyrimidin-5-one

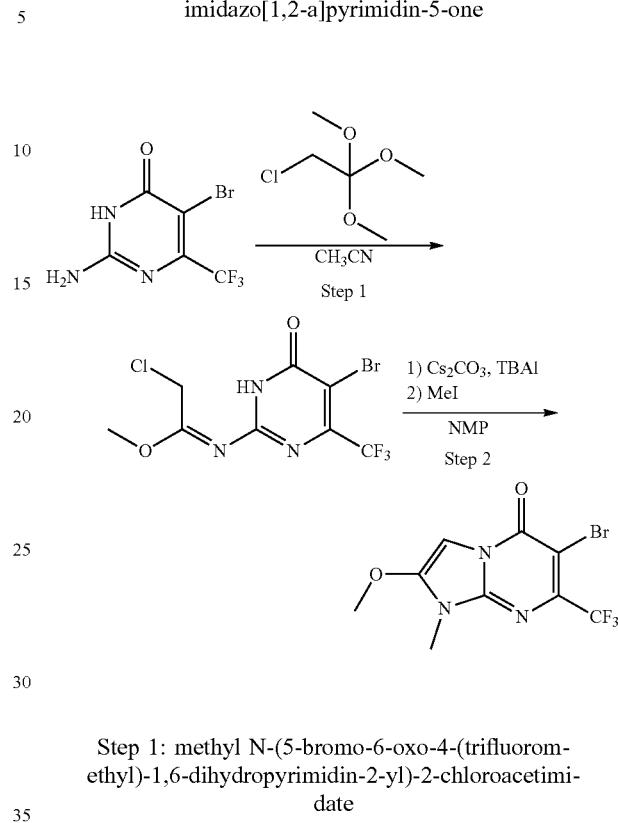

Step 1: methyl N-(5-bromo-6-oxo-4-(trifluoromethyl)-1,6-dihydropyrimidin-2-yl)-2-chloroacetimidate A mixture of 2-amino-5-bromo-4-(trifluoromethyl)-1H-pyrimidin-6-one (1 g, 3.88 mmol) and 2-chloro-1,1,1-trimethoxyethane (3.0 mL, 22.26 mmol) in MeCN (10 mL) was heated at 100° C. for 16 h. After cooling to rt, the mixture was evaporated under reduced pressure to give methyl N-(5-bromo-6-oxo-4-(trifluoromethyl)-1,6-dihydropyrimidin-2-yl)-2-chloroacetimidate (1.35 g, 3.88 mmol). The crude was used in the next step without further purification. LC/MS (ESI) m/z=348.0/350.0/351.9 [M+H]$^+$.

Step 2: 6-bromo-2-methoxy-1-methyl-7-(trifluoromethyl)imidazo[1,2-a]pyrimidin-5-one The crude methyl N-(5-bromo-6-oxo-4-(trifluoromethyl)-1,6-dihydropyrimidin-2-yl)-2-chloroacetimidate (1.35 g, 3.88 mmol) was suspended in NMP (13 mL) and tetrabutylammonium iodide (143.2 mg, 0.39 mmol) and cesium carbonate (2.53 g, 7.75 mmol) were added. The resulting mixture was heated at 100° C. for 1 h, then cooled to rt. MeI (0.27 mL, 4.26 mmol) was added and the reaction was stirred at 40° C. for 16 h. The mixture was treated with H$_2$O and extracted with EtOAc (2×). The combined organic phases were dried over Na$_2$SO$_4$, filtered and concentrated under reduced pressure. The crude was purified by flash chromatography (SiO$_2$, 0-60% EtOAc/cyclohexane) to give 6-bromo-2-methoxy-1-methyl-7-(trifluoromethyl)imidazo[1,2-a]pyrimidin-5-one. LC/MS (ESI$^+$) m/z=326.0/328.0 [M+H]$^+$.

Intermediate 24A 1-(2,2,3,3,3-Pentafluoropropyl)-4-(4,4,5,5-tetramethyl-1,3,2-dioxaborolan-2-yl)pyrazole

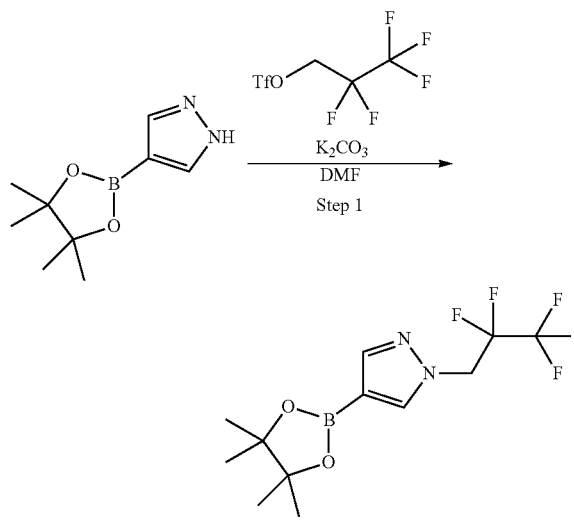

Step 1: 1-(2,2,3,3,3-Pentafluoropropyl)-4-(4,4,5,5-tetramethyl-1,3,2-dioxaborolan-2-yl)pyrazole A resealable vial was charged 4-pyrazoleboronic acid pinacol ester (0.5 g, 2.6 mmol) potassium carbonate (0.7 g, 5 mmol), DMF (3 ml), and 2,2,3,3,3-pentafluoropropyl trifluoromethanesulfonate (1.0 g, 3.5 mmol, Matrix Scientific). The reaction mixture was heated at 80° C. for 12 h. The reaction mixture was cooled to rt and partitioned between water and EtOAc. The organic layer was dried over Na$_2$SO$_4$, filtered, and adsorbed onto a pad of silica gel. Purification by flash chromatography (SiO$_2$, 0-60% EtOAc/heptane) afforded 1-(2,2,3,3,3-pentafluoropropyl)-4-(4,4,5,5-tetramethyl-1,3,2-dioxaborolan-2-yl)pyrazole (289 mg, 0.9 mmol, 34% yield) which was carried forward in the next reaction without further purification. $^1$H NMR (400 MHz, CDCl$_3$) δ 1.32 (s, 16H) 4.75 (t, J=14.10 Hz, 2H) 7.80 (s, 1H) 7.84 (s, 1H).

Intermediate 25A 4-(4,4,5,5-Tetramethyl-1,3,2-dioxaborolan-2-yl)-1-(3,3,3-trifluoropropyl)pyrazole

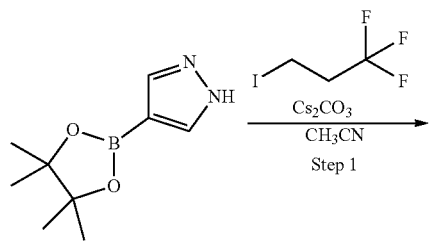

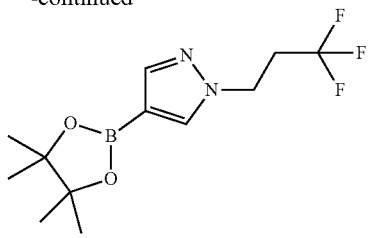

Step 1: 4-(4,4,5,5-Tetramethyl-1,3,2-dioxaborolan-2-yl)-1-(3,3,3-trifluoropropyl)pyrazole A resealable vial was charged with 4-pyrazoleboronic acid pinacol ester (500 mg, 2.6 mmol), acetonitrile (5 mL), cesium carbonate (1.7 g, 5.1 mmol), and 1,1,1-trifluoro-3-iodopropane (604 µl, 5.15 mmol, Oakwood). The reaction mixture was heated at 80° C. for 12 h. The reaction mixture was cooled to rt and filtered with EtOAc through a pad of celite. The filtrate was washed with brine and the organic phase was dried over Na$_2$SO$_4$, filtered and concentrated under reduced pressure. The residue was purified by flash chromatography (SiO$_2$, 0-60% EtOAc/heptane) to afford 4-(4,4,5,5-tetramethyl-1,3,2-dioxaborolan-2-yl)-1-(3,3,3-trifluoropropyl)-1H-pyrazole (137 mg, 0.47 mmol, 18% yield). $^1$H NMR (400 MHz, CDCl$_3$) δ 1.32 (s, 13H) 2.74 (dt, J=10.37, 7.36 Hz, 2H) 4.37 (t, J=7.36 Hz, 2H) 7.71 (s, 1H) 7.81 (s, 1H).

Intermediate 26A

Potassium trifluoro-[1-(2,2,3,3,3-pentafluoropropyl)pyrazol-4-yl]boranuide

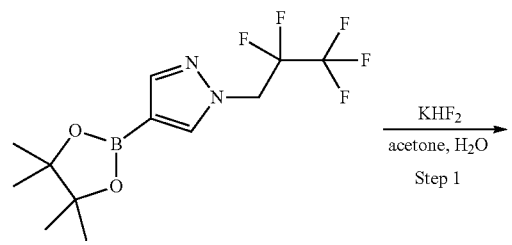

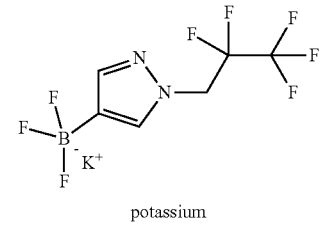

Step 1: Potassium trifluoro-[1-(2,2,3,3,3-pentafluoropropyl)pyrazol-4-yl]boranuide A mixture of 1-(2,2,3,3,3-pentafluoropropyl)-4-(4,4,5,5-tetramethyl-1,3,2-dioxaborolan-2-yl)pyrazole (Intermediate 24A, 1.0 g, 3.07 mmol) and potassium bifluoride (0.79 g, 10.12 mmol) in acetone (15 mL) and water (5 mL) was stirred at rt for 2 h. The solvent was evaporated, the residue suspended in hot acetone (25 mL) and filtered to remove undissolved salts. The solvent was evaporated, residue redissolved in hot acetone, cooled to rt and allowed to stand overnight. The crystallized product was collected, washed with cold acetone and dried under vacuum to give potassium trifluoro-[1-(2,2,3,3,3-pentafluoropropyl)pyrazol-4-yl]boranuide (270 mg, 0.88 mmol, 29% yield). H NMR (400 MHz, DMSO-$d_6$) δ 4.98 (t, J=15.30 Hz, 2H), 7.03-7.33 (m, 2H).

Intermediate 27A

1-[(2,2-difluorocyclopropyl)methyl]-4-(4,4,5,5-tetramethyl-1,3,2-dioxaborolan-2-yl)pyrazole

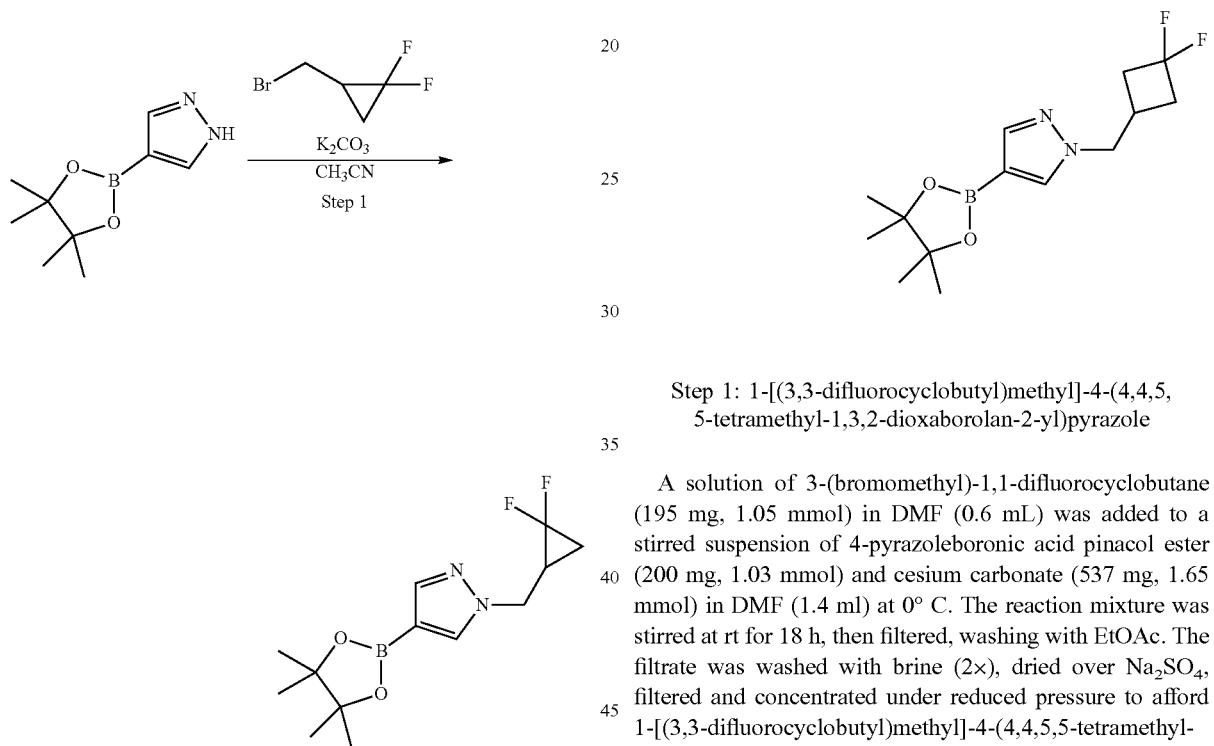

Step 1: 1-[(2,2-difluorocyclopropyl)methyl]-4-(4,4,5,5-tetramethyl-1,3,2-dioxaborolan-2-yl)pyrazole A resealable vial was charged with 4-pyrazoleboronic acid pinacol ester (1 g, 5.15 mmol), potassium carbonate (1.42 g, 10.3 mmol), acetonitrile (20 ml), and 2-(bromomethyl)-1,1-difluorocyclopropane (1.06 g, 6.18 mmol). The reaction mixture was heated at 80° C. for 4 h, then cooled to rt and filtered, washing with MeCN. The filtrate was concentrated under reduced pressure and purified by flash chromatography (SiO$_2$, 0-50% EtOAc/cyclohexane) to afford 1-[(2,2-difluorocyclopropyl)methyl]-4-(4,4,5,5-tetramethyl-1,3,2-dioxaborolan-2-yl)pyrazole (460 mg, 1.62 mmol, 31% yield) as colorless oil. LC/MS (ESI$^+$) m/z=285.2 [M+H]$^+$.

Intermediate 28A

1-[(3,3-difluorocyclobutyl)methyl]-4-(4,4,5,5-tetramethyl-1,3,2-dioxaborolan-2-yl)pyrazole

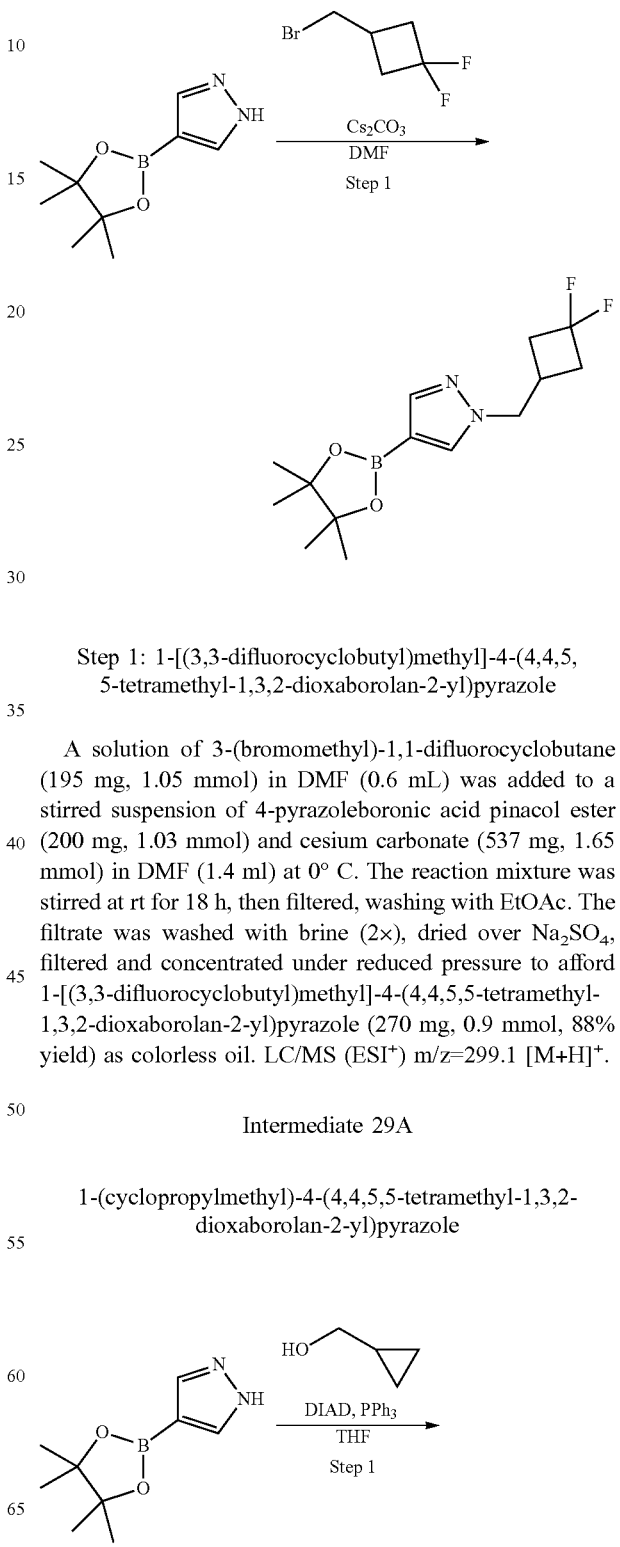

Step 1: 1-[(3,3-difluorocyclobutyl)methyl]-4-(4,4,5, 5-tetramethyl-1,3,2-dioxaborolan-2-yl)pyrazole A solution of 3-(bromomethyl)-1,1-difluorocyclobutane (195 mg, 1.05 mmol) in DMF (0.6 mL) was added to a stirred suspension of 4-pyrazoleboronic acid pinacol ester (200 mg, 1.03 mmol) and cesium carbonate (537 mg, 1.65 mmol) in DMF (1.4 ml) at 0° C. The reaction mixture was stirred at rt for 18 h, then filtered, washing with EtOAc. The filtrate was washed with brine (2×), dried over Na$_2$SO$_4$, filtered and concentrated under reduced pressure to afford 1-[(3,3-difluorocyclobutyl)methyl]-4-(4,4,5,5-tetramethyl-1,3,2-dioxaborolan-2-yl)pyrazole (270 mg, 0.9 mmol, 88% yield) as colorless oil. LC/MS (ESI$^+$) m/z=299.1 [M+H]$^+$.

Intermediate 29A 1-(cyclopropylmethyl)-4-(4,4,5,5-tetramethyl-1,3,2-dioxaborolan-2-yl)pyrazole -continued

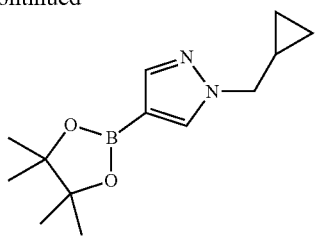

Step 1: 1-(cyclopropylmethyl)-4-(4,4,5,5-tetramethyl-1,3,2-dioxaborolan-2-yl)pyrazole Cyclopropanemethanol (0.89 g, 12.37 mmol) was added dropwise to a stirred solution of 4-pyrazoleboronic acid pinacol ester (2.0 g, 10.31 mmol), triphenylphosphine (2.7 g, 10.31 mmol) and DIAD (2.0 mL, 10.31 mmol) in THF (30 mL) under nitrogen atmosphere at 0° C. The reaction mixture was allowed to warm to rt and stirred for 24 h. The mixture was concentrated under reduced pressure, cyclohexane was added and the resulting precipitate was filtered off. The filtrate was evaporated and the crude material was purified by flash chromatography (SiO$_2$, 0-50% EtOAc/cyclohexane) affording 1-(cyclopropylmethyl)-4-(4,4,5,5-tetramethyl-1,3,2-dioxaborolan-2-yl)pyrazole (1.78 g, 7.17 mmol, 70% yield) as a white solid. LC/MS (ESI$^+$) m/z=249.1 [M+H]$^+$.

Intermediate 30A 1-(2,2,3,3,3-pentafluoropropyl)-3-(4,4,5,5-tetramethyl-1,3,2-dioxaborolan-2-yl)pyrazole

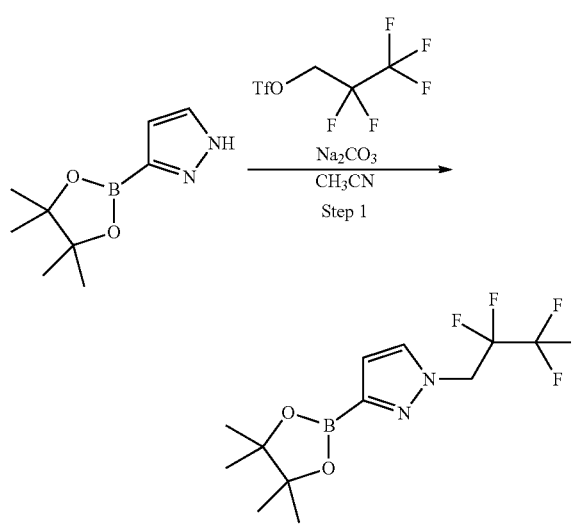

Step 1: 1-(2,2,3,3,3-pentafluoropropyl)-3-(4,4,5,5-tetramethyl-1,3,2-dioxaborolan-2-yl)pyrazole A resealable vial was charged with 3-(4,4,5,5-tetramethyl-1,3,2-dioxaborolan-2-yl)-1H-pyrazole (1.0 g, 5.15 mmol), sodium carbonate (1.09 g, 10.31 mmol), MeCN (5 mL) and 2,2,3,3,3-pentafluoropropyl trifluoromethanesulfonate (1.32 mL, 7.99 mmol). The mixture was heated at 80° C. for 20 h, then cooled to rt and partitioned between water and EtOAc. The organic phases were dried over Na$_2$SO$_4$, filtered and evaporated under reduced pressure to give 1-(2,2,3,3,3-pentafluoropropyl)-3-(4,4,5,5-tetramethyl-1,3,2-dioxaborolan-2-yl)pyrazole (1 g, 3.07 mmol, 60% yield) which was carried forward in the next reaction without further purification. LC/MS (ESI) m/z=327.2 [M+H]$^+$.

Intermediate 31A 4,4,5,5-tetramethyl-2-[4-(2,2,2-trifluoroethoxy)phenyl]-1,3,2-dioxaborolane

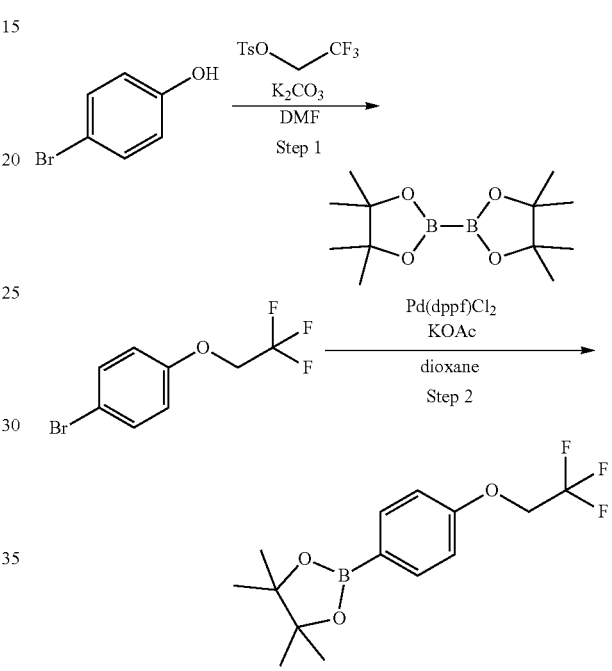

Step 1: 1-bromo-4-(2,2,2-trifluoroethoxy)benzene 4-methylbenzenesulfonic acid 2,2,2-trifluoroethyl ester (14.7 g, 57.9 mmol) was added to a stirred mixture of 4-bromophenol (10 g, 57.8 mmol) and potassium carbonate (39.9 g, 289 mmol) in DMF (80 mL) at 0° C. The reaction mixture was heated at 110° C. for 16 h. After cooling to rt, the mixture was partitioned between water and EtOAc. The organic layer was dried over Na$_2$SO$_4$, filtered and concentrated under reduced pressure. Purification by flash chromatography (SiO$_2$, 50% EtOAc/cyclohexane) afforded 1-bromo-4-(2,2,2-trifluoroethoxy)benzene (10.9 g, 42.73 mmol, 74% yield). $^1$H NMR (400 MHz, DMSO-d$_6$) δ 4.78 (q, J=8.88 Hz, 2H), 7.02-7.08 (m, 2H), 7.48-7.56 (m, 2H).

Step 2: 4,4,5,5-tetramethyl-2-[4-(2,2,2-trifluoroethoxy)phenyl]-1,3,2-dioxaborolane A mixture of 1-bromo-4-(2,2,2-trifluoroethoxy)benzene (5.0 g, 19.61 mmol), bis(pinacolato)diboron (5.48 g, 21.57 mmol), potassium acetate (5.77 g, 58.82 mmol) and [1,1'-bis(diphenylphosphino)ferrocene]dichloropalladium(II) (719 mg, 0.98 mmol) in 1,4-dioxane (50 ml) was purged with nitrogen for 5 min, then heated at 110° C. for 4 h. After cooling to rt, the mixture was filtered with EtOAc through a pad of celite. The filtrate was concentrated under reduced pressure and the residue was purified by flash chromatography (SiO$_2$, 0-3% EtOAc/cyclohexane) to give 4,4,5,5-tetramethyl-2-[4-(2,2,2-trifluoroethoxy)phenyl]-1,3,2-dioxaborolane (2.76 g, 9.13 mmol, 47% yield) as colorless oil. LC/MS (ESI$^+$) m/z=303.1 [M+H]$^+$.

Intermediate 32A 1-(oxetan-3-ylmethyl)-4-(4,4,5,5-tetramethyl-1,3,2-dioxaborolan-2-yl)pyrazole

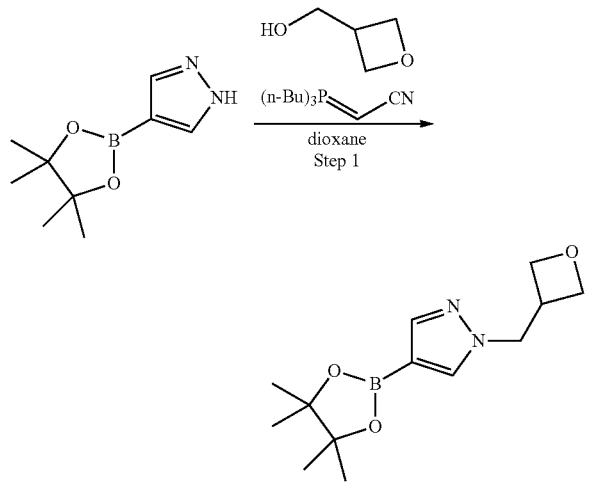

Step 1: 1-(oxetan-3-ylmethyl)-4-(4,4,5,5-tetramethyl-1,3,2-dioxaborolan-2-yl)pyrazole A microwave vial was charged with 4-pyrazoleboronic acid pinacol ester (194 mg, 1 mmol), oxetan-3-ylmethanol (88 mg, 1 mmol), 2-tributylphosphoranylideneacetonitrile (0.52 ml, 2 mmol) and 1,4-dioxane (3 mL). The resulting mixture was subjected to microwave irradiation at 150° C. for 45 min. After cooling to rt, the mixture was partitioned between water and EtOAc. The organic layer was dried over Na$_2$SO$_4$, filtered and concentrated under reduced pressure. The crude material was purified by flash chromatography (SiO$_2$, 50-90% EtOAc/cyclohexane) obtaining 1-(oxetan-3-ylmethyl)-4-(4,4,5,5-tetramethyl-1,3,2-dioxaborolan-2-yl)pyrazole (270 mg, 1 mmol, 100% yield) as brown oil. LC/MS (ESI$^+$) m/z=265.0 [M+H]$^+$.

Intermediate 33A

Trimethyl-[2-[[4-(4,4,5,5-tetramethyl-1,3,2-dioxaborolan-2-yl)pyrazol-1-yl]methoxy]ethyl]silane

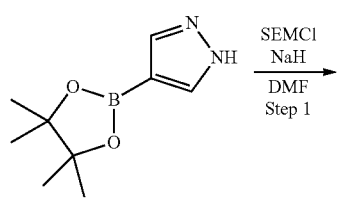

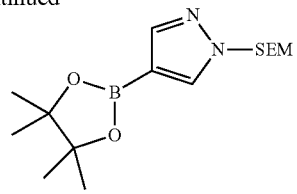

Step 1: Trimethyl-[2-[[4-(4,4,5,5-tetramethyl-1,3,2-dioxaborolan-2-yl)pyrazol-1-yl]methoxy]ethyl]silane Sodium hydride (60% in mineral oil, 309 mg, 7.73 mmol) was added to a stirred solution of 4-pyrazoleboronic acid pinacol ester (1 g, 5.15 mmol) in anhydrous DMF (10 mL) at 0° C. The mixture was stirred at 0° C. for 5 min, then at rt for 30 min. The mixture was again cooled to 0° C. and 2-(chloromethoxy)ethyl-trimethylsilane (1.19 mL, 6.7 mmol) was added. The reaction was allowed to reach rt and stirred for 4 h, then poured into satd. aq. NH$_4$Cl solution and extracted with EtOAc (2×). The combined organic phases were dried over Na$_2$SO$_4$, filtered and evaporated. The crude material was purified by flash chromatography (SiO$_2$, 0-20% EtOAc/cyclohexane) to afford trimethyl-[2-[[4-(4,4,5,5-tetramethyl-1,3,2-dioxaborolan-2-yl)pyrazol-1-yl]methoxy]ethyl]silane (830 mg, 2.56 mmol, 50% yield) as a colorless oil. LC/MS (ESI$^+$) m/z=325.3 [M+H]$^+$.

Intermediate 34A

[1-(2-bromoethyl)cyclopropyl]oxy-tert-butyl-dimethylsilane

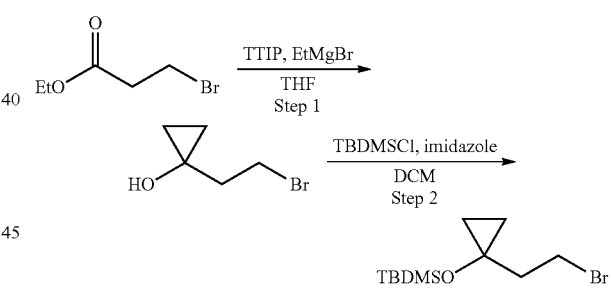

Step 1: 1-(2-bromoethyl)cyclopropan-1-ol

Titanium(IV) isopropoxide (3.14 g, 11.05 mmol) was added to a solution of 3-bromopropanoic acid ethyl ester (2.0 g, 11.05 mmol) in anhydrous THF (40 mL). The mixture was cooled to −5° C. then ethyl magnesium bromide (1 M solution in THF, 24.3 mL, 24.31 mmol) was added drop wise over a period of 2 h, maintaining the temperature below 4° C. The reaction mixture was stirred at rt for 2 h, then quenched with satd. aq. NH$_4$Cl solution and extracted with EtOAc. The organic phase was dried over Na$_2$SO$_4$, filtered and concentrated under reduced pressure. The crude material was purified by flash chromatography (SiO$_2$, 0-50% EtOAc/cyclohexane) to afford 1-(2-bromoethyl)cyclopropan-1-ol (417 mg, 2.53 mmol, 23% yield) as a brown oil. $^1$H NMR (400 MHz, CDCl$_3$) δ 0.61-0.53 (m, 2H), 0.88-0.81 (m, 2H), 1.99 (s, 1H), 2.15 (tt, J=7.1, 0.6 Hz, 2H), 3.65 (t, J=7.2 Hz, 2H).

Step 2: [1-(2-bromoethyl)cyclopropyl]oxy-tert-butyl-dimethylsilane

Tert-butyl-chloro-dimethylsilane (685.5 mg, 4.55 mmol) was added portion wise to a mixture of 1-(2-bromoethyl)cyclopropan-1-ol (417 mg, 2.53 mmol) and imidazole (344.0 mg, 5.05 mmol) in DCM (10 mL) at 0° C. The mixture was stirred at rt overnight, then partitioned between water and DCM. Phases were separated and the organic one was dried over $Na_2SO_4$, filtered and concentrated under reduced pressure. The residue was purified by flash chromatography ($SiO_2$, 100% cyclohexane) to afford [1-(2-bromoethyl)cyclopropyl]oxy-tert-butyl-dimethylsilane (536 mg, 1.92 mmol, 76% yield) as a colorless oil. $^1$H NMR (400 MHz, $CDCl_3$) δ −0.12 (s, 6H), 0.54-0.48 (m, 2H), 0.80-0.73 (m, 2H), 0.87 (s, 9H), 2.06 (ddt, J=8.1, 7.5, 0.7 Hz, 2H), 3.63-3.55 (m, 2H).

SYNTHESIS OF EXAMPLES

Method 1

Example 1: 6-[1-(2,2,3,3,3-pentafluoropropyl)-1H-pyrazol-4-yl]-7-(trifluoromethyl)-5H-[1,3]thiazolo[3,2-a]pyrimidin-5-one

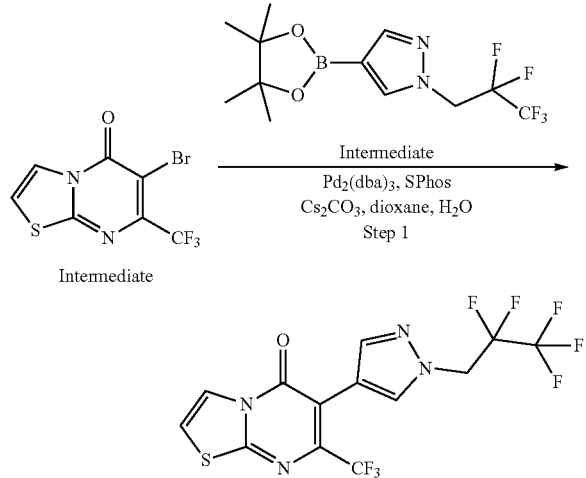

Step 1: 6-[1-(2,2,3,3,3-pentafluoropropyl)-1H-pyrazol-4-yl]-7-(trifluoromethyl)-5H-[1,3]thiazolo[3,2-a]pyrimidin-5-one A screw-capped vial was charged with 6-bromo-7-(trifluoromethyl)-[1,3]thiazolo[3,2-a]pyrimidin-5-one (Intermediate 1A, 100 mg, 0.33 mmol), 1,4-dioxane (5.5 ml), water (0.55 ml), cesium carbonate (274 mg, 0.84 mmol), 1-(2,2,3,3,3-pentafluoropropyl)-4-(4,4,5,5-tetramethyl-1,3,2-dioxaborolan-2-yl)pyrazole (Intermediate 24A, 142 mg, 0.43 mmol), 2-dicyclohexylphosphino-2',6'-dimethoxybiphenyl (27 mg, 0.07 mmol) and tris(dibenzylideneacetone)dipalladium(0) (31 mg, 0.033 mmol). The mixture was purged with nitrogen for 10 min then heated at 90° C. for 2 h. The reaction mixture was cooled to room temperature and filtered through a pad of celite. The filtrate was concentrated under reduced pressure and purified by flash chromatography ($SiO_2$, 20-100% EtOAc/cyclohexane) to afford 6-[1-(2,2,3,3,3-pentafluoropropyl)-1H-pyrazol-4-yl]-7-(trifluoromethyl)-5H-[1,3]thiazolo[3,2-a]pyrimidin-5-one (95 mg, 0.23 mmol, 68% yield) as a white solid. LC/MS (ESI$^+$) m/z=419.1 [M+H]$^+$. $^1$H NMR (400 MHz, DMSO-$d_6$) δ 8.12 (d, J=5.04 Hz, 1H), 8.00 (s, 1H), 7.72 (d, J=4.82 Hz, 1H), 7.64 (s, 1H), 5.27 (t, J=15.02 Hz, 2H).

Example 2: 2-methyl-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one

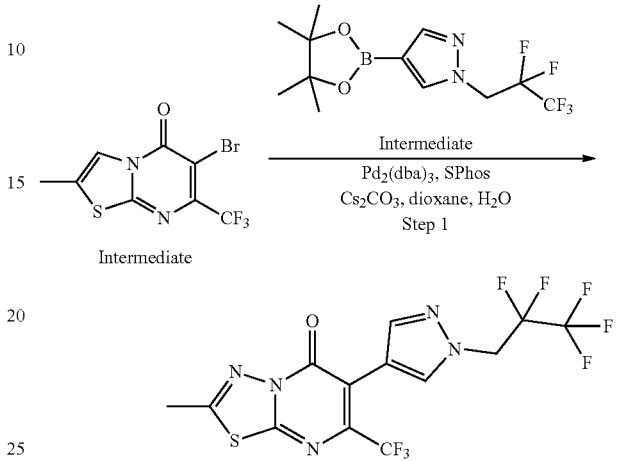

Step 1: 2-methyl-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one A screw-capped vial was charged with 6-bromo-2-methyl-7-(trifluoromethyl)-[1,3,4]thiadiazolo[3,2-a]pyrimidin-5-one (Intermediate 3A, 1.63 g, 5.19 mmol), 1,4-dioxane (15 mL), water (3 mL), cesium carbonate (4.25 g, 12.97 mmol), 1-(2,2,3,3,3-pentafluoropropyl)-4-(4,4,5,5-tetramethyl-1,3,2-dioxaborolan-2-yl)pyrazole (Intermediate 24A, 3.38 g, 10.37 mmol), 2-dicyclohexylphosphino-2',6'-dimethoxybiphenyl (639 mg, 1.56 mmol) and tris(dibenzylideneacetone)dipalladium(0) (475 mg, 0.52 mmol). The mixture was purged with nitrogen for 10 min then heated at 90° C. for 5 h. After cooling to rt, the reaction mixture was concentrated under reduced pressure. The crude material was purified by flash chromatography (C18, 3-80% MeCN/0.1% formic acid in water followed by $SiO_2$, 10-90% EtOAc/Cyclohexane) to afford 2-methyl-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one (1.10 g, 2.55 mmol, 49% yield) as a white solid. LC/MS (ESI$^+$) m/z=434.17 [M+H]$^+$. $^1$H NMR (500 MHz, DMSO-$d_6$) δ 2.77 (s, 3H), 5.29 (t, J=15.0 Hz, 2H), 7.66 (s, 1H), 8.05 (s, 1H).

Alternatively, Example 2 may be prepared as follows:

A screw-capped vial was charged with 6-bromo-2-methyl-7-(trifluoromethyl)-[1,3,4]thiadiazolo[3,2-a]pyrimidin-5-one (Intermediate 3A, 105 mg, 0.33 mmol), 1,4-dioxane (0.8 mL), water (0.2 mL), cesium carbonate (329 mg, 1.00 mmol), 1-(2,2,3,3,3-pentafluoropropyl)-4-(4,4,5,5-tetramethyl-1,3,2-dioxaborolan-2-yl)pyrazole (Intermediate 24A, 171 mg, 0.52 mmol) and chloro(2-dicyclohexylphosphino-2',6'-diisopropoxy-1,1'-biphenyl)[2-(2'-amino-1,1'-biphenyl)]palladium(II) (34 mg, 0.04 mmol). The mixture was purged with nitrogen for 10 min then heated at 110° C. for 50 min. After cooling to rt, the mixture was partitioned between water and EtOAc. The organic phase was dried over $Na_2SO_4$, filtered and concentrated under reduced pressure.

The residue was purified by flash chromatography (SiO$_2$, 50-100% EtOAc/Cyclohexane) to afford 2-methyl-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one (108 mg, 0.25 mmol, 75% yield). LC/MS (ESI$^+$) m/z=434.1 [M+H]$^+$. $^1$H NMR (500 MHz, DMSO-d$_6$) δ 2.77 (s, 3H), 5.29 (t, J=15.0 Hz, 2H), 7.66 (s, 1H), 8.05 (s, 1H).

Example 3: 1-methyl-6-[1-(2,2,3,3,3-pentafluoropropyl)-1H-pyrazol-4-yl]-7-(trifluoromethyl)-1H,2H,3H,5H-imidazo[1,2-a]pyrimidine-2,5-dione

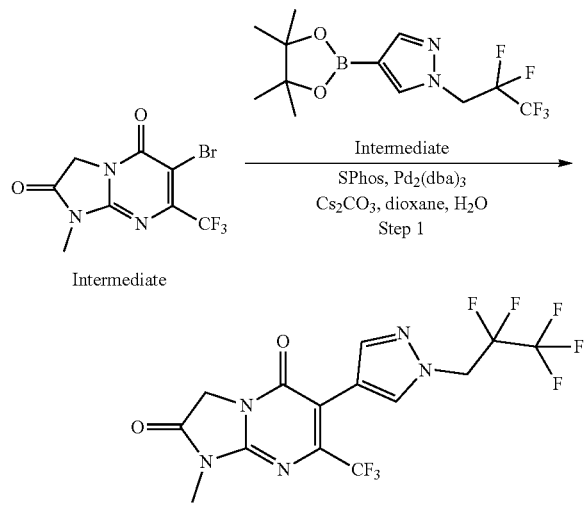

Step 1: 1-methyl-6-[1-(2,2,3,3,3-pentafluoropropyl)-1H-pyrazol-4-yl]-7-(trifluoromethyl)-1H,2H,3H,5H-imidazo[1,2-a]pyrimidine-2,5-dione A screw-capped vial was charged with 6-bromo-1-methyl-7-(trifluoromethyl)-3H-imidazo[1,2-a]pyrimidine-2,5-dione (Intermediate 15A, 1.12 g, 3.34 mmol), 1,4-dioxane (35 mL), water (3.5 mL), cesium carbonate (2.74 g, 8.35 mmol), 1-(2,2,3,3,3-pentafluoropropyl)-4-(4,4,5,5-tetramethyl-1,3,2-dioxaborolan-2-yl)pyrazole (Intermediate 24A, 2.18 g, 6.68 mmol), 2-dicyclohexylphosphino-2',6'-dimethoxybiphenyl (274 mg, 0.67 mmol) and tris(dibenzylideneacetone)dipalladium(0) (306 mg, 0.33 mmol). The mixture was purged with nitrogen for 10 min then heated at 80° C. for 2 h. After cooling to rt, the mixture was filtered with EtOAc through a pad of celite. The filtrate was washed with brine, dried over Na$_2$SO$_4$, filtered and concentrated under reduced pressure. The crude material was purified by flash chromatography (SiO$_2$, 0-50% EtOAc/cyclohexane followed by (C18, 0-70% acetonitrile/water) to afford 1-methyl-6-[1-(2,2,3,3,3-pentafluoropropyl)-1H-pyrazol-4-yl]-7-(trifluoromethyl)-1H,2H,3H,5H-imidazo[1,2-a]pyrimidine-2,5-dione (445 mg, 1.03 mmol, 31% yield) as a white solid. LC/MS (ESI$^+$) m/z=432.7 [M+H]$^+$. $^1$H NMR (500 MHz, DMSO-d$_6$) δ 3.12 (s, 3H), 4.55 (s, 2H), 5.27 (t, J=14.96 Hz, 2H), 7.61 (s, 1H), 8.00 (s, 1H).

Examples 4-36 listed in Table 7 below were prepared following the procedure described in Method 1, Step 1, above as follows.

TABLE 7

| Ex. # | Chemical Structure | Name | Condition Changes | Reagent |
|---|---|---|---|---|
| 4 | 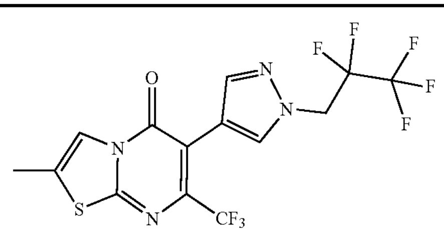 | 2-methyl-6-[1-(2,2,3,3,3-pentafluoropropyl)-1H-pyrazol-4-yl]-7-(trifluoromethyl)-5H-[1,3]thiazolo[3,2-a]pyrimidin-5-one | Heated at 90° C. for 4 h. Purification by flash chromatography (SiO$_2$, Cy/DCM/EtOAc 6:2:2) | 6-bromo-2-methyl-7-(trifluoromethyl)-[1,3]thiazolo[3,2-a]pyrimidin-5-one (Intermediate 1B) and 1-(2,2,3,3,3-pentafluoropropyl)-4-(4,4,5,5-tetramethyl-1,3,2-dioxaborolan-2-yl)pyrazole (Intermediate 24A) |
| 5 | 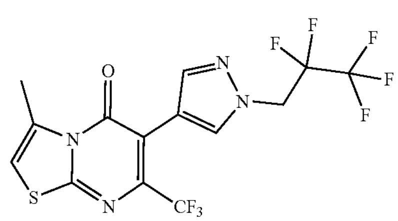 | 3-methyl-6-[1-(2,2,3,3,3-pentafluoropropyl)-1H-pyrazol-4-yl]-7-(trifluoromethyl)-5H-[1,3]thiazolo[3,2-a]pyrimidin-5-one | Heated at 90° C. for 2 h. Purification by flash chromatography (SiO$_2$, 10-50% EtOAC/Cy) | 6-bromo-3-methyl-7-(trifluoromethyl)-[1,3]thiazolo[3,2-a]pynmidin-5-one Intermediate 1C) and 1-(2,2,3,3,3-pentafluoropropyl)-4-(4,4,5,5-tetramethyl-1,3,2-dioxaborolan-2-yl)pyrazole (Intermediate 24A) |

TABLE 7-continued

| Ex. # | Chemical Structure | Name | Condition Changes | Reagent |
|---|---|---|---|---|
| 6 | 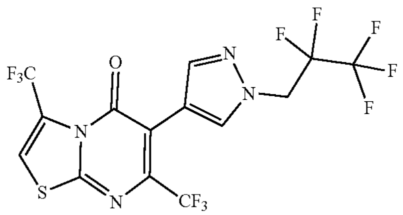 | 6-[1-(2,2,3,3,3-pentafluoropropyl)-1H-pyrazol-4-yl]-3,7-bis(trifluoromethyl)-5H-[1,3]thiazolo[3,2-a]pyrimidin-5-one | Heated at 90° C. for 2 h. Purification by flash chromatography (SiO₂, 0-20% EtOAC/Cy) | 6-bromo-3,7-bis(trifluoromethyl)-[1,3]thiazolo[3,2-a]pyrimidin-5-one (Intermediate 1D) and 1-(2,2,3,3,3-pentafluoropropyl)-4-(4,4,5,5-tetramethyl-1,3,2-dioxaborolan-2-yl)pyrazole (Intermediate 24A) |
| 7 | 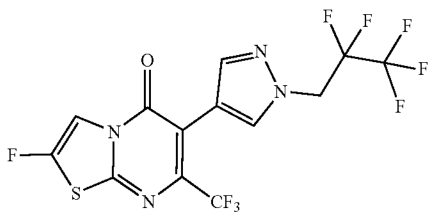 | 2-fluoro-6-[1-(2,2,3,3,3-pentafluoropropyl)-1H-pyrazol-4-yl]-7-(trifluoromethyl)-5H-[1,3]thiazolo[3,2-a]pyrimidin-5-one | Heated at 90° C. for 4 h. Purification by flash chromatography (SiO₂, 0-50% EtOAC/Cy) | 6-bromo-2-fluoro-7-(trifluoromethyl)-[1,3]thiazolo[3,2-a]pyrimidin-5-one (Intermediate 1E) and 1-(2,2,3,3,3-pentafluoropropyl)-4-(4,4,5,5-tetramethyl-1,3,2-dioxaborolan-2-yl)pyrazole (Intermediate 24A) |
| 8 | 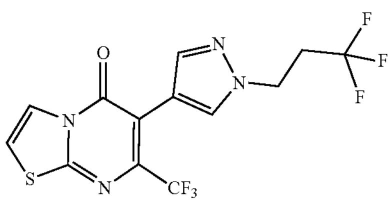 | 7-(trifluoromethyl)-6-[1-(3,3,3-trifluoropropyl)-1H-pyrazol-4-yl]-5H-[1,3]thiazolo[3,2-a]pyrimidin-5-one | Heated at 90° C. for 6 h. Purification by flash chromatography (SiO₂, 0-80% EtOAC/Cy) | 6-bromo-7-(trifluoromethyl)-[1,3]thiazolo[3,2-a]pyrimidin-5-one (Intermediate 1A) and 4-(4,4,5,5-tetramethyl-1,3,2-dioxaborolan-2-yl)-1-(3,3,3-trifluoropropyl)pyrazole (Intermediate 25A) |
| 9 | 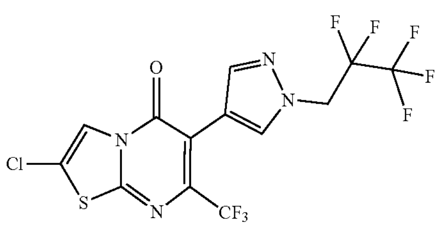 | 2-chloro-6-[1-(2,2,3,3,3-pentafluoropropyl)-1H-pyrazol-4-yl]-7-(trifluoromethyl)-5H-[1,3]thiazolo[3,2-a]pyrimidin-5-one | Heated at 90° C. for 3 h. Purification by flash chromatography (SiO₂, 0-50% EtOAC/Cy followed by RP HPLC, 40-100% MeCN/0.1% HCOOH in H₂O) | 6-bromo-2-chloro-7-(trifluoromethyl)-[1,3]thiazolo[3,2-a]pyrimidin-5-one (Intermediate 1F) and 1-(2,2,3,3,3-pentafluoropropyl)-4-(4,4,5,5-tetramethyl-1,3,2-dioxaborolan-2-yl)pyrazole (Intermediate 24A) |
| 10 | 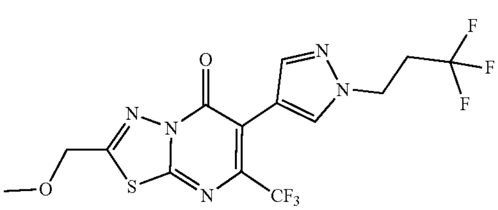 | 2-(methoxymethyl)-7-(trifluoromethyl)-6-[1-(3,3,3-trifluoropropyl)-1H-pyrazol-4-yl]-5H-[1,3,4]thiadiazolo[3,2-a]pyrimidin-5-one | Heated at 90° C. for 2 h. Purification by flash chromatography (SiO₂, 30-50% EtOAC/Cy) | 6-bromo-2-(methoxymethyl-7-(trifluoromethyl-[1,3,4]thiadiazolo[3,2-a]pyrimidin-5-one (Intermediate 2A) and 4-(4,4,5,5-Tetramethyl-1,3,2-dioxaborolan-2-yl)-1-(3,3,3-trifluoropropyl)pyrazole (Intermediate 25A) |

TABLE 7-continued

| Ex. # | Chemical Structure | Name | Condition Changes | Reagent |
|---|---|---|---|---|
| 11 | 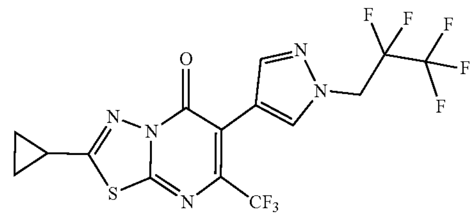 | 2-cyclopropyl-6-[1-(2,2,3,3,3-pentafluoropropyl)-1H-pyrazol-4-yl]-7-(trifluoromethyl)-5H-[1,3,4]thiadiazolo-[3,2-a]pyrimidin-5-one | Heated at 90° C. for 1 h. Purification by flash chromatography (SiO$_2$, 5-80% EtOAC/Cy) | 6-bromo-2-cyclopropyl-7-(trifluoromethyl)-[1,3,4]thiadiazolo-[3,2-a]pyrimidin-5-one (Intermediate 1L) and 1-(2,2,3,3,3-pentafluoropropyl)-4-(4,4,5,5-tetramethyl-1,3,2-dioxaborolan-2-yl)pyrazole (Intermediate 24A) |
| 12 | 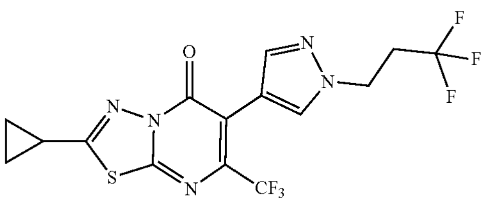 | 2-cyclopropyl-7-(trifluoromethyl)-6-[1-(3,3,3-trifluoropropyl)-1H-pyrazol-4-yl]-5H-[1,3,4]thiadiazolo[3,2-a]pyrimidin-5-one | Heated at 90° C. for 1 h. Purification by flash chromatography (SiO$_2$, 5-80% EtOAC/Cy) | 6-bromo-2-cyclopropyl-7-(trifluoromethyl)-[1,3,4]thiadiazolo[3,2-a]pyrimidin-5-one (Intermediate 1L) and 4-(4,4,5,5-Tetramethyl-1,3,2-dioxaborolan-2-yl)-1-(3,3,3-trifluoropropyl)pyrazole (Intermediate 25A) |
| 13 | 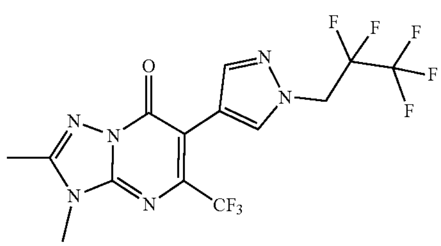 | 2,3-dimethyl-6-[1-(2,2,3,3,3-pentafluoropropyl)-1H-pyrazol-4-yl]-5-(trifluoromethyl)-3H,7H-[1,2,4]-triazolo[1,5-a]pyrimidin-7-one | Heated at 90° C. for 9 h. Purification by flash chromatography (SiO$_2$, 30-100% EtOAC/Cy followed by C18, 5-50% MeCN/0.1% HCOOH in H$_2$O) | 6-bromo-2,3-dimethyl-5-(trifluoromethyl)-[1,2,4]triazolo-[1,5-a]pyrimidin-7-one (Intermediate 5B) and 1-(2,2,3,3,3-pentafluoropropyl)-4-(4,4,5,5-tetramethyl-1,3,2-dioxaborolan-2-yl)pyrazole (Intermediate 24A) |
| 14 | 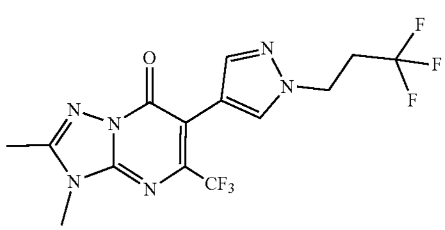 | 2,3-dimethyl-5-(trifluoromethyl)-6-[1-(3,3,3-trifluoropropyl)-1H-pyrazol-4-yl]-3H,7H-[1,2,4]-triazolo[1,5-a]pyrimidin-7-one | Heated at 90° C. for 24 h. Purification by flash chromatography (C18, 5-50% MeCN/0.1% HCOOH in H$_2$O followed by SiO$_2$, 0-5% MeOH/DCM) | 6-bromo-2,3-dimethyl-5-(trifluoromethyl)-[1,2,4]triazolo[1,5-a]pyrimidin-7-one (Intermediate 5B) and 4-(4,4,5,5-Tetramethyl-1,3,2-dioxaborolan-2-yl)-1-(3,3,3-trifluoropropyl)pyrazole (Intermediate 25A) |
| 15 | 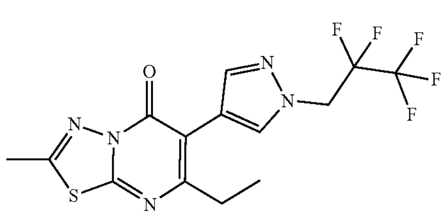 [SMILES: CCc1nc2sc(C)nn2c(=O)c1-c1cnn(CC(F)(F)C(F)(F)F)c1] | 7-ethyl-2-methyl-6-[1-(2,2,3,3,3-pentafluoropropyl)-1H-pyrazol-4-yl]-5H-[1,3,4]thiadiazolo[3,2-a]pyrimidin-5-one | Heated at 90° C. for 1 h. Purification by flash chromatography (C18, 5-100% MeCN/0.1% HCOOH in H$_2$O followed by SiO$_2$, 5-80% EtOAc/Cy) | 6-bromo-7-ethyl-2-methyl-[1,3,4]thiadiazolo[3,2-a]pyrimidin-5-one (Intermediate 1M) and 1-(2,2,3,3,3-pentafluoropropyl)-4-(4,4,5,5-tetramethyl-1,3,2-dioxaborolan-2-yl)pyrazole (Intermediate 24A) |

TABLE 7-continued

| Ex. # | Chemical Structure | Name | Condition Changes | Reagent |
|---|---|---|---|---|
| 16 | 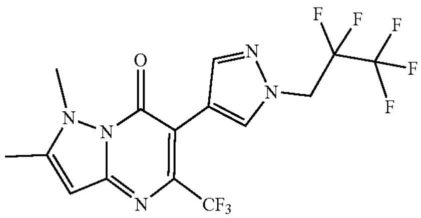 [SMILES: Cc1cc2nc(C(F)(F)F)c(-c3cnn(CC(F)(F)C(F)(F)F)c3)c(=O)n2n1C] | 1,2-dimethyl-6-[1-(2,2,3,3,3-pentafluoropropyl)-1H-pyrazol-4-yl]-5-(trifluoromethyl)-1H,7H-pyrazolo[1,5-a]pyrimidin-7-one | Heated at 80° C. for 5 h. Purification by flash chromatography (SiO$_2$, 0-80% EtOAc/Cy followed by C18, 0-50% MeCN/H$_2$O) | 6-bromo-1,2-dimethyl-5-(trifluoromethyl)-pyrazolo[1,5-a]pyrimidin-7-one (Intermediate 1G) and 1-(2,2,3,3,3-pentafluoropropyl)-4-(4,4,5,5-tetramethyl-1,3,2-dioxaborolan-2-yl)pyrazole (Intermediate 24A) |
| 17 | 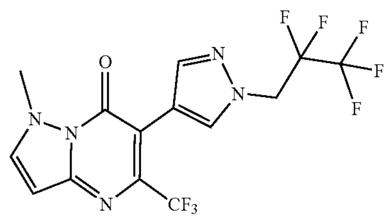 | 1-methyl-6-[1-(2,2,3,3,3-pentafluoropropyl)-1H-pyrazol-4-yl]-5-(trifluoromethyl)-1H,7H-pyrazolo[1,5-a]pyrimidin-7-one | Heated at 80° C. for 5 h. Purification by flash chromatography [SiO$_2$, 0-100% (10% MeOH in EtOAc)/Cy] | 6-bromo-1-methyl-5-(trifluoromethyl)-pyrazolo[1,5-a]pyrimidin-7-one (Intermediate 1H) and 1-(2,2,3,3,3-pentafluoropropyl)-4-(4,4,5,5-tetramethyl-1,3,2-dioxaborolan-2-yl)pyrazole (Intermediate 24A) |
| 18 | 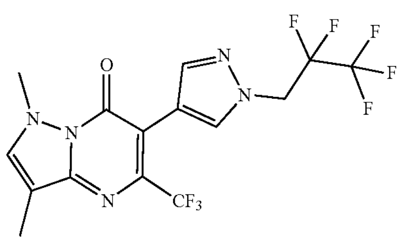 | 1,3-dimethyl-6-[1-(2,2,3,3,3-pentafluoropropyl)-1H-pyrazol-4-yl]-5-(trifluoromethyl)-1H,7H-pyrazolo[1,5-a]pyrimidin-7-one | Heated at 80° C. for 6 h. Purification by flash chromatography SiO$_2$, 0-100% (10% MeOH in EtOAc)/Cy followed by C18, 0-70% MeCN/H$_2$O] | 6-bromo-1,3-dimethyl-5-(trifluoromethyl)-pyrazolo[1,5-a]pyrimidin-7-one (Intermediate 1I) and 1-(2,2,3,3,3-pentafluoropropyl)-4-(4,4,5,5-tetramethyl-1,3,2-dioxaborolan-2-yl)pyrazole (Intermediate 24A) |
| 19 | 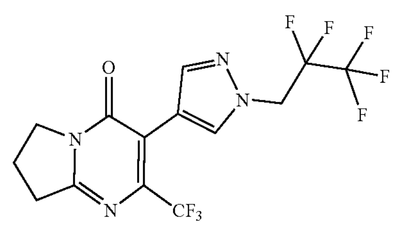 | 341-(2,2,3,3,3-pentafluoropropyl)-1H-pyrazol-4-yl]-2-(trifluoromethyl)-4H,6H,7H,8H-pyrrolo[1,2-a]pyrimidin-4-one | Heated at 90° C. for 3 h. Purification by flash chromatography (C18, 0-60% MeCN/0.1% HCOOH in H$_2$O followed by SiO$_2$, 0-40% EtOAc/Cy) | 3-bromo-2-(trifluoromethyl)-7,8-dihydro-6H-pyrrolo[1,2-a]pyrimidin-4-one (Intermediate 6A) and 1-(2,2,3,3,3-pentafluoropropyl)-4-(4,4,5,5-tetramethyl-1,3,2-dioxaborolan-2-yl)pyrazole (Intermediate 24A) |
| 20 | 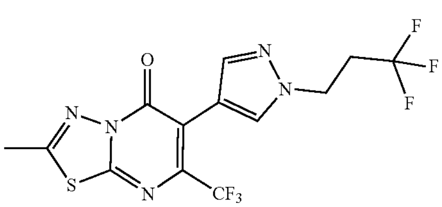 [SMILES: Cc1nn2c(=O)c(-c3cnn(CCC(F)(F)F)c3)c(C(F)(F)F)nc2s1] | 2-methyl-7-(trifluoromethyl)-6-[1-(3,3,3-trifluoropropyl)-1H-pyrazol-4-yl]-5H-[1,3,4]thiadiazolo[3,2-a]pyrimidin-5-one | Heated at 90° C. for 5 h. Purification by flash chromatography (SiO$_2$, 10-90% EtOAc/Cy followed by C18, 5-100% MeCN/0.1% HCOOH in H$_2$O) | 6-bromo-2-methyl-7-(trifluoromethyl)-[1,3,4]thiadiazolo[3,2-a]pyrimidin-5-one (Intermediate 3A) and 4-(4,4,5,5-Tetramethyl-1,3,2-dioxaborolan-2-yl)-1-(3,3,3-trifluoropropyl)-pyrazole (Intermediate 25A) |

TABLE 7-continued

| Ex. # | Chemical Structure | Name | Condition Changes | Reagent |
|---|---|---|---|---|
| 21 | 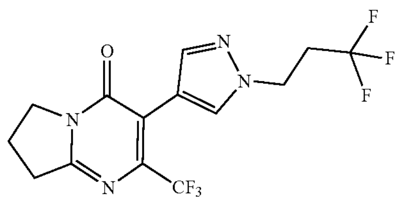 | 2-(trifluoromethyl)-3-[1-(3,3,3-trifluoropropyl)-1H-pyrazol-4-yl]-4H,6H,7H,8H-pyrrolo[1,2-a]pyrimidin-4-one | Heated at 90° C. for 7 h. Purification by flash chromatography (C18, 5-50% MeCN/0.1% HCOOH in $H_2O$ followed by $SiO_2$, 0-50% EtOAc/Cy) | 3-bromo-2-(trifluoromethyl)-7,8-dihydro-6H-pyrrolo[1,2-a]pyrimidin-4-one (Intermediate 6A) and 4-(4,4,5,5-Tetramethyl-1,3,2-dioxaborolan-2-yl)-1-(3,3,3-trifluoropropyl)-pyrazole (Intermediate 25A) |
| 22 | 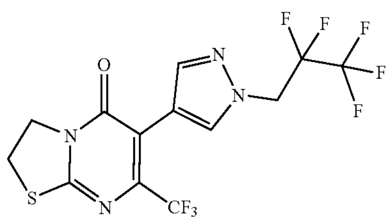 | 6-[1-(2,2,3,3,3-pentafluoropropyl)-1H-pyrazol-4-yl]-7-(trifluoromethyl)-2H,3H,5H-[1,3]thiazolo[3,2-a]pyrimidin-5-one | Heated at 80° C. for 5 h. Purification by flash chromatography ($SiO_2$, 0-80% EtOAc/Cy) | 6-bromo-7-(trifluoromethyl)-2,3-dihydro-[1,3]thiazolo[3,2-a]pyrimidin-5-one (Intermediate 11A) and 1-(2,2,3,3,3-pentafluoropropyl)-4-(4,4,5,5-tetramethyl-1,3,2-dioxaborolan-2-yl)pyrazole (Intermediate 24A) |
| 23 | 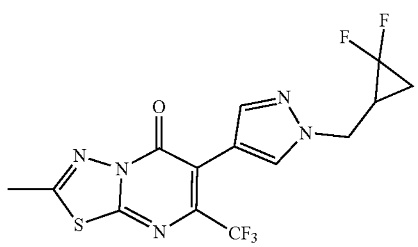 | 6-{1-[(2,2-difluorocyclopropyl)-methyl]-1H-pyrazol-4-yl}-2-methyl-7-(trifluoromethyl)-5H-[1,3,4]thiadiazolo[3,2-a]pyrimidin-5-one | Heated at 90° C. for 4 h. Purification by flash chromatography ($SiO_2$, 20% Cy in EtOAc) | 6-bromo-2-methyl-7-(trifluoromethyl)-[1,3,4]thiadiazolo[3,2-a]pyrimidin-5-one (Intermediate 3A) and 1-[(2,2-difluorocyclo-propyl)methyl]-4-(4,4,5,5-tetramethyl-1,3,2-dioxaborolan-2-yl)pyrazole (Intermediate 27A) |
| 24 | 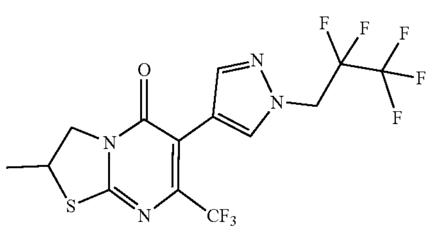 [SMILES: CC1Cn2c(nc(C(F)(F)F)c(-c3cnn(CC(F)(F)C(F)(F)F)c3)c2=O)S1] | 2-methyl-6-[1-(2,2,3,3,3-pentafluoropropyl)-1H-pyrazol-4-yl]-7-(trifluoromethyl)-2H,3H,5H-[1,3]thiazolo[3,2-a]pyrimidin-5-one | Heated at 85° C. for 3 h. Purification by flash chromatography ($SiO_2$, 0-100% (10% MeOH in EtOAc)/Cy) | 6-bromo-2-methyl-7-(trifluoromethyl)-2,3-dihydro-[1,3]thiazolo[3,2-a]pyrimidin-5-one (Intermediate 8A) and 1-(2,2,3,3,3-pentafluoropropyl)-4-(4,4,5,5-tetralmethyl-1,3,2-dioxaborolan-2-yl)pyrazole (Intermediate 24A) |
| 25 | 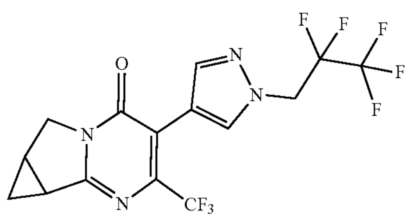 [SMILES: O=c1c(-c2cnn(CC(F)(F)C(F)(F)F)c2)c(C(F)(F)F)nc2n1CC1CC21] | 8-[1-(2,2,3,3,3-pentafluoropropyl)-1H-pyrazol-4-yl]-9-(trifluoromethyl)-6,10-diazatricyclo[4.4.0.0$^{2,4}$]deca-1(10),8-dien-7-one | Heated at 90° C. for 3 h. Purification by flash chromatography ($SiO_2$, 0-50% EtOAc/Cy followed by C18, 5-60% MeCN/$H_2O$) | 3-bromo-2-(trifluoromethyl)-6,6a,7,7a-tetrahydrocyclo-propa[1,2]pyrrolo-[4,5-a]pyrimidin-4-one (Intermediate 7A) and 1-(2,2,3,3,3-pentafluoropropyl)-4-(4,4,5,5-tetramethyl-1,3,2-dioxaborolan-2-yl)pyrazole (Intermediate 24A) |

TABLE 7-continued

| Ex. # | Chemical Structure | Name | Condition Changes | Reagent |
|---|---|---|---|---|
| 26 | 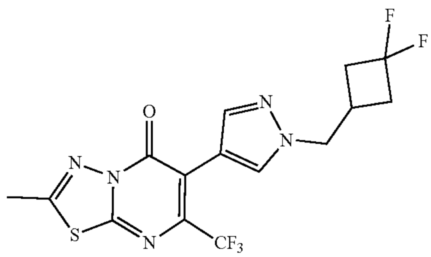 | 6-{1-[(3,3-difluorocyclobutyl)methyl]-1H-pyrazol-4-yl}-2-methyl-7-(trifluoromethyl)-5H-[1,3,4]thiadiazolo[3,2-a]pyrimidin-5-one | Heated at 90° C. for 24 h. Purification by flash chromatography (C18, 5-80% MeCN/0.1% HCOOH in H$_2$O followed by SiO$_2$, 20% Cy in EtOAc) | 6-bromo-2-methyl-7-(trifluoromethyl)-[1,3,4]thiadiazolo-[3,2-a]pyrimidin-5-one (Intermediate 3A) and 1-[(3,3-difluorocyclobutyl)methyl]-4-(4,4,5,5-tetramethyl-1,3,2-dioxaborolan-2-yl)pyrazole (Intermediate 28A) |
| 27 | 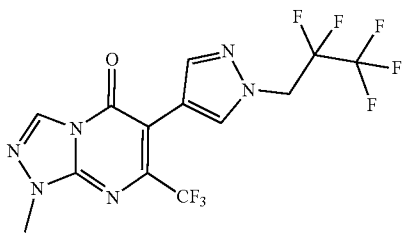 [SMILES: Cn1ncn2c(=O)c(-c3cnn(CC(F)(F)C(F)(F)F)c3)c(C(F)(F)F)nc12] | 1-methyl-6-[1-(2,2,3,3,3-pentafluoropropyl)-1H-pyrazol-4-yl]-7-(trifluoromethyl)-1H,5H-[1,2,4]triazolo[4,3-a]pyrimidin-5-one | Heated at 85° C. for 1 h. Purification by flash chromatography (SiO$_2$, 0-80% EtOAc/Cy) | 6-bromo-1-methyl-7-(trifluoromethyl)-[1,2,4]triazolo[4,3-a]pyrimidin-5-one (Intermediate 1J) and 1-(2,2,3,3,3-pentafluoropropyl)-4-(4,4,5,5-tetramethyl-1,3,2-dioxaborolan-2-yl)pyrazole (Intermediate 24A) |
| 28 | 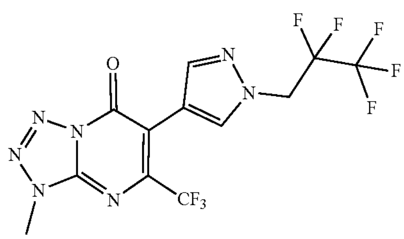 | 3-methyl-6-[1-(2,2,3,3,3-pentafluoropropyl)-1H-pyrazol-4-yl]-5-(trifluoromethyl)-3H,7H-[1,2,3,4]tetrazolo[1,5-a]pyrimidin-7-one | Heated at 85° C. for 3 h. Purification by flash chromatography (SiO$_2$, 0-50% EtOAc/Cy) | 6-bromo-3-methyl-5-(trifluoromethyl)-tetrazolo[1,5-a]pyrimidin-7-one (Intermediate 1K) and 1-(2,2,3,3,3-pentafluoropropyl)-4-(4,4,5,5-tetramethyl-1,3,2-dioxaborolan-2-yl)pyrazole (Intermediate 24A) |
| 29 | 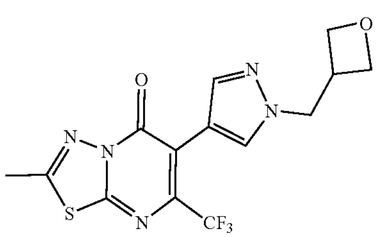 [SMILES: Cc1nn2c(=O)c(-c3cnn(CC4COC4)c3)c(C(F)(F)F)nc2s1] | 2-methyl-6-{1-[(oxetan-3-yl)methyl]-1H-pyrazol-4-yl}-7-(trifluoromethyl)-5H-[1,3,4]thiadiazolo[3,2-a]pyrimidin-5-one | Heated at 90° C. for 3 h. Purification by flash chromatography (C18, 5-60% MeCN/0.1% HCOOH in H$_2$O followed by SiO$_2$, 0-5% MeOH/DCM) | 6-bromo-2-methyl-7-(trifluoromethyl)-[1,3,4]thiadiazolo-[3,2-a]pyrimidin-5-one (Intermediate 3A) and 1-(oxetan-3-ylmethyl)-4-(4,4,5,5-tetramethyl-1,3,2-dioxaborolan-2-yl)pyrazole (Intermediate 32A) |
| 30 | 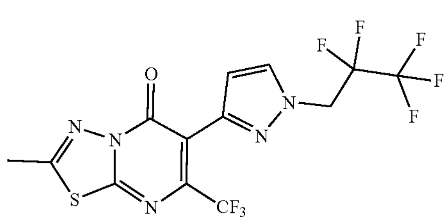 [SMILES: Cc1nn2c(=O)c(-c3ccn(CC(F)(F)C(F)(F)F)n3)c(C(F)(F)F)nc2s1] | 2-methyl-6-[1-(2,2,3,3,3-pentafluoropropyl)-1H-pyrazol-3-yl]-7-(trifluoromethyl)-5H-[1,3,4]thiadiazolo[3,2-a]pyrimidin-5-one | Heated at 90° C. for 2 h. Purification by flash chromatography (SiO$_2$, 30-80% EtOAc/Cy) | 6-bromo-2-methyl-7-(trifluoromethyl)-[1,3,4]thiadiazolo-[3,2-a]pyrimidin-5-one (Intermediate 3A) and 1-(2,2,3,3,3-pentafluoropropyl)-3-(4,4,5,5-tetramethyl-1,3,2-dioxaborolan-2-yl)pyrazole (Intermediate 30A) |

TABLE 7-continued

| Ex. # | Chemical Structure | Name | Condition Changes | Reagent |
|---|---|---|---|---|
| 31 | 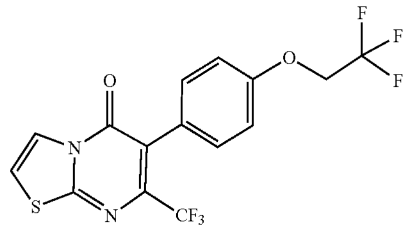 [SMILES: O=c1c(-c2ccc(OCC(F)(F)F)cc2)c(C(F)(F)F)nc2sccn12] | 6-[4-(2,2,2-trifluoroethoxy)phenyl]-7-(trifluoromethyl)-5H-[1,3]thiazolo[3,2-a]pyrimidin-5-one | Heated at 90° C. for 3 h. Purification by flash chromatography (SiO$_2$, 20-80% EtOAc/Cy followed by C18, 40-80% MeCN/0.1% HCOOH in H$_2$O) | 6-bromo-7-(trifluoromethyl)-[1,3]thiazolo[3,2-a]pyrimidin-5-one (Intermediate 1A) and tetramethyl-2-[4-(2,2,2-trifluoroethoxy)phenyl]-1,3,2-dioxaborolane (Intermediate 31A) |
| 32 | 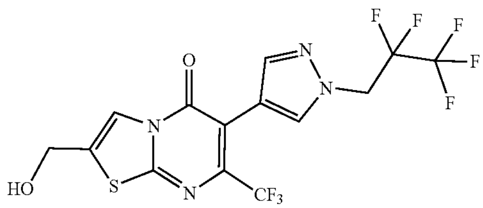 [SMILES: O=c1c(-c2cnn(CC(F)(F)C(F)(F)F)c2)c(C(F)(F)F)nc2sc(CO)cn12] | 2-(hydroxymethyl)-6-[1-(2,2,3,3,3-pentafluoropropyl)-1H-pyrazol-4-yl]-7-(trifluoromethyl)-5H-[1,3]thiazolo[3,2-a]pyrimidin-5-one | Heated at 90° C. for 2 h. Purification by flash chromatography (SiO$_2$, 20-80% EtOAc/Cy) | 6-bromo-2-(hydroxymethyl)-7-(trifluoromethyl)-[1,3]thiazolo[3,2-a]pyrimidin-5-one (Intermediate 4B) and 1-(2,2,3,3,3-pentafluoropropyl)-4-(4,4,5,5-tetramethyl-1,3,2-dioxaborolan-2-yl)pyrazole (Intermediate 24A) |
| 33 | 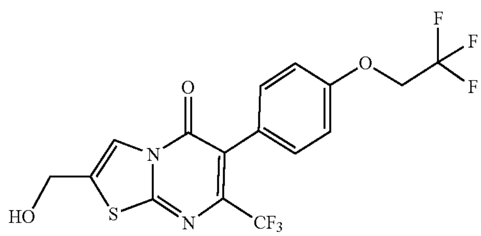 [SMILES: O=c1c(-c2ccc(OCC(F)(F)F)cc2)c(C(F)(F)F)nc2sc(CO)cn12] | 2-(hydroxymethyl)-6-[4-(2,2,2-trifluoroethoxy)phenyl]-7-(trifluoromethyl)-5H-[1,3]thiazolo[3,2-a]pyrimidin-5-one | Heated at 90° C. for 2 h. Purification by flash chromatography (SiO$_2$, 20-100% EtOAc/Cy followed by C18, 0-100% MeCN/0.1% HCOOH in H$_2$O) | 6-bromo-2-(hydroxymethyl)-7-(trifluoromethyl)-[1,3]thiazolo[3,2-a]pyrimidin-5-one (Intermediate 4B) and 4,4,5,5-tetramethyl-2-[4-(2,2,2-trifluoroethoxy)phenyl]-1,3,2-dioxaborolane (Intermediate 31A) |
| 34 | 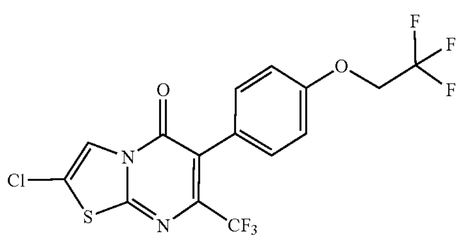 [SMILES: O=c1c(-c2ccc(OCC(F)(F)F)cc2)c(C(F)(F)F)nc2sc(Cl)cn12] | 2-chloro-6-[4-(2,2,2-trifluoroethoxy)phenyl]-7-(trifluoromethyl)-5H-[1,3]thiazolo[3,2-a]pyrimidin-5-one | Heated at 90° C. for 3 h. Purification by flash chromatography (SiO$_2$, 0-50% EtOAc/Cy followed by C18, 0-80% MeCN/0.1% HCOOH in H$_2$O) | 6-bromo-2-chloro-7-(trifluoromethyl)-[1,3]thiazolo[3,2-a]pyrimidin-5-one (Intermediate 1F) and 4,4,5,5-tetramethyl-2-[4-[2,2,2-trifluoroethoxy)phenyl]-1,3,2-dioxaborolane (Intermediate 31A) |
| 35 | 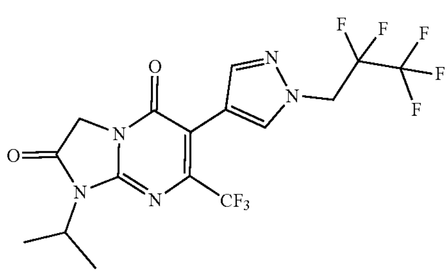 | 6-[1-(2,2,3,3,3-pentafluoropropyl)-1H-pyrazol-4-yl]-1-(propan-2-yl)-7-(trifluoromethyl)-1H,2H,3H,5H-imidazo[1,2-a]pyrimidine-2,5-dione | Heated at 80° C. for 6 h. Purification by flash chromatography (SiO$_2$, 0-60% EtOAc/Cy followed by C18, 0-70% MeCN/H$_2$O) | 6-bromo-1-propan-2-yl-7-(trifluoromethyl)-3H-imidazo[1,2-a]pyrimidine-2,5-dione (Intermediate 16A) and 1-(2,2,3,3,3-pentafluoropropyl)-4-(4,4,5,5-tetramethyl-1,3,2-dioxaborolan-2-yl)pyrazole (Intermediate 24A) |

TABLE 7-continued

| Ex. # | Chemical Structure | Name | Condition Changes | Reagent |
|---|---|---|---|---|
| 36 | 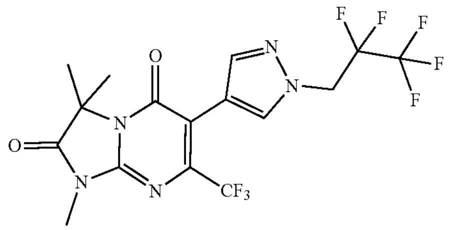 | 1,3,3-trimethyl-6-[1-(2,2,3,3,3-pentafluoropropyl)-1H-pyrazol-4-yl]-7-(trifluoromethyl)-1H,2H,3H,5H-imidazo[1,2-a]pyrimidine-2,5-dione | Heated at 80° C. for 16 h. Purification by flash chromatography (SiO$_2$, 0-50% EtOAc/Cy) | 6-bromo-1,3,3-trimethyl-7-(trifluoromethyl)-imidazo[1,2-a]pyrimidine-2,5-dione (Intermediate 17A) and 1-(2,2,3,3,3-pentafluoropropyl)-4-(4,4,5,5-tetramethyl-1,3,2-dioxaborolan-2-yl)pyrazole (Intermediate 24A) |

Method 2

Example 37: 1-methyl-6-[1-(2,2,3,3,3-pentafluoropropyl)-1H-pyrazol-4-yl]-7-(trifluoromethyl)-1H,5H-imidazo[1,2-a]pyrimidin-5-one

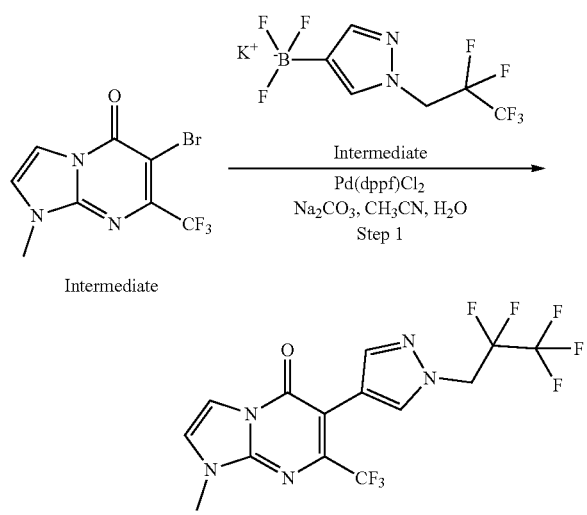

Step 1: 1-methyl-6-[1-(2,2,3,3,3-pentafluoropropyl)-1H-pyrazol-4-yl]-7-(trifluoromethyl)-1H,5H-imidazo[1,2-a]pyrimidin-5-one A microwave vial was charged with 6-bromo-1-methyl-7-(trifluoromethyl)imidazo[1,2-a]pyrimidin-5-one (Intermediate 10A, 50 mg, 0.17 mmol), MeCN (2.3 mL), sodium carbonate (1M solution in water, 0.42 mL, 0.42 mmol), potassium trifluoro-[1-(2,2,3,3,3-pentafluoropropyl)pyrazol-4-yl]boranuide (Intermediate 26A, 77.50 mg, 0.25 mmol) and [1,1'-bis(diphenylphosphino)ferrocene]dichloropalladium(II) (12.40 mg, 0.02 mmol). The mixture was purged with nitrogen for 10 min then subjected to microwave irradiation at 120° C. for 30 minutes. The reaction mixture was cooled to room temperature and filtered with EtOAc through a pad of celite. The filtrate was washed with water and brine, dried over Na$_2$SO$_4$, filtered and concentrated under reduced pressure. The residue was purified by flash chromatography (SiO$_2$, 0-100% EtOAc/cyclohexane followed by C18, 0-70% MeCN in water) to afford 1-methyl-6-[1-(2,2,3,3,3-pentafluoropropyl)-1H-pyrazol-4-yl]-7-(trifluoromethyl)-1H,5H-imidazo[1,2-a]pyrimidin-5-one (42 mg, 0.10 mmol, 44% yield) as a white solid. LC/MS (ESI$^+$) m/z=416.4 [M+H]. $^1$H NMR (500 MHz, DMSO-d$_6$) δ 3.74 (s, 3H), 5.24 (t, J=14.96 Hz, 2H), 7.56 (s, 1H), 7.72-7.78 (m, 1H), 7.78-7.83 (m, 1H), 7.88 (s, 1H).

Examples 38-39 listed in Table 8 below were prepared following the procedure described in Method 2, Step 1, above as follows:

TABLE 8

| Ex. # | Chemical Structure | Name | Condition Changes | Reagents |
|---|---|---|---|---|
| 38 | 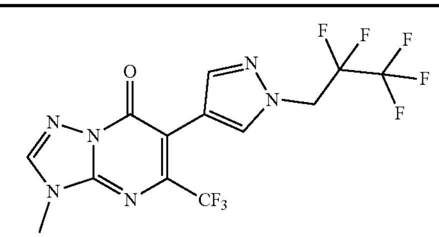 | 3-methyl-6-[1-(2,2,3,3,3-pentafluoropropyl)-1H-pyrazol-4-yl]-5-(trifluoromethyl)-3H,7H-[1,2,4]triazolo[1,5-a]pyrimidin-7-one | Purification by flash chromatography (SiO$_2$, 2-5% MeOH/DCM followed by RP HPLC, 3-100% 0.1% HCOOH in MeCN/0.1% HCOOH in H$_2$O) | 6-bromo-3-methyl-5-(trifluoromethyl)-[1,2,4]triazolo[1,5-a]pyrimidin-7-one (Intermediate 5A) and potassium trifluoro-[1-(2,2,3,3,3-pentafluoropropyl)pyrazol-4-yl]boranuide (Intermediate 26A) |

TABLE 8-continued

| Ex. # | Chemical Structure | Name | Condition Changes | Reagents |
|---|---|---|---|---|
| 39 | 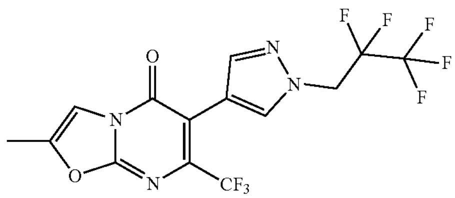 [SMILES: Cc1cn2c(=O)c(-c3cnn(CC(F)(F)C(F)(F)F)c3)c(C(F)(F)F)nc2o1] | 2-methyl-6-[1-(2,2,3,3,3-pentafluoropropyl)-1H-pyrazol-4-yl]-7-(trifluoromethyl)-5H-[1,3]oxazolo[3,2-a]pyrimidin-5-one | Heated at 120° C. for 1 h. Purification by flash chromatography (SiO$_2$, 30-60% EtOAc/Cy) | 6-bromo-2-methyl-7-(trifluoromethyl)-[1,3]oxazolo[3,2-a]pyrimidin-5-one (Intermediate 12A) and potassium trifluoro-[1-(2,2,3,3,3-pentafluoro-propyl)pyrazol-4-yl]boranuide (Intermediate 26A) |

Method 3

Example 40: 2-methyl-6-[4-(2,2,2-trifluoroethoxy)phenyl]-7-(trifluoromethyl)-5H-[1,3,4]thiadiazolo[3,2-a]pyrimidin-5-one

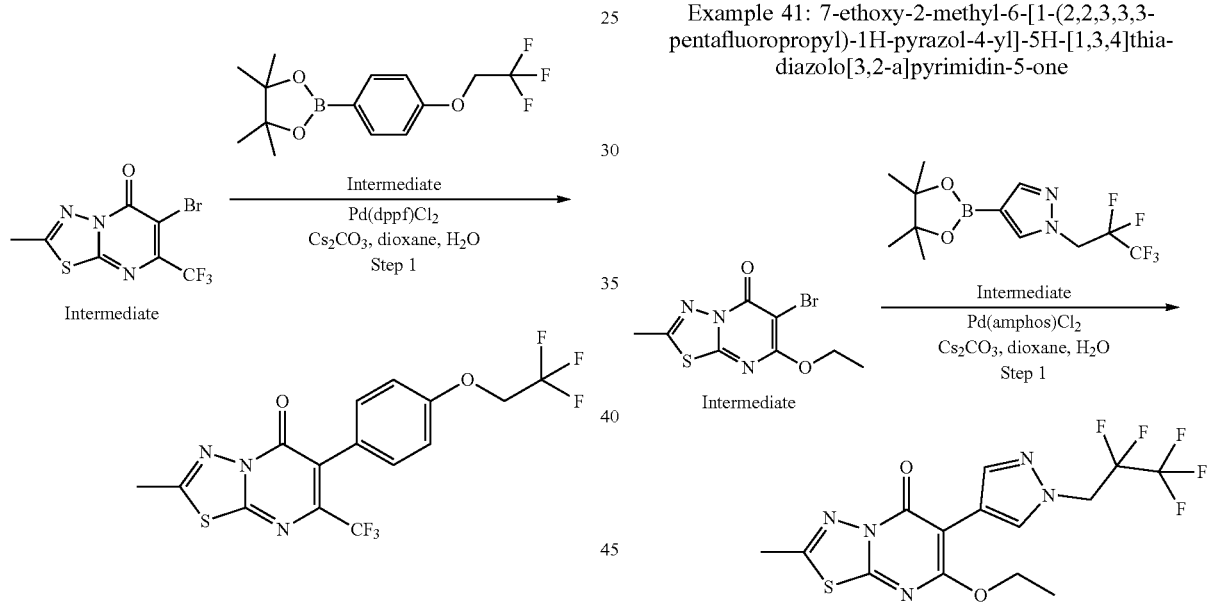

Step 1: 2-methyl-6-[4-(2,2,2-trifluoroethoxy)phenyl]-7-(trifluoromethyl)-5H-[1,3,4]thiadiazolo[3,2-a]pyrimidin-5-one A screw-capped vial was charged with 6-bromo-2-methyl-7-(trifluoromethyl)-[1,3,4]thiadiazolo[3,2-a]pyrimidin-5-one (Intermediate 3A, 200 mg, 0.64 mmol), 1,4-dioxane (1.8 mL), water (0.36 mL), cesium carbonate (622 mg, 1.91 mmol), 4,4,5,5-tetramethyl-2-[4-(2,2,2-trifluoroethoxy)phenyl]-1,3,2-dioxaborolane (Intermediate 31A, 385 mg, 1.27 mmol), and [1,1'-bis(diphenylphosphino)ferrocene]dichloropalladium(II) (70 mg, 0.10 mmol). The mixture was purged with nitrogen for 10 min then heated at 95° C. for 45 min. The reaction mixture was cooled to room temperature and filtered with EtOAc through a pad of celite. The filtrate was concentrated under reduced pressure and purified by flash chromatography (SiO$_2$, 0-100% EtOAc/cyclohexane followed by C18, 0-50% acetonitrile/0.1% formic acid in water) to afford 2-methyl-6-[4-(2,2,2-trifluoroethoxy)phenyl]-7-(trifluoromethyl)-5H-[1,3,4]thiadiazolo[3,2-a]pyrimidin-5-one (140 mg, 0.34 mmol, 54% yield). LC/MS (ESI$^+$) m/z=410.0 [M+H]$^+$. 1H NMR (500 MHz, DMSO-d$_6$) δ 2.77 (s, 3H), 4.82 (q, J=8.9 Hz, 2H), 7.13 (d, J=8.8 Hz, 2H), 7.25 (d, J=8.8 Hz, 2H).

Method 4

Example 41: 7-ethoxy-2-methyl-6-[1-(2,2,3,3,3-pentafluoropropyl)-1H-pyrazol-4-yl]-5H-[1,3,4]thiadiazolo[3,2-a]pyrimidin-5-one

Step 1: 7-ethoxy-2-methyl-6-[1-(2,2,3,3,3-pentafluoropropyl)-1H-pyrazol-4-yl]-5H-[1,3,4]thiadiazolo[3,2-a]pyrimidin-5-one A screw-capped vial was charged with 6-bromo-7-ethoxy-2-methyl-[1,3,4]thiadiazolo[3,2-a]pyrimidin-5-one (Intermediate 9A, 40.0 mg, 0.140 mmol), 1,4-dioxane (1.4 mL), water (0.28 mL), cesium carbonate (135 mg, 0.41 mmol), 1-(2,2,3,3,3-pentafluoropropyl)-4-(4,4,5,5-tetramethyl-1,3,2-dioxaborolan-2-yl)pyrazole (Intermediate 24A, 89.91 mg, 0.280 mmol) and bis(di-tert-butyl(4-dimethylaminophenyl)phosphine)dichloropalladium(II) (9.8 mg, 0.01 mmol). The mixture was purged with nitrogen for 10 min then heated at 100° C. for 30 min. The reaction mixture was cooled to room temperature and filtered with EtOAc through a pad of celite. The filtrate was concentrated under reduced pressure and purified by flash chromatography (C18, 0-50% acetonitrile/0.1% formic acid in water) to afford 7-ethoxy-2-methyl-6-

[1-(2,2,3,3,3-pentafluoropropyl)-1H-pyrazol-4-yl]-5H-[1,3,4]thiadiazolo[3,2-a]pyrimidin-5-one (21 mg, 0.051 mmol, 37% yield). LC/MS (ESI+) m/z=410.4 [M+H]+. 1H NMR (500 MHz, DMSO-d6) δ 1.42 (t, J=7.0 Hz, 3H), 2.73 (s, 3H), 4.50 (q, J=7.0 Hz, 2H), 5.28 (t, J=15.1 Hz, 2H), 8.23 (s, 1H), 8.52 (s, 1H).

Method 5

Example 42: 2-(methoxymethyl)-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one

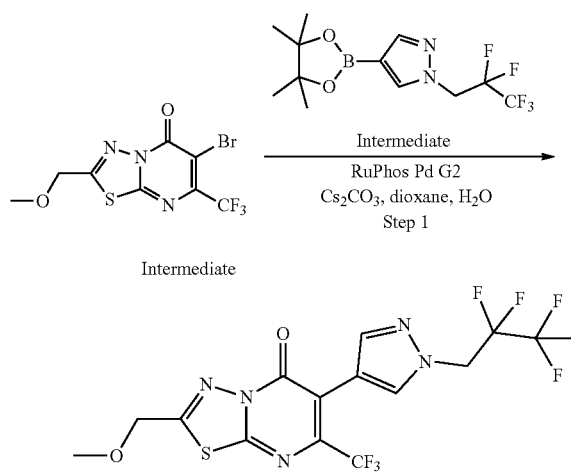

Intermediate

Step 1: 2-(methoxymethyl)-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one A screw-capped vial was charged with 6-bromo-2-(methoxymethyl)-7-(trifluoromethyl)-[1,3,4]thiadiazolo[3,2-a]pyrimidin-5-one (Intermediate 2A, 295 mg, 0.86 mmol), 1,4-dioxane (4.7 mL), water (1.2 mL), cesium carbonate (843 mg, 2.57 mmol), 1-(2,2,3,3,3-pentafluoropropyl)-4-(4,4,5,5-tetramethyl-1,3,2-dioxaborolan-2-yl)pyrazole (Intermediate 24A, 608 mg, 1.71 mmol) and chloro(2-dicyclohexylphosphino-2',6'-diisopropoxy-1,1'-biphenyl)[2-(2'-amino-1,1'-biphenyl)]palladium(II) (100 mg, 0.13 mmol). The mixture was purged with nitrogen for 10 min then heated at 110° C. for 1.5 h. After cooling to rt, the mixture was partitioned between water and EtOAc and extracted with EtOAc (2×). The organic phase was dried over Na2SO4, filtered and concentrated under reduced pressure. The residue was purified by flash chromatography (SiO2, 30-80% EtOAc/cyclohexane followed by C18, 20-80% acetonitrile/0.1% formic acid in water) to afford 2-(methoxymethyl)-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one (224 mg, 0.48 mmol, 48% yield) as a white solid. LC/MS (ESI+) m/z=464.1 [M+H]+. 1H NMR (500 MHz, DMSO-d6) δ 3.46 (s, 3H), 4.88 (s, 2H), 5.30 (t, J=15.10 Hz, 2H), 7.67 (s, 1H), 8.06 (s, 1H).

Method 6

Example 43: 2-methoxy-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one

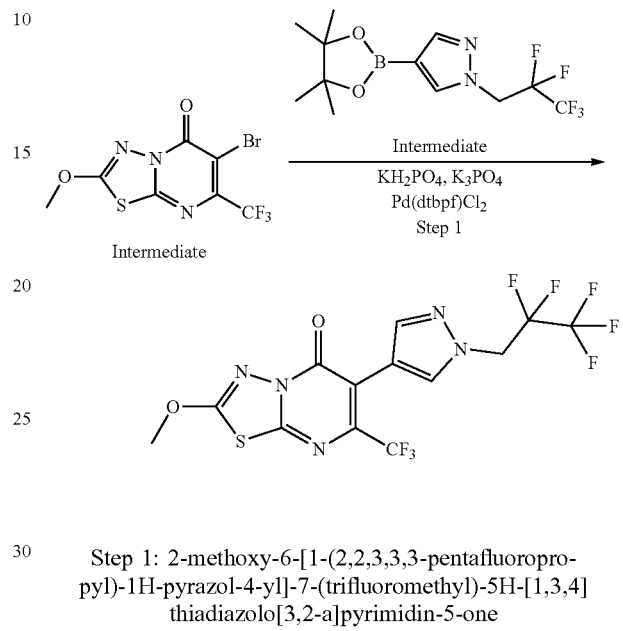

Step 1: 2-methoxy-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one A mixture of 1,2-dimethoxyethane (12.4 mL), ethanol (7.4 mL) and water (2.5 mL) was purged with nitrogen for 10 min. 6-Bromo-2-methoxy-7-(trifluoromethyl)-[1,3,4]thiadiazolo[3,2-a]pyrimidin-5-one (Intermediate 4A, 121 mg, 0.36 mmol), 1-(2,2,3,3,3-pentafluoropropyl)-4-(4,4,5,5-tetramethyl-1,3,2-dioxaborolan-2-yl)pyrazole (Intermediate 24A, 176 mg, 0.54 mmol), potassium dihydrogen phosphate (50.5 mg, 0.37 mmol) and tripotassium phosphate (79.4 mg, 0.37 mmol) were added and the mixture was purged with nitrogen for 10 min. [1,1'-Bis(di-tert-butylphosphino)ferrocene]dichloropalladium(II) (23.5 mg, 0.04 mmol) was added and the reaction mixture was stirred at 40° C. overnight. Further 1-(2,2,3,3,3-pentafluoropropyl)-4-(4,4,5,5-tetramethyl-1,3,2-dioxaborolan-2-yl)pyrazole (Intermediate 24A, 176 mg, 0.54 mmol), [1,1'-bis(di-tert-butylphosphino)ferrocene]dichloropalladium(II) (23.5 mg, 0.04 mmol), potassium dihydrogen phosphate (50.5 mg, 0.37 mmol) and tripotassium phosphate (79.4 mg, 0.37 mmol) were added and stirring was continued for 48 h. The reaction mixture was partitioned between EtOAc and H2O, phases were separated and the organic one was dried over Na2SO4, filtered and concentrated. The crude material was purified by flash chromatography (SiO2, 0-80% EtOAc/cyclohexane) to afford 2-methoxy-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one (14 mg, 0.031 mmol, 9% yield) as a white solid. LC/MS (EST*) m/z=449.9 [M+H]+. 1H NMR (500 MHz, DMSO-d6) δ 4.23 (s, 3H), 5.29 (t, J=15.0 Hz, 2H), 7.66 (s, 1H), 8.04 (s, 1H).

Method 7

Example 44: 3-chloro-1-methyl-6-[1-(2,2,3,3,3-pentafluoropropyl)-1H-pyrazol-4-yl]-7-(trifluoromethyl)-1H,5H-imidazo[1,2-a]pyrimidin-5-one

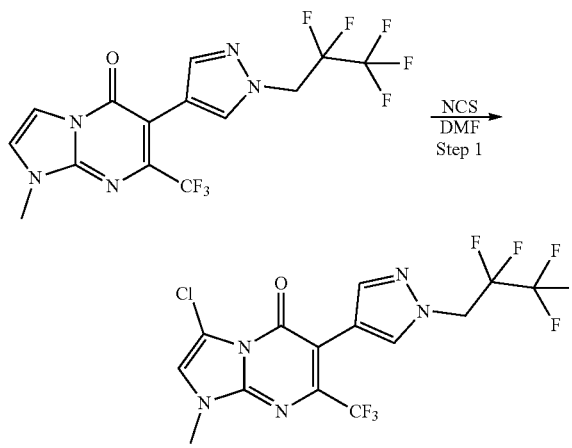

Step 1: 3-chloro-1-methyl-6-[1-(2,2,3,3,3-pentafluoropropyl)-1H-pyrazol-4-yl]-7-(trifluoromethyl)-1H,5H-imidazo[1,2-a]pyrimidin-5-one A solution of 1-methyl-6-[1-(2,2,3,3,3-pentafluoropropyl)-1H-pyrazol-4-yl]-7-(trifluoromethyl)-1H,5H-imidazo[1,2-a]pyrimidin-5-one (Example 37, 24.9 mg, 0.06 mmol) and N-chlorosuccinimide (9.6 mg, 0.07 mmol) in DMF (0.6 mL) was heated at 80° C. for 1 h. After cooling to rt, the reaction mixture was diluted with EtOAc and washed with water. The organic layer was dried over Na$_2$SO$_4$, filtered and concentrated under reduced pressure. The residue was purified by flash chromatography (SiO$_2$, 0-50% EtOAc/cyclohexane) to afford 3-chloro-1-methyl-6-[1-(2,2,3,3,3-pentafluoropropyl)-1H-pyrazol-4-yl]-7-(trifluoromethyl)-1H,5H-imidazo[1,2-a]pyrimidin-5-one (9.3 mg, 0.021 mmol, 34% yield). LC/MS (ESI$^+$) m/z=450.4/452.3 [M+H]$^+$. 1H NMR (500 MHz, DMSO-d$_6$) δ 3.65 (s, 3H), 5.24 (t, J=14.82 Hz, 2H), 7.54 (s, 1H), 7.87 (s, 1H), 7.90 (s, 1H).

Method 8

Example 45: 2-(hydroxymethyl)-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one

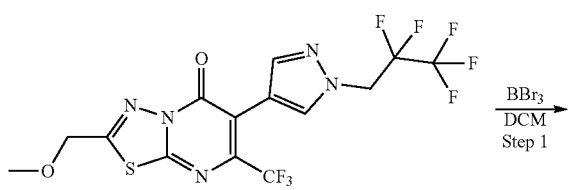

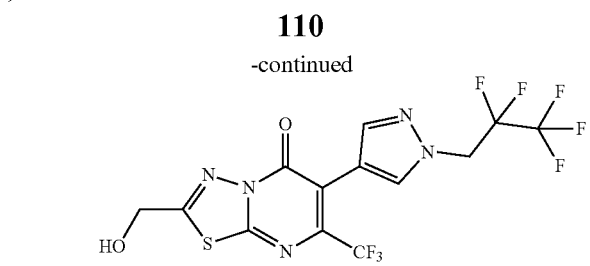

Step 1: 2-(hydroxymethyl)-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one Boron tribromide (1 M solution in DCM, 1.9 mL, 1.9 mmol) was added dropwise to a stirred solution of 2-(methoxymethyl)-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one (Example 42, 220 mg, 0.47 mmol) in anhydrous DCM (43 mL) cooled to 0° C. The reaction mixture was stirred at 0° C. for 4 h then at rt overnight. The solution was cooled to 0° C., treated with satd. aq. NaHCO$_3$ solution and brine and extracted with DCM (2×). The combined organic phases were dried over Na$_2$SO$_4$, filtered and concentrated under reduced pressure. The residue was purified by flash chromatography (SiO$_2$, 50-70% EtOAc/cyclohexane followed by C18, 5-50% acetonitrile/0.1% formic acid in water) to afford 2-(hydroxymethyl)-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one (160 mg, 0.36 mmol, 75% yield) as a white solid. LC/MS (ESI$^+$) m/z=450.4 [M+H]$^+$. 1H NMR (400 MHz, DMSO-d$_6$) δ 4.87 (d, J=5.7 Hz, 2H), 5.30 (t, J=15.0 Hz, 2H), 6.68 (t, J=5.9 Hz, 1H), 7.67 (s, 1H), 8.06 (s, 1H).

Example 46: 2-(hydroxymethyl)-7-(trifluoromethyl)-6-[1-(3,3,3-trifluoropropyl)-1H-pyrazol-4-yl]-5H-[1,3,4]thiadiazolo[3,2-a]pyrimidin-5-one

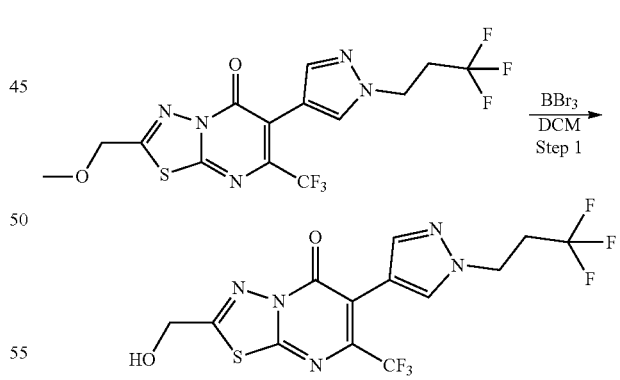

Step 1: 2-(hydroxymethyl)-7-(trifluoromethyl)-6-[1-(3,3,3-trifluoropropyl)-1H-pyrazol-4-yl]-5H-[1,3,4]thiadiazolo[3,2-a]pyrimidin-5-one The title compound was prepared using the procedure described for Example 45, Step 1 with the following modification: the reaction was performed with 2-(methoxymethyl)-7-(trifluoromethyl)-6-[1-(3,3,3-trifluoropropyl)-1H-pyrazol-4-yl]-5H-[1,3,4]thiadiazolo[3,2-a]pyrimidin-5-one (Example 10). Product purification by flash chromatography (C18, 5-40% acetonitrile/0.1% formic acid in water followed by SiO$_2$, 70% EtOAc/cyclohexane). LC/MS (ESI) m/z=414.1 [M+H]$^+$. $^1$H NMR (400 MHz, DMSO-d$_6$) δ 2.80-3.06 (m, 2H), 4.47 (t, J=6.8 Hz, 2H), 4.87 (d, J=5.3 Hz, 2H), 6.67 (t, J=5.6 Hz, 1H), 7.57 (s, 1H), 8.02 (s, 1H).

Method 9

Example 47: 6-[1-(2,2,3,3,3-pentafluoropropyl)-1H-pyrazol-4-yl]-7-(trifluoromethyl)-1H,2H,3H,5H-imidazo[1,2-a]pyrimidine-2,5-dione

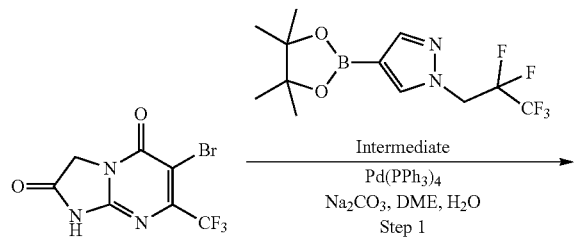

Step 1: 6-[1-(2,2,3,3,3-pentafluoropropyl)-1H-pyrazol-4-yl]-7-(trifluoromethyl)-1H,2H,3H,5H-imidazo[1,2-a]pyrimidine-2,5-dione A screw-capped vial was charged with 6-bromo-7-(trifluoromethyl)-1,3-dihydroimidazo[1,2-a]pyrimidine-2,5-dione (Intermediate 14A, 700 mg, 1.9 mmol), 1,2-dimethoxyethane (24 mL), water (3.7 mL), 1-(2,2,3,3,3-pentafluoropropyl)-4-(4,4,5,5-tetramethyl-1,3,2-dioxaborolan-2-yl)pyrazole (Intermediate 24A, 1.55 g, 4.75 mmol), sodium carbonate (604 mg, 5.7 mmol) and tetrakis(triphenylphosphine)palladium(0) (329 mg, 0.29 mmol). The reaction mixture was purged with nitrogen for 10 min then heated at 100° C. for 6 h. After cooling to rt, the mixture was diluted with water, treated with HCl 1 M aq solution until pH=4 and extracted with EtOAc. The organic layer was dried over Na$_2$SO$_4$, filtered and concentrated under reduced pressure. The residue was purified by flash chromatography (C18, 0-40% MeCN/0.1% formic acid in water) to afford 6-[1-(2,2,3,3,3-pentafluoropropyl)-1H-pyrazol-4-yl]-7-(trifluoromethyl)-1H,2H,3H,5H-imidazo[1,2-a]pyrimidine-2,5-dione (152 mg, 0.36 mmol, 19% yield) as a white solid. LC/MS (ESI$^+$) m/z=418.6 [M+H]$^+$. $^1$H NMR (500 MHz, DMSO-d$_6$) δ 12.51 (br. s., 1H), 7.97 (s, 1H), 7.59 (s, 1H), 5.26 (t, J=14.96 Hz, 2H), 4.48 (s, 2H).

Method 11

Example 48: 2-chloro-1-methyl-6-[1-(2,2,3,3,3-pentafluoropropyl)-1H-pyrazol-4-yl]-7-(trifluoromethyl)-1H,5H-imidazo[1,2-a]pyrimidin-5-one

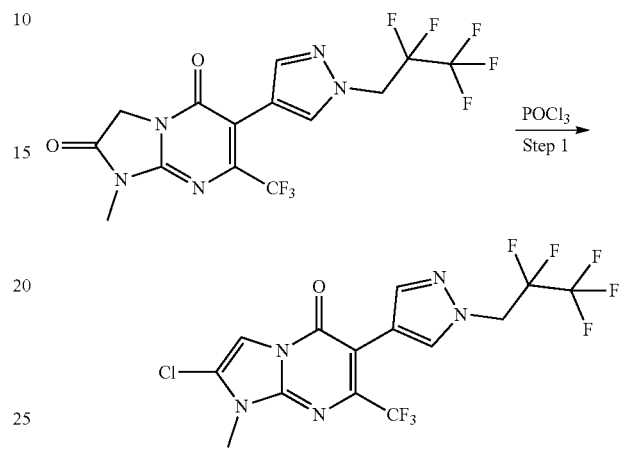

Step 1: 2-chloro-1-methyl-6-[1-(2,2,3,3,3-pentafluoropropyl)-1H-pyrazol-4-yl]-7-(trifluoromethyl)-1H,5H-imidazo[1,2-a]pyrimidin-5-one A mixture of 1-methyl-6-[1-(2,2,3,3,3-pentafluoropropyl)-1H-pyrazol-4-yl]-7-(trifluoromethyl)-1H,2H,3H,5H-imidazo[1,2-a]pyrimidine-2,5-dione (Example 3, 95.0 mg, 0.22 mmol) in phosphorus(V) oxychloride (2.18 mL, 23.35 mmol) was heated at 150° C. for 3 days. After cooling to rt, the mixture was poured into iced water and extracted with EtOAc (2×). The combined organic phases were washed with brine, dried over Na$_2$SO$_4$, filtered and concentrated under reduced pressure. The crude material was purified by flash chromatography (SiO$_2$, 0-50% EtOAc/cyclohexane) to give 2-chloro-1-methyl-6-[1-(2,2,3,3,3-pentafluoropropyl)-1H-pyrazol-4-yl]-7-(trifluoromethyl)-1H,5H-imidazo[1,2-a]pyrimidin-5-one (19 mg, 0.04 mmol, 19% yield). LC/MS (ESI$^+$) m/z=450.3/452.3 [M+H]$^+$. $^1$H NMR (400 MHz, DMSO-d$_6$) δ 3.67 (s, 3H), 5.25 (t, J=14.91 Hz, 2H), 7.57 (s, 1H), 7.90 (s, 1H), 8.13 (s, 1H).

Example 49: 2-chloro-6-[1-(2,2,3,3,3-pentafluoropropyl)-1H-pyrazol-4-yl]-7-(trifluoromethyl)-1H,5H-imidazo[1,2-a]pyrimidin-5-one

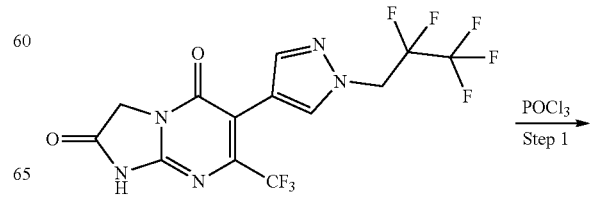

-continued

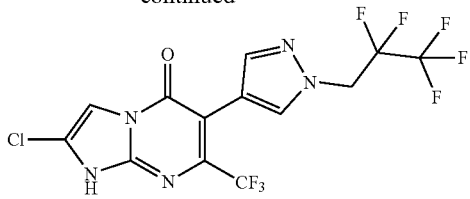

Step 1: 2-chloro-6-[1-(2,2,3,3,3-pentafluoropropyl)-1H-pyrazol-4-yl]-7-(trifluoromethyl)-1H,5H-imidazo[1,2-a]pyrimidin-5-one The title compound was prepared using the procedure described for Example 48, Step 1 with the following modification: the reaction was performed with 6-[1-(2,2,3,3,3-pentafluoropropyl)-1H-pyrazol-4-yl]-7-(trifluoromethyl)-1H,2H,3H,5H-imidazo[1,2-a]pyrimidine-2,5-dione (Example 47) and heating the mixture at 90° C. for 5 h. Product purification by flash chromatography (C18, 0-60% acetonitrile/0.1% formic acid in water). LC/MS (ESI$^+$) m/z=436.0/438.0 [M+H]$^+$. $^1$H NMR (400 MHz, DMSO-d$_6$) δ 5.23 (t, J=14.9 Hz, 2H), 7.55 (s, 1H), 7.75-7.90 (m, 2H).

Method 11

Example 50: 2-cyclopropyl-1-methyl-6-[1-(2,2,3,3,3-pentafluoropropyl)-1H-pyrazol-4-yl]-7-(trifluoromethyl)-1H,5H-imidazo[1,2-a]pyrimidin-5-one

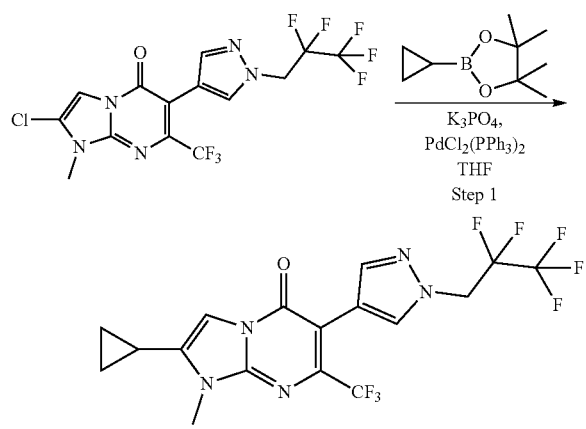

Step 1: 2-cyclopropyl-1-methyl-6-[1-(2,2,3,3,3-pentafluoropropyl)-1H-pyrazol-4-yl]-7-(trifluoromethyl)-1H,5H-imidazo[1,2-a]pyrimidin-5-one A screw-capped vial was charged with 2-chloro-1-methyl-6-[1-(2,2,3,3,3-pentafluoropropyl)-1H-pyrazol-4-yl]-7-(trifluoromethyl)-1H,5H-imidazo[1,2-a]pyrimidin-5-one (Example 48, 20 mg, 0.04 mmol), THF (2.5 mL), tripotassium phosphate (18.9 mg, 0.09 mmol), 2-cyclopropyl-4,4,5,5-tetramethyl-1,3,2-dioxaborolane (18.7 mg, 0.11 mmol) and bis(triphenylphosphine)palladium(II) dichloride (3.1 mg, 0.004 mmol). The mixture was purged with nitrogen and heated at 75° C. overnight. Further 2-cyclopropyl-4,4,5,5-tetramethyl-1,3,2-dioxaborolane (18.7 mg, 0.11 mmol), tripotassium phosphate (18.9 mg, 0.09 mmol) and bis(triphenylphosphine)palladium(II) dichloride (3.1 mg, 0.004 mmol) were added and heating was continued for 7 h. The reaction mixture was cooled to rt, diluted with EtOAc and washed with water and brine. The organic phase was dried over Na$_2$SO$_4$, filtered and concentrated in vacuo. The residue was purified by flash chromatography (C18, 5-55% MeCN/0.1% formic acid in water) followed by HPLC (40/60% v/v n-hexane/ethanol) to afford 2-cyclopropyl-1-methyl-6-[1-(2,2,3,3,3-pentafluoropropyl)-1H-pyrazol-4-yl]-7-(trifluoromethyl)-1H,5H-imidazo[1,2-a]pyrimidin-5-one (1 mg, 0.002 mmol, 5% yield) as a white solid. LC/MS (ESI$^+$) m/z=456.1 [M+H]$^+$. $^1$H NMR (500 MHz, CDCl$_3$) δ 0.78-0.83 (m, 2H), 1.11-1.12 (m, 1H), 1.11-1.18 (m, 1H), 1.76-1.86 (m, 1H), 3.85 (s, 3H), 4.79 (t, J=13.9 Hz, 2H), 7.28 (d, J=1.1 Hz, 1H), 7.68-7.75 (m, 2H).

Method 12

Example 51: 2-chloro-1-methyl-7-(trifluoromethyl)-6-[1-(3,3,3-trifluoropropyl)-1H-pyrazol-4-yl]-1H,5H-imidazo[1,2-a]pyrimidin-5-one

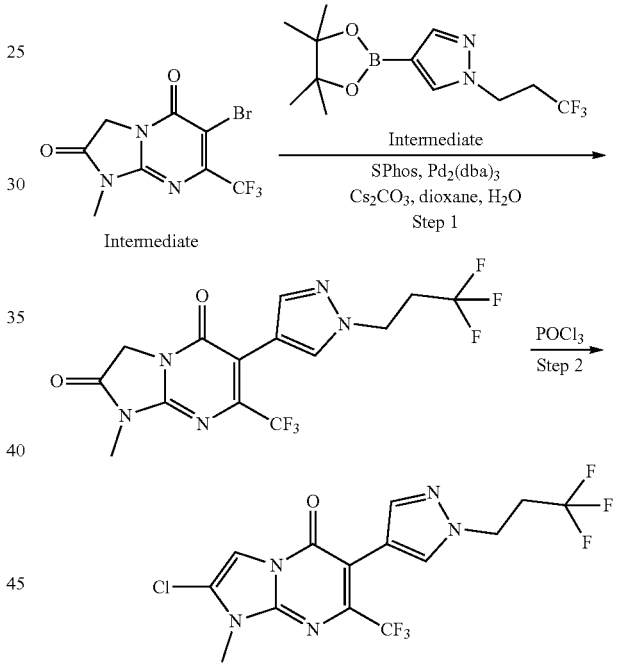

Step 1: 1-methyl-7-(trifluoromethyl)-6-[1-(3,3,3-trifluoropropyl)pyrazol-4-yl]-3H-imidazo[1,2-a]pyrimidine-2,5-dione The title compound was prepared using the procedure described for Example 3, Step 1 with the following modification: the reaction was performed with 6-bromo-1-methyl-7-(trifluoromethyl)-3H-imidazo[1,2-a]pyrimidine-2,5-dione (Intermediate 15A) and 4-(4,4,5,5-tetramethyl-1,3,2-dioxaborolan-2-yl)-1-(3,3,3-trifluoropropyl)pyrazole (Intermediate 25A). LC/MS (ESI$^+$) m/z=396.1 [M+H]$^+$.

Step 2: 2-chloro-1-methyl-7-(trifluoromethyl)-6-[1-(3,3,3-trifluoropropyl)-1H-pyrazol-4-yl]-1H,5H-imidazo[1,2-a]pyrimidin-5-one The title compound was prepared using the procedure described for Example 48, Step 1 with the following modification: the reaction was performed with 1-methyl-7-(trifluoromethyl)-6-[1-(3,3,3-trifluoropropyl)pyrazol-4-yl]-3H-imidazo[1,2-a]pyrimidine-2,5-dione and stirring the mixture at 160° C. for 24 h. Product purification by flash chromatography (SiO₂, 0-50% EtOAc/Cyclohexane followed by C18, 0-60% acetonitrile/water). LC/MS (ESI⁺) m/z=414.1/416.0 [M+H]⁺. ¹H NMR (500 MHz, DMSO-d₆) δ 2.88 (qt, J=11.2, 6.8 Hz, 2H), 3.66 (s, 3H), 4.43 (t, J=6.7 Hz, 2H), 7.47 (s, 1H), 7.86 (s, 1H), 8.11 (s, 1H).

Method 13

Example 52: 1,2-dimethyl-6-[1-(2,2,3,3,3-pentafluoropropyl)-1H-pyrazol-4-yl]-7-(trifluoromethyl)-1H,5H-imidazo[1,2-a]pyrimidin-5-one

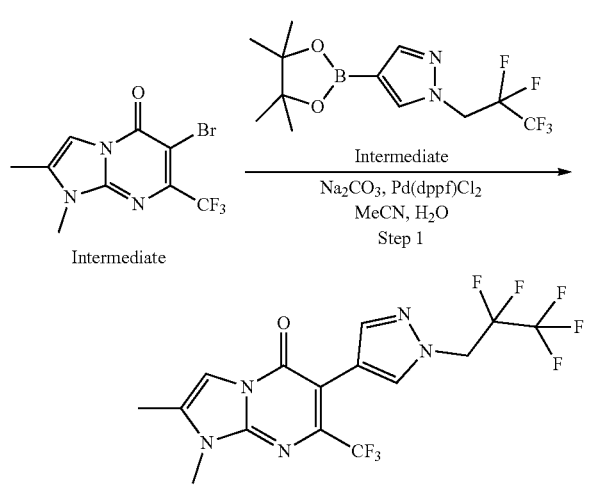

Step 1: 1,2-dimethyl-6-[1-(2,2,3,3,3-pentafluoropropyl)-1H-pyrazol-4-yl]-7-(trifluoromethyl)-1H,5H-imidazo[1,2-a]pyrimidin-5-one A screw-capped vial was charged with 6-bromo-1,2-dimethyl-7-(trifluoromethyl)imidazo[1,2-a]pyrimidin-5-one (Intermediate 19A, 355 mg, 1.14 mmol), acetonitrile (14.2 mL), water (3.6 mL), sodium carbonate (303.4 mg, 2.86 mmol), 1-(2,2,3,3,3-pentafluoropropyl)-4-(4,4,5,5-tetramethyl-1,3,2-dioxaborolan-2-yl)pyrazole (Intermediate 24A, 560 mg, 1.72 mmol) and [1,1'-bis(diphenylphosphino)ferrocene]dichloropalladium(II) (84 mg, 0.11 mmol). The mixture was purged with nitrogen for 10 min then heated at 110° C. for 1 h. After cooling to rt, the mixture was diluted with EtOAc and washed with water and brine. The organic phase was dried over Na₂SO₄, filtered and concentrated under reduced pressure. The resulting crude material was purified by flash chromatography (SiO₂, 0-100% EtOAc/cyclohexane followed by C18, 0-50% MeCN/water) to afford 1,2-dimethyl-6-[1-(2,2,3,3,3-pentafluoropropyl)-1H-pyrazol-4-yl]-7-(trifluoromethyl)-1H,5H-imidazo[1,2-a]pyrimidin-5-one (155 mg, 0.36 mmol, 32% yield) as a white solid. LC/MS (ESI⁺) m/z=430.3 [M+H]⁺. ¹H NMR (500 MHz, DMSO-d₆) δ 2.38 (d, J=1.1 Hz, 3H), 3.65 (s, 3H), 5.24 (t, J=15.0 Hz, 2H), 7.54-7.57 (m, 1H), 7.58-7.62 (m, 1H), 7.88 (s, 1H).

Example 53: 1,2-dimethyl-7-(trifluoromethyl)-6-[1-(3,3,3-trifluoropropyl)-1H-pyrazol-4-yl]-1H,5H-imidazo[1,2-a]pyrimidin-5-one

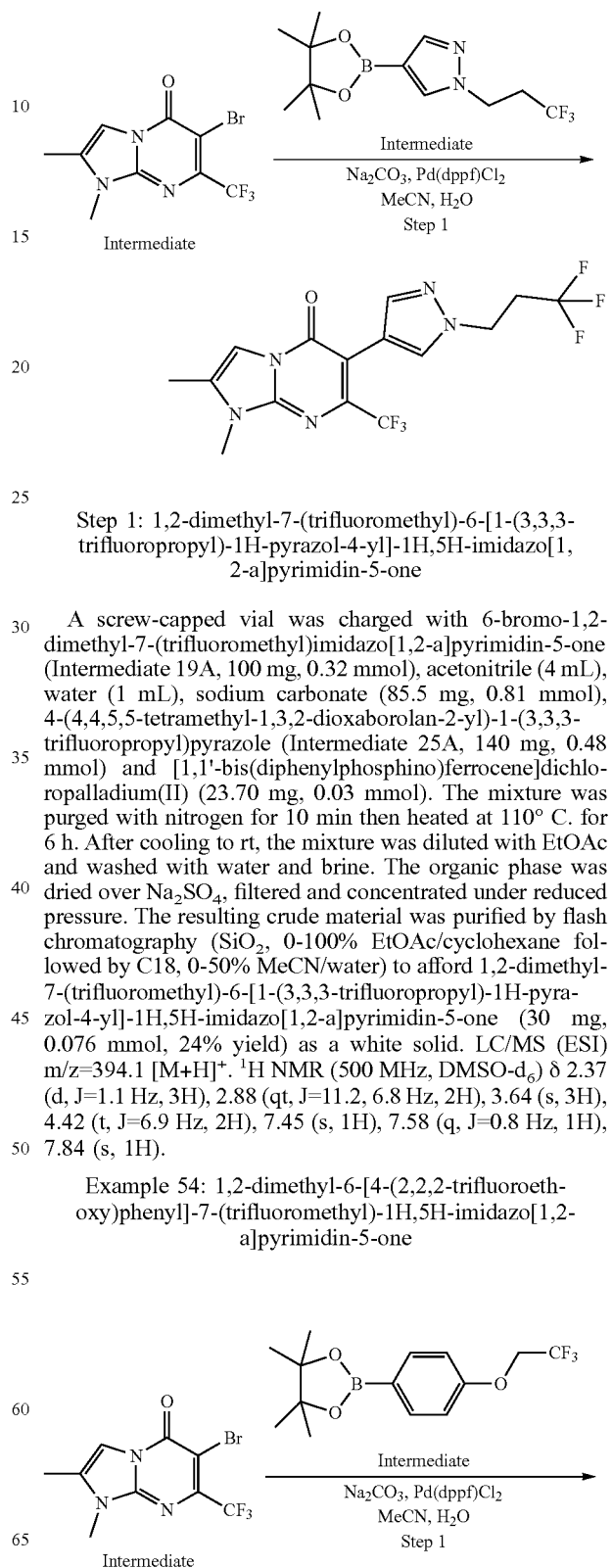

Step 1: 1,2-dimethyl-7-(trifluoromethyl)-6-[1-(3,3,3-trifluoropropyl)-1H-pyrazol-4-yl]-1H,5H-imidazo[1,2-a]pyrimidin-5-one A screw-capped vial was charged with 6-bromo-1,2-dimethyl-7-(trifluoromethyl)imidazo[1,2-a]pyrimidin-5-one (Intermediate 19A, 100 mg, 0.32 mmol), acetonitrile (4 mL), water (1 mL), sodium carbonate (85.5 mg, 0.81 mmol), 4-(4,4,5,5-tetramethyl-1,3,2-dioxaborolan-2-yl)-1-(3,3,3-trifluoropropyl)pyrazole (Intermediate 25A, 140 mg, 0.48 mmol) and [1,1'-bis(diphenylphosphino)ferrocene]dichloropalladium(II) (23.70 mg, 0.03 mmol). The mixture was purged with nitrogen for 10 min then heated at 110° C. for 6 h. After cooling to rt, the mixture was diluted with EtOAc and washed with water and brine. The organic phase was dried over Na₂SO₄, filtered and concentrated under reduced pressure. The resulting crude material was purified by flash chromatography (SiO₂, 0-100% EtOAc/cyclohexane followed by C18, 0-50% MeCN/water) to afford 1,2-dimethyl-7-(trifluoromethyl)-6-[1-(3,3,3-trifluoropropyl)-1H-pyrazol-4-yl]-1H,5H-imidazo[1,2-a]pyrimidin-5-one (30 mg, 0.076 mmol, 24% yield) as a white solid. LC/MS (ESI) m/z=394.1 [M+H]⁺. ¹H NMR (500 MHz, DMSO-d₆) δ 2.37 (d, J=1.1 Hz, 3H), 2.88 (qt, J=11.2, 6.8 Hz, 2H), 3.64 (s, 3H), 4.42 (t, J=6.9 Hz, 2H), 7.45 (s, 1H), 7.58 (q, J=0.8 Hz, 1H), 7.84 (s, 1H).

Example 54: 1,2-dimethyl-6-[4-(2,2,2-trifluoroethoxy)phenyl]-7-(trifluoromethyl)-1H,5H-imidazo[1,2-a]pyrimidin-5-one -continued

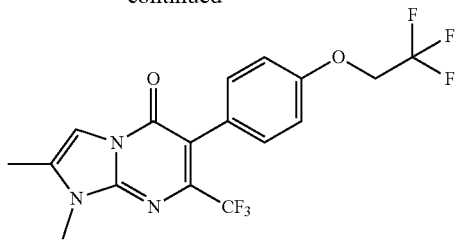

Step 1: 1,2-dimethyl-6-[4-(2,2,2-trifluoroethoxy) phenyl]-7-(trifluoromethyl)-1H,5H-imidazo[1,2-a] pyrimidin-5-one A screw-capped vial was charged with 6-bromo-1,2-dimethyl-7-(trifluoromethyl)imidazo[1,2-a]pyrimidin-5-one (Intermediate 19A, 60 mg, 0.19 mmol), acetonitrile (2.4 mL), water (0.6 mL), sodium carbonate (51.3 mg, 0.48 mmol), 4,4,5,5-tetramethyl-2-[4-(2,2,2-trifluoroethoxy)phenyl]-1,3,2-dioxaborolane (Intermediate 31A, 58.5 mg, 0.19 mmol) and [1,1'-bis(diphenylphosphino)ferrocene]dichloropalladium(II) (14.2 mg, 0.02 mmol). The mixture was purged with nitrogen for 10 min then heated at 110° C. for 1 h. After cooling to rt, the mixture was filtered with EtOAc through a pad of celite. The filtrate was concentrated under reduced pressure and purified by flash chromatography (SiO$_2$, 0-10% EtOAc/cyclohexane followed by C18, 0-50% MeCN/0.1% formic acid in water) to afford 1,2-dimethyl-6-[4-(2,2,2-trifluoroethoxy)phenyl]-7-(trifluoromethyl)-1H,5H-imidazo[1,2-a]pyrimidin-5-one (27 mg, 0.067 mmol, 34% yield) as a white solid. LC/MS (ESI$^+$) m/z=406.1 [M+H]$^+$. $^1$H NMR (500 MHz, DMSO-d$_6$) δ 2.38 (s, 3H), 3.66 (s, 3H), 4.80 (q, J=8.9 Hz, 2H), 7.03-7.11 (m, 2H), 7.18 (d, J=8.5 Hz, 2H), 7.59 (d, J=1.1 Hz, 1H).

Examples 55-70 listed in Table 9 below were prepared following the procedure described in Method 13, Step 1, above as follows.

TABLE 9

| Ex. # | Chemical Structure | Name | Method Changes | Reagent |
|---|---|---|---|---|
| 55 | 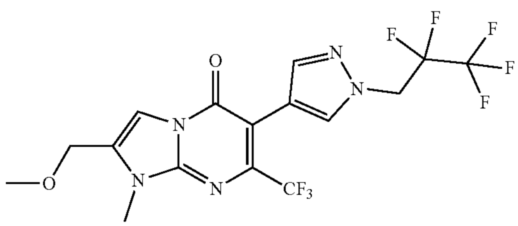 [SMILES: COCc1cn2c(=O)c(-c3cnn(CC(F)(F)C(F)(F)F)c3)c(C(F)(F)F)nc2n1C] | 2-(methoxymethyl)-1-methyl-6-[1-(2,2,3,3,3-pentafluoropropyl)-1H-pyrazol-4-yl]-7-(trifluoromethyl)-1H,5H-imidazo[1,2-a]pyrimidin-5-one | MW irradiation at 110° C. for 30 min. Purification by flash chromatography (SiO$_2$, 0-25% MeCN/DCM followed by C18, 0-55% MeCN/0.1% HCOOH in H$_2$O) | 6-bromo-2-(methoxymethyl)-1-methyl-7-(trifluoromethyl)imidazo[1,2-a]pyrimidin-5-one (Intermediate 20A) and 1-(2,2,3,3,3-pentafluoropropyl)-4-(4,4,5,5-tetramethyl-1,3,2-dioxaborolan-2-yl)pyrazole (Intermediate 24A) |
| 56 | 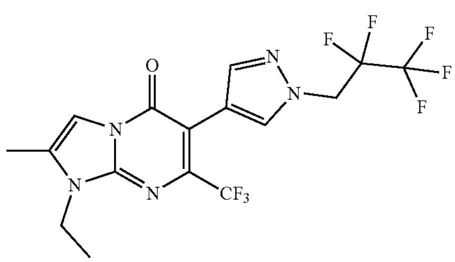 [SMILES: CCn1c(C)cn2c(=O)c(-c3cnn(CC(F)(F)C(F)(F)F)c3)c(C(F)(F)F)nc12] | 1-ethyl-2-methyl-6-[1-(2,2,3,3,3-pentafluoropropyl)-1H-pyrazol-4-yl]-7-(trifluoromethyl)-1H,5H-imidazo[1,2-a]pyrimidin-5-one | Heated at 110° C. for 1 h. Purification by flash chromatography (SiO$_2$, 0-25% MeCN/DCM) | 6-bromo-1-ethyl-2-methyl-7-(trifluoromethyl)imidazo[1,2-a]pyrimidin-5-one (Intermediate 19B) and 1-(2,2,3,3,3-pentafluoropropyl)-4-(4,4,5,5-tetramethyl-1,3,2-dioxaborolan-2-yl)pyrazole |
| 57 | 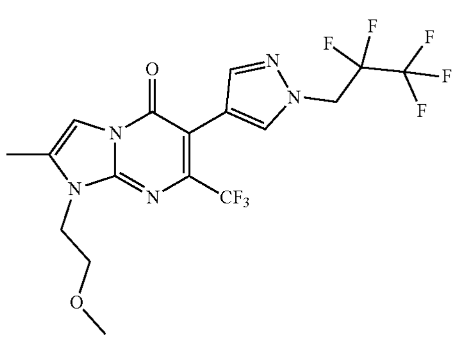 [SMILES: COCCn1c(C)cn2c(=O)c(-c3cnn(CC(F)(F)C(F)(F)F)c3)c(C(F)(F)F)nc12] | 1-(2-methoxyethyl)-2-methyl-6-[1-(2,2,3,3,3-pentafluoropropyl)-1H-pyrazol-4-yl]-7-(trifluoromethyl)-1H,5H-imidazo[1,2-a]pyrimidin-5-one | Heated at 110° C. for 30 min. Purification by flash chromatography (SiO$_2$, 0-25% MeCN/DCM followed by C18, 0-55% MeCN/0.1% HCOOH in H$_2$O) | 6-bromo-1-(2-methoxyethyl)-2-methyl-7-(trifluoromethyl)imidazo[1,2-a]pyrimidin-5-one (Intermediate 19C) and 1-(2,2,3,3,3-pentafluoropropyl)-4-(4,4,5,5-tetramethyl-1,3,2-dioxaborolan-2-yl)pyrazole (Intermediate 24A) |

TABLE 9-continued

| Ex. # | Chemical Structure | Name | Method Changes | Reagent |
|---|---|---|---|---|
| 58 | 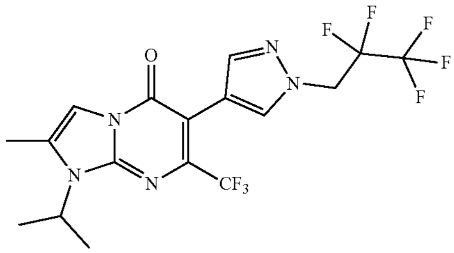 [SMILES: Cc1cn2c(=O)c(-c3cnn(CC(F)(F)C(F)(F)F)c3)c(C(F)(F)F)nc2n1C(C)C] | 2-methyl-6-[1-(2,2,3,3,3-pentafluoropropyl)-1H-pyrazol-4-yl]-1-(propan-2-yl)-7-(trifluoromethyl)-1H,5H-imidazo[1,2-a]pyrimidin-5-one | Heated at 110° C. for 1 h. Purification by flash chromatography (SiO$_2$, 0-25% MeCN/DCM) | 6-bromo-2-methyl-1-propan-2-yl-7-(trifluoromethyl)imidazo[1,2-a]pyrimidin-5-one (Intermediate 19D) and 1-(2,2,3,3,3-pentafluoropropyl)-4-(4,4,5,5-tetramethyl-1,3,2-dioxaborolan-2-yl)pyrazole (Intermediate 24A) |
| 59 | 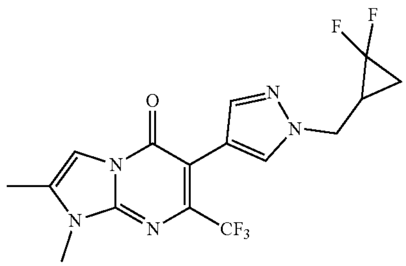 [SMILES: Cc1cn2c(=O)c(-c3cnn(CC4CC4(F)F)c3)c(C(F)(F)F)nc2n1C] | 6-{1-[(2,2-difluorocyclopropyl)methyl]-1H-pyrazol-4-yl}-1,2-dimethyl-7-(trifluoromethyl)-1H,5H-imidazo[1,2-a]pyrimidin-5-one | Heated at 90° C. for 4 h. Purification by flash chromatography (SiO$_2$, 0-5% MeOH/EtOAc) | 6-bromo-1,2-dimethyl-7-(trifluoromethyl)imidazo[1,2-a]pyrimidin-5-one (Intermediate 19A) and 1-[(2,2-difluorocyclopropyl)methyl]-4-(4,4,5,5-tetramethyl-1,3,2-dioxaborolan-2-yl)pyrazole (Intermediate 27A) |
| 60 | 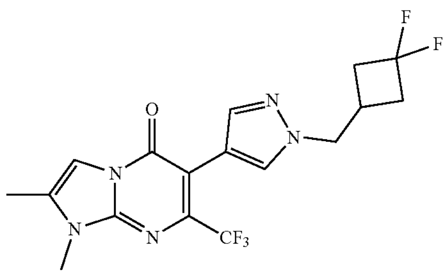 [SMILES: Cc1cn2c(=O)c(-c3cnn(CC4CC(F)(F)C4)c3)c(C(F)(F)F)nc2n1C] | 6-{1-[(3,3-difluorocyclobutyl)methyl]-1H-pyrazol-4-yl}-1,2-dimethyl-7-(trifluoromethyl)-1H,5H-imidazo[1,2-a]pyrimidin-5-one | Heated at 90° C. for 18 h. Purification by flash chromatography (SiO$_2$, 50-100% EtOAc/Cy) | 6-bromo-1,2-dimethyl-7-(trifluoromethyl)imidazo[1,2-a]pyrimidin-5-one (Intermediate 19A) and 1-[(3,3-difluorocyclobutyl)methyl]-4-(4,4,5,5-tetramethyl-1,3,2-dioxaborolan-2-yl)pyrazole (Intermediate 28A) |
| 61 | 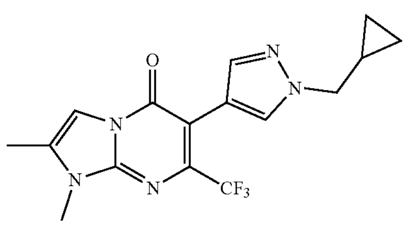 [SMILES: Cc1cn2c(=O)c(-c3cnn(CC4CC4)c3)c(C(F)(F)F)nc2n1C] | 6-[1-(cyclopropylmethyl)-1H-pyrazol-4-yl]-1,2-dimethyl-7-(trifluoromethyl)-1H,5H-imidazo[1,2-a]pyrimidin-5-one | Heated at 90° C. for 4 h. Purification by flash chromatography (SiO$_2$, 0-100% EtOAc/Cy) | 6-bromo-1,2-dimethyl-7-(trifluoromethyl)imidazo[1,2-a]pyrimidin-5-one (Intermediate 19A) and 1-(cyclopropylmethyl)-4-(4,4,5,5-tetramethyl-1,3,2-dioxaborolan-2-yl)pyrazole (Intermediate 29A) |
| 62 | 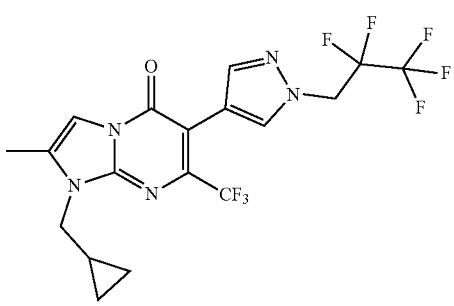 [SMILES: Cc1cn2c(=O)c(-c3cnn(CC(F)(F)C(F)(F)F)c3)c(C(F)(F)F)nc2n1CC1CC1] | 1-(cyclopropylmethyl)-2-methyl-6-[1-(2,2,3,3,3-pentafluoropropyl)-1H-pyrazol-4-yl]-7-(trifluoromethyl)-1H,5H-imidazo[1,2-a]pyrimidin-5-one | Heated at 110° C. for 1 h. Purification by flash chromatography (SiO$_2$, 0-100% EtOAc/Cy followed by C18, 0-70% MeCN/H$_2$O) | 6-bromo-1-(cyclopropylmethyl)-2-methyl-7-(trifluoromethyl)imidazo[1,2-a]pyrimidin-5-one (Intermediate 21B) and 1-(2,2,3,3,3-pentafluoropropyl)-4-(4,4,5,5-tetramethyl-1,3,2-dioxaborolan-2-yl)pyrazole (Intermediate 24A) |

TABLE 9-continued

| Ex. # | Chemical Structure | Name | Method Changes | Reagent |
|---|---|---|---|---|
| 63 | 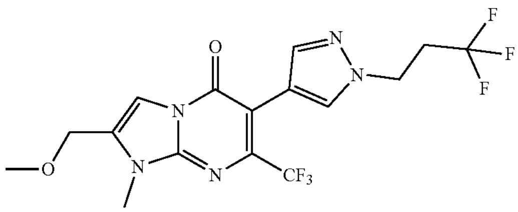 [SMILES: COCc1cn2c(=O)c(-c3cnn(CCC(F)(F)F)c3)c(C(F)(F)F)nc2n1C] | 2-(methoxymethyl)-1-methyl-7-(trifluoromethyl)-6-[1-(3,3,3-trifluoropropyl)-1H-pyrazol-4-yl]-1H,5H-imidazo[1,2-a]pyrimidin-5-one | MW irradiation at 110° C. for 30 min. Purification by flash chromatography (SiO$_2$, 0-30% MeCN/DCM followed by C18, 0-50% MeCN/0.1% HCOOH in H$_2$O) | 6-bromo-2-(methoxymethyl)-1-methyl-7-(trifluoromethyl) imidazo[1,2-a]pyrimidin-5-one (Intermediate 20A) and 4-(4,4,5,5-tetramethyl-1,3,2-dioxaborolan-2-yl)-1-(3,3,3-trifluoropropyl) pyrazole (Intermediate 25A) |
| 64 | 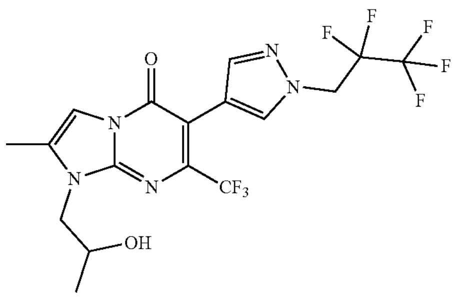 [SMILES: Cc1cn2c(=O)c(-c3cnn(CC(F)(F)C(F)(F)F)c3)c(C(F)(F)F)nc2n1CC(C)O] | 1-(2-hydroxypropyl)-2-methyl-6-[1-(2,2,3,3,3-pentafluoropropyl)-1H-pyrazol-4-yl]-7-(trifluoromethyl)-1H,5H-imidazo[1,2-a]pyrimidin-5-one | Heated at 110° C. for 3 h. Purification by flash chromatography (SiO$_2$, 0-100% EtOAc/Cy followed by C18, 0-50% MeCN/H$_2$O) | 6-bromo-1-(2-hydroxypropyl)-2-methyl-7-(trifluoromethyl) imidazo[1,2-a]pyrimidin-5-one (Intermediate 22A) and 1-(2,2,3,3,3-pentafluoro-propyl)-4-(4,4,5,5-tetramethyl-1,3,2-dioxaborolan-2-yl)pyrazole (Intermediate 24A) |
| 65 | 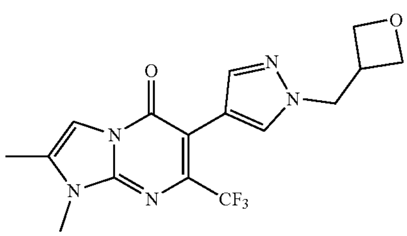 [SMILES: Cc1cn2c(=O)c(-c3cnn(CC4COC4)c3)c(C(F)(F)F)nc2n1C] | 1,2-dimethyl-6-{1-[(oxetan-3-yl)methyl]-1H-pyrazol-4-yl}-7-(trifluoromethyl)-1H,5H-imidazo[1,2-a]pyrimidin-5-one | 1,4-Dioxane as solvent. Heated at 90° C. for 24 h. Purification by flash chromatography (C18, 5-60% MeCN/0.1% HCOOH in H$_2$O followed by SiO$_2$, 0-5% MeOH/DCM) | 6-bromo-1,2-dimethyl-7-(trifluoromethyl) imidazo[1,2-a]pyrimidin-5-one (Intermediate 19A) and 1-(oxetan-3-ylmethyl)-4-(4,4,5,5-tetramethyl-1,3,2-dioxaborolan-2-yl)pyrazole (Intermediate 32A) |
| 66 | 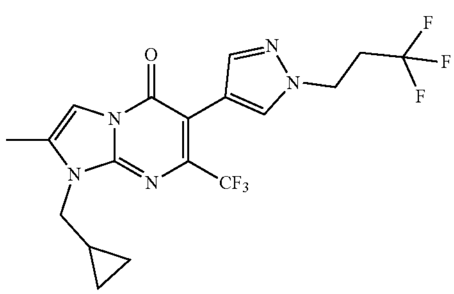 [SMILES: Cc1cn2c(=O)c(-c3cnn(CCC(F)(F)F)c3)c(C(F)(F)F)nc2n1CC1CC1] | 1-(cyclo-propylmethyl)-2-methyl-7-(trifluoromethyl)-6-[1-(3,3,3-trifluoropropyl)-1H-pyrazol-4-yl]-1H,5H-imidazo[1,2-a]pyrimidin-5-one | 1,4-Dioxane as solvent. Heated at 110° C. for 5 h. Purification by flash chromatography (SiO$_2$, 0-100% EtOAc/Cy followed by C18, 0-80% MeCN/0.1% HCOOH in H$_2$O) | 6-bromo-1-(cyclo-propylmethyl)-2-methyl-7-(trifluoromethyl) imidazo[1,2-a]pyrimidin-5-one (Intermediate 21B) and 4-(4,4,5,5-tetramethyl-1,3,2-dioxaborolan-2-yl)-1-(3,3,3-trifluoropropyl) pyrazole (Intermediate 25A) |
| 67 | 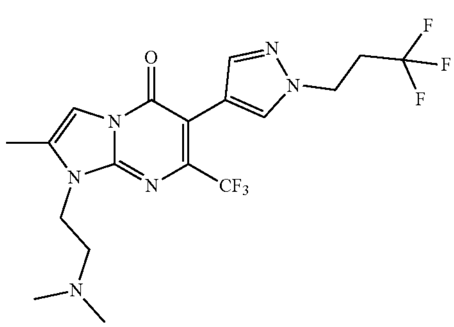 [SMILES: Cc1cn2c(=O)c(-c3cnn(CCC(F)(F)F)c3)c(C(F)(F)F)nc2n1CCN(C)C] | 1-[2-(dimethyl-amino)ethyl]-2-methyl-7-(trifluoromethyl)-6-[1-(3,3,3-trifluoropropyl)-1H-pyrazol-4-yl]-1H,5H-imidazo[1,2-a]pyrimidin-5-one | 1,4-Dioxane as solvent. Heated at 110° C. for 2 h. Purification by flash chromatography (SiO$_2$, 0-10% MeOH/DCM followed by C18, 0-30% MeCN/0.1% HCOOH in H$_2$O) | 6-bromo-1-[2-(dimethylamino) ethyl]-2-methyl-7-(trifluoromethyl) imidazo[1,2-a]pyrimidin-5-one (Intermediate 21C) and 4-(4,4,5,5-tetramethyl-1,3,2-dioxaborolan-2-yl)-1-(3,3,3-trifluoropropyl) pyrazole (Intermediate 25A) |

TABLE 9-continued

| Ex. # | Chemical Structure | Name | Method Changes | Reagent |
|---|---|---|---|---|
| 68 | 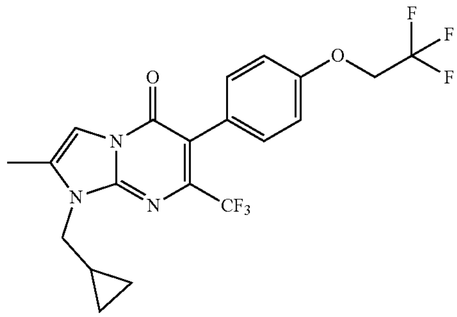 [SMILES: Cc1cn2c(=O)c(-c3ccc(OCC(F)(F)F)cc3)c(C(F)(F)F)nc2n1CC1CC1] | 1-(cyclo-propylmethyl)-2-methyl-6-[4-(2,2,2-trifluoro-ethoxy)phenyl]-7-(trifluoromethyl)-1H,5H-imidazo[1,2-a]pyrimidin-5-one | 1,4-Dioxane as solvent. Heated at 110° C. for 2 h. Purification by flash chromatography (SiO$_2$, 0-70% EtOAc/Cy followed by C18, 0-30% MeCN/0.1% HCOOH in H$_2$O) | 6-bromo-1-(cyclopropyl-methyl)-2-methyl-7-(trifluoromethyl)imidazo[1,2-a]pyrimidin-5-one (Intermediate 21B) and 4,4,5,5-tetramethyl-2-[4-(2,2,2-trifluoroethoxy)phenyl]-1,3,2-dioxaborolane (Intermediate 31A) |
| 69 | 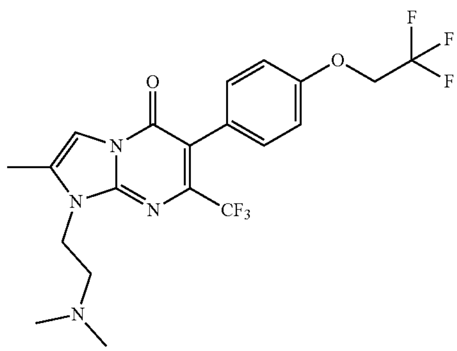 [SMILES: Cc1cn2c(=O)c(-c3ccc(OCC(F)(F)F)cc3)c(C(F)(F)F)nc2n1CCN(C)C] | 1-[2-(dimethyl-amino)ethyl]-2-methyl-6-[4-(2,2,2-trifluoro-ethoxy)phenyl]-7-(trifluoromethyl)-1H,5H-imidazo[1,2-a]pyrimidin-5-one | 1,4-Dioxane as solvent. Heated at 110° C. for 2 h. Purification by flash chromatography (SiO$_2$, 0-5% MeOH/DCM followed by C18, 0-30% MeCN/0.1% HCOOH in H$_2$O) | 6-bromo-1-[2-(dimethylamino)ethyl]-2-methyl-7-(trifluoromethyl)imidazo[1,2-a]pyrimidin-5-one (Intermediate 21C) and 4,4,5,5-tetramethyl-2-[4-(2,2,2-trifluoroethoxy)phenyl]-1,3,2-dioxaborolane (Intermediate 31A) |
| 70 | 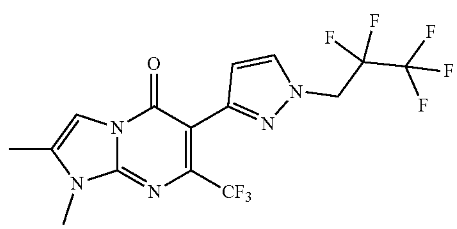 [SMILES: Cc1cn2c(=O)c(-c3ccn(CC(F)(F)C(F)(F)F)n3)c(C(F)(F)F)nc2n1C] | 1,2-dimethyl-6-[1-(2,2,3,3,3-pentafluoropropyl)-1H-pyrazol-3-yl]-7-(trifluoromethyl)-1H,5H-imidazo[1,2-a]pyrimidin-5-one | 1,4-Dioxane as solvent. Heated at 90° C. for 18 h. Purification by flash chromatography (C18, 5-100% MeCN/0.1% HCOOH in H$_2$O followed by SiO$_2$, 70-100% EtOAc/Cy) | 6-bromo-1,2-dimethyl-7-(trifluoromethyl)imidazo[1,2-a]pyrimidin-5-one (Intermediate 19A) and 1-(2,2,3,3,3-pentafluoropropyl)-3-(4,4,5,5-tetramethyl-1,3,2-dioxaborolan-2-yl)pyrazole (Intermediate 30A) |

Method 15

Example 71: 2-methoxy-1-methyl-6-[1-(2,2,3,3,3-pentafluoropropyl)-1H-pyrazol-4-yl]-7-(trifluoromethyl)-1H,5H-imidazo[1,2-a]pyrimidin-5-one

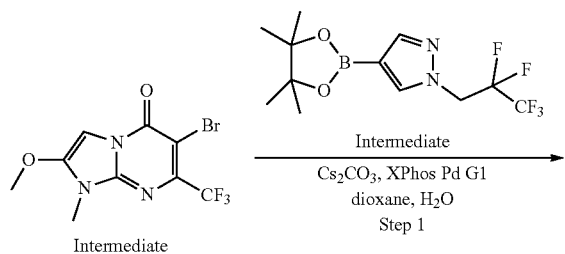

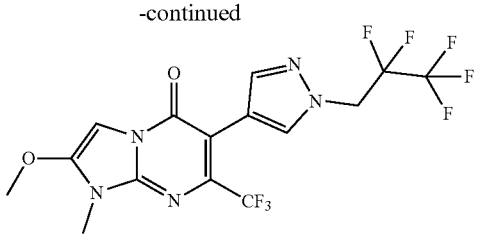

Step 1: 2-methoxy-1-methyl-6-[1-(2,2,3,3,3-pentafluoropropyl)-1H-pyrazol-4-yl]-7-(trifluoromethyl)-1H,5H-imidazo[1,2-a]pyrimidin-5-one A screw-capped vial was charged with 6-bromo-2-methoxy-1-methyl-7-(trifluoromethyl)imidazo[1,2-a]pyrimidin-5-one (Intermediate 23A, 70 mg, 0.21 mmol), 1,4-dioxane (1.75 mL), water (0.35 mL), cesium carbonate (210 mg, 0.64 mmol), 1-(2,2,3,3,3-pentafluoropropyl)-4-(4,4,5,5-tetramethyl-1,3,2-dioxaborolan-2-yl)pyrazole (Intermediate 24A, 140 mg, 0.43 mmol) and (2-dicyclohexylphosphino-2',4',6'-triisopropyl-1,1'-biphenyl)[2-(2-aminoethyl)phenyl)]palladium(II) chloride (16 mg, 0.02 mmol). The mixture was purged with nitrogen for 10 min then heated at 100° C. for 20 min. After cooling to rt, the mixture was filtered with EtOAc through a pad of celite. The filtrate was concentrated under reduced pressure and purified by flash chromatography (SiO$_2$, 0-60% MeCN/DCM) to afford 2-methoxy-1-methyl-6-[1-(2,2,3,3,3-pentafluoropropyl)-1H-pyrazol-4-yl]-7-(trifluoromethyl)-1H,5H-imidazo[1,2-a]pyrimidin-5-one (40 mg, 0.09 mmol, 42% yield) as a white solid. LC/MS (ESI$^+$) m/z=446.1 [M+H]$^+$. $^1$H NMR (500 MHz, DMSO-d$_6$) δ 3.53 (s, 3H), 4.03 (s, 3H), 5.24 (t, J=15.0 Hz, 2H), 7.30 (s, 1H), 7.57 (s, 1H), 7.89 (s, 1H).

Example 72: 2-methoxy-1-methyl-7-(trifluoromethyl)-6-[1-(3,3,3-trifluoropropyl)-1H-pyrazol-4-yl]-1H,5H-imidazo[1,2-a]pyrimidin-5-one

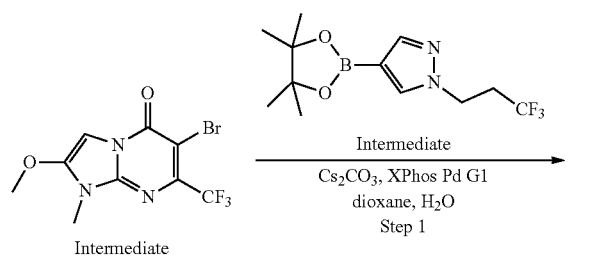

Intermediate

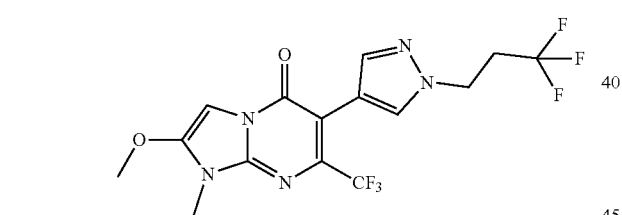

Step 1: 2-methoxy-1-methyl-7-(trifluoromethyl)-6-[1-(3,3,3-trifluoropropyl)-1H-pyrazol-4-yl]-1H,5H-imidazo[1,2-a]pyrimidin-5-one The title compound was prepared using the procedure described for Example 71, Step 1 with the following modification: the reaction was performed with 6-bromo-2-methoxy-1-methyl-7-(trifluoromethyl)imidazo[1,2-a]pyrimidin-5-one (Intermediate 23A) and 4-(4,4,5,5-tetramethyl-1,3,2-dioxaborolan-2-yl)-1-(3,3,3-trifluoropropyl)pyrazole (Intermediate 25A). Purification by flash chromatography (SiO$_2$, 0-60% MeCN/DCM followed by SiO$_2$, 20% EtOAc in Cyclohexane). LC/MS (ESI$^+$) m/z=410.2 [M+H]$^+$. $^1$H NMR (400 MHz, DMSO-d$_6$) δ 2.88 (qt, J=11.2, 6.7 Hz, 2H), 3.52 (s, 3H), 4.03 (s, 3H), 4.43 (t, J=6.8 Hz, 2H), 7.28 (s, 1H), 7.46 (s, 1H), 7.84 (s, 1H).

Method 15

Example 73: 2-methyl-6-[1-(2,2,3,3,3-pentafluoropropyl)-1H-pyrazol-4-yl]-7-(trifluoromethyl)-1H,5H-imidazo[1,2-a]pyrimidin-5-one

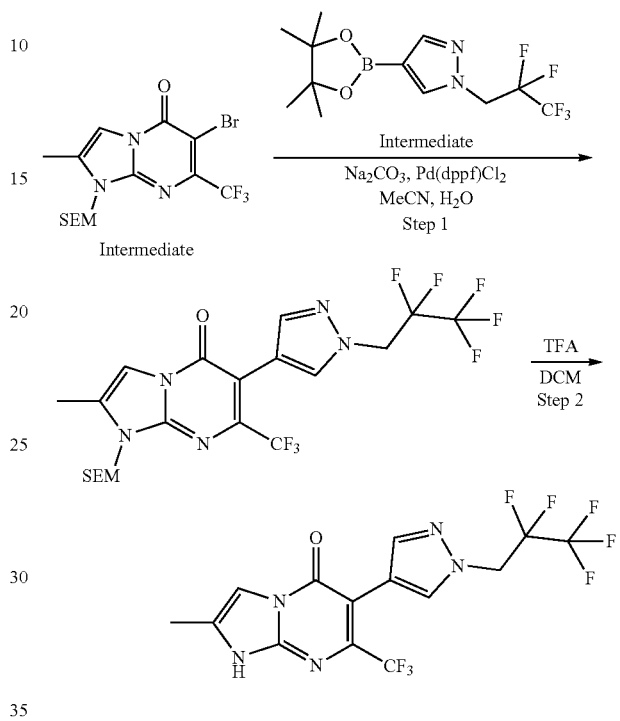

Step 1: 2-methyl-6-[1-(2,2,3,3,3-pentafluoropropyl)pyrazol-4-yl]-7-(trifluoromethyl)-1-(2-trimethylsilylethoxymethyl)imidazo[1,2-a]pyrimidin-5-one A screw-capped vial was charged with 6-bromo-2-methyl-7-(trifluoromethyl)-1-(2-trimethylsilylethoxymethyl)imidazo[1,2-a]pyrimidin-5-one (Intermediate 21A, 3 g, 7.04 mmol), 1,4-dioxane (100 mL), sodium carbonate (1M aq solution, 21.11 mL, 21.11 mmol), 1-(2,2,3,3,3-pentafluoropropyl)-4-(4,4,5,5-tetramethyl-1,3,2-dioxaborolan-2-yl)pyrazole (Intermediate 24A, 4.59 g, 14.07 mmol) and [1,1'-bis(diphenylphosphino)ferrocene]dichloropalladium(II) (516 mg, 0.7 mmol). The mixture was purged with nitrogen for 10 min and heated at 110° C. for 3 h. After cooling to rt, the mixture was filtered with EtOAc through a pad of celite. The filtrate was washed with water and brine, dried over Na$_2$SO$_4$, filtered and evaporated under vacuum. The crude material was purified by flash chromatography (SiO$_2$, 0-60% EtOAc/cyclohexane followed by C18, 0-80% MeCN/water) to obtain 2-methyl-6-[1-(2,2,3,3,3-pentafluoropropyl)pyrazol-4-yl]-7-(trifluoromethyl)-1-(2-trimethylsilylethoxymethyl)imidazo[1,2-a]pyrimidin-5-one (2.17 g, 3.978 mmol, 57% yield). LC/MS (ESI$^+$) m/z=546.0 [M+H].

Step 2: 2-methyl-6-[1-(2,2,3,3,3-pentafluoropropyl)-1H-pyrazol-4-yl]-7-(trifluoromethyl)-1H,5H-imidazo[1,2-a]pyrimidin-5-one TFA (42 mL, 3.94 mmol) was added to a stirred solution of 2-methyl-6-[1-(2,2,3,3,3-pentafluoropropyl)pyrazol-4-yl]-7-(trifluoromethyl)-1-(2-trimethylsilylethoxymethyl)

imidazo[1,2-a]pyrimidin-5-one (2.17 g, 3.94 mmol) in DCM (42 mL) cooled to 0° C. The mixture was stirred at rt for 6 h, then concentrated under reduced pressure. The residue was dissolved in EtOAc, washed with satd. aq. NaHCO₃ solution and brine, dried over Na₂SO₄, filtered and evaporated under vacuum. Et₂O was added and the precipitate was collected by filtration and dried under vacuum to afford 2-methyl-6-[1-(2,2,3,3,3-pentafluoropropyl)-1H-pyrazol-4-yl]-7-(trifluoromethyl)-1H,5H-imidazo[1,2-a]pyrimidin-5-one (1.34 g, 3.23 mmol, 82% yield) as a white solid. LC/MS (ESI⁺) m/z=416.0 [M+H]⁺. ¹H NMR (500 MHz, DMSO-d6) δ2.31 (d, J=1.4 Hz, 3H), 5.23 (t, J=15.0 Hz, 2H), 7.48 (d, J=1.1 Hz, 1H), 7.55 (s, 1H), 7.86 (s, 1H), 13.23 (br s, 1H).

Example 74: 2-methyl-7-(trifluoromethyl)-6-[1-(3,3,3-trifluoropropyl)-1H-pyrazol-4-yl]-1H,5H-imidazo[1,2-a]pyrimidin-5-one

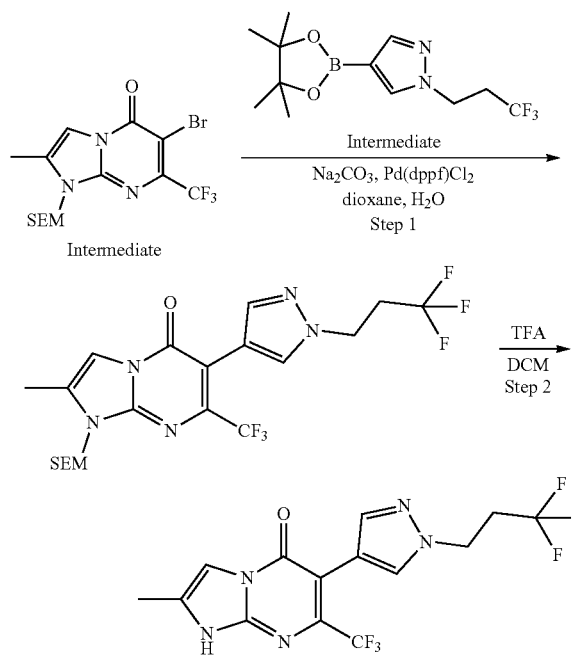

Step 1: 2-methyl-7-(trifluoromethyl)-6-[1-(3,3,3-trifluoropropyl)pyrazol-4-yl]-1-(2-trimethylsilylethoxymethyl)imidazo[1,2-a]pyrimidin-5-one A screw-capped vial was charged with 6-bromo-2-methyl-7-(trifluoromethyl)-1-(2-trimethylsilylethoxymethyl)imidazo[1,2-a]pyrimidin-5-one (Intermediate 21A, 1.11 g, 2.6 mmol), 1,4-dioxane (20 mL), water (7.8 mL), sodium carbonate (827.9 mg, 7.81 mmol), 4-(4,4,5,5-tetramethyl-1,3,2-dioxaborolan-2-yl)-1-(3,3,3-trifluoropropyl) pyrazole (Intermediate 25A, 1.51 g, 5.21 mmol) and [1,1'-bis(diphenylphosphino)ferrocene]dichloropalladium(II) (191 mg, 0.26 mmol). The mixture was purged with nitrogen for 10 min then heated at 100° C. for 3 h. After cooling to rt, the mixture was diluted with EtOAc and washed with water and brine. The organic phase was dried over Na₂SO₄, filtered and evaporated under vacuum. The crude material was purified by flash chromatography (SiO₂, 0-60% EtOAc/cyclohexane) to afford 2-methyl-7-(trifluoromethyl)-6-[1-(3,3,3-trifluoropropyl)pyrazol-4-yl]-1-(2-trimethylsilylethoxymethyl)imidazo[1,2-a]pyrimidin-5-one (502 mg, 0.99 mmol, 38% yield). LC/MS (ESI⁺) m/z=510.2 [M+H]⁺.

Step 2: 2-methyl-7-(trifluoromethyl)-6-[1-(3,3,3-trifluoropropyl)-1H-pyrazol-4-yl]-1H,5H-imidazo[1,2-a]pyrimidin-5-one TFA (2.0 mL, 0 mmol) was added to a stirred solution of 2-methyl-7-(trifluoromethyl)-6-[1-(3,3,3-trifluoropropyl) pyrazol-4-yl]-1-(2-trimethylsilylethoxymethyl)imidazo[1,2-a]pyrimidin-5-one (502 mg, 0.99 mmol) in DCM (10 mL) cooled to 0° C. The mixture was stirred at rt overnight then diluted with EtOAc washed with water and brine. The organic phase was dried over Na₂SO₄, filtered and concentrated under reduced pressure. The crude material was purified by flash chromatography (SiO₂, 0-100% EtOAc/ cyclohexane followed by C18, 0-50% MeCN/0.1% formic acid in water) to afford 2-methyl-7-(trifluoromethyl)-6-[1-(3,3,3-trifluoropropyl)-1H-pyrazol-4-yl]-1H,5H-imidazo[1, 2-a]pyrimidin-5-one (225 mg, 0.59 mmol, 61% yield) as a white solid. LC/MS (ESI) m/z=380.1 [M+H]⁺. ¹H NMR (500 MHz, DMSO-d₆) δ 2.31 (s, 3H), 2.80-2.94 (m, 2H), 4.42 (t, J=6.8 Hz, 2H), 7.38-7.49 (m, 2H), 7.81 (s, 1H), 13.21 (br s, 1H).

Example 75: 2-methyl-6-[4-(2,2,2-trifluoroethoxy) phenyl]-7-(trifluoromethyl)-1H,5H-imidazo[1,2-a] pyrimidin-5-one

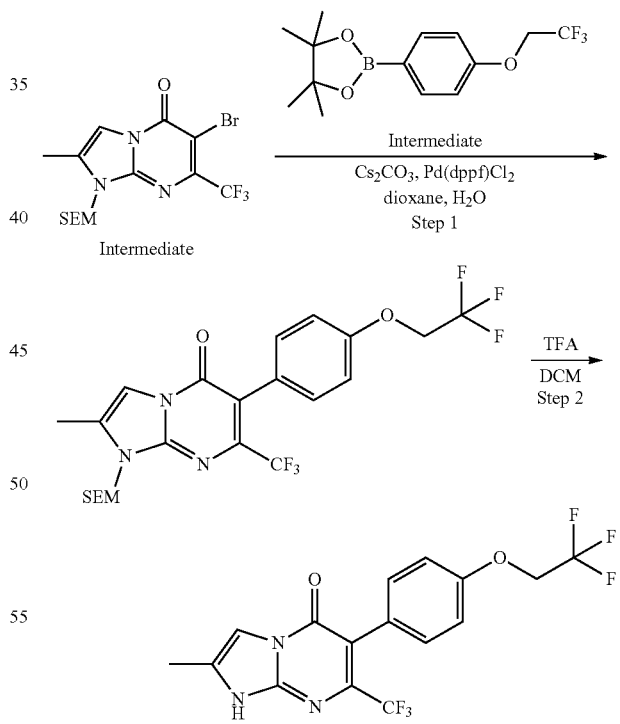

Step 1: 2-methyl-6-[4-(2,2,2-trifluoroethoxy)phenyl]-7-(trifluoromethyl)-1-(2-trimethylsilylethoxymethyl)imidazo[1,2-a]pyrimidin-5-one A screw-capped vial was charged with 6-bromo-2-methyl-7-(trifluoromethyl)-1-(2-trimethylsilylethoxymethyl)imidazo[1,2-a]pyrimidin-5-one (Intermediate 21A, 200 mg, 0.46 mmol), 1,4-dioxane (3.6 mL), water (2.0 mL), cesium carbonate (449.4 mg, 1.38 mmol), 4,4,5,5-tetramethyl-2-[4-(2,2,2-trifluoroethoxy)phenyl]-1,3,2-dioxaborolane (Intermediate 31A, 278 mg, 0.920 mmol) and [1,1'-bis(diphenylphosphino)ferrocene]dichloropalladium(II) (33.80 mg, 0.05 mmol). The mixture was purged with nitrogen for 10 min then heated at 110° C. for 30 min. After cooling to rt, the mixture was filtered with EtOAc through a pad of celite. The filtrate was concentrated under reduced pressure and purified by flash chromatography (SiO$_2$, 0-50% EtOAc/cyclohexane) to afford 2-methyl-6-[4-(2,2,2-trifluoroethoxy)phenyl]-7-(trifluoromethyl)-1-(2-trimethylsilylethoxymethyl)imidazo[1,2-a]pyrimidin-5-one (160 mg, 0.31 mmol, 67% yield). LC/MS (ESI$^+$) m/z=522.0 [M+H]$^+$.

Step 2: 2-methyl-6-[4-(2,2,2-trifluoroethoxy)phenyl]-7-(trifluoromethyl)-1H,5H-imidazo[1,2-a]pyrimidin-5-one TFA (4.2 mL, 54.54 mmol) was added to a stirred solution of 2-methyl-6-[4-(2,2,2-trifluoroethoxy)phenyl]-7-(trifluoromethyl)-1-(2-trimethylsilylethoxymethyl)imidazo[1,2-a]pyrimidin-5-one (165 mg, 0.32 mmol) in DCM (3.1 mL) cooled to 0° C. The mixture was stirred at rt 3 h, then evaporated under reduced pressure and purified by flash chromatography (C18, 0-50% MeCN/0.1% formic acid in water) to afford 2-methyl-6-[4-(2,2,2-trifluoroethoxy)phenyl]-7-(trifluoromethyl)-1H,5H-imidazo[1,2-a]pyrimidin-5-one (52 mg, 0.13 mmol, 42% yield) as a white solid. LC/MS (ESI$^+$) m/z=392.0 [M+H]$^+$. $^1$H NMR (500 MHz, DMSO-d$_6$) δ 2.31 (d, J=1.1 Hz, 3H), 4.80 (q, J=9.1 Hz, 2H), 7.06 (br d, J=8.7 Hz, 2H), 7.18 (d, J=8.7 Hz, 2H), 7.46 (s, 1H), 13.13 (br s, 1H).

Example 76: 6-{1-[(2,2-difluorocyclopropyl)methyl]-1H-pyrazol-4-yl}-2-methyl-7-(trifluoromethyl)-1H,5H-imidazo[1,2-a]pyrimidin-5-one

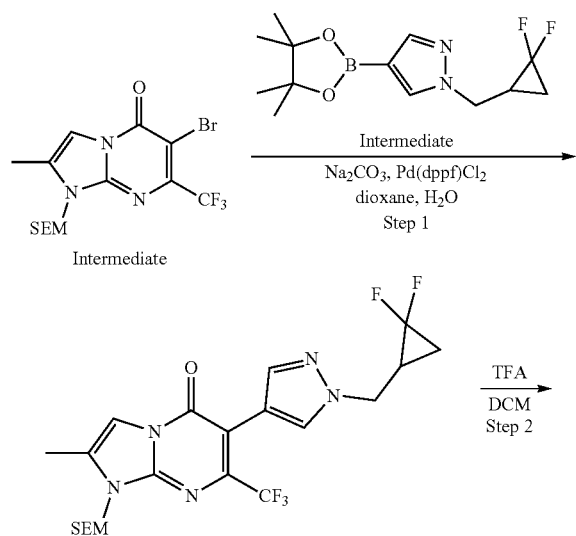

Step 1: 6-[1-[(2,2-difluorocyclopropyl)methyl]pyrazol-4-yl]-2-methyl-7-(trifluoromethyl)-1-(2-trimethylsilylethoxymethyl)imidazo[1,2-a]pyrimidin-5-one

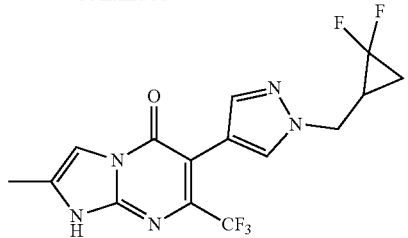

A screw-capped vial was charged with 6-bromo-2-methyl-7-(trifluoromethyl)-1-(2-trimethylsilylethoxymethyl)imidazo[1,2-a]pyrimidin-5-one (Intermediate 21A, 130 mg, 0.30 mmol), 1,4-dioxane (5 mL), sodium carbonate (1M aq solution, 0.91 mL, 0.91 mmol), 1-[(2,2-difluorocyclopropyl)methyl]-4-(4,4,5,5-tetramethyl-1,3,2-dioxaborolan-2-yl)pyrazole (Intermediate 27A, 173 mg, 0.61 mmol) and [1,1'-bis(diphenylphosphino)ferrocene]dichloropalladium(II) (22 mg, 0.03 mmol). The mixture was purged with nitrogen for 10 min then heated at 100° C. for 3 h. After cooling to rt, the mixture was filtered with EtOAc through a pad of celite. The filtrate was washed with water and brine, dried over Na$_2$SO$_4$, filtered and concentrated under reduced pressure. The crude material was purified by flash chromatography (SiO$_2$, 0-60% EtOAc/cyclohexane) to afford 6-[1-[(2,2-difluorocyclopropyl)methyl]pyrazol-4-yl]-2-methyl-7-(trifluoromethyl)-1-(2-trimethylsilylethoxymethyl)imidazo[1,2-a]pyrimidin-5-one (92 mg, 0.18 mmol, 60% yield). LC/MS (ESI$^+$) m/z=504.1 [M+H]$^+$.

Step 2: 6-{1-[(2,2-difluorocyclopropyl)methyl]-1H-pyrazol-4-yl}-2-methyl-7-(trifluoromethyl)-1H,5H-imidazo[1,2-a]pyrimidin-5-one TFA (0.5 mL, 31.49 mmol) was added to a stirred solution of 6-[1-[(2,2-difluorocyclopropyl)methyl]pyrazol-4-yl]-2-methyl-7-(trifluoromethyl)-1-(2-trimethylsilylethoxymethyl)imidazo[1,2-a]pyrimidin-5-one (92 mg, 0.18 mmol) in DCM (2 mL) cooled to 0° C. The mixture was stirred at rt overnight, then 0.1 mL of water were added and stirring was continued for 3 h. The mixture was diluted with DCM, washed with water and brine, dried over Na$_2$SO$_4$, filtered and concentrated under reduced pressure. The residue was purified by flash chromatography (SiO$_2$, 0-100% EtOAc/cyclohexane followed by C18, 0-50% MeCN/0.1% formic acid in water) to afford 6-{1-[(2,2-difluorocyclopropyl)methyl]-1H-pyrazol-4-yl}-2-methyl-7-(trifluoromethyl)-1H,5H-imidazo[1,2-a]pyrimidin-5-one (25 mg, 0.07 mmol, 37% yield) as a white solid. LC/MS (ESI) m/z=374.1 [M+H]$^+$. $^1$H NMR (400 MHz, DMSO-d$_6$) δ 1.48 (dtd, J=13.5, 7.7, 7.7, 3.9 Hz, 1H), 1.68 (tdd, J=12.0, 12.0, 7.7, 4.9 Hz, 1H), 2.17-2.29 (m, 1H), 2.31 (s, 3H), 4.28 (d, J=7.7 Hz, 2H), 7.45 (s, 2H), 7.78 (s, 1H), 13.20 (br s, 1H).

Method 16

Example 77: 1-($^2$H$_3$)methyl-2-methyl-6-[1-(2,2,3,3,3-pentafluoropropyl)-1H-pyrazol-4-yl]-7-(trifluoromethyl)-1H,5H-imidazo[1,2-a]pyrimidin-5-one

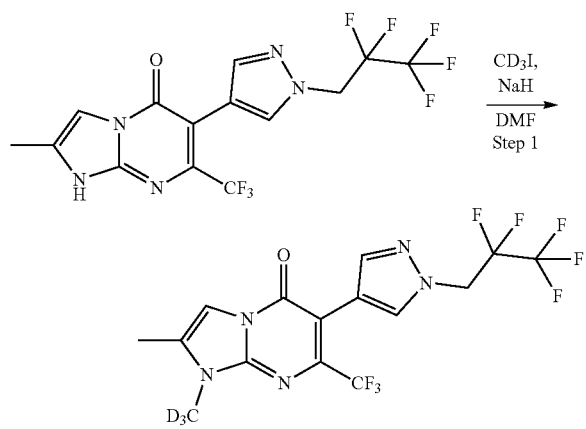

Step 1: 1-($^2$H$_3$)methyl-2-methyl-6-[1-(2,2,3,3,3-pentafluoropropyl)-1H-pyrazol-4-yl]-7-(trifluoromethyl)-1H,5H-imidazo[1,2-a]pyrimidin-5-one Sodium hydride (60% in mineral oil, 8.7 mg, 0.22 mmol) was added to a stirred solution of 2-methyl-6-[1-(2,2,3,3,3-pentafluoropropyl)-1H-pyrazol-4-yl]-7-(trifluoromethyl)-1H,5H-imidazo[1,2-a]pyrimidin-5-one (Example 73.75 mg, 0.18 mmol) in anhydrous DMF (1.9 mL) cooled to 0° C. The mixture was stirred at rt for 15 min, then trideuterio(iodo)methane (12 μL, 0.20 mmol) was added and the reaction mixture was stirred at room temperature for 1 h. Satd. aq. NH$_4$Cl solution was added and the mixture was extracted with EtOAc. The organic phase was washed with brine (2×), dried over Na$_2$SO$_4$, filtered and concentrated under reduced pressure. The crude material was purified by flash chromatography (C18, 5-80% MeCN/0.1% formic acid in water) to give 1-($^2$H$_3$)methyl-2-methyl-6-[1-(2,2,3,3,3-pentafluoropropyl)-1H-pyrazol-4-yl]-7-(trifluoromethyl)-1H,5H-imidazo[1,2-a]pyrimidin-5-one (43 mg, 0.099 mmol, 55% yield) as a white solid. LC/MS (ESI$^+$) m/z=433.1 [M+H]$^+$. $^1$H NMR (500 MHz, DMSO-d$_6$) δ 2.38 (d, J=1.1 Hz, 3H), 5.23 (t, J=14.8 Hz, 2H), 7.56 (s, 1H), 7.60 (q, J=0.9 Hz, 1H), 7.82-7.95 (m, 1H).

Example 78: 1-($^2$H$_3$)methyl-2-methyl-7-(trifluoromethyl)-6-[1-(3,3,3-trifluoropropyl)-1H-pyrazol-4-yl]-1H,5H-imidazo[1,2-a]pyrimidin-5-one

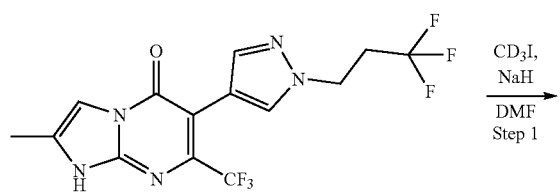

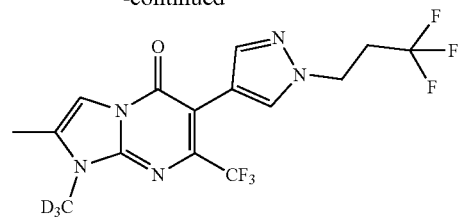

Step 1: 1-($^2$H$_3$)methyl-2-methyl-7-(trifluoromethyl)-6-[1-(3,3,3-trifluoropropyl)-1H-pyrazol-4-yl]-1H,5H-imidazo[1,2-a]pyrimidin-5-one The title compound was prepared using the procedure described for Example 77, Step 1 with the following modification: the reaction was performed with 2-methyl-7-(trifluoromethyl)-6-[1-(3,3,3-trifluoropropyl)-1H-pyrazol-4-yl]-1H,5H-imidazo[1,2-a]pyrimidin-5-one (Example 74) and stirring the reaction mixture at rt for 4 h. Purification by flash chromatography (SiO$_2$, 0-100% EtOAc/cyclohexane). LC/MS (ESI$^+$) m/z=397.1 [M+H]$^+$. $^1$H NMR (500 MHz, DMSO-d$_6$) δ 2.37 (s, 3H), 2.80-2.99 (m, 2H), 4.43 (t, J=6.7 Hz, 2H), 7.45 (s, 1H), 7.58 (d, J=1.4 Hz, 1H), 7.84 (s, 1H).

Example 79: 1-(2-hydroxyethyl)-2-methyl-6-[1-(2,2,3,3,3-pentafluoropropyl)-1H-pyrazol-4-yl]-7-(trifluoromethyl)-1H,5H-imidazo[1,2-a]pyrimidin-5-one

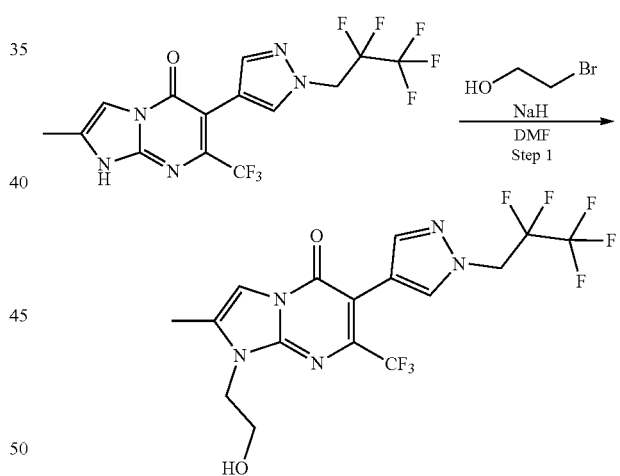

Step 1: 1-(2-hydroxyethyl)-2-methyl-6-[1-(2,2,3,3,3-pentafluoropropyl)-1H-pyrazol-4-yl]-7-(trifluoromethyl)-1H,5H-imidazo[1,2-a]pyrimidin-5-one Sodium hydride (60% in mineral oil, 12 mg, 0.29 mmol) was added to a stirred solution of 2-methyl-6-[1-(2,2,3,3,3-pentafluoropropyl)-1H-pyrazol-4-yl]-7-(trifluoromethyl)-1H,5H-imidazo[1,2-a]pyrimidin-5-one (Example 73, 100 mg, 0.24 mmol) in anhydrous DMF (4 mL) cooled to 0° C. After stirring for 15 min at rt, 2-bromoethanol (0.1 mL, 1.44 mmol) was added and the mixture was heated at 70° C. for 16 h. Satd. aq. NH$_4$Cl solution was added and the mixture was extracted with EtOAc. The organic phase was washed with brine (2×), dried over Na$_2$SO$_4$, filtered and concentrated under reduced pressure. The crude material was purified by flash chromatography (SiO₂, 10-70% EtOAc/cyclohexane followed by C18, 5-80% MeCN/0.1% formic acid in water) to afford 1-(2-hydroxyethyl)-2-methyl-6-[1-(2,2,3,3,3-pentafluoropropyl)-1H-pyrazol-4-yl]-7-(trifluoromethyl)-1H,5H-imidazo[1,2-a]pyrimidin-5-one (36 mg, 0.08 mmol, 33% yield) as a white solid. LC/MS (ESI) m/z=460.0 [M+H]⁺. ¹H NMR (600 MHz, DMSO-d₆) δ 2.41 (d, J=1.0 Hz, 3H), 3.75 (q, J=5.6 Hz, 2H), 4.17 (t, J=5.4 Hz, 2H), 4.96 (t, J=5.8 Hz, 1H), 5.24 (t, J=15.0 Hz, 2H), 7.56 (s, 1H), 7.59 (m, J=1.3 Hz, 1H), 7.88 (s, 1H).

Examples 80-85 listed in Table 10 below were prepared following the procedure described in Method 16, Step 1, above as follows.

TABLE 10

| Ex. # | Chemical Structure | Name | Method Changes | Reagent |
|---|---|---|---|---|
| 80 | 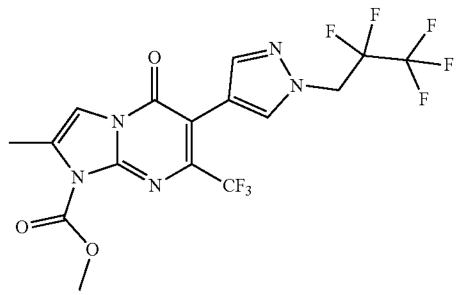 [SMILES: COC(=O)n1c(C)cn2c(=O)c(-c3cnn(CC(F)(F)C(F)(F)F)c3)c(C(F)(F)F)nc12] | methyl 2-methyl-5-oxo-6-[1-(2,2,3,3,3-pentafluoropropyl)-1H-pyrazol-4-yl]-7-(trifluoromethyl)-1H,5H-imidazo[1,2-a]pyrimidine-1-carboxylate | Stirred at rt for 5 h. Purification by flash chromatography (SiO₂, 0-100% EtOAc/Cy followed by C18, 0-50% MeCN/H₂O) | 2-methyl-6-[1-(2,2,3,3,3-pentafluoropropyl)-1H-pyrazol-4-yl]-7-(trifluoromethyl)-1H,5H-imidazo[1,2-a]pyrimidin-5-one (Example 73) and carbonochloridic acid methyl ester |
| 81 | 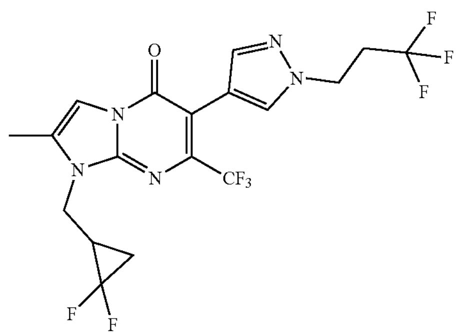 [SMILES: Cc1cn2c(=O)c(-c3cnn(CCC(F)(F)F)c3)c(C(F)(F)F)nc2n1CC1CC1(F)F] | 1-[(2,2-difluorocyclopropyl)methyl]-2-methyl-7-(trifluoromethyl)-6-[1-(3,3,3-trifluoropropyl)-1H-pyrazol-4-yl]-1H,5H-imidazo[1,2-a]pyrimidin-5-one | Heated at 70° C. for 24 h. Purification by flash chromatography (SiO₂, 0-100% EtOAc/Cy followed by C18, 0-50% MeCN/H₂O) | 2-methyl-7-(trifluoromethyl)-6-[1-(3,3,3-trifluoropropyl)-1H-pyrazol-4-yl]-1H,5H-imidazo[1,2-a]pyrimidin-5-one (Example 74) and 1-bromomethyl-2,2-difluorocyclopropane |
| 82 | 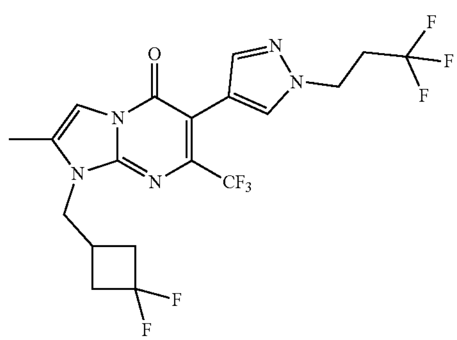 [SMILES: Cc1cn2c(=O)c(-c3cnn(CCC(F)(F)F)c3)c(C(F)(F)F)nc2n1CC1CC(F)(F)C1] | 1-[(3,3-difluorocyclobutyl)methyl]-2-methyl-7-(trifluoromethyl)-6-[1-(3,3,3-trifluoropropyl)-1H-pyrazol-4-yl]-1H,5H-imidazo[1,2-a]pyrimidin-5-one | Heated at 70° C. for 16 h. Purification by flash chromatography (SiO₂, 10-100% EtOAc/Cy followed by SiO₂, 50-100% EtOAc/Cy) | 2-methyl-7-(trifluoromethyl)-6-[1-(3,3,3-trifluoropropyl)-1H-pyrazol-4-yl]-1H,5H-imidazo[1,2-a]pyrimidin-5-one (Example 74) and 3-(bromomethyl)-1,1-difluorocyclobutan |
| 83 | 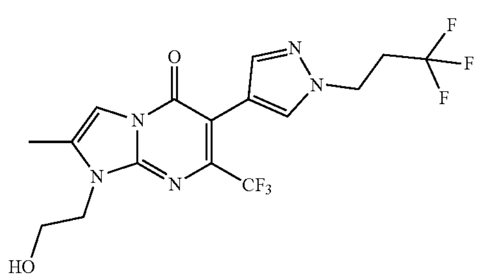 [SMILES: Cc1cn2c(=O)c(-c3cnn(CCC(F)(F)F)c3)c(C(F)(F)F)nc2n1CCO] | 1-(2-hydroxyethyl)-2-methyl-7-(trifluoromethyl)-6-[1-(3,3,3-trifluoropropyl)-1H-pyrazol-4-yl]-1H,5H-imidazo[1,2-a]pyrimidin-5-one | Heated at 70° C. for 16 h. Purification by flash chromatography (C18, 5-80% MeCN/0.1% HCOOH in H₂O followed by SiO₂, 100% EtOAc) | 2-methyl-7-(trifluoromethyl)-6-[1-(3,3,3-trifluoropropyl)-1H-pyrazol-4-yl]-1H,5H-imidazo[1,2-a]pyrimidin-5-one (Example 74) and 2-bromoethanol |

TABLE 10-continued

| Ex. # | Chemical Structure | Name | Method Changes | Reagent |
|---|---|---|---|---|
| 84 | 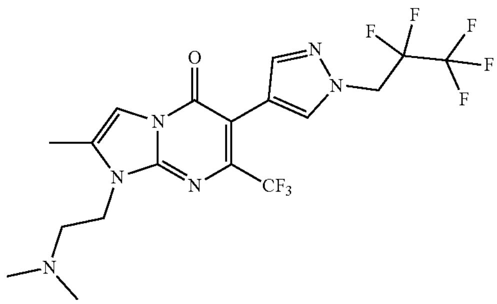 [SMILES: Cc1cn2c(=O)c(-c3cnn(CC(F)(F)C(F)(F)F)c3)c(C(F)(F)F)nc2n1CCN(C)C] | 1-[2-(dimethyl-amino)ethyl]-2-methyl-6-[1-(2,2,3,3,3-pentafluoropropyl)-1H-pyrazol-4-yl]-7-(trifluoromethyl)-1H,5H-imidazo[1,2-a]pyrimidin-5-one | Heated at 60° C. for 6 h. Purification by flash chromatography (SiO$_2$, 0-10% MeOH/DCM followed by C18, 0-20% MeCN/0.1% HCOOH in H$_2$O) | 2-methyl-6-[1-(2,2,3,3,3-pentafluoro-propyl)-1H-pyrazol-4-yl]-7-(trifluoromethyl)-1H,5H-imidazo[1,2-a]pyrimidin-5-one (Example 73) and 2-chloro-N,N-dimethyl-ethanamine hydrochloride |
| 85 | 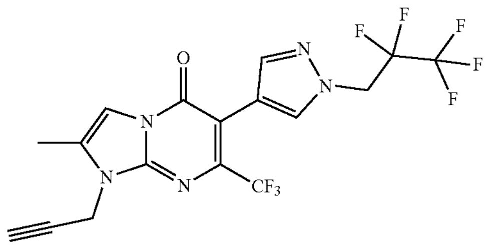 [SMILES: C#CCn1c(C)cn2c(=O)c(-c3cnn(CC(F)(F)C(F)(F)F)c3)c(C(F)(F)F)nc12] | 2-methyl-6-[1-(2,2,3,3,3-pentafluoropropyl)-1H-pyrazol-4-yl]-1-(prop-2-yn-1-yl)-7-(trifluoromethyl)-1H,5H-imidazo[1,2-a]pyrimidin-5-one | Heated at 70° C. for 24 h. Purification by flash chromatography (SiO$_2$, 0-100% EtOAc/Cy followed by C18, 0-100% MeCN/0.1% HCOOH in H$_2$O) | 2-methyl-6-[1-(2,2,3,3,3-pentafluoro-propyl)-1H-pyrazol-4-yl]-7-(trifluoromethyl)-1H,5H-imidazo[1,2-a]pyrimidin-5-one (Example 73) and 3-bromo-1-propyne |

Method 17

Example 86: 2-{2-methyl-5-oxo-6-[1-(2,2,3,3,3-pentafluoropropyl)-1H-pyrazol-4-yl]-7-(trifluoromethyl)-1H,5H-imidazo[1,2-a]pyrimidin-1-yl}acetonitrile

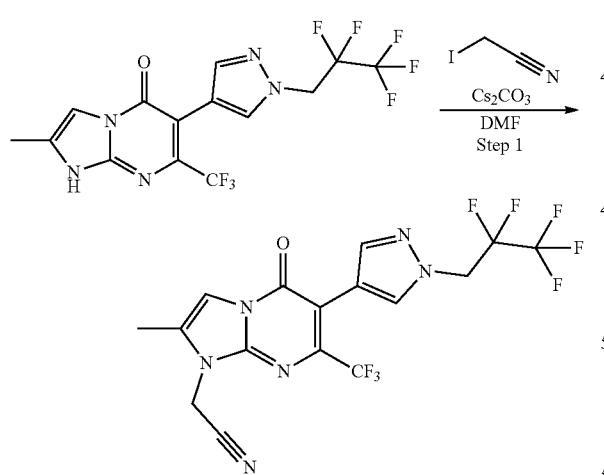

Step 1: 2-{2-methyl-5-oxo-6-[1-(2,2,3,3,3-pentafluoropropyl)-1H-pyrazol-4-yl]-7-(trifluoromethyl)-1H,5H-imidazo[1,2-a]pyrimidin-1-yl}acetonitrile Iodoacetonitile (18 µL, 0.24 mmol) was added to a stirred solution of 2-methyl-6-[1-(2,2,3,3,3-pentafluoropropyl)-1H-pyrazol-4-yl]-7-(trifluoromethyl)-1H,5H-imidazo[1,2-a]pyrimidin-5-one (Example 73, 100 mg, 0.22 mmol) and cesium carbonate (144 mg, 0.44 mmol) in DMF (1.85 mL) cooled to 0° C. The reaction mixture was stirred at rt overnight then diluted with iced water and extracted with EtOAc (2×). The combined organic phases were washed with water and brine, dried over Na$_2$SO$_4$, filtered and evaporated under reduced pressure. The crude material was purified by flash chromatography (SiO$_2$, 0-100% EtOAc/cyclohexane) to afford 2-{2-methyl-5-oxo-6-[1-(2,2,3,3,3-pentafluoropropyl)-1H-pyrazol-4-yl]-7-(trifluoromethyl)-1H,5H-imidazo[1,2-a]pyrimidin-1-yl}acetonitrile (40 mg, 0.09 mmol, 40% yield) as a white solid. LC/MS (ESI) m/z=455.2 [M+H]$^+$. $^1$H NMR (500 MHz, DMSO-d$_6$) δ 2.44 (d, J=1.1 Hz, 3H), 5.25 (t, J=15.0 Hz, 2H), 5.43 (s, 2H), 7.58 (s, 1H), 7.67 (q, J=1.4 Hz, 1H), 7.91 (s, 1H).

Example 87: 2-[2-methyl-5-oxo-7-(trifluoromethyl)-6-[1-(3,3,3-trifluoropropyl)-1H-pyrazol-4-yl]-1H,5H-imidazo[1,2-a]pyrimidin-1-yl]acetonitrile

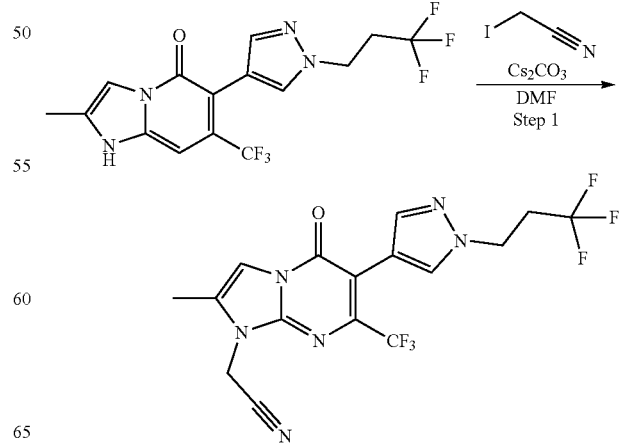

Step 1: 2-[2-methyl-5-oxo-7-(trifluoromethyl)-6-[1-(3,3,3-trifluoropropyl)-1H-pyrazol-4-yl]-1H,5H-imidazo[1,2-a]pyrimidin-1-yl]acetonitrile Iodoacetonitrile (13 μL, 0.17 mmol) was added to a stirred solution of 2-methyl-7-(trifluoromethyl)-6-[1-(3,3,3-trifluoropropyl)-1H-pyrazol-4-yl]-1H,5H-imidazo[1,2-a]pyrimidin-5-one (Example 74, 60 mg, 0.16 mmol) and cesium carbonate (103 mg, 0.32 mmol) in DMF (1.2 mL) cooled to 0° C. The reaction mixture was stirred at rt overnight then quenched with 0.5 M aq HCl solution and extracted with EtOAc (2×). The combined organic phases were dried over $Na_2SO_4$, filtered, evaporated under reduced pressure. The crude material was purified by flash chromatography [$SiO_2$, 0-5% (0.1% formic acid in MeCN)/DCM] to afford 2-[2-methyl-5-oxo-7-(trifluoromethyl)-6-[1-(3,3,3-trifluoropropyl)-1H-pyrazol-4-yl]-1H,5H-imidazo[1,2-a]pyrimidin-1-yl]acetonitrile (40 mg, 0.096 mmol, 60% yield) as a white solid. LC/MS (ESI) m/z=419.2 [M+H]$^+$. $^1$H NMR (500 MHz, DMSO-$d_6$) δ 2.44 (d, J=1.4 Hz, 3H), 2.88 (qt, J=11.2, 6.7 Hz, 2H), 4.44 (t, J=6.7 Hz, 2H), 5.42 (s, 2H), 7.48 (s, 1H), 7.65 (q, J=1.2 Hz, 1H), 7.87 (s, 1H).

Example 88: 1-(2-hydroxy-2-methylpropyl)-2-methyl-6-[1-(2,2,3,3,3-pentafluoropropyl)-1H-pyrazol-4-yl]-7-(trifluoromethyl)-1H,5H-imidazo[1,2-a]pyrimidin-5-one

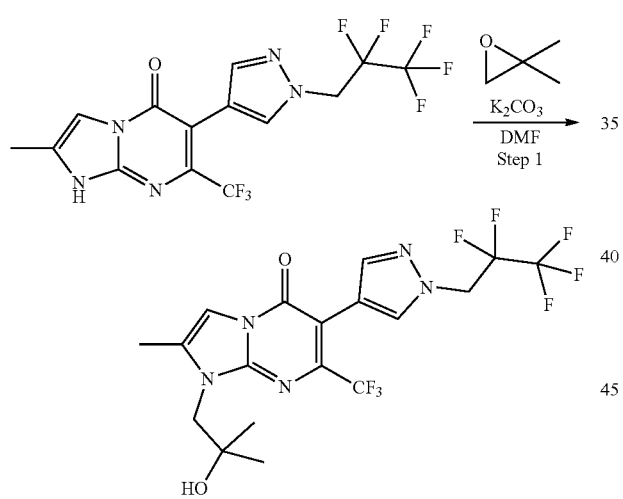

Step 1: 1-(2-hydroxy-2-methylpropyl)-2-methyl-6-[1-(2,2,3,3,3-pentafluoropropyl)-1H-pyrazol-4-yl]-7-(trifluoromethyl)-1H,5H-imidazo[1,2-a]pyrimidin-5-one The title compound was prepared using the procedure described for Example 86 Step 1 with the following modification: the reaction was performed with 2-methyl-6-[1-(2,2,3,3,3-pentafluoropropyl)-1H-pyrazol-4-yl]-7-(trifluoromethyl)-1H,5H-imidazo[1,2-a]pyrimidin-5-one (Example 73), potassium carbonate and 2,2-dimethyloxirane and the mixture was heated at 110° C. for 16 h. Product purification by flash chromatography ($SiO_2$, 80-100% EtOAc/Cyclohexane followed by C18, 0-100% acetonitrile/0.1% formic acid in water). LC/MS (ESI$^+$) m/z=488.2 [M+H]$^+$. $^1$H NMR (400 MHz, DMSO-$d_6$) δ 1.18 (s, 6H), 2.44 (d, J=1.2 Hz, 3H), 4.05 (s, 2H), 4.85 (s, 1H), 5.23 (t, J=15.0 Hz, 2H), 7.57 (s, 1H), 7.60 (d, J=1.2 Hz, 1H), 7.89 (s, 1H).

Example 89: 1-[2-(1-hydroxycyclopropyl)ethyl]-2-methyl-6-[1-(2,2,3,3,3-pentafluoropropyl)-1H-pyrazol-4-yl]-7-(trifluoromethyl)-1H,5H-imidazo[1,2-a]pyrimidin-5-one

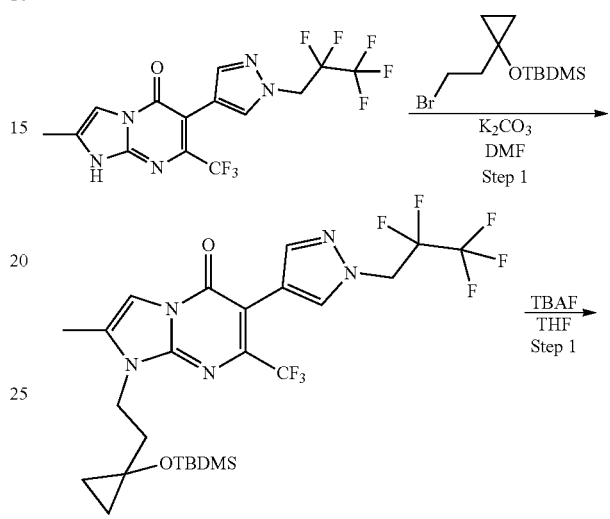

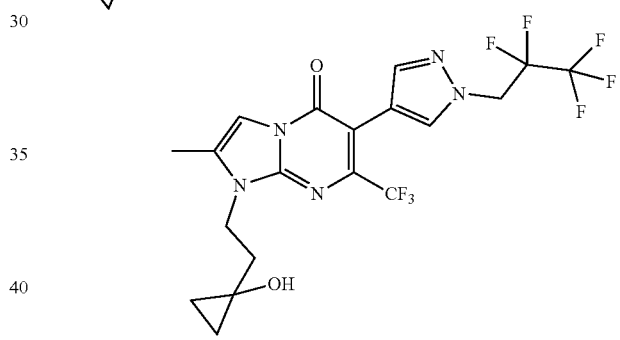

Step 1: 1-[2-[1-[tert-butyl(dimethyl)silyl]oxycyclopropyl]ethyl]-2-methyl-6-[1-(2,2,3,3,3-pentafluoropropyl)pyrazol-4-yl]-7-(trifluoromethyl)imidazo[1,2-a]pyrimidin-5-one The title compound was prepared using the procedure described for Example 86, Step 1 with the following modification: the reaction was performed with 2-methyl-6-[1-(2,2,3,3,3-pentafluoropropyl)-1H-pyrazol-4-yl]-7-(trifluoromethyl)-1H,5H-imidazo[1,2-a]pyrimidin-5-one (Example 73), potassium carbonate and [1-(2-bromoethyl)cyclopropyl]oxy-tert-butyl-dimethylsilane (Intermediate 34A) and the mixture was heated at 80° C. for 16 h. Product purification by flash chromatography ($SiO_2$, 0-40% EtOAc/Cyclohexane). LC/MS (ESI$^+$) m/z=614.2 [M+H]$^+$.

Step 2: 1-[2-(1-hydroxycyclopropyl)ethyl]-2-methyl-6-[1-(2,2,3,3,3-pentafluoropropyl)-1H-pyrazol-4-yl]-7-(trifluoromethyl)-1H,5H-imidazo[1,2-a]pyrimidin-5-one A mixture of 1-[2-[1-[tert-butyl(dimethyl)silyl]oxycyclopropyl]ethyl]-2-methyl-6-[1-(2,2,3,3,3-pentafluoropropyl)

pyrazol-4-yl]-7-(trifluoromethyl)imidazo[1,2-a]pyrimidin-5-one (134 mg, 0.22 mmol) and tetrabutylammonium fluoride (1 M in THF, 0.66 mL, 0.66 mmol) in anhydrous THF (5 mL) was stirred at rt for 30 min. Water was added and the mixture was extracted with EtOAc. The organic phase was dried over Na$_2$SO$_4$, filtered and concentrated. The crude material was purified by flash chromatography (SiO$_2$, 10-100% EtOAc/cyclohexane) to afford 1-[2-(1-hydroxycyclopropyl)ethyl]-2-methyl-6-[1-(2,2,3,3,3-pentafluoropropyl)-1H-pyrazol-4-yl]-7-(trifluoromethyl)-1H,5H-imidazo[1,2-a]pyrimidin-5-one (65 mg, 0.13 mmol, 60% yield) as a white solid. LC/MS (ESI$^+$) m/z=500.2 [M+H]$^+$. $^1$H NMR (500 MHz, DMSO-d$_6$) δ 0.21-0.28 (m, 2H), 0.47-0.55 (m, 2H), 1.91 (t, J=6.9 Hz, 2H), 2.43 (d, J=1.4 Hz, 3H), 4.30 (t, J=6.9 Hz, 2H), 5.18-5.31 (m, 3H), 7.57 (s, 1H), 7.60 (d, J=1.4 Hz, 1H), 7.88 (s, 1H).

Method 18

Example 90: 2-methyl-1-[(oxetan-3-yl)methyl]-6-[1-(2,2,3,3,3-pentafluoropropyl)-1H-pyrazol-4-yl]-7-(trifluoromethyl)-1H,5H-imidazo[1,2-a]pyrimidin-5-one

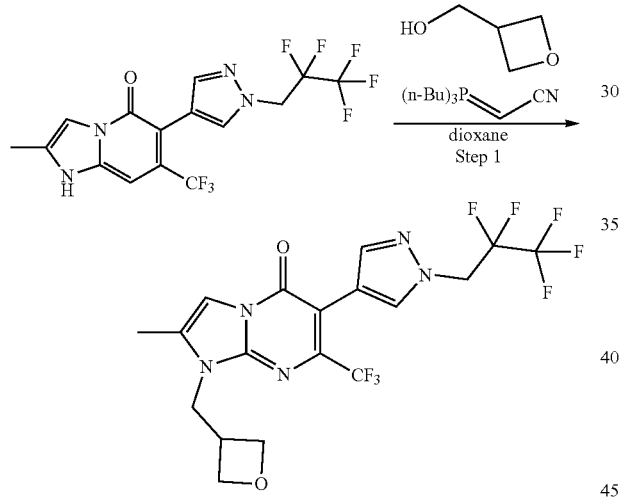

Step 1: 2-methyl-1-[(oxetan-3-yl)methyl]-6-[1-(2,2,3,3,3-pentafluoropropyl)-1H-pyrazol-4-yl]-7-(trifluoromethyl)-1H,5H-imidazo[1,2-a]pyrimidin-5-one A microwave vial was charged with 2-methyl-6-[1-(2,2,3,3,3-pentafluoropropyl)-1H-pyrazol-4-yl]-7-(trifluoromethyl)-1H,5H-imidazo[1,2-a]pyrimidin-5-one (Example 73.50 mg, 0.12 mmol), 1,4-dioxane (0.5 mL), oxetan-3-ylmethanol (13 mg, 0.14 mmol) and 2-tributylphosphoranylideneacetonitrile (58 mg, 0.24 mmol). The solution was purged with nitrogen for 5 min then submitted to microwave irradiation at 150° C. for 1 h. After cooling to rt, the mixture was diluted with water and extracted with EtOAc (2×). The organic phase was dried over Na$_2$SO$_4$, filtered and concentrated under vacuum. The crude material was purified by flash chromatography (SiO$_2$, 10-40% EtOAc/cyclohexane followed by C18, 20-100% MeCN/0.1% formic acid in water) to afford 2-methyl-1-[(oxetan-3-yl)methyl]-6-[1-(2,2,3,3,3-pentafluoropropyl)-1H-pyrazol-4-yl]-7-(trifluoromethyl-1H,5H-imidazo[1,2-a]pyrimidin-5-one (13 mg, 0.027 mmol, 22% yield) as a white solid. LC/MS (ESI$^+$) m/z=486.1 [M+H]$^+$. $^1$H NMR (400 MHz, DMSO-d$_6$) δ 2.38 (d, J=0.9 Hz, 3H), 3.40-3.54 (m, 1H), 4.44 (d, J=7.3 Hz, 2H), 4.52 (t, J=6.2 Hz, 2H), 4.63 (dd, J=7.7, 6.3 Hz, 2H), 5.23 (t, J=15.0 Hz, 2H), 7.56 (s, 1H), 7.59 (br q, J=1.3 Hz, 1H), 7.88 (s, 1H).

Example 91: 2-methyl-1-(oxetan-3-yl)-6-[1-(2,2,3,3,3-pentafluoropropyl)-1H-pyrazol-4-yl]-7-(trifluoromethyl)-1H,5H-imidazo[1,2-a]pyrimidin-5-one

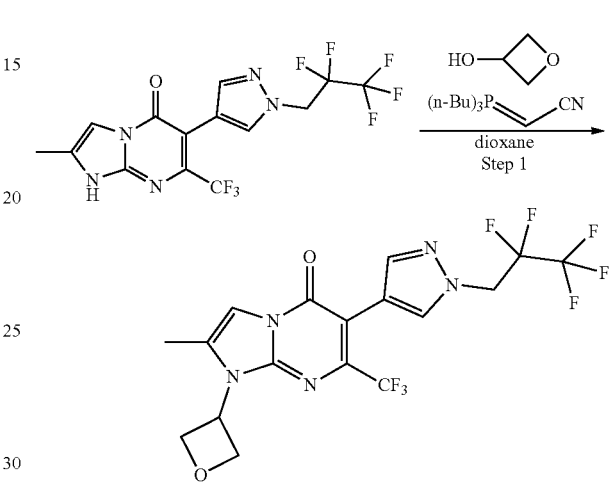

Step 1: 2-methyl-1-(oxetan-3-yl)-6-[1-(2,2,3,3,3-pentafluoropropyl)-1H-pyrazol-4-yl]-7-(trifluoromethyl)-1H,5H-imidazo[1,2-a]pyrimidin-5-one The title compound was prepared using the procedure described for Example 90, Step 1 with the following modification: the reaction was performed with 2-methyl-6-[1-(2,2,3,3,3-pentafluoropropyl)-1H-pyrazol-4-yl]-7-(trifluoromethyl)-1H,5H-imidazo[1,2-a]pyrimidin-5-one (Example 73) and 3-oxetanol. Purification by flash chromatography (SiO$_2$, 80-100% EtOAc/Cyclohexane). LC/MS (ESI) m/z=472.0 [M+H]$^+$. $^1$H NMR (600 MHz, DMSO-d$_6$) δ 2.41 (d, J=1.0 Hz, 3H), 4.89 (dd, J=8.1, 7.1 Hz, 2H), 5.24 (t, J=15.0 Hz, 2H), 5.35 (t, J=6.9 Hz, 2H), 5.68 (quin, J=7.6 Hz, 1H), 7.58 (s, 1H), 7.62 (br q, J=1.0 Hz, 1H), 7.90 (s, 1H).

Method 19

Example 92: 1,2-dimethyl-6-[1-(2,2,3,3,3-pentafluoropropyl)-1H-pyrazol-4-yl]-7-(trifluoromethyl)-1H,5H-imidazo[1,2-a]pyrimidine-5-thione

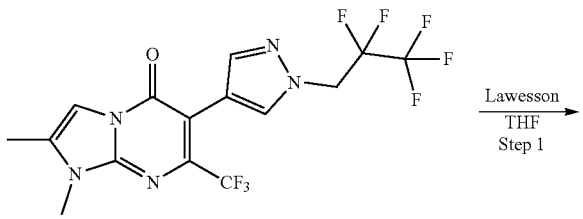

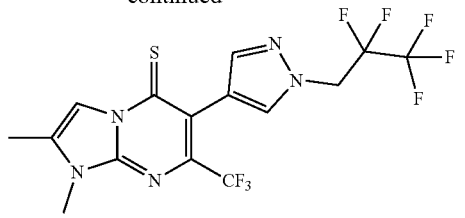

Step 1: 1,2-dimethyl-6-[1-(2,2,3,3,3-pentafluoropropyl)-1H-pyrazol-4-yl]-7-(trifluoromethyl)-1H,5H-imidazo[1,2-a]pyrimidine-5-thione A mixture of 1,2-dimethyl-6-[1-(2,2,3,3,3-pentafluoropropyl)-1H-pyrazol-4-yl]-7-(trifluoromethyl)-1H,5H-imidazo[1,2-a]pyrimidin-5-one (Example 52, 70 mg, 0.16 mmol) and Lawesson's reagent (2,4-bis(4-methoxyphenyl)-1,3,2,4-dithiadiphosphetane-2,4-dithione, 78.4 mg, 0.2 mmol) in THF (0.58 mL) was heated to reflux for 16 h. After cooling to rt, the mixture was concentrated under reduced pressure. The residue was purified by flash chromatography (C18, 0-100% MeCN/0.1% formic acid in water followed by $SiO_2$, 0-60% EtOAc/cyclohexane) to afford 1,2-dimethyl-6-[1-(2,2,3,3,3-pentafluoropropyl)-1H-pyrazol-4-yl]-7-(trifluoromethyl)-1H,5H-imidazo[1,2-a]pyrimidine-5-thione (22 mg, 0.05 mmol, 31% yield) as yellow solid. LC/MS (ESI+) m/z=446.0 [M+H]+. $^1$H NMR (500 MHz, DMSO-$d_6$) δ 2.48 (d, J=0.8 Hz, 3H), 3.76 (s, 3H), 5.24 (t, J=14.7 Hz, 2H), 7.51 (s, 1H), 7.81 (s, 1H), 8.12-8.17 (m, 1H).

Method 20

Example 93: 2-methyl-6-[1-(2,2,3,3,3-pentafluoropropyl)-1H-pyrazol-4-yl]-1-(pyridin-2-yl)-7-(trifluoromethyl)-1H,5H-imidazo[1,2-a]pyrimidin-5-one

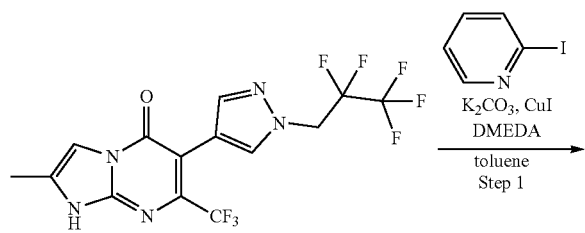

Step 1: 2-methyl-6-[1-(2,2,3,3,3-pentafluoropropyl)-1H-pyrazol-4-yl]-1-(pyridin-2-yl)-7-(trifluoromethyl)-1H,5H-imidazo[1,2-a]pyrimidin-5-one A screw-capped vial was charged with 2-methyl-6-[1-(2,2,3,3,3-pentafluoropropyl)-1H-pyrazol-4-yl]-7-(trifluoromethyl)-1H,5H-imidazo[1,2-a]pyrimidin-5-one (Example 73, 200 mg, 0.47 mmol), toluene (2.6 mL), potassium carbonate (161 mg, 1.17 mmol), 2-iodopyridine (75 μL, 0.7 mmol), copper(I) iodide (22.2 mg, 0.12 mmol) and N,N'-dimethyl ethylenediamine (25.14 μL, 0.23 mmol). The mixture was purged with nitrogen flow for 5 min with nitrogen then heated at 120° C. for 16 h. More 2-iodopyridine (50 μL, 0.47 mmol), copper(I) iodide (18 mg, 0.09 mmol) and N,N-dimethylethylenediamine (19 μL, 0.18 mmol) were added and heating was continued for 24 h. After cooling to rt, the mixture was filtered with EtOAc through a pad of celite. The filtrate was washed with water and brine, dried over $Na_2SO_4$, filtered and concentrated in vacuo. The crude material was purified by flash chromatography ($SiO_2$, 10-50% EtOAc/cyclohexane followed by C18, 10-80% MeCN/0.1% formic acid in water) to afford 2-methyl-6-[1-(2,2,3,3,3-pentafluoropropyl)-1H-pyrazol-4-yl]-1-(pyridin-2-yl)-7-(trifluoromethyl)-1H,5H-imidazo[1,2-a]pyrimidin-5-one (34 mg, 0.07 mmol, 15% yield) as a white solid. LC/MS (ESI+) m/z=493.1 [M+H]+. $^1$H NMR (400 MHz, DMSO-$d_6$) δ 2.36 (s, 3H), 5.25 (t, J=14.9 Hz, 2H), 7.59-7.67 (m, 2H), 7.80 (d, J=1.1 Hz, 1H), 7.89 (d, J=7.9 Hz, 1H), 7.93 (s, 1H), 8.18 (td, J=7.8, 2.0 Hz, 1H), 8.67-8.74 (m, 1H).

Examples 94-96 listed in Table 11 below were prepared following the procedure described in Method 20, Step 1, above as follows.

TABLE 11

| Ex. # | Chemical Structure | Name | Method Changes | Reagent |
|---|---|---|---|---|
| 94 | 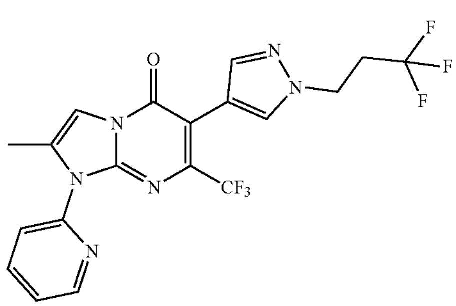 [SMILES: Cc1cn2c(=O)c(-c3cnn(CCC(F)(F)F)c3)c(C(F)(F)F)nc2n1-c1ccccn1] | 2-methyl-1-(pyridin-2-yl)-7-(trifluoromethyl)-6-[1-(3,3,3-trifluoropropyl)-1H-pyrazol-4-yl]-1H,5H-imidazo[1,2-a]pyrimidin-5-one | Heated at 120° C. for 22 h. Purification by flash chromatography (C18, 0-60% MeCN/0.1% HCOOH in $H_2O$ followed by $SiO_2$, 0-50% EtOAc/Cy) | 2-methyl-7-(trifluoromethyl)-6-[1-(3,3,3-trifluoropropyl)-1H-pyrazol-4-yl]-1H,5H-imidazo[1,2-a]pyrimidin-5-one (Example 74) and 2-iodopyridine |

TABLE 11-continued

| Ex. # | Chemical Structure | Name | Method Changes | Reagent |
|---|---|---|---|---|
| 95 | 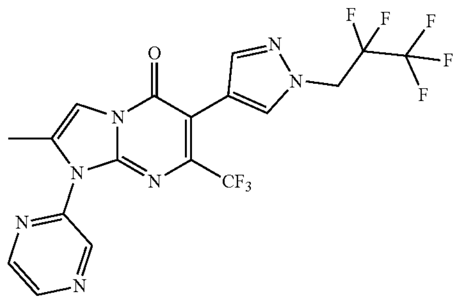 [SMILES: Cc1cn2c(=O)c(-c3cnn(CC(F)(F)C(F)(F)F)c3)c(C(F)(F)F)nc2n1-c1cnccn1] | 2-methyl-6-[1-(2,2,3,3,3-pentafluoropropyl)-1H-pyrazol-4-yl]-1-(pyrazin-2-yl)-7-(trifluoromethyl)-1H,5H-imidazo[1,2-a]pyrimidin-5-one | Heated at 120° C. for 16 h. Purification by flash chromatography ($SiO_2$, 0-20% EtOAc/Cy followed by C18, 0-60% MeCN/$H_2O$) | 2-methyl-6-[1-(2,2,3,3,3-pentafluoropropyl)-1H-pyrazol-4-yl]-7-(trifluoromethyl)-1H,5H-imidazo[1,2-a]pyrimidin-5-one (Example 73) and 2-iodopyrazine |
| 96 | 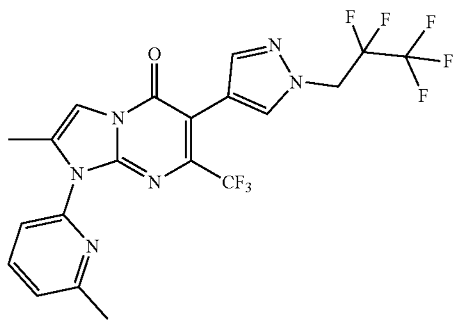 [SMILES: Cc1cccc(-n2c(C)cn3c(=O)c(-c4cnn(CC(F)(F)C(F)(F)F)c4)c(C(F)(F)F)nc23)n1] | 2-methyl-1-(6-methylpyridin-2-yl)-6-[1-(2,2,3,3,3-pentafluoropropyl)-1H-pyrazol-4-yl]-7-(trifluoromethyl)-1H,5H-imidazo[1,2-a]pyrimidin-5-one | Heated at 120° C. for 16 h. Purification by flash chromatography ($SiO_2$, 40-80% EtOAc/Cy) | 2-methyl-6-[1-(2,2,3,3,3-pentafluoropropyl)-1H-pyrazol-4-yl]-7-(trifluoromethyl)-1H,5H-imidazo[1,2-a]pyrimidin-5-one (Example 73) and 2-iodo-6-methylpyridine (Combiblocks Inc.) |

Method 21

Example 97: 2-methyl-1-(1-methyl-1H-pyrazol-4-yl)-6-[1-(2,2,3,3,3-pentafluoropropyl)-1H-pyrazol-4-yl]-7-(trifluoromethyl)-1H,5H-imidazo[1,2-a]pyrimidin-5-one

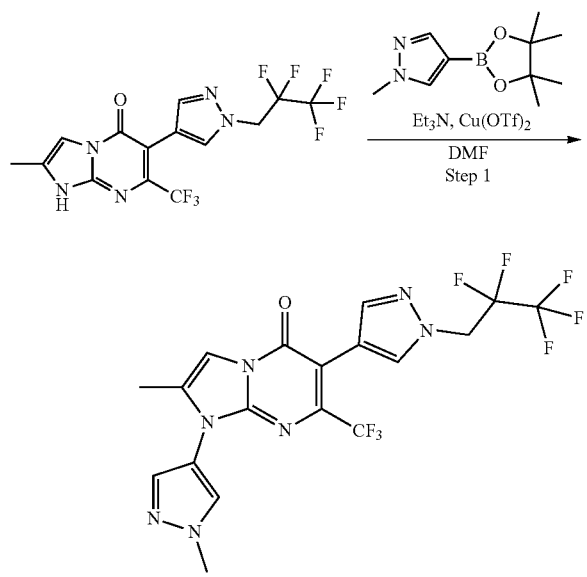

Step 1: 2-methyl-1-(1-methyl-1H-pyrazol-4-yl)-6-[1-(2,2,3,3,3-pentafluoropropyl)-1H-pyrazol-4-yl]-7-(trifluoromethyl)-1H,5H-imidazo[1,2-a]pyrimidin-5-one Triethylamine (48 μL, 0.34 mmol), 1-methyl-4-(4,4,5,5-tetramethyl-1,3,2-dioxaborolan-2-yl)pyrazole (38.7 mg, 0.19 mmol) and copper trifluoromethanesulfonate (56.0 mg, 0.16 mmol) were added to a solution of 2-methyl-6-[1-(2,2,3,3,3-pentafluoropropyl)-1H-pyrazol-4-yl]-7-(trifluoromethyl)-1H,5H-imidazo[1,2-a]pyrimidin-5-one (Example 73, 70 mg, 0.16 mmol) in DMF (3.2 mL). The mixture was stirred at room temperature in the presence of air for 16 h, then diluted with EtOAc and washed with 10% $NH_4OH$ aq solution and brine. The organic phase was dried over $Na_2SO_4$, filtered and concentrated under reduced pressure. The residue was purified by flash chromatography ($SiO_2$, 30-70% EtOAc/cyclohexane followed by C18, 5-80% acetonitrile/0.1% formic acid in water) to afford 2-methyl-1-(1-methyl-1H-pyrazol-4-yl)-6-[1-(2,2,3,3,3-pentafluoropropyl)-1H-pyrazol-4-yl]-7-(trifluoromethyl)-1H,5H-imidazo[1,2-a]pyrimidin-5-one (25 mg, 0.05 mmol, 33% yield) as a white solid. LC/MS (ESI$^+$) m/z=496.2 [M+H]$^+$. $^1$H NMR (400 MHz, DMSO-$d_6$) δ 2.25 (d, J=1.0 Hz, 3H), 3.95 (s, 3H), 5.24 (t, J=15.0 Hz, 2H), 7.58 (s, 1H), 7.74 (q, J=1.2 Hz, 1H), 7.81 (s, 1H), 7.90 (s, 1H), 8.21 (s, 1H).

Examples 98-102 listed in Table 12 were prepared following the procedure described in Method 21, Step 1, above as follows.

TABLE 12

| Ex. # | Chemical Structure | Name | Method Changes | Reagent |
|---|---|---|---|---|
| 98 | 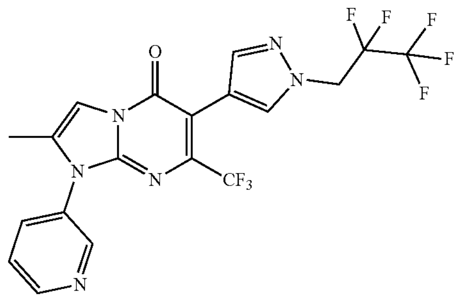 [SMILES: Cc1cn2c(=O)c(-c3cnn(CC(F)(F)C(F)(F)F)c3)c(C(F)(F)F)nc2n1-c1cccnc1] | 2-methyl-6-[1-(2,2,3,3,3-pentafluoropropyl)-1H-pyrazol-4-yl]-1-(pyridin-3-yl)-7-(trifluoromethyl)-1H,5H-imidazo[1,2-a]pyrimidin-5-one | Stirred at rt in the presence of air for 5 h. Purification by flash chromatography (SiO$_2$, 0-100% EtOAc/Cy followed by SiO$_2$, 0-50% MeCN/EtOAc) | 2-methyl-6-[1-(2,2,3,3,3-pentafluoro-propyl)-1H-pyrazol-4-yl]-7-(trifluoromethyl)-1H,5H-imidazo[1,2-a]pyrimidin-5-one (Example 73) and 3-(4,4,5,5-tetramethyl-1,3,2-dioxaborolan-2-yl)pyridine |
| 99 | 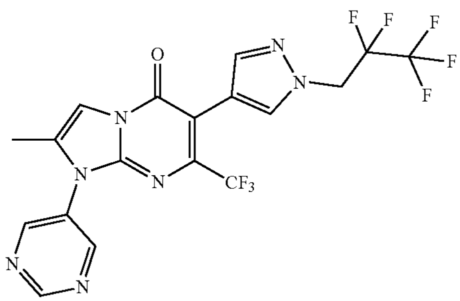 [SMILES: Cc1cn2c(=O)c(-c3cnn(CC(F)(F)C(F)(F)F)c3)c(C(F)(F)F)nc2n1-c1cncnc1] | 2-methyl-6-[1-(2,2,3,3,3-pentafluoropropyl)-1H-pyrazol-4-yl]-1-(pyrimidin-5-yl)-7-(trifluoromethyl)-1H,5H-imidazo[1,2-a]pyrimidin-5-one | Stirred at rt in the presence of air for 16 h. Purification by flash chromatography (C18, 20-100% MeCN/0.1% HCOOH in H$_2$O followed by SiO$_2$, 50-90% EtOAc/Cy) | 2-methyl-6-[1-(2,2,3,3,3-pentafluoro-propyl)-1H-pyrazol-4-yl]-7-(trifluoromethyl)-1H,5H-imidazo[1,2-a]pyrimidin-5-one (Example 73) and 5-pyrimidine-boronic acid |
| 100 | 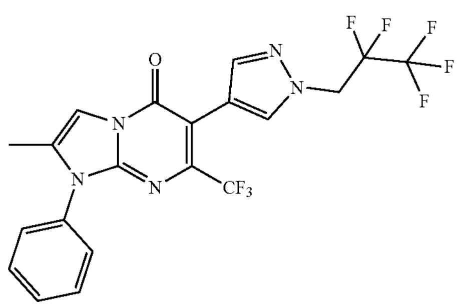 [SMILES: Cc1cn2c(=O)c(-c3cnn(CC(F)(F)C(F)(F)F)c3)c(C(F)(F)F)nc2n1-c1ccccc1] | 2-methyl-6-[1-(2,2,3,3,3-pentafluoropropyl)-1H-pyrazol-4-yl]-1-phenyl-7-(trifluoromethyl)-1H,5H-imidazo[1,2-a]pyrimidin-5-one | Stirred at rt in the presence of air for 16 h. Purification by flash chromatography (C18, 0-60% MeCN/0.1% HCOOH in H$_2$O followed by SiO$_2$, 0-80% EtOAc/Cy) | 2-methyl-6-[1-(2,2,3,3,3-pentafluoro-propyl)-1H-pyrazol-4-yl]-7-(trifluoromethyl)-1H,5H-imidazo[1,2-a]pyrimidin-5-one (Example 73) and phenylboronic acid |
| 101 | 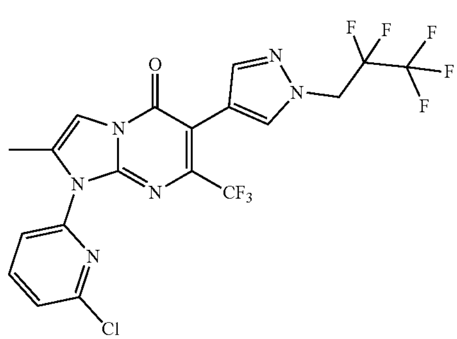 [SMILES: Cc1cn2c(=O)c(-c3cnn(CC(F)(F)C(F)(F)F)c3)c(C(F)(F)F)nc2n1-c1cccc(Cl)n1] | 1-(6-chloropyridin-2-yl)-2-methyl-6-[1-(2,2,3,3,3-pentafluoropropyl)-1H-pyrazol-4-yl]-7-(trifluoromethyl)-1H,5H-imidazo[1,2-a]pyrimidin-5-one | Stirred at rt in the presence of air for 36 h. Purification by flash chromatography (SiO$_2$, 0-100% EtOAc/Cy followed by C18, 10-100% MeCN/0.1% HCOOH in H$_2$O) | 2-methyl-6-[1-(2,2,3,3,3-pentafluoro-propyl)-1H-pyrazol-4-yl]-7-(trifluoromethyl)-1H,5H-imidazo[1,2-a]pyrimidin-5-one (Example 73) and 6-chloropyridine-2-boronic acid pinacol ester |

TABLE 12-continued

| Ex. # | Chemical Structure | Name | Method Changes | Reagent |
|---|---|---|---|---|
| 102 | 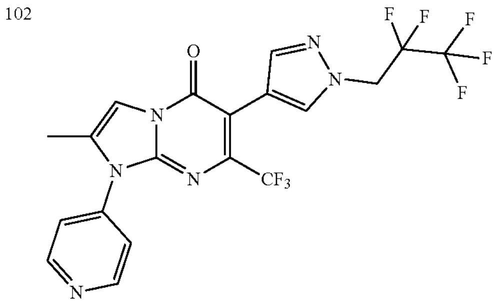 | 2-methyl-6-[1-(2,2,3,3,3-pentafluoropropyl)-1H-pyrazol-4-yl]-1-(pyridin-4-yl)-7-(trifluoromethyl)-1H,5H-imidazo[1,2-a]pyrimidin-5-one | Stirred at rt in the presence of air for 40 h. Purification by flash chromatography (SiO₂, 50% EtOAc/Cy) | 2-methyl-6-[1-(2,2,3,3,3-pentafluoropropyl)-1H-pyrazol-4-yl]-7-(trifluoromethyl)-1H,5H-imidazo[1,2-a]pyrimidin-5-one (Example 73) and 4-(4,4,5,5-tetramethyl-1,3,2-dioxaborolan-2-yl)pyridine |

Method 22

Example 103: 2-methyl-6-[1-(2,2,3,3,3-pentafluoropropyl)-1H-pyrazol-4-yl]-1-(1H-pyrazol-4-yl)-7-(trifluoromethyl)-1H,5H-imidazo[1,2-a]pyrimidin-5-one

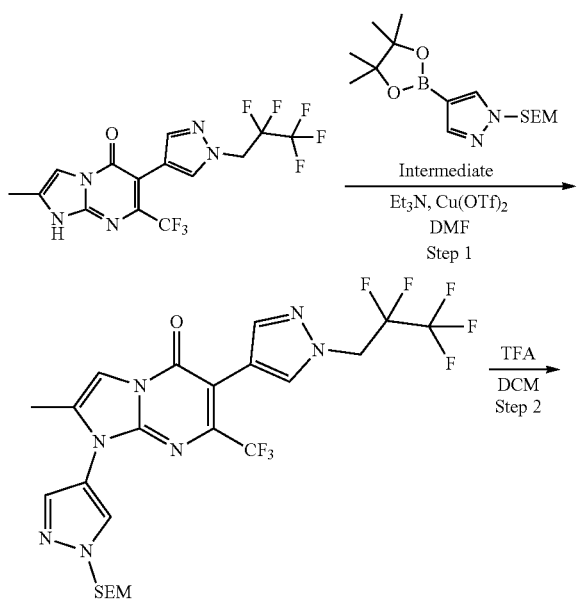

Step 1: 2-methyl-6-[1-(2,2,3,3,3-pentafluoropropyl)pyrazol-4-yl]-7-(trifluoromethyl)-1-[1-(2-trimethylsilylethoxymethyl)pyrazol-4-yl]imidazo[1,2-a]pyrimidin-5-one The title compound was prepared using the procedure described for Example 97, Step 1 with the following modification: the reaction was performed with 2-methyl-6-[1-(2,2,3,3,3-pentafluoropropyl)-1H-pyrazol-4-yl]-7-(trifluoromethyl)-1H,5H-imidazo[1,2-a]pyrimidin-5-one (Example 73) and trimethyl-[2-[[4-(4,4,5,5-tetramethyl-1,3,2-dioxaborolan-2-yl)pyrazol-1-yl]methoxy]ethyl]silane (Intermediate 33A) and the mixture was stirred at rt in the presence of air for 16 h. Product purification by flash chromatography (SiO₂, 30-70% EtOAc/Cyclohexane). LC/MS (ESI⁺) m/z=612.4 [M+H]⁺.

Step 2: 2-methyl-6-[1-(2,2,3,3,3-pentafluoropropyl)-1H-pyrazol-4-yl]-1-(1H-pyrazol-4-yl)-7-(trifluoromethyl)-1H,5H-imidazo[1,2-a]pyrimidin-5-one The title compound was prepared using the procedure described for Example 73, Step 2 with the following modification: the reaction was performed with 2-methyl-6-[1-(2,2,3,3,3-pentafluoropropyl)pyrazol-4-yl]-7-(trifluoromethyl)-1-[1-(2-trimethylsilylethoxymethyl)pyrazol-4-yl]imidazo[1,2-a]pyrimidin-5-one and the mixture was stirred at rt for 24 h. Product purification by flash chromatography (C18, 5-80% acetonitrile/0.1% ammonia in water). LC/MS (ESI⁺) m/z=482.1 [M+H]⁺. ¹H NMR (500 MHz, DMSO-d₆) δ 2.26 (d, J=1.1 Hz, 3H), 5.25 (t, J=15.0 Hz, 2H), 7.58 (s, 1H), 7.66-8.50 (m, 2H), 7.75 (d, J=1.4 Hz, 1H), 7.91 (s, 1H), 13.40 (br s, 1H).

Method 23

Example 104: 2-(fluoromethyl)-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one

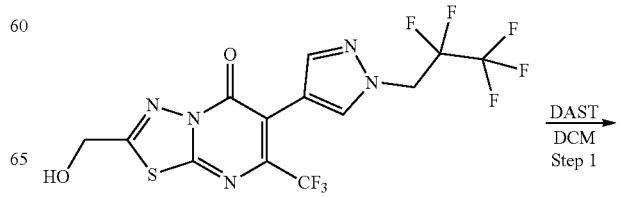

-continued

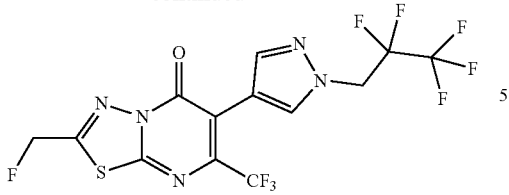

Step 1: 2-(fluoromethyl)-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one 2-(Hydroxymethyl)-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one (Example 45, 55.0 mg, 0.12 mmol) was added to a stirred solution of (diethylamino)sulfur trifluoride (20 µL, 0.16 mmol) in anhydrous DCM (1 mL) at −78° C. The reaction mixture was allowed to reach rt over 10 h, then it was partitioned between DCM and water. The organic phase was washed with brine, dried over $Na_2SO_4$, filtered and concentrated under reduced pressure. The crude material was purified by flash chromatography (C18, 40-80% acetonitrile/0.1% formic acid in water) to afford 2-(fluoromethyl)-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one (15 mg, 0.033 mmol, 27% yield) as a white solid. LC/MS (ESI$^+$) m/z=452.1 [M+H]$^+$. $^1$H NMR (400 MHz, DMSO-d$_6$) δ 5.30 (t, J=15.0 Hz, 2H), 5.91 (d, J=45.6 Hz, 2H), 7.68 (s, 1H), 8.08 (s, 1H).

Method 24

Example 105: 2-[(dimethylamino)methyl]-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one

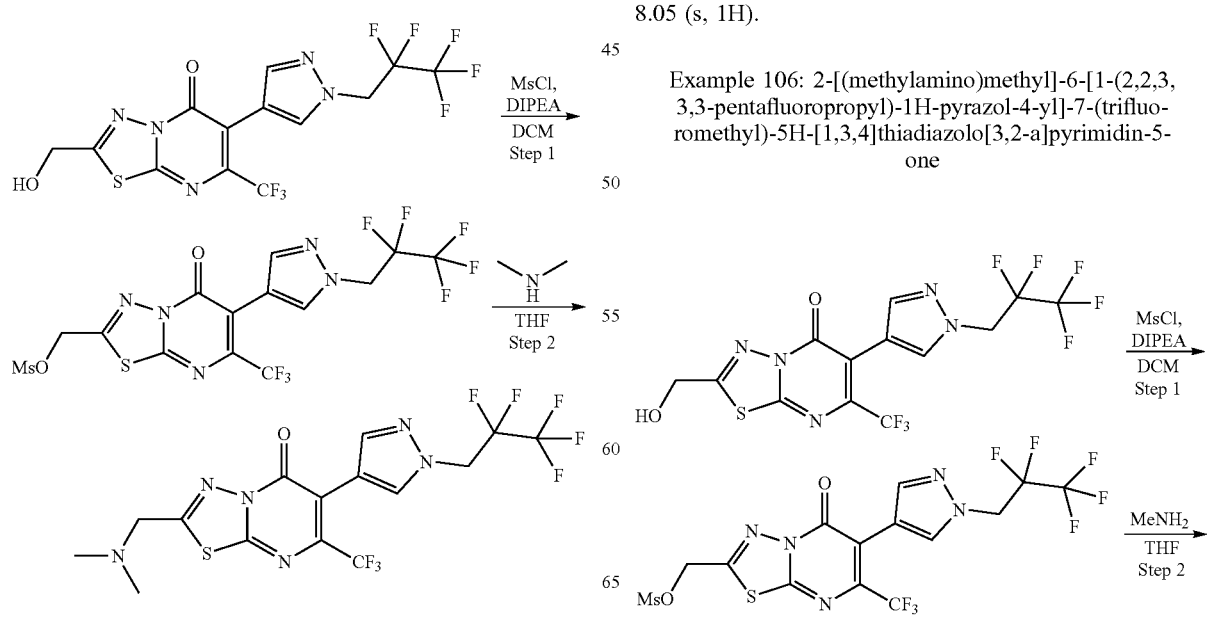

Step 1: [5-oxo-6-[1-(2,2,3,3,3-pentafluoropropyl)pyrazol-4-yl]-7-(trifluoromethyl)-[1,3,4]thiadiazolo[3,2-a]pyrimidin-2-yl]methyl methanesulfonate N,N-Diisopropylethylamine (87 µL, 0.50 mmol) and methanesulfonyl chloride (16 µL, 0.20 mmol) were added consecutively to a solution of 2-(hydroxymethyl)-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one (Example 45, 75.0 mg, 0.17 mmol) in DCM (1.25 mL) at 0° C. The reaction mixture was stirred at rt for 2 h, then 10% $NaHCO_3$ aq solution was added. Phases were separated and the organic layer was washed with brine, dried over $Na_2SO_4$, filtered and concentrated under reduced pressure to afford [5-oxo-6-[1-(2,2,3,3,3-pentafluoropropyl)pyrazol-4-yl]-7-(trifluoromethyl)-[1,3,4]thiadiazolo[3,2-a]pyrimidin-2-yl]methyl methanesulfonate (88 mg, 0.17 mmol, 100% yield) which was carried forward in the next step without further purification. LC/MS (ESI$^+$) m/z=528.2 [M+H]$^+$.

Step 2: 2-[(dimethylamino)methyl]-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one N-Methylmethanamine (2M solution in THF, 0.42 mL, 0.83 mmol) was added to a stirred solution of [5-oxo-6-[1-(2,2,3,3,3-pentafluoropropyl)pyrazol-4-yl]-7-(trifluoromethyl)-[1,3,4]thiadiazolo[3,2-a]pyrimidin-2-yl]methyl methanesulfonate (88.0 mg, 0.17 mmol) in anhydrous THF (0.7 mL) at rt. The reaction mixture was heated at 75° C. for 16 h, then cooled to rt, diluted with DCM and washed with brine. The organic phase was dried over $Na_2SO_4$, filtered and concentrated under reduced pressure. The crude material was purified by flash chromatography (SiO$_2$, 50-80% EtOAc/cyclohexane followed by SiO$_2$, 20-50% EtOAc/cyclohexane) to afford 2-[(dimethylamino)methyl]-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one (20 mg, 0.042 mmol, 25% yield) as a white solid. LC/MS (ESI$^+$) m/z=477.2 [M+H]$^+$. $^1$H NMR (500 MHz, DMSO-d$_6$) δ 2.35 (s, 6H), 3.88 (s, 2H), 5.30 (t, J=15.0 Hz, 2H), 7.66 (s, 1H), 8.05 (s, 1H).

Example 106: 2-[(methylamino)methyl]-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one

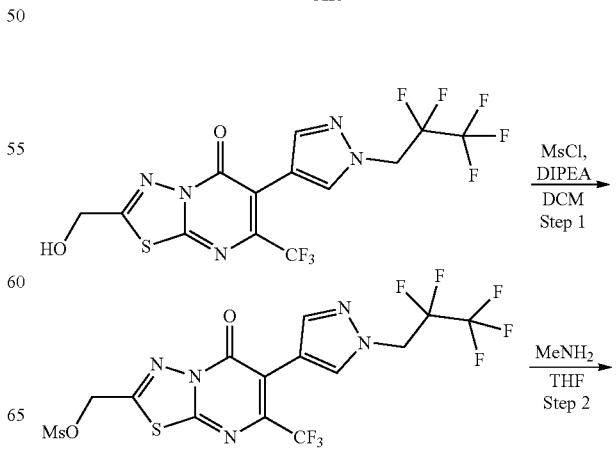

-continued

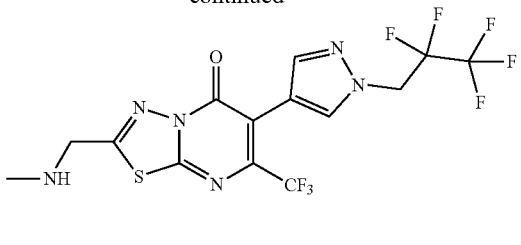

Step 1: [5-oxo-6-[1-(2,2,3,3,3-pentafluoropropy)pyrazol-4-yl]-7-(trifluoromethy)-[1,3,4]thiadiazolo[3,2-a]pyrimidin-2-yl]methyl methanesulfonate The title compound was prepared using the procedure described for Example 105, Step 1. LC/MS (ESI⁺) m/z=528.2 [M+H]⁺.

Step 2: 2-[(methylamino)methyl]-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one The title compound was prepared using the procedure described for Example 105, Step 2 with the following modification: the reaction was performed with [5-oxo-6-[1-(2,2,3,3,3-pentafluoropropyl)pyrazol-4-yl]-7-(trifluoromethyl)-[1,3,4]thiadiazolo[3,2-a]pyrimidin-2-yl]methyl methanesulfonate and methanamine (2M solution in THF) and the reaction mixture was stirred at rt for 48 h. Purification by flash chromatography (SiO₂, 50-100% EtOAc/cyclohexane followed by SiO₂, 80-100% EtOAc/cyclohexane). LC/MS (ESI⁺) m/z=463.1 [M+H]⁺. $^1$H NMR (400 MHz, DMSO-$d_6$) δ 2.83 (d, J=4.7 Hz, 3H), 3.77 (s, 2H), 5.27 (t, J=14.9 Hz, 2H), 7.65 (s, 1H), 7.72 (s, 1H), 8.02 (s, 1H).

Method 25

Examples 107 and 108: 6-(1-{[(1R)-2,2-difluorocyclopropyl]methyl}-1H-pyrazol-4-yl)-2-methyl-7-(trifluoromethyl)-1H,5H-imidazo[1,2-a]pyrimidin-5-one and 6-(1-{[(1S)-2,2-difluorocyclopropyl]methyl}-1H-pyrazol-4-yl)-2-methyl-7-(trifluoromethyl)-1H,5H-imidazo[1,2-a]pyrimidin-5-one

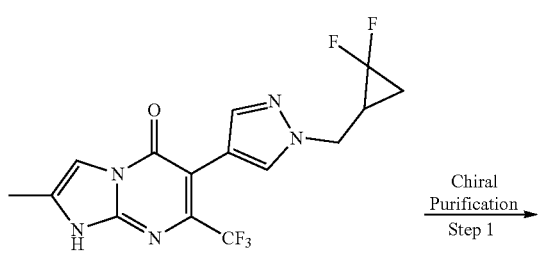

Chiral Purification Step 1

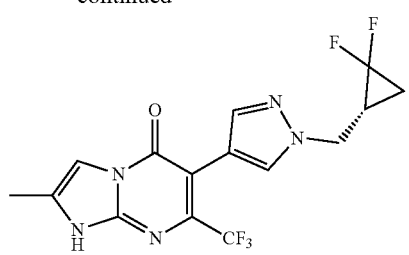

1$^{st}$-eluting isomer

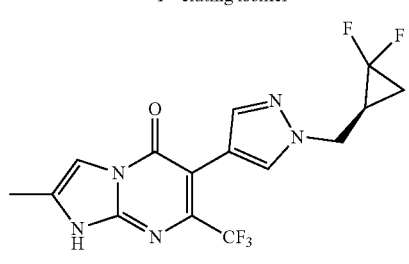

2$^{nd}$-eluting isomer

Step 1: 6-(1-{[(1R)-2,2-difluorocyclopropyl]methyl}-1H-pyrazol-4-yl)-2-methyl-7-(trifluoromethyl)-1H,5H-imidazo[1,2-a]pyrimidin-5-one and 6-(1-{[(1S)-2,2-difluorocyclopropyl]methyl}-1H-pyrazol-4-yl)-2-methyl-7-(trifluoromethyl)-1H,5H-imidazo[1,2-a]pyrimidin-5-one The racemic mixture of 6-{1-[(2,2-difluorocyclopropyl)methyl]-1H-pyrazol-4-yl}-2-methyl-7-(trifluoromethyl)-1H,5H-imidazo[1,2-a]pyrimidin-5-one (Example 76.19 mg, 0.05 mmol) was purified by chiral SFC (Chiralcel OD-H column, 25×0.46 cm, 5 m, 10% (EtOH+0.1% isopropylamine)/CO₂, flow rate 2.5 ml/min, 120 bar) to obtain two peaks: 1$^{st}$ eluting isomer (5.5 mg, 0.015 mmol) and 2$^{nd}$ eluting isomer (6 mg, 0.016 mmol). The stereochemistry of the isomers was assigned arbitrarily to be 6-(1-{[(1R)-2,2-difluorocyclopropyl]methyl}-1H-pyrazol-4-yl)-2-methyl-7-(trifluoromethyl)-1H,5H-imidazo[1,2-a]pyrimidin-5-one as 1$^{st}$ eluting isomer and 6-(1-{[(1S)-2,2-difluorocyclopropyl]methyl}-1H-pyrazol-4-yl)-2-methyl-7-(trifluoromethyl)-1H,5H-imidazo[1,2-a]pyrimidin-5-one as 2″a eluting isomer. 1$^{st}$ Eluting isomer: LC/MS (ESI) m/z=374.1 [M+H]⁺; $^1$H NMR (500 MHz, methanol-$d_4$) δ 1.40 (dtd, J=13.4, 7.8, 7.8, 3.8 Hz, 1H), 1.55-1.66 (m, 1H), 2.22 (ddq, J=13.0, 11.4, 7.5, 7.5, 7.5 Hz, 1H), 2.38 (d, J=1.1 Hz, 3H), 4.25-4.41 (m, 2H), 7.39 (d, J=1.1 Hz, 1H), 7.52 (s, 1H), 7.70 (s, 1H). 2″a Eluting isomer: LC/MS (ESI⁺) m/z=374.1 [M+H]⁺; $^1$H NMR (500 MHz, methanol-$d_4$) δ 1.36-1.46 (m, 1H), 1.56-1.66 (m, 1H), 2.22 (ddq, J=13.1, 11.5, 7.5, 7.5, 7.5 Hz, 1H), 2.38 (s, 3H), 4.18-4.46 (m, 2H), 7.39 (d, J=1.1 Hz, 1H), 7.52 (s, 1H), 7.70 (s, 1H).

The Examples 109-116 listed in Table 13 below were obtained following the procedure described in Method 25, Step 1 above as follows.

TABLE 13

| Ex. # | Chemical Structure | Name | Racemic SM / separation conditions |
|---|---|---|---|
| 109 | 1st-eluting isomer | 6-(1-{[(1R)-2,2-difluorocyclo-propyl]methyl}-1H-pyrazol-4-yl)-1,2-dimethyl-7-(trifluoromethyl)-1H,5H-imidazo[1,2-a]pyrimidin-5-one | Example 59/chiral HPLC: Chiralcel OD-H column, 25 × 0.46 cm, 5 µm, 60/40% v/v n-Hexane/(EtOH + 0.1% isopropylamine), 1 ml/min |
| 110 | 2nd-eluting isomer | 6-(1-{[(1S)-2,2-difluorocyclo-propyl]methyl}-1H-pyrazol-4-yl)-1,2-dimethyl-7-(trifluoromethyl)-1H,5H-imidazo[1,2-a]pyrimidin-5-one | Example 59/chiral HPLC: Chiralcel OD-H column, 25 × 0.46 cm, 5 µm, 60/40 % v/v n-Hexane/(EtOH + 0.1% isopropylamine), 1 ml/min |
| 111 | 1st-eluting isomer | 6-(1-{[(1R)-2,2-difluorocyclo-propyl]methyl}-1H-pyrazol-4-yl)-2-methyl-7-(trifluoromethyl)-5H-[1,3,4]thiadiazolo[3,2-a]pyrimidin-5-one | Example 23/chiral HPLC: Chiralpak IC column, 25 × 0.46 cm, 5 µm, 50/50 % v/v n-Hexane/(EtOH + 0.1% isopropylamine), 1 ml/min |
| 112 | 2nd-eluting isomer | 6-(1-{[(1S)-2,2-difluorocyclo-propyl]methyl}-1H-pyrazol-4-yl)-2-methyl-7-(trifluoromethyl)-5H-[1,3,4]thiadiazolo[3,2-a]pyrimidin-5-one | Example 23/chiral HPLC: Chiralpak IC column, 25 × 0.46 cm, 5 µm, 50/50 % v/v n-Hexane/(EtOH + 0.1% isopropylamine), 1 ml/min |
| 113 | 1st-eluting isomer | (2S)-2-methyl-6-[1-(2,2,3,3,3-pentafluoro-propyl)-1H-pyrazol-4-yl]-7-(trifluoromethyl)-2H,3H,5H-[1,3]thiazolo[3,2-a]pyrimidin-5-one | Example 24/chiral SFC: Chiralcel OD-H column, 25 × 0.46 cm, 5 µm, 20% (EtOH + 0.1% isopropylamine)/ $CO_2$, 2.5 ml/min, 120 bar |

TABLE 13-continued

| Ex. # | Chemical Structure | Name | Racemic SM / separation conditions |
|---|---|---|---|
| 114 | (structure) 2nd-eluting isomer | (2R)-2-methyl-6-[1-(2,2,3,3,3-pentafluoropropyl)-1H-pyrazol-4-yl]-7-(trifluoromethyl)-2H,3H,5H,6H,7H-[1,3]thiazolo[3,2-a]pyrimidin-5-one | Example 24/chiral SFC: Chiralcel OD-H column, 25 × 0.46 cm, 5 μm, 20% (EtOH + 0.1% isopropylamine)/ $CO_2$, 2.5 ml/min, 120 bar |
| 115 | (structure) 1st-eluting isomer | 1-{[(1S)-2,2-difluorocyclopropyl]methyl}-2-methyl-7-(trifluoromethyl)-6-[1-(3,3,3-trifluoropropyl)-1H-pyrazol-4-yl]-1H,5H-imidazo[1,2-a]pyrimidin-5-one | Example 81/chiral HPLC: Chiralpak AS-H column, 25 × 0.46 cm, 5 μm, 65/35% v/v n-Hexane/(2-propanol + 0.1% isopropylamine), 1 ml/min |
| 116 | (structure) 2nd-eluting isomer | 1-{[(1R)-2,2-difluorocyclopropyl]methyl}-2-methyl-7-(trifluoromethyl)-6-[1-(3,3,3-trifluoropropyl)-1H-pyrazol-4-yl]-1H,5H-imidazo[1,2-a]pyrimidin-5-one | Example 81/chiral HPLC: Chiralpak AS-H column, 25 × 0.46 cm, 5 μm, 65/35% v/v n-Hexane/(2-propanol + 0.1% isopropylamine), 1 ml/min |

TABLE 14

Analytical Data

| Ex. # | LRMS: m/z (ESI, +ve ion): $(M + H)^+$ | NMR |
|---|---|---|
| 4 | 433.0 | $^1$H NMR (500 MHz, DMSO-$d_6$) δ 2.49 (br. s., 3H), 5.28 (t, J = 14.96 Hz, 2H), 7.65 (s, 1H), 7.99 (q, J = 1.40 Hz, 1H), 8.02 (s, 1H) |
| 5 | 433.3 | $^1$H NMR (500 MHz, DMSO-$d_6$) δ 2.70 (s, 3H), 5.27 (t, J = 14.96 Hz, 2H), 7.23 (s, 1H), 7.62 (s, 1H), 7.99 (s, 1H) |
| 6 | 487.1 | $^1$H NMR (500 MHz, DMSO-$d_6$) δ 5.29 (t, J = 14.96 Hz, 2H), 7.66 (s, 1H), 8.08 (s, 1H), 8.50 (s, 1H) |
| 7 | 437.1 | $^1$H NMR (500 MHz, CDCl$_3$) δ 4.82 (t, J = 13.72 Hz, 2H), 7.76 (s, 1H), 7.80 (s, 1H), 7.86 (s, 1H) |
| 8 | 383.1 | $^1$H NMR (400 MHz, DMSO-$d_6$) δ 2.81-2.97 (m, 2H), 4.46 (t, J = 6.65 Hz, 2H), 7.56 (s, 1H), 7.72 (d, J = 4.70 Hz, 1H), 7.98 (s, 1H), 8.12 (d, J = 4.70 Hz, 1H). |
| 9 | 453.3/455.3 | $^1$H NMR (500 MHz, DMSO-$d_6$) δ 5.27 (t, J = 14.92 Hz, 2H), 7.65 (s, 1H), 8.03 (s, 1H), 8.44 (s, 1H) |
| 10 | 428.1 | $^1$H NMR (500 MHz, DMSO-$d_6$) δ 2.90 (qt, J = 11.21, 6.79 Hz, 2H), 3.46 (s, 3H), 4.48 (t, J = 6.72 Hz, 2H), 4.87 (s, 2H), 7.57 (s, 1H), 8.02 (s, 1H) |
| 11 | 460.1 | $^1$H NMR (400 MHz, DMSO-$d_6$) δ 1.13-1.19 (m, 2H), 1.30-1.39 (m, 2H), 2.61 (tt, J = 8.24, 4.77 Hz, 1H), 5.29 (t, J = 14.87 Hz, 2H), 7.65 (s, 1H), 8.03 (s, 1H) |
| 12 | 424.1 | $^1$H NMR (500 MHz, DMSO-$d_6$) δ 1.13-1.18 (m, 2H), 1.30-1.36 (m, 2H), 2.60 (tt, J = 8.23, 4.80 Hz, 1H), 2.82-2.99 (m, 2H), 4.47 (t, J = 6.72 Hz, 2H), 7.55 (s, 1H), 7.99 (s, 1H) |
| 13 | 431.1 | $^1$H NMR (500 MHz, DMSO-$d_6$) δ 2.56 (s, 3H), 3.63 (s, 3H), 5.26 (t, J = 15.0 Hz, 2H), 7.59 (s, 1H), 7.93 (s, 1H) |
| 14 | 395.1 | $^1$H NMR (500 MHz, DMSO-$d_6$) δ 2.55 (s, 3H), 2.89 (qt, J = 11.2, 6.8 Hz, 2H), 3.62 (s, 3H), 4.44 (t, J = 6.7 Hz, 2H), 7.48 (s, 1H), 7.89 (s, 1H) |
| 15 | 394.3 | $^1$H NMR (500 MHz, DMSO-$d_6$) δ 1.17 (t, J = 7.5 Hz, 3H), 2.63 (q, J = 7.5 Hz, 2H), 2.71 (s, 3H), 5.26 (t, J = 15.2 Hz, 2H), 7.74 (s, 1H), 8.09 (s, 1H) |
| 16 | 430.1 | $^1$H NMR (500 MHz, DMSO-$d_6$) δ 2.46 (s, 3H), 4.18 (s, 3H), 5.23 (t, J = 14.9 Hz, 2H), 6.53 (d, J = 0.7 Hz, 1H), 7.56 (s, 1H), 7.88 (s, 1H) |

TABLE 14-continued

Analytical Data

| Ex. # | LRMS: m/z (ESI, +ve ion): (M + H)+ | NMR |
|---|---|---|
| 17 | 416.3 | ¹H NMR (400 MHz, CDCl₃) δ 4.42 (s, 3H), 4.80 (t, J = 13.9 Hz, 2H), 6.54 (d, J = 3.5 Hz, 1H), 7.63 (d, J = 3.5 Hz, 1H), 7.70 (s, 1H), 7.73 (s, 1H) |
| 18 | 430.3 | ¹H NMR (500 MHz, CDCl₃) δ 2.29 (d, J = 1.1 Hz, 3H), 4.30 (s, 3H), 4.80 (t, J = 13.9 Hz, 2H), 7.42-7.45 (m, 1H), 7.70 (s, 1H), 7.73 (s, 1H) |
| 19 | 403.3 | ¹H NMR (500 MHz, DMSO-d₆) δ 2.19 (quin, J = 7.7 Hz, 2H), 3.13 (t, J = 8.0 Hz, 2H), 3.99-4.15 (m, 2H), 5.27 (t, J = 15.1 Hz, 2H), 7.63 (s, 1H), 8.02 (s, 1H) |
| 20 | 398.3 | ¹H NMR (500 MHz, DMSO-d₆) δ 2.76 (s, 3H), 2.90 (qt, J = 11.2, 6.8 Hz, 2H), 4.47 (t, J = 6.7 Hz, 2H), 7.56 (s, 1H), 8.01 (s, 1H) |
| 21 | 367.1 | ¹H NMR (500 MHz, DMSO-d₆) δ 2.15-2.22 (m, 2H), 2.88 (br d, J = 11.3 Hz, 2H), 3.12 (t, J = 8.1 Hz, 2H), 4.02-4.07 (m, 2H), 4.45 (t, J = 6.7 Hz, 2H), 7.54 (s, 1H), 7.98 (s, 1H) |
| 22 | 421.0 | ¹H NMR (500 MHz, CDCl₃) δ 3.57 (t, J = 7.8 Hz, 2H), 4.55 (t, J = 7.7 Hz, 2H), 4.79 (t, J = 13.9 Hz, 2H), 7.76 (s, 1H), 7.83 (s, 1H) |
| 23 | 392.1 | ¹H NMR (400 MHz, CDCl₃) δ 1.25-1.37 (m, 1H), 1.58-1.67 (m, 1H), 2.20 (tq, J = 12.1, 7.5 Hz, 1H), 2.81 (s, 3H), 4.25-4.37 (m, 2H), 7.78 (s, 1H), 7.86 (s, 1H) |
| 24 | 435.1 | ¹H NMR (500 MHz, CDCl₃) δ 1.63 (d, J = 6.6 Hz, 3H), 4.07-4.16 (m, 1H), 4.16-4.23 (m, 1H), 4.57 (dd, J = 12.9, 7.4 Hz, 1H), 4.79 (t, J = 13.9 Hz, 2H), 7.76 (s, 1H), 7.83 (s, 1H) |
| 25 | 415.1 | ¹H NMR (500 MHz, DMSO-d₆) δ 0.88-0.97 (m, 1H), 1.37 (td, J = 8.2, 4.7 Hz, 1H), 2.27-2.34 (m, 1H), 2.66-2.74 (m, 1H), 4.01-4.18 (m, 2H), 5.26 (t, J = 15.0 Hz, 2H), 7.61 (s, 1H), 7.99 (s, 1H) |
| 26 | 406.3 | ¹H NMR (500 MHz, DMSO-d₆) δ 2.38-2.48 (m, 2H), 2.56-2.67 (m, 3H), 2.76 (s, 3H), 4.32 (d, J = 5.5 Hz, 2H), 7.55 (s, 1H), 7.98 (s, 1H) |
| 27 | 417.0 | ¹H NMR (500 MHz, CDCl₃) δ 4.04 (s, 3H), 4.81 (t, J = 13.9 Hz, 2H), 7.71 (s, 2H), 8.66 (s, 1H) |
| 28 | 418.0 | ¹H NMR (500 MHz, DMSO-d₆) δ 4.11 (s, 3H), 5.29 (t, J = 14.8 Hz, 2H), 7.63 (s, 1H), 8.00 (s, 1H) |
| 29 | 372.0 | ¹H NMR (500 MHz, DMSO-d₆) δ 2.76 (s, 3H), 3.38-3.49 (m, 1H), 4.43 (t, J = 6.1 Hz, 2H), 4.48 (d, J = 7.3 Hz, 2H), 4.64 (dd, J = 7.8, 6.0 Hz, 2H), 7.53 (s, 1H), 7.97 (s, 1H) |
| 30 | 434.1 | ¹H NMR (600 MHz, DMSO-d₆) δ 2.77 (s, 3H), 5.24 (t, J = 14.8 Hz, 2H), 6.48 (d, J = 2.6 Hz, 1H), 7.95 (d, J = 2.3 Hz, 1H) |
| 31 | 395.1 | ¹H NMR (400 MHz, DMSO-d₆) δ 4.82 (q, J = 9.0 Hz, 2H), 7.12 (d, J = 9.0 Hz, 1H), 7.25 (d, J = 8.8 Hz, 1H), 7.73 (d, J = 4.8 Hz, 1H), 8.13 (d, J = 4.8 Hz, 1H) |
| 32 | 449.1 | ¹H NMR (500 MHz, CDCl₃) δ 2.39 (br s, 1H), 4.81 (t, J = 13.9 Hz, 2H), 4.90 (br s, 2H), 7.79 (s, 1H), 7.83 (s, 1H), 7.96 (d, J = 1.1 Hz, 1H) |
| 33 | 425.1 | ¹H NMR (400 MHz, CDCl₃) δ 2.34 (br t, J = 5.6 Hz, 1H), 4.36-4.40 (m, 1H), 4.40-4.45 (m, 1H), 4.89 (d, J = 4.6 Hz, 2H), 7.03 (d, J = 8.8 Hz, 2H), 7.25-7.31 (m, 2H), 7.95 (s, 1H) |
| 34 | 429.0/ 431.0 | ¹H NMR (500 MHz, DMSO-d₆) δ 4.82 (q, J = 9.0 Hz, 2H), 7.10-7.15 (m, 2H), 7.21-7.27 (m, 2H), 8.45 (s, 1H) |
| 35 | 460.3 | ¹H NMR (400 MHz, DMSO-d₆) δ 1.44 (d, J = 7.02 Hz, 6H), 4.32-4.60 (m, 3H), 5.27 (t, J = 14.91 Hz, 2H), 7.61 (s, 1H), 8.00 (s, 1H) |
| 36 | 460.4 | ¹H NMR (400 MHz, CDCl₃) δ 1.81 (s, 6H), 3.32 (s, 3H), 4.79 (t, J = 13.81 Hz, 2H), 7.73 (s, 1H), 7.79 (s, 1H) |
| 38 | 417.3 | ¹H NMR (500 MHz, DMSO-d₆) δ 3.71 (s, 3H), 5.26 (t, J = 14.96 Hz, 2H), 7.59 (s, 1H), 7.94 (s, 1H), 9.02 (s, 1H) |
| 39 | 417.1 | ¹H NMR (500 MHz, DMSO-d₆) δ 2.41 (d, J = 1.37 Hz, 3H), 5.27 (t, J = 14.96 Hz, 2H), 7.62 (s, 1H), 7.93 (d, J = 1.37 Hz, 1H), 7.98 (s, 1H) |
| 55 | 460.1 | ¹H NMR (400 MHz, CDCl₃) δ 3.42 (s, 3H), 3.82 (s, 3H), 4.56 (s, 2H), 4.80 (t, J = 13.8 Hz, 2H), 7.63 (s, 1H), 7.72 (s, 2H) |
| 56 | 444.5 | ¹H NMR (500 MHz, DMSO-d₆) δ 1.33 (t, J = 7.3 Hz, 3H), 2.41 (d, J = 1.4 Hz, 3H), 4.16 (q, J = 7.3 Hz, 2H), 5.24 (t, J = 15.0 Hz, 2H), 7.56 (s, 1H), 7.60 (d, J = 1.4 Hz, 1H), 7.88 (s, 1H) |
| 57 | 474.0 | ¹H NMR (500 MHz, CDCl₃) δ 2.43 (d, J = 1.1 Hz, 3H), 3.34 (s, 3H), 3.72-3.81 (m, 2H), 4.31 (t, J = 5.1 Hz, 2H), 4.79 (t, J = 13.7 Hz, 2H), 7.39 (s, 1H), 7.73 (s, 2H) |
| 58 | 458.5 | ¹H NMR (500 MHz, DMSO-d₆) δ 1.60 (d, J = 6.9 Hz, 6H), 2.42 (d, J = 1.1 Hz, 3H), 4.74 (quin, J = 6.9 Hz, 1H), 5.23 (t, J = 15.0 Hz, 2H), 7.56 (s, 1H), 7.59 (q, J = 1.4 Hz, 1H), 7.85-7.91 (m, 1H) |
| 59 | 388.1 | ¹H NMR (400 MHz, CDCl₃) δ 1.25-1.37 (m, 1H), 1.55-1.66 (m, 1H), 2.12-2.27 (m, 1H), 2.41 (d, J = 1.1 Hz, 3H), 3.73 (s, 3H), 4.20-4.29 (m, 1H), 4.29-4.38 (m, 2H), 7.42 (q, J = 1.1 Hz, 1H), 7.65 (s, 1H), 7.67 (s, 1H) |
| 60 | 402.1 | ¹H NMR (500 MHz, CDCl₃) δ 0.37-0.44 (m, 2H), 0.64-0.71 (m, 2H), 1.30-1.40 (m, 1H), 2.41 (d, J = 1.1 Hz, 3H), 3.73 (s, 3H), 4.04 (d, J = 7.1 Hz, 2H), 7.42 (q, J = 1.1 Hz, 1H), 7.64 (s, 1H), 7.73 (s, 1H) |
| 61 | 352.1 | ¹H NMR (500 MHz, CDCl₃) δ 0.37-0.44 (m, 2H), 0.64-0.71 (m, 2H), 1.30-1.40 (m, 1H), 2.41 (d, J = 1.1 Hz, 3H), 3.73 (s, 3H), 4.04 (d, J = 7.1 Hz, 2H), 7.42 (q, J = 1.1 Hz, 1H), 7.64 (s, 1H), 7.73 (s, 1H) |
| 62 | 470.0 | ¹H NMR (500 MHz, DMSO-d₆) δ 0.45-0.58 (m, 4H), 1.24-1.34 (m, 1H), 2.44 (s, 3H), 4.02 (d, J = 7.1 Hz, 2H), 5.24 (t, J = 15.0 Hz, 2H), 7.57 (s, 1H), 7.62 (s, 1H), 7.89 (s, 1H) |
| 63 | 424.1 | ¹H NMR (500 MHz, CDCl₃) δ 2.81 (qt, J = 10.4, 7.4 Hz, 2H), 3.42 (s, 3H), 3.82 (s, 3H), 4.38-4.45 (m, 2H), 4.56 (s, 2H), 7.63 (s, 2H), 7.67 (s, 1H) |
| 64 | 474.1 | ¹H NMR (500 MHz, DMSO-d₆) δ 1.15 (d, J = 6.0 Hz, 3H), 2.40 (d, J = 1.1 Hz, 3H), 3.88-3.97 (m, 1H), 4.03-4.16 (m, 2H), 5.00 (d, J = 4.7 Hz, 1H), 5.24 (t, J = 15.0 Hz, 2H), 7.57 (s, 1H), 7.59 (q, J = 1.4 Hz, 1H), 7.88 (s, 1H) |
| 65 | 368.0 | ¹H NMR (500 MHz, DMSO-d₆) δ 2.37 (d, J = 1.1 Hz, 3H), 3.37-3.47 (m, 3H), 3.64 (s, 3H), 4.40-4.47 (m, 4H), 4.64 (dd, J = 7.7, 6.0 Hz, 2H), 7.42 (s, 1H), 7.58 (d, J = 1.1 Hz, 1H), 7.80 (s, 1H) |
| 66 | 434.1 | ¹H NMR (600 MHz, DMSO-d₆) δ 0.45-0.56 (m, 4H), 1.21-1.32 (m, 1H), 2.44 (d, J = 1.0 Hz, 3H), 2.88 (qt, J = 11.2, 6.9 Hz, 2H), 4.02 (d, J = 6.9 Hz, 2H), 4.43 (t, J = 6.8 Hz, 2H), 7.46 (s, 1H), 7.59-7.62 (m, 1H), 7.84 (s, 1H) |
| 67 | 451.2 | ¹H NMR (400 MHz, DMSO-d₆) δ 2.20 (s, 6H), 2.41 (d, J = 0.9 Hz, 3H), 2.61 (t, J = 6.1 Hz, 2H), 2.79-2.98 (m, 2H), 4.21 (t, J = 6.1 Hz, 2H), 4.43 (t, J = 6.8 Hz, 2H), 7.46 (s, 1H), 7.58 (d, J = 1.3 Hz, 1H), 7.84 (s, 1H) |
| 68 | 446.1 | ¹H NMR (400 MHz, DMSO-d₆) δ 0.43-0.60 (m, 4H), 1.19-1.37 (m, 1H), 2.44 (d, J = 0.9 Hz, 3H), 4.03 (d, J = 7.0 Hz, 2H), 4.80 (q, J = 8.8 Hz, 2H), 7.08 (d, J = 8.7 Hz, 2H), 7.20 (d, J = 8.7 Hz, 2H), 7.62 (d, J = 1.2 Hz, 1H) |
| 69 | 463.2 | ¹H NMR (400 MHz, DMSO-d₆) δ 2.21 (s, 6H), 2.42 (d, J = 0.7 Hz, 3H), 2.62 (t, J = 6.2 Hz, 2H), 4.22 (t, J = 6.1 Hz, 2H), 4.80 (q, J = 8.8 Hz, 2H), 7.07 (d, J = 8.8 Hz, 2H), 7.20 (d, J = 8.8 Hz, 2H), 7.59 (d, J = 1.1 Hz, 1H) |
| 70 | 430.2 | ¹H NMR (600 MHz, DMSO-d₆) δ 2.38 (d, J = 0.7 Hz, 3H), 3.66 (s, 3H), 5.19 (t, J = 14.8 Hz, 2H), 6.37 (d, J = 2.3 Hz, 1H), 7.61 (q, J = 1.0 Hz, 1H), 7.87 (d, J = 2.3 Hz, 1H) |
| 80 | 474.1 | ¹H NMR (400 MHz, DMSO-d₆) δ 2.48 (d, J = 1.1 Hz, 3H), 4.03 (s, 3H), 5.26 (t, J = 14.9 Hz, 2H), 7.62 (s, 1H), 7.70 (d, J = 1.1 Hz, 1H), 7.98 (s, 1H) |
| 81 | 470.1 | ¹H NMR (500 MHz, DMSO-d₆) δ 1.52-1.79 (m, 2H), 2.27-2.40 (m, 1H), 2.42 (d, J = 0.8 Hz, 3H), 2.88 (qt, J = 11.2, 6.8 Hz, 2H), 4.17-4.37 (m, 2H), 4.43 (t, J = 6.7 Hz, 2H), 7.47 (s, 1H), 7.61 (d, J = 1.4 Hz, 1H), 7.85 (s, 1H) |

TABLE 14-continued

Analytical Data

| Ex. # | LRMS: m/z (ESI, +ve ion): (M + H)+ | NMR |
|---|---|---|
| 82 | 484.2 | $^1$H NMR (400 MHz, CDCl$_3$) δ 2.42 (d, J = 1.1 Hz, 3H), 2.46-2.64 (m, 2H), 2.67-2.87 (m, 5H), 4.26 (d, J = 6.4 Hz, 2H), 4.37-4.45 (m, 2H), 7.42 (d, J = 1.3 Hz, 1H), 7.63 (s, 1H), 7.66 (s, 1H) |
| 83 | 424.2 | $^1$H NMR (400 MHz, DMSO-d$_6$) δ 2.40 (d, J = 0.9 Hz, 3H), 2.76-3.00 (m, 2H), 3.75 (q, J = 5.5 Hz, 2H), 4.16 (t, J = 5.4 Hz, 2H), 4.43 (t, J = 6.8 Hz, 2H), 4.96 (t, J = 5.8 Hz, 1H), 7.46 (s, 1H), 7.51-7.66 (m, 1H), 7.84 (s, 1H) |
| 84 | 487.3 | $^1$H NMR (500 MHz, DMSO-d$_6$) δ 2.21 (br s, 6H), 2.42 (d, J = 1.1 Hz, 3H), 2.63 (br dd, J = 3.6, 1.9 Hz, 2H), 4.12-4.31 (m, 2H), 5.24 (t, J = 15.0 Hz, 2H), 7.57 (s, 1H), 7.60 (d, J = 1.4 Hz, 1H), 7.89 (s, 1H) |
| 85 | 454.3 | $^1$H NMR (500 MHz, DMSO-d$_6$) δ 2.46 (d, J = 1.1 Hz, 3H), 3.54 (t, J = 2.5 Hz, 1H), 5.04 (d, J = 2.5 Hz, 2H), 5.24 (t, J = 15.0 Hz, 2H), 7.57 (s, 1H), 7.65 (d, J = 1.4 Hz, 1H), 7.89 (s, 1H) |
| 94 | 457.2 | $^1$H NMR (400 MHz, DMSO-d$_6$) δ 2.36 (d, J = 0.9 Hz, 3H), 2.79-3.00 (m, 2H), 4.44 (t, J = 6.8 Hz, 2H), 7.50 (s, 1H), 7.58-7.68 (m, 1H), 7.74-7.82 (m, 1H), 7.84-7.94 (m, 2H), 8.18 (td, J = 7.8, 2.0 Hz, 1H), 8.70 (dd, J = 4.8, 1.3 Hz, 1H) |
| 95 | 494.2 | $^1$H NMR (400 MHz, DMSO-d$_6$) δ 2.41 (d, J = 0.9 Hz, 3H), 5.26 (t, J = 14.9 Hz, 2H), 7.62 (s, 1H), 7.85 (d, J = 1.3 Hz, 1H), 7.95 (s, 1H), 8.82 (dd, J = 2.5, 1.4 Hz, 1H), 8.86 (d, J = 2.4 Hz, 1H), 9.22 (d, J = 1.3 Hz, 1H) |
| 96 | 507.2 | $^1$H NMR (400 MHz, DMSO-d$_6$) δ 2.35 (d, J = 0.9 Hz, 3H), 2.57 (s, 3H), 5.25 (br t, J = 14.9 Hz, 2H), 7.48 (d, J = 7.7 Hz, 1H), 7.60 (s, 1H), 7.67 (d, J = 7.9 Hz, 1H), 7.79 (d, J = 1.1 Hz, 1H), 7.93 (s, 1H), 8.05 (t, J = 7.8 Hz, 1H) |
| 98 | 493.1 | $^1$H NMR (400 MHz, DMSO-d$_6$) δ 2.24 (d, J = 1.0 Hz, 3H), 5.25 (t, J = 15.0 Hz, 2H), 7.59 (s, 1H), 7.71 (dd, J = 8.2, 4.9 Hz, 1H), 7.83 (d, J = 1.4 Hz, 1H), 7.92 (s, 1H), 8.07-8.16 (m, 1H), 8.79 (dd, J = 4.8, 1.5 Hz, 1H), 8.85 (d, J = 2.2 Hz, 1H) |
| 99 | 494.2 | $^1$H NMR (500 MHz, DMSO-d$_6$) δ 2.31 (d, J = 1.4 Hz, 3H), 5.26 (t, J = 15.0 Hz, 2H), 7.60 (s, 1H), 7.86 (q, J = 1.4 Hz, 1H), 7.93 (s, 1H), 9.19 (s, 2H), 9.40 (s, 1H) |
| 100 | 492.1 | $^1$H NMR (500 MHz, DMSO-d$_6$) δ 2.19 (d, J = 1.1 Hz, 3H), 5.25 (t, J = 15.0 Hz, 2H), 7.56-7.69 (m, 6H), 7.80 (d, J = 1.4 Hz, 1H), 7.89-7.92 (m, 1H) |
| 101 | 527.1/ 529.1 | $^1$H NMR (500 MHz, DMSO-d$_6$) δ 2.40 (d, J = 1.1 Hz, 3H), 5.26 (t, J = 14.8 Hz, 2H), 7.61 (s, 1H), 7.77 (d, J = 8.0 Hz, 1H), 7.81 (d, J = 1.1 Hz, 1H), 7.94 (s, 1H), 7.96 (d, J = 8.0 Hz, 1H), 8.25 (t, J = 8.0 Hz, 1H) |
| 102 | 493.1 | $^1$H NMR (500 MHz, DMSO-d$_6$) δ 2.29 (d, J = 1.1 Hz, 3H), 5.25 (t, J = 15.0 Hz, 2H), 7.60 (s, 1H), 7.70-7.78 (m, 2H), 7.81-7.86 (m, 1H), 7.93 (s, 1H), 8.82-8.92 (m, 2H) |
| 109 | 388.1 | $^1$H NMR (400 MHz, CDCl$_3$) δ 1.30 (dtd, J = 13.1, 7.8, 7.8, 3.7 Hz, 1H), 1.53-1.67 (m, 1H), 2.19 (ddq, J = 12.9, 11.4, 7.4, 7.4, 7.4 Hz, 1H), 2.41 (d, J = 1.3 Hz, 3H), 3.73 (s, 3H), 4.17-4.40 (m, 2H), 7.42 (d, J = 1.3 Hz, 1H), 7.62-7.71 (m, 2H) |
| 110 | 388.1 | $^1$H NMR (400 MHz, CDCl$_3$) δ 1.24-1.38 (m, 1H), 1.49-1.74 (m, 1H), 2.10-2.29 (m, 1H), 2.41 (d, J = 1.1 Hz, 3H), 3.73 (s, 3H), 4.17-4.43 (m, 2H), 7.42 (d, J = 1.1 Hz, 1H), 7.61-7.75 (m, 2H) |
| 111 | 392.1 | $^1$H NMR (400 MHz, CDCl$_3$) δ 1.25-1.37 (m, 1H), 1.58-1.67 (m, 1H), 2.20 (tq, J = 12.1, 7.5 Hz, 1H), 2.81 (s, 3H), 4.25-4.37 (m, 2H), 7.78 (s, 1H), 7.86 (s, 1H) |
| 112 | 392.1 | $^1$H NMR (400 MHz, CDCl$_3$) δ 1.25-1.37 (m, 1H), 1.58-1.67 (m, 1H), 2.20 (tq, J = 12.1, 7.5 Hz, 1H), 2.81 (s, 3H), 4.25-4.37 (m, 2H), 7.78 (s, 1H), 7.86 (s, 1H) |
| 113 | 435.1 | $^1$H NMR (400 MHz, CDCl$_3$) δ 1.63 (d, J = 6.8 Hz, 3H), 4.11 (sxt, J = 6.7 Hz, 1H), 4.16-4.25 (m, 1H), 4.57 (dd, J = 12.9, 7.2 Hz, 1H), 4.79 (t, J = 13.8 Hz, 2H), 7.76 (s, 1H), 7.83 (s, 1H) |
| 114 | 435.1 | $^1$H NMR (400 MHz, CDCl$_3$) δ 1.63 (d, J = 6.6 Hz, 3H), 4.06-4.16 (m, 1H), 4.16-4.23 (m, 1H), 4.57 (dd, J = 12.8, 7.3 Hz, 1H), 4.79 (t, J = 13.7 Hz, 2H), 7.76 (s, 1H), 7.83 (s, 1H) |
| 115 | 470.1 | $^1$H NMR (500 MHz, DMSO-d$_6$) δ 1.52-1.79 (m, 2H), 2.27-2.40 (m, 1H), 2.42 (d, J = 0.8 Hz, 3H), 2.88 (qt, J = 11.2, 6.8 Hz, 2H), 4.17-4.37 (m, 2H), 4.43 (t, J = 6.7 Hz, 2H), 7.47 (s, 1H), 7.61 (d, J = 1.4 Hz, 1H), 7.85 (s, 1H) |
| 116 | 470.1 | $^1$H NMR (500 MHz, DMSO-d$_6$) δ 1.52-1.79 (m, 2H), 2.27-2.40 (m, 1H), 2.42 (d, J = 0.8 Hz, 3H), 2.88 (qt, J = 11.2, 6.8 Hz, 2H), 4.17-4.37 (m, 2H), 4.43 (t, J = 6.7 Hz, 2H), 7.47 (s, 1H), 7.61 (d, J = 1.4 Hz, 1H), 7.85 (s, 1H) |

BIOLOGICAL EVALUATION

Provided in this section is the biological evaluation of the specific examples provided herein. See Tables 15-18.

In Vitro Measurement of Delta-5-Desaturase Inhibitory Activity Using DGLA-CoA and Arachidonyl-CoA Mass Spectrometric Assays Membrane preparations of D5D-overexpressing HEK293 6E cells were prepared in which the total protein concentration was 5.6 mg/mL. Stock D5D membrane preparations were diluted in D5D assay buffer (25 mM 2-amino-2-(hydroxymethyl)-1,3-propanediol, pH 7.5 containing 10 mM MgCl$_2$, 1 mM octyl glucoside (SigmaAldrich O-8001), 1 mM tris(2-carboxyethyl)phosphine hydrochloride (SigmaAldrich 646547)) to a final D5D membrane concentration of 10 μg/mL in an assay plate containing serially diluted test compounds. To 15 μL of this D5D preparation was added 15 μL of a substrate solution (0.25 mM NADH (nicotinamide adenine dinucleotide, Roche Diag. 10107735001), 0.25 mM adenosine triphosphate (SigmaAldrich A-3377), 0.05 mM coenzyme A hydrate (SigmaAldrich C-4282), and 0.01 mM DGLA (dihomo-g-linolenic acid, Sigma E-4504) in the same D5D assay buffer. After one-hour incubation at ambient temperature acetonitrile (30 μL) was added to quench the reaction and plates were centrifuged for 10 min @ 3,000 rpm. Mass spectrometric analysis involved a Rapidfire 360 SPE system coupled to an ABSciex API4000 Triple Quadrupole mass spectrometer using a C18 SPE cartridge (G9203-80105) with ionization in negative mode (solvent A=100% water; solvent B=100% acetonitrile, each solvent containing 5 mM ammonium acetate). DGLA-CoA and Arachidonyl-CoA were detected by multiple reaction monitoring (MRM) of the doubly charged parent ions at m/z 526.6 and 525.6, respectively.

The % of inhibition was expressed as percentage of the maximal inhibition value obtained in the absence of enzyme according to the formula: % inhibition=100−(100*(Sx−Sc)/(So−Sc)). Sx is value from unknown sample, So is value from DMSO alone and Sc is value from no enzyme well. For CRC analysis, the % of inhibitions were analysed with 4 Parameter Logistic Model or Sigmoidal Dose-Response Model using XLfit (IDBS, Guilford, UK). The potency of the test item was expressed as IC50 nM, corresponding to the test item concentration able to inhibit the 50% of the enzyme maximal response. IC$_{50}$ values were averaged values determined by at least two independent runs.

The results presented in Table 15 have been generated with the in vitro assay described above. This assay may be used to test any of the compounds described herein to assess and characterize a compound's ability to inhibit D5D.

TABLE 15

| Example Number | D5D IC$_{50}$ (uM) |
| --- | --- |
| 1 | 0.0038 |
| 2 | 0.0196 |
| 3 | 0.0257 |
| 4 | 0.0178 |
| 5 | 0.482 |
| 6 | 0.271 |
| 7 | 0.0013 |
| 8 | 0.0046 |
| 9 | 0.0064 |
| 10 | 0.0274 |
| 11 | 0.133 |
| 12 | 0.248 |
| 13 | 0.249 |
| 14 | 1.43 |
| 15 | 1.51 |
| 16 | 9.41 |
| 17 | 0.363 |
| 18 | 3.63 |
| 19 | 0.0463 |
| 20 | 0.0329 |
| 21 | 0.235 |
| 22 | 0.0143 |
| 23 | 0.158 |
| 24 | 0.168 |
| 25 | 0.354 |
| 26 | 0.104 |
| 27 | 0.0026 |
| 28 | 0.0060 |
| 29 | 1.58 |
| 30 | 17.9 |
| 31 | 0.0023 |
| 32 | 0.0456 |
| 33 | 0.0009 |
| 34 | 0.0048 |
| 35 | 0.118 |
| 36 | >67 |
| 37 | 0.0115 |
| 38 | 0.0673 |
| 39 | 0.0188 |
| 40 | 0.224 |
| 41 | 0.877 |
| 42 | 0.0274 |
| 43 | 0.0340 |
| 44 | 3.21 |
| 45 | 0.0211 |
| 46 | 0.0361 |
| 47 | 4.95 |
| 48 | 0.0068 |
| 49 | 0.331 |
| 50 | 0.120 |
| 51 | 0.0368 |
| 52 | 0.0475 |
| 53 | 0.0064 |
| 54 | 0.0171 |
| 55 | 0.210 |
| 56 | 0.0343 |
| 57 | 0.146 |
| 58 | 0.0315 |
| 59 | 0.011 |
| 60 | 0.0578 |
| 61 | 0.0737 |
| 62 | 0.0029 |
| 63 | 0.160 |
| 64 | 0.239 |
| 65 | 0.815 |
| 66 | 0.0066 |
| 67 | 1.48 |
| 68 | 0.356 |
| 69 | 13.5 |
| 70 | 5.15 |
| 71 | 0.0328 |
| 72 | 0.135 |
| 73 | 0.0357 |
| 74 | 0.0047 |
| 75 | 0.0063 |
| 76 | 0.026 |
| 77 | 0.024 |
| 78 | 0.028 |
| 79 | 0.0117 |
| 80 | 0.0547 |
| 81 | 0.105 |
| 82 | 2.03 |
| 83 | 0.0115 |
| 84 | 0.193 |
| 85 | 0.0071 |
| 86 | 0.0109 |
| 87 | 0.0037 |
| 88 | 0.631 |
| 89 | 0.0533 |
| 90 | 0.105 |
| 91 | 0.0101 |
| 92 | 0.132 |
| 93 | 0.678 |
| 94 | 0.777 |
| 95 | 0.247 |
| 96 | 0.0194 |
| 97 | 0.0293 |
| 98 | 2.40 |
| 99 | 36.1 |
| 100 | 4.12 |
| 101 | 0.397 |
| 102 | 8.40 |
| 103 | 0.301 |
| 104 | 0.100 |
| 105 | 10.5 |
| 106 | 61.5 |
| 107 | 0.0125 |
| 108 | 0.0120 |
| 109 | 0.0286 |
| 110 | 0.0241 |
| 111 | 0.452 |
| 112 | 0.861 |
| 113 | 0.0118 |
| 114 | 0.0494 |
| 115 | 0.039 |
| 116 | 1.17 |

In Vivo Measurement of Delta-5-Desaturase Inhibitory Activity

Diet-induced obese (DIO; Jackson Laboratories strain #3800050) mice were used to screen for pharmacodynamic (PD) activity of test compounds. Generally, 14 to 24 week old DIO mice, were administered test compounds formulated in the vehicle of 2% hydroxypropyl methylcellulose (HPMC) and 1% Tween80. Animals were dosed on body weight by oral gavage with a single dose (30 mg/kg) for PD studies. Necropsy included plasma collection for PUFA analysis. 10 µl of plasma or standards diluted in surrogate matrix (65 g/l bovine serum albumin in Dulbecco's phosphate-buffered saline) were mixed with 10 µl of an internal standard (100 µM alpha-linolenic acid-d$_{14}$ (ALA-d$_{14}$, Cayman Chemical)) in a 96 well plate. 100 µl of 2N NAOH was added to the mixture for subsequent saponification at 65° C. for 1 hour. The mixture was then acidified with 50 µl of formic acid followed by two consecutive hexane extractions. Hexane (500 µl) was added and the mixture thoroughly mixed by vortexing, followed by centrifugation at 4,000 rpm for 15 min. The hexane phase was transferred to a new 1 ml 96 well plate and the remaining aqueous layer was extracted with hexane. The organic extracts were combined and the solvent was removed by placing the plate under nitrogen gas at 55° C. 250 µl of 90% methanol was added to the plate followed by vortexing for 2 minutes. 200 μl of the samples were transferred to a new 96 well polypropylene plate. The samples were analyzed on a LC-MS/MS for the following PUFAs: arachidonic acid (AA), dihomo-gamma-linolenic acid (DGLA), with ALA-$d_{14}$ as the internal standard. Description of the LC-MS/MS method: 5 μl of sample was injected onto a Poroshell 120 EC-C18 3.0×50 mm, 1.9 μm id column. Mobile phases were 20% acetonitrile containing 5 mM ammonium acetate for mobile phase A and 99.8% acetonitrile containing 2 mM ammonium acetate for mobile phase B. The LC gradient was a 11.30 min long method at a flow rate of 0.5 mL/minute consisting of 0% B to 45% B from 0 to 2.25 min, followed by a 45% B to 71% B from 6.0 to 9.5 min, followed by a 71% B to 95% B from 9.5 to 9.6 min; the system was then maintained at 95% B from 9.6 min to 10.10 min and returned to 0% B from 10.20 min to 11.30 min at the end of the method. The PUFA peak areas were quantified by using the SCIEX Analyst software. To determine the degree of D5D inhibition, the product/substrate ratio, AA/DGLA ratio was calculated by dividing the AA content (retention time 8.25 min) by the DGLA content (retention time 9.31 min). The relative decrease of the AA/DGLA ratio of the test compound administered group relative to the vehicle administered group was calculated and used as an index for the degree of D5D inhibition.

This procedure was used to show that the compounds provided herein inhibited in vivo D5D enzyme activity with changes in polyunsaturated fatty acids (PUFAs).

The results presented in Table 16 were obtained using certain compounds described herein in the in vivo protocol described above.

TABLE 16

| Example Number | Average % D5D Inhibition expressed as Plasma Endogenous AA/DGLA Ratio |
| --- | --- |
| 2 | 66 |
| 48 | 68 |
| 52 | 74 |

Assessment of D5D Inhibitor in Diet-Induced Obese (DIO) Mice

Male C57BL/6J DIO mice (Jackson Laboratories, Stock No.: 380050) were fed high-fat diet (Research Diets, Inc., D12492) for 12 weeks. All animals were given free access to water and chow. Animals were acclimated to per os dosing for 3 days prior to the start of the experiment. Animals were randomized on body weight, fat mass, lean mass, and blood glucose concentrations in to groups of 8 to 10 animals per group. Animals were twice daily dosed per os with either: vehicle (2% hydroxypropyl methylcellulose and 1% tween 80 in water), Example 2 at 10 mg/kg, or 30 mg/kg (formulated in 2% hydroxypropyl methylcellulose and 1% tween 80 in water), or Example 45 at 3 mg/kg, or 10 mg/kg (formulated in 2% hydroxypropyl methylcellulose and 1% tween 80 in water). Three-day average (Example 2) or daily average (Example 45) food consumption was measured at the indicated times as shown in Table 17 and Table 18. Body composition (EchoMRI) was determined on day 78 for Example 2 and day 22 for Example 45. For Example 2, a non-fasted blood collection was performed on day 81; blood glucose was immediately measured, and plasma samples created from the remaining blood and used to measure DGLA and AA concentrations. On day 84, a 4-hour fasted blood collection was performed, and plasma samples were created from the blood and used to measure cholesterol, triglycerides, low-density lipoprotein (LDL) cholesterol, insulin, and adipokine (adiponectin, leptin, and resistin) levels. For Example 45, 4 hour fasted blood samples were collected on day 25 and blood glucose was measured immediately and the plasma samples created from the remaining blood were used to measure cholesterol, triglycerides, LDL cholesterol, insulin, DGLA and AA concentration. At the end of the studies, liver, epididymal white adipose tissue, inguinal white adipose tissue, mesenteric (only Example 2) white adipose tissue weights were recorded. Data was analyzed using GraphPad Prism v 7.04. All data are presented in Table 17 and Table 18.

The D5D inhibitor dose-dependently led to weight loss over the course of the experiment (Table 17 and Table 18) compared to vehicle controls. Consistently fat mass was reduced, along with lower inguinal, epididymal and mesenteric white adipose tissue (WAT) weights at necropsy. Blood glucose and plasma insulin levels were both reduced by the D5D inhibitor, along with reductions in plasma cholesterol and triglycerides. Evidence of target engagement was established by observing increases in plasma DGLA and decreases in plasma AA.

TABLE 17

|  | measurement day | Vehicle | Example 2 | Example 2 |
| --- | --- | --- | --- | --- |
| Dose (mg/kg) |  |  | 10 | 30 |
| Body weight (g) | 84 | 53.1 ± 1.1 | 38.1 ± 1.0* | 32.3 ± 0.9* |
| Blood glucose (mg/dL) | 81 | 201.6 ± 10.2 | 165.3 ± 4.6* | 152.1 ± 6.1* |
| Insulin (ng/mL) | 84 | 15.8 ± 2.3 | 1.8 ± 0.3* | 1.4 ± 0.2* |
| Cholesterol (mg/dL) | 84 | 341.3 ± 17.2 | 224.5 ± 7.3* | 207.5 ± 4.8* |
| LDL cholesterol (mg/dL) | 84 | 110.2 ± 9.5 | 85.9 ± 3.8* | 80.6 ± 3.9* |
| Triglycerides (mg/dL) | 84 | 29.9 ± 3.6 | 14.3 ± 1.2* | 12.8 ± 1.0* |
| Fat mass (g) | 78 | 22.9 ± 0.6 | 11.4 ± 0.6* | 5.7 ± 0.6* |
| Lean mass (g) | 78 | 29.5 ± 0.7 | 26.4 ± 0.6* | 26.1 ± 0.4* |
| Food consumption(g/day) | 0-2 | 2.7 ± 0.1 | 2.5 ± 0.2 | 2.5 ± 0.2 |
| Food consumption(g/day) | 70-72 | 2.8 ± 0.1 | 2.5 ± 0.1* | 2.7 ± 0.1 |
| Liver weights (g) | 84 | 2.7 ± 0.2 | 3.0 ± 0.2 | 3.2 ± 0.1 |
| inguinal WAT (g) | 84 | 2.7 ± 0.1 | 1.2 ± 0.1* | 0.5 ± 0.1* |
| epididymal WAT (g) | 84 | 1.5 ± 0.2 | 1.2 ± 0.1 | 0.75 ± 0.1* |
| mesenteric WAT (g) | 84 | 1.1 ± 0.1 | 0.4 ± 0.0* | 0.2 ± 0.0* |
| DGLA (μg/mL) | 81 | 80.0 ± 4.4 | 167.8 ± 11.1* | 137.7 ± 6.5* |
| AA (μg/mL) | 81 | 175.2 ± 7.7 | 14.5 ± 0.9* | 10.7 ± 0.6* |
| Adiponectin (ng/mL) | 84 | 42.0 ± 23.0 | 48.3 ± 17.7 | 51.0 ± 24.4 |
| Leptin (ng/mL) | 84 | 21.9 ± 6.2 | 10.7 ± 3.6 | 3.2 ± 1.6 |
| Resisten (ng/mL) | 84 | 1.7 ± 0.4 | 0.9 ± 0.2 | 0.7 ± 0.2 |

*$P < 0.05$ vs. vehicle, one-way ANOVA with Dunnett's posthoc test

TABLE 18

|  | measurement day | Vehicle | Example 45 | Example 45 |
| --- | --- | --- | --- | --- |
| Dose (mg/kg) |  |  | 3 | 10 |
| Body weight (g) | 27 | 49.8 ± 2.7 | 47.8 ± 2.8 | 43.8 ± 3.1* |
| Blood glucose (mg/dL) | 25 | 203.9 ± 21.1 | 176.1 ± 9.4 | 156.1 ± 19.8* |
| Insulin (ng/mL) | 25 | 11.1 ± 2.2 | 7.2 ± 1.8 | 5.2 ± 0.7* |
| Cholesterol (mg/dL) | 25 | 218.0 ± 29.3 | 160.4 ± 43.7* | 162.8 ± 10.0* |
| LDL cholesterol (mg/dL) | 25 | 146.5 ± 22.4 | 130.6 ± 25.1 | 129.0 ± 15.7 |

TABLE 18-continued

| | measurement day | Vehicle | Example 45 | Example 45 |
|---|---|---|---|---|
| Triglycerides (mg/dL) | 25 | 43.3 ± 6.6 | 32.6 ± 5.2* | 26.3 ± 5.5* |
| Fat mass (g) | 22 | 21.4 ± 1.6 | 19.7 ± 2.2 | 16.9 ± 2.3* |
| Lean mass (g) | 22 | 27.1 ± 1.4 | 27.4 ± 1.5 | 26.7 ± 1.1 |
| Food consumption(g/day) | 0 | 2.6 ± 0.2 | 2.5 ± 0.3 | 2.6 ± 0.3 |
| Food consumption(g/day) | 7 | 2.8 ± 0.3 | 3.0 ± 0.3 | 2.6 ± 0.3 |
| Food consumption(g/day) | 14 | 3.0 ± 0.2 | 2.7 ± 0.3 | 2.4 ± 0.2* |
| Food consumption(g/day) | 21 | 2.9 ± 0.2 | 2.7 ± 0.2 | 2.5 ± 0.2* |
| Food consumption(g/day) | 27 | 2.8 ± 0.3 | 2.5 ± 0.2 | 2.4 ± 0.2 |
| Liver weights (g) | 27 | 2.0 ± 0.5 | 2.6 ± 0.4* | 2.6 ± 0.5* |
| inguinal WAT (g) | 27 | 2.7 ± 0.3 | 2.2 ± 0.5* | 1.9 ± 0.2* |
| epididymal WAT (g) | 27 | 1.9 ± 0.3 | 1.8 ± 0.3 | 1.7 ± 0.3 |
| DGLA (µg/mL) | 25 | 61.3 ± 22.4 | 286.9 ± 47.7* | 212.6 ± 23.7* |
| AA (ng/mL) | 25 | 791.6 ± 175.5 | 88.6 ± 18.9* | 38.2 ± 3.6* |

*$P < 0.05$ vs. vehicle, one-way ANOVA with Dunnett's posthoc test

REFERENCES

Baugh S D et al., Design, synthesis, and in vivo activity of novel inhibitors of delta-5 desaturase for the treatment of metabolic syndrome, *Bioorg. Med. Chem. Lett.* 25(18): 3836-3839 (2015).

Chopra M et al., A global response to a global problem: the epidemic of overnutrition, *Bull. World Health Organ.* 80:952-958 (2002).

Di Marzo V and Matias I, Endocannabinoid control of food intake and energy balance, *Nat. Neurosci.* 8(5):585-589 (2005).

Dupuis J, New genetic loci implicated in fasting glucose homeostasis and their impact on type 2 diabetes risk, *Nat. Genet.* 42(2):105-116 (2010).

Fumagalli M et al., Greenlandic Inuit show genetic signatures of diet and climate adaptation, *Science* 349(6254): 1343-1347 (2015).

Haidar Y M and Cosman B C, Obesity epidemiology, *Clin. Colon Rectal Surg.* 24:205-210 (2011).

Harizi H et al., Arachidonic-acid-derived eicosanoids: roles in biology and immunopathology, *Trends Mol. Med.* 14(10):461-469 (2008).

Kroeger J and Schulze M B, Recent insights into the relation of delta5 desaturase and delta6 desaturase activity to the development of type 2 diabetes, *Curr. Opin. Lipidol.* 23(1):4-10 (2012).

Mendis S et al., World Health Organization (WHO) and International Society of Hypertension (ISH) risk prediction charts: assessment of cardiovascular risk for prevention and control of cardiovascular disease in low and middle-income countries, *J Hypertens.* 25:1578-1582 (2007).

Merino D M et al., Genetic variation in lipid desaturases and its impact on the development of human disease, *Lipids Health Dis.* 9:63 (2010).

Merino D M et al., Polymorphisms in FADS1 and FADS2 alter desaturase activity in young Caucasian and Asian adults, *Mol. Genet. Metab.* 103(2):171-178 (2011).

Miyahisa I et al., T-3364366 Targets the Desaturase Domain of Delta-5 Desaturase with Nanomolar Potency and a Multihour Residence Time, *ACS Med. Chem. Lett.* 7(9): 868-872 (2016).

Monteiro C A et al., Socioeconomic status and obesity in adult populations of developing countries: a review. *Bull. World Health Organ.* 82:940-946 (2004).

Obukowicz M G et al., Novel, selective delta6 or delta5 fatty acid desaturase inhibitors as antiinflammatory agents in mice, *J. Pharmacol. Exp. Ther.* 287(1):157-166 (1998).

Powell D R et al., Fatty acid desaturase 1 knockout mice are lean with improved glycemic control and decreased development of atheromatous plaque, *Diabetes Metab. Syndr. Obes.* 9:185-199 (2016).

Tosi F et al., Delta-5 and delta-6 desaturases: crucial enzymes in polyunsaturated fatty acid-related pathways with pleiotropic influences in health and disease, *Adv. Exp. Med. Biol.* 824:61-81 (2014).

Willer C J et al., Discovery and refinement of loci associated with lipid levels, *Nat. Genet.* 45(11):1274-1283 (2013).

Yashiro H et al., A Novel Selective Inhibitor of Delta-5 Desaturase Lowers Insulin Resistance and Reduces Body Weight in Diet-Induced Obese C57BL/6J Mice, PLoS One 11(11):e0166198 (2016).

All references, for example, a scientific publication or patent application publication, cited herein are incorporated herein by reference in their entirety and for all purposes to the same extent as if each reference was specifically and individually indicated to be incorporated by reference in its entirety for all purposes.

What is claimed is:

1. A compound of Formula I

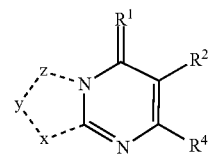

or a tautomer thereof, or a pharmaceutically acceptable salt of said compound or said tautomer,
wherein

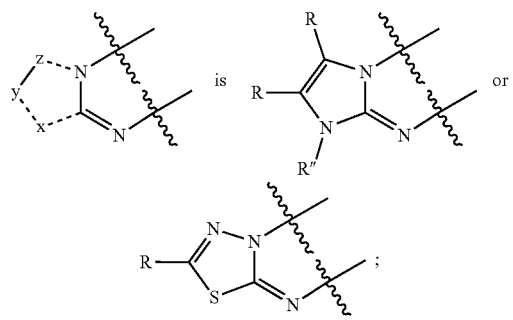

each instance of R is independently selected from H, halogen, —OH, —CN, —CO($C_{1-4}$alkyl), —S(O)$_n$($C_{1-4}$alkyl), —COOH, —COO($C_{1-4}$alkyl), —CONH$_2$, —CONH($C_{1-4}$alkyl), —CO(di$C_{1-4}$alkylamino), —NH$_2$, $C_{1-4}$alkylamino, di$C_{1-4}$alkylamino, —NH(COC$_{1-4}$alkyl), —N($C_{1-4}$alkyl)C(=O)F, $C_{1-4}$alkyl, —(CH$_2$)$_m$($C_{3-5}$cycloalkyl), —CH$_2$($C_{3-5}$heterocycloalkyl), $C_{1-4}$deuteroalkyl, $C_{3-5}$cycloalkyl, $C_{3-4}$heterocycloalkyl, C$_{2-4}$alkenyl, C$_{2-4}$alkynyl, C$_{1-4}$alkoxy, C$_{1-4}$deuteroalkoxy, 5-membered heteroaryl, and 6-membered heteroaryl;
wherein the C$_{1-4}$alkyl group is optionally substituted with 1 to 4 F atoms or is optionally substituted with a substituent selected from —OH, —CN, C$_{1-4}$alkoxy, —NH$_2$, C$_{1-4}$alkylamino, diC$_{1-4}$alkylamino, and —S(O)$_n$(C$_{1-4}$alkyl);
wherein the C$_{1-4}$alkoxy group is optionally substituted with 1 to 4 independently selected halogens or optionally substituted with a substituent selected from —OH, —CN, C$_{1-4}$alkoxy, —NH$_2$, C$_{1-4}$alkylamino, diC$_{1-4}$alkylamino, and —S(O)$_n$(C$_{1-4}$alkyl);
wherein the —CH$_2$(C$_{3-5}$cycloalkyl), C$_{3-4}$heterocycloalkyl, 5-membered heteroaryl, and 6-membered heteroaryl groups are optionally substituted with 1 to 4 substituents independently selected from halogen, —OH, —CN, C$_{1-4}$alkoxy, C$_{1-4}$alkyl, —NH$_2$, C$_{1-4}$alkylamino, diC$_{1-4}$alkylamino, and —S(O)$_n$(C$_{1-4}$alkyl); and
wherein R of a first CR group and R of a second CR group, if present, may, together with the atoms to which they are attached, form a C$_{3-5}$carbocycle;
each R", if present, is independently selected from H, —OH, —CO(C$_{1-4}$alkyl), —S(O)$_n$(C$_{1-4}$alkyl), —COO(C$_{1-4}$alkyl), —CONH$_2$, —CONH(C$_{1-4}$alkyl), —CO(diC$_{1-4}$alkylamino), C$_{1-4}$alkyl, —(CH$_2$)$_m$(C$_{3-5}$cycloalkyl), —CH$_2$(C$_{3-5}$heterocycloalkyl), C$_{1-4}$deuteroalkyl, C$_{3-5}$cycloalkyl, C$_{3-4}$heterocycloalkyl, C$_{2-4}$alkenyl, C$_{2-4}$alkynyl, 5-membered heteroaryl, and 6-membered heteroaryl;
wherein the C$_{1-4}$alkyl group is optionally substituted with 1 to 4 F atoms or is optionally substituted with a substituent selected from —OH, —CN, C$_{1-4}$alkoxy, —NH$_2$, C$_{1-4}$alkylamino, diC$_{1-4}$alkylamino, and —S(O)$_n$(C$_{1-4}$alkyl); and
wherein the —(CH$_2$)$_m$(C$_{3-5}$cycloalkyl), C$_{3-4}$heterocycloalkyl, 5-membered heteroaryl, or 6-membered heteroaryl groups are optionally substituted with 1 to 4 substituents independently selected from halogen, —OH, —CN, C$_{1-4}$alkoxy, C$_{1-4}$alkyl, —NH$_2$, C$_{1-4}$alkylamino, diC$_{1-4}$alkylamino, and —S(O)$_n$(C$_{1-4}$alkyl);
R$^1$ is O, S, or NH;
R$^2$ is

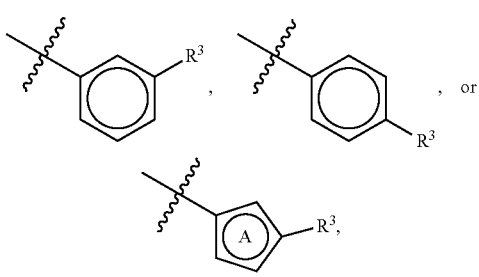

wherein
Ring A is a 5-membered heteroaryl containing one heteroatom selected from N, S, and O and optionally one or two further N atoms with the remaining ring atoms of the 5-membered heteroaryl being carbon, wherein
i) Ring A is attached via a C atom to the bicyclic core and R$^3$ is attached via an N atom; or
ii) Ring A is attached via an N atom to the bicyclic core and R$^3$ is attached via a C atom; or
iii) Ring A is attached via a C atom to the bicyclic core and R$^3$ is attached via a C atom;
and wherein the

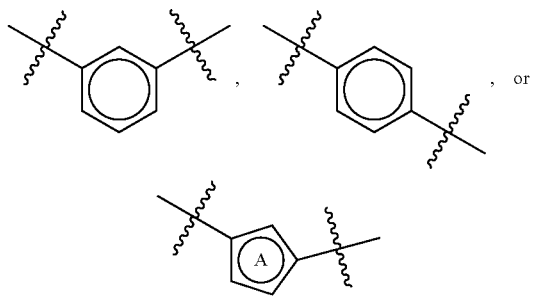

portion of R$^2$ is further optionally substituted with one or two independently selected substituents R$^{3'}$;
R$^3$ is C$_{1-6}$alkyl, C$_{3-5}$cycloalkyl, C$_{2-6}$alkoxy, C$_{1-6}$alkylamino, diC$_{1-6}$alkylamino, —S(O)$_n$(C$_{1-6}$alkyl), —CH$_2$(C$_{3-5}$cycloalkyl), —OCH$_2$(C$_{3-5}$cycloalkyl), —NHCH$_2$(C$_{3-5}$cycloalkyl), —S(O)$_n$CH$_2$(C$_{3-5}$cycloalkyl), —CH$_2$(C$_{3-5}$heterocycloalkyl), or phenyl; wherein the C$_{1-6}$alkyl, C$_{3-5}$cycloalkyl, C$_{2-6}$alkoxy, C$_{1-6}$alkylamino, diC$_{1-6}$alkylamino, —S(O)$_n$(C$_{1-6}$alkyl), —CH$_2$(C$_{3-5}$cycloalkyl), —OCH$_2$(C$_{3-5}$cycloalkyl), —NHCH$_2$(C$_{3-5}$cycloalkyl), and —S(O)$_n$CH$_2$(C$_{3-5}$cycloalkyl) groups are optionally substituted with 1-9 halogen atoms and are optionally substituted with —CN and wherein the phenyl is optionally substituted with 1-3 substituents selected from halogen, C$_{1-4}$alkyl, C$_{1-4}$haloalkyl, C$_{1-4}$alkoxy, and C$_{1-4}$haloalkoxy;
R$^{3'}$, if present, is independently halogen, C$_{1-4}$alkyl, C$_{1-4}$haloalkyl, C$_{1-4}$alkoxy, or C$_{1-4}$haloalkoxy;
R$^4$ is C$_{1-3}$alkyl, C$_{1-4}$haloalkyl, C$_{1-4}$alkoxy, C$_{1-4}$haloalkoxy, C$_{3-5}$cycloalkyl, or C$_{3-5}$cyclohaloalkyl;
n is 0, 1, or 2; and
m is 1 or 2.

2. The compound according to claim 1, or a tautomer thereof, or a pharmaceutically acceptable salt of said compound or said tautomer, wherein
each R is independently selected from H, halogen, —COO(C$_{1-4}$alkyl), C$_{1-4}$alkyl, —(CH$_2$)$_m$(C$_{3-5}$ cycloalkyl), —CH$_2$(C$_{3-5}$heterocycloalkyl), C$_{1-4}$deuteroalkyl, C$_{3-5}$cycloalkyl, C$_{3-4}$heterocycloalkyl, C$_{2-4}$alkynyl, C$_{1-4}$alkoxy, 5-membered heteroaryl, and 6-membered heteroaryl;
wherein the C$_{1-4}$alkyl group is optionally substituted with 1 to 4 F atoms or is optionally substituted with a substituent selected from —OH, —CN, C$_{1-4}$alkoxy, C$_{1-4}$alkylamino, and diC$_{1-4}$alkylamino; and
wherein the —(CH$_2$)$_m$(C$_{3-5}$cycloalkyl), 5-membered heteroaryl, and 6-membered heteroaryl groups are optionally substituted with 1 to 4 substituents independently selected from halogen, —OH, and C$_{1-4}$alkyl.

3. The compound according to claim 1, or a tautomer thereof, or a pharmaceutically acceptable salt of said compound or said tautomer, wherein
each R is independently selected from H, halogen, —COO(C$_{1-4}$alkyl), C$_{1-4}$alkyl, —(CH$_2$)$_m$(C$_{3-5}$ cycloalkyl), —CH$_2$(C$_{3-5}$heterocycloalkyl), C$_{1-4}$deuteroalkyl, C$_{3-5}$cycloalkyl, C$_{3-4}$heterocycloalkyl, C$_{2-4}$alkynyl, C$_{1-4}$alkoxy, 5-membered heteroaryl, and 6-membered heteroaryl;
wherein the C$_{1-4}$alkyl group is optionally substituted with 1 to 4 F atoms or is optionally substituted with a substituent selected from —OH, —CN, and C$_{1-4}$alkoxy.

4. The compound according to claim 1, or a tautomer thereof, or a pharmaceutically acceptable salt of said compound or said tautomer, wherein
each R is independently selected from H, C$_{1-4}$alkyl, C$_{1-4}$deuteroalkyl, and C$_{1-4}$alkoxy; wherein the C$_{1-4}$alkyl group is optionally substituted with a substituent selected from —OH and —CN.

5. The compound according to claim 1, or a tautomer thereof, or a pharmaceutically acceptable salt of said compound or said tautomer, wherein each R is independently selected from H and methyl.

6. The compound according to claim 1, or a tautomer thereof, or a pharmaceutically acceptable salt of said compound or said tautomer, wherein
each R", if present, is independently selected from H, —COO(C$_{1-4}$alkyl), C$_{1-4}$alkyl, —(CH$_2$)$_m$(C$_{3-5}$cycloalkyl), —CH$_2$(C$_{3-5}$heterocycloalkyl), C$_{1-4}$deuteroalkyl, C$_{3-5}$cycloalkyl, C$_{3-4}$heterocycloalkyl, C$_{2-4}$alkynyl, 5-membered heteroaryl, and 6-membered heteroaryl;
wherein the C$_{1-4}$alkyl group is optionally substituted with 1 to 4 F or optionally substituted with a substituent selected from —OH, —CN, C$_{1-4}$alkoxy, C$_{1-4}$alkylamino, and diC$_{1-4}$alkylamino; and
wherein the —(CH$_2$)$_m$(C$_{3-5}$cycloalkyl), 5-membered heteroaryl, and 6-membered heteroaryl groups are optionally substituted with 1 to 4 substituents independently selected from halogen, —OH, and C$_{1-4}$alkyl.

7. The compound according to claim 1, or a tautomer thereof, or a pharmaceutically acceptable salt of said compound or said tautomer, wherein
each R", if present, is independently selected from H, —COOMe, methyl, ethyl, isopropyl, fluoromethyl, trifluoromethyl, 2-hydroxyethyl, 2-hydroxy-2-methylpropyl, CH$_2$CN, 2-hydroxypropyl, —CH$_2$OCH$_3$, —CH$_2$CH$_2$OCH$_3$, dimethylaminomethyl, 2-(dimethylamino)ethyl, cyclopropylmethyl, (2,2-difluorocyclopropyl)methyl, (3,3-difluorocyclobutyl)methyl, (1-hydroxycyclopropyl)ethyl, -CD$_3$, cyclopropyl, (oxetan-3-yl)methyl, oxetan-3-yl, prop-2-yn-1-yl, pyrazolyl, 1-methyl-pyrazol-4-yl, pyridinyl, pyrazinyl, pyrimidinyl, 6-methylpyridin-2-yl, and 6-chloropyridin-2-yl.

8. The compound according to claim 1, or a tautomer thereof, or a pharmaceutically acceptable salt of said compound or said tautomer, wherein R$^1$ is O.

9. The compound according to claim 1, or a tautomer thereof, or a pharmaceutically acceptable salt of said compound or said tautomer, wherein
R$^2$ is

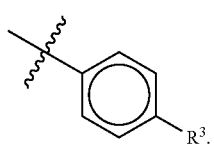

10. The compound according to claim 1, or a tautomer thereof, or a pharmaceutically acceptable salt of said compound or said tautomer, wherein
R$^2$ is

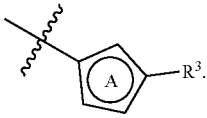

11. The compound according to claim 1, or a tautomer thereof, or a pharmaceutically acceptable salt of said compound or said tautomer, wherein
R$^2$ is

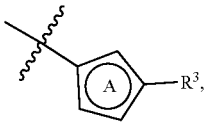

wherein A is a 5-membered heteroaryl containing two N atoms.

12. The compound according to claim 1, or a tautomer thereof, or a pharmaceutically acceptable salt of said compound or said tautomer, wherein
R$^2$ is

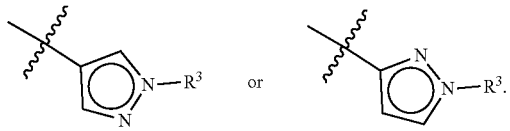

13. The compound according to claim 1, or a tautomer thereof, or a pharmaceutically acceptable salt of said compound or said tautomer, wherein
R$^2$ is

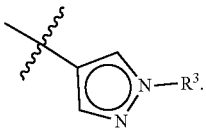

14. The compound according to claim 1, or a tautomer thereof, or a pharmaceutically acceptable salt of said compound or said tautomer, wherein
R$^3$ is C$_{1-6}$alkyl, C$_{2-6}$alkoxy, —CH$_2$(C$_{3-5}$cycloalkyl), —OCH$_2$(C$_{3-5}$cycloalkyl), —CH$_2$(C$_{3-5}$heterocycloalkyl), or phenyl; wherein the C$_{1-6}$alkyl, C$_{2-6}$alkoxy, —CH$_2$(C$_{3-5}$cycloalkyl), and —OCH$_2$(C$_{3-5}$cycloalkyl) groups are optionally substituted with 1-9 halogen atoms and are optionally substituted with —CN and wherein the phenyl is optionally substituted with one halogen substituent.

15. The compound according to claim 1, or a tautomer thereof, or a pharmaceutically acceptable salt of said compound or said tautomer, wherein
R$^3$ is 2,2,2-trifluoroethyl, propyl, 2,2-difluoropropyl, 3,3,3-trifluoropropyl, 4,4,4-trifluorobutyl, 2,2,3,3,3-pentafluoropropyl, —OCH₂CN, —OC(CH₃)₂CN, difluoromethoxy, trifluoromethoxy, —OCH(CN)CH₃, 2-fluoroethoxy, 2,2,-difluoroethoxy, 2,2,2-trifluoroethoxy, 2,2-difluoropropoxy, 2,2,3,3-tetrafluoropropoxy, 2,2,3,3,3-pentafluoropropoxy, cyclopropylmethyl, (2,2-difluorocyclopropyl)methyl, (3,3-difluorocyclobutyl)methyl, cyclopropylmethoxy, (2,2-difluorocyclopropyl)methoxy, (oxetan-3-yl)methyl, phenyl, 3-fluorophenyl, or 4-fluorophenyl.

16. The compound according to claim 1, or a tautomer thereof, or a pharmaceutically acceptable salt of said compound or said tautomer, wherein
R³ is C₁₋₆alkyl, C₂₋₆alkoxy, —CH₂(C₃₋₅cycloalkyl), or —CH₂(C₃₋₅heterocycloalkyl); wherein the C₁₋₆alkyl, C₂₋₆alkoxy, and —CH₂(C₃₋₅cycloalkyl) groups are substituted with 2-5 halogen atoms.

17. The compound according to claim 1, or a tautomer thereof, or a pharmaceutically acceptable salt of said compound or said tautomer, wherein
R⁴ is C₁₋₃alkyl, C₁₋₄haloalkyl, C₁₋₄alkoxy, or C₃₋₅cycloalkyl.

18. The compound according to claim 1, or a tautomer thereof, or a pharmaceutically acceptable salt of said compound or said tautomer, wherein R⁴ is C₁₋₄haloalkyl.

19. The compound according to claim 1, or a tautomer thereof, or a pharmaceutically acceptable salt of said compound or said tautomer, wherein
R⁴ is methyl, ethyl, fluoromethyl, difluoromethyl, trifluoromethyl, methoxy, ethoxy, or cyclopropyl.

20. The compound according to claim 1, or a tautomer thereof, or a pharmaceutically acceptable salt of said compound or said tautomer, wherein the compound is
1-methyl-6-[1-(2,2,3,3,3-pentafluoropropyl)-1H-pyrazol-4-yl]-7-(trifluoromethyl)-1H,5H-imidazo[1,2-a]pyrimidin-5-one;
3-chloro-1-methyl-6-[1-(2,2,3,3,3-pentafluoropropyl)-1H-pyrazol-4-yl]-7-(trifluoromethyl)-1H,5H-imidazo[1,2-a]pyrimidin-5-one;
2-chloro-1-methyl-6-[1-(2,2,3,3,3-pentafluoropropyl)-1H-pyrazol-4-yl]-7-(trifluoromethyl)-1H,5H-imidazo[1,2-a]pyrimidin-5-one;
2-chloro-6-[1-(2,2,3,3,3-pentafluoropropyl)-1H-pyrazol-4-yl]-7-(trifluoromethyl)-1H,5H-imidazo[1,2-a]pyrimidin-5-one;
2-cyclopropyl-1-methyl-6-[1-(2,2,3,3,3-pentafluoropropyl)-1H-pyrazol-4-yl]-7-(trifluoromethyl)-1H,5H-imidazo[1,2-a]pyrimidin-5-one;
2-chloro-1-methyl-7-(trifluoromethyl)-6-[1-(3,3,3-trifluoropropyl)-1H-pyrazol-4-yl]-1H,5H-imidazo[1,2-a]pyrimidin-5-one;
1,2-dimethyl-6-[1-(2,2,3,3,3-pentafluoropropyl)-1H-pyrazol-4-yl]-7-(trifluoromethyl)-1H,5H-imidazo[1,2-a]pyrimidin-5-one;
1,2-dimethyl-7-(trifluoromethyl)-6-[1-(3,3,3-trifluoropropyl)-1H-pyrazol-4-yl]-1H,5H-imidazo[1,2-a]pyrimidin-5-one;
1,2-dimethyl-6-[4-(2,2,2-trifluoroethoxy)phenyl]-7-(trifluoromethyl)-1H,5H-imidazo[1,2-a]pyrimidin-5-one;
2-(methoxymethyl)-1-methyl-6-[1-(2,2,3,3,3-pentafluoropropyl)-1H-pyrazol-4-yl]-7-(trifluoromethyl)-1H,5H-imidazo[1,2-a]pyrimidin-5-one;
1-ethyl-2-methyl-6-[1-(2,2,3,3,3-pentafluoropropyl)-1H-pyrazol-4-yl]-7-(trifluoromethyl)-1H,5H-imidazo[1,2-a]pyrimidin-5-one;
1-(2-methoxyethyl)-2-methyl-6-[1-(2,2,3,3,3-pentafluoropropyl)-1H-pyrazol-4-yl]-7-(trifluoromethyl)-1H,5H-imidazo[1,2-a]pyrimidin-5-one;
2-methyl-6-[1-(2,2,3,3,3-pentafluoropropyl)-1H-pyrazol-4-yl]-1-(propan-2-yl)-7-(trifluoromethyl)-1H,5H-imidazo[1,2-a]pyrimidin-5-one;
6-{1-[(2,2-difluorocyclopropyl)methyl]-1H-pyrazol-4-yl}-1,2-dimethyl-7-(trifluoromethyl)-1H,5H-imidazo[1,2-a]pyrimidin-5-one;
6-{1-[(3,3-difluorocyclobutyl)methyl]-1H-pyrazol-4-yl}-1,2-dimethyl-7-(trifluoromethyl)-1H,5H-imidazo[1,2-a]pyrimidin-5-one;
6-[1-(cyclopropylmethyl)-1H-pyrazol-4-yl]-1,2-dimethyl-7-(trifluoromethyl)-1H,5H-imidazo[1,2-a]pyrimidin-5-one;
1-(cyclopropylmethyl)-2-methyl-6-[1-(2,2,3,3,3-pentafluoropropyl)-1H-pyrazol-4-yl]-7-(trifluoromethyl)-1H,5H-imidazo[1,2-a]pyrimidin-5-one;
2-(methoxymethyl)-1-methyl-7-(trifluoromethyl)-6-[1-(3,3,3-trifluoropropyl)-1H-pyrazol-4-yl]-1H,5H-imidazo[1,2-a]pyrimidin-5-one;
1-(2-hydroxypropyl)-2-methyl-6-[1-(2,2,3,3,3-pentafluoropropyl)-1H-pyrazol-4-yl]-7-(trifluoromethyl)-1H,5H-imidazo[1,2-a]pyrimidin-5-one;
1,2-dimethyl-6-{1-[(oxetan-3-yl)methyl]-1H-pyrazol-4-yl}-7-(trifluoromethyl)-1H,5H-imidazo[1,2-a]pyrimidin-5-one;
1-(cyclopropylmethyl)-2-methyl-7-(trifluoromethyl)-6-[1-(3,3,3-trifluoropropyl)-1H-pyrazol-4-yl]-1H,5H-imidazo[1,2-a]pyrimidin-5-one;
1-[2-(dimethylamino)ethyl]-2-methyl-7-(trifluoromethyl)-6-[1-(3,3,3-trifluoropropyl)-1H-pyrazol-4-yl]-1H,5H-imidazo[1,2-a]pyrimidin-5-one;
1-(cyclopropylmethyl)-2-methyl-6-[4-(2,2,2-trifluoroethoxy)phenyl]-7-(trifluoromethyl)-1H,5H-imidazo[1,2-a]pyrimidin-5-one;
1-[2-(dimethylamino)ethyl]-2-methyl-6-[4-(2,2,2-trifluoroethoxy)phenyl]-7-(trifluoromethyl)-1H,5H-imidazo[1,2-a]pyrimidin-5-one;
1,2-dimethyl-6-[1-(2,2,3,3,3-pentafluoropropyl)-1H-pyrazol-3-yl]-7-(trifluoromethyl)-1H,5H-imidazo[1,2-a]pyrimidin-5-one;
2-methoxy-1-methyl-6-[1-(2,2,3,3,3-pentafluoropropyl)-1H-pyrazol-4-yl]-7-(trifluoromethyl)-1H,5H-imidazo[1,2-a]pyrimidin-5-one;
2-methoxy-1-methyl-7-(trifluoromethyl)-6-[1-(3,3,3-trifluoropropyl)-1H-pyrazol-4-yl]-1H,5H-imidazo[1,2-a]pyrimidin-5-one;
2-methyl-6-[1-(2,2,3,3,3-pentafluoropropyl)-1H-pyrazol-4-yl]-7-(trifluoromethyl)-1H,5H-imidazo[1,2-a]pyrimidin-5-one;
2-methyl-7-(trifluoromethyl)-6-[1-(3,3,3-trifluoropropyl)-1H-pyrazol-4-yl]-1H,5H-imidazo[1,2-a]pyrimidin-5-one;
2-methyl-6-[4-(2,2,2-trifluoroethoxy)phenyl]-7-(trifluoromethyl)-1H,5H-imidazo[1,2-a]pyrimidin-5-one;
6-{1-[(2,2-difluorocyclopropyl)methyl]-1H-pyrazol-4-yl}-2-methyl-7-(trifluoromethyl)-1H,5H-imidazo[1,2-a]pyrimidin-5-one;
1-(²H₃)methyl-2-methyl-6-[1-(2,2,3,3,3-pentafluoropropyl)-1H-pyrazol-4-yl]-7-(trifluoromethyl)-1H,5H-imidazo[1,2-a]pyrimidin-5-one;
1-(²H₃)methyl-2-methyl-7-(trifluoromethyl)-6-[1-(3,3,3-trifluoropropyl)-1H-pyrazol-4-yl]-1H,5H-imidazo[1,2-a]pyrimidin-5-one;
1-(2-hydroxyethyl)-2-methyl-6-[1-(2,2,3,3,3-pentafluoropropyl)-1H-pyrazol-4-yl]-7-(trifluoromethyl)-1H,5H-imidazo[1,2-a]pyrimidin-5-one;

methyl 2-methyl-5-oxo-6-[1-(2,2,3,3,3-pentafluoropropyl)-1H-pyrazol-4-yl]-7-(trifluoromethyl)-1H,5H-imidazo[1,2-a]pyrimidine-1-carboxylate;

1-[(2,2-difluorocyclopropyl)methyl]-2-methyl-7-(trifluoromethyl)-6-[1-(3,3,3-trifluoropropyl)-1H-pyrazol-4-yl]-1H,5H-imidazo[1,2-a]pyrimidin-5-one;

1-[(3,3-difluorocyclobutyl)methyl]-2-methyl-7-(trifluoromethyl)-6-[1-(3,3,3-trifluoropropyl)-1H-pyrazol-4-yl]-1H,5H-imidazo[1,2-a]pyrimidin-5-one;

1-(2-hydroxyethyl)-2-methyl-7-(trifluoromethyl)-6-[1-(3,3,3-trifluoropropyl)-1H-pyrazol-4-yl]-1H,5H-imidazo[1,2-a]pyrimidin-5-one;

1-[2-(dimethylamino)ethyl]-2-methyl-6-[1-(2,2,3,3,3-pentafluoropropyl)-1H-pyrazol-4-yl]-7-(trifluoromethyl)-1H,5H-imidazo[1,2-a]pyrimidin-5-one;

2-methyl-6-[1-(2,2,3,3,3-pentafluoropropyl)-1H-pyrazol-4-yl]-1-(prop-2-yn-1-yl)-7-(trifluoromethyl)-1H,5H-imidazo[1,2-a]pyrimidin-5-one;

2-{2-methyl-5-oxo-6-[1-(2,2,3,3,3-pentafluoropropyl)-1H-pyrazol-4-yl]-7-(trifluoromethyl)-1H,5H-imidazo[1,2-a]pyrimidin-1-yl}acetonitrile;

2-[2-methyl-5-oxo-7-(trifluoromethyl)-6-[1-(3,3,3-trifluoropropyl)-1H-pyrazol-4-yl]-1H,5H-imidazo[1,2-a]pyrimidin-1-yl]acetonitrile;

1-(2-hydroxy-2-methylpropyl)-2-methyl-6-[1-(2,2,3,3,3-pentafluoropropyl)-1H-pyrazol-4-yl]-7-(trifluoromethyl)-1H,5H-imidazo[1,2-a]pyrimidin-5-one;

1-[2-(1-hydroxycyclopropyl)ethyl]-2-methyl-6-[1-(2,2,3,3,3-pentafluoropropyl)-1H-pyrazol-4-yl]-7-(trifluoromethyl)-1H,5H-imidazo[1,2-a]pyrimidin-5-one;

2-methyl-1-[(oxetan-3-yl)methyl]-6-[1-(2,2,3,3,3-pentafluoropropyl)-1H-pyrazol-4-yl]-7-(trifluoromethyl)-1H,5H-imidazo[1,2-a]pyrimidin-5-one;

2-methyl-1-(oxetan-3-yl)-6-[1-(2,2,3,3,3-pentafluoropropyl)-1H-pyrazol-4-yl]-7-(trifluoromethyl)-1H,5H-imidazo[1,2-a]pyrimidin-5-one;

1,2-dimethyl-6-[1-(2,2,3,3,3-pentafluoropropyl)-1H-pyrazol-4-yl]-7-(trifluoromethyl)-1H,5H-imidazo[1,2-a]pyrimidine-5-thione;

2-methyl-6-[1-(2,2,3,3,3-pentafluoropropyl)-1H-pyrazol-4-yl]-1-(pyridin-2-yl)-7-(trifluoromethyl)-1H,5H-imidazo[1,2-a]pyrimidin-5-one;

2-methyl-1-(pyridin-2-yl)-7-(trifluoromethyl)-6-[1-(3,3,3-trifluoropropyl)-1H-pyrazol-4-yl]-1H,5H-imidazo[1,2-a]pyrimidin-5-one;

2-methyl-6-[1-(2,2,3,3,3-pentafluoropropyl)-1H-pyrazol-4-yl]-1-(pyrazin-2-yl)-7-(trifluoromethyl)-1H,5H-imidazo[1,2-a]pyrimidin-5-one;

2-methyl-1-(6-methylpyridin-2-yl)-6-[1-(2,2,3,3,3-pentafluoropropyl)-1H-pyrazol-4-yl]-7-(trifluoromethyl)-1H,5H-imidazo[1,2-a]pyrimidin-5-one;

2-methyl-1-(1-methyl-1H-pyrazol-4-yl)-6-[1-(2,2,3,3,3-pentafluoropropyl)-1H-pyrazol-4-yl]-7-(trifluoromethyl)-1H,5H-imidazo[1,2-a]pyrimidin-5-one;

2-methyl-6-[i-(2,2,3,3,3-pentafluoropropyl)-1H-pyrazol-4-yl]-1-(pyridin-3-yl)-7-(trifluoromethyl)-1H,5H-imidazo[1,2-a]pyrimidin-5-one;

1-(6-chloropyridin-2-yl)-2-methyl-6-[1-(2,2,3,3,3-pentafluoropropyl)-1H-pyrazol-4-yl]-7-(trifluoromethyl)-1H,5H-imidazo[1,2-a]pyrimidin-5-one;

2-methyl-6-[i-(2,2,3,3,3-pentafluoropropyl)-1H-pyrazol-4-yl]-1-(pyridin-4-yl)-7-(trifluoromethyl)-1H,5H-imidazo[1,2-a]pyrimidin-5-one;

2-methyl-6-[1-(2,2,3,3,3-pentafluoropropyl)-1H-pyrazol-4-yl]-1-(1H-pyrazol-4-yl)-7-(trifluoromethyl)-1H,5H-imidazo[1,2-a]pyrimidin-5-one;

6-(1-{[(1R)-2,2-difluorocyclopropyl]methyl}-1H-pyrazol-4-yl)-2-methyl-7-(trifluoromethyl)-1H,5H-imidazo[1,2-a]pyrimidin-5-one;

6-(1-{[(1S)-2,2-difluorocyclopropyl]methyl}-1H-pyrazol-4-yl)-2-methyl-7-(trifluoromethyl)-1H,5H-imidazo[1,2-a]pyrimidin-5-one;

6-(1-{[(1R)-2,2-difluorocyclopropyl]methyl}-1H-pyrazol-4-yl)-1,2-dimethyl-7-(trifluoromethyl)-1H,5H-imidazo[1,2-a]pyrimidin-5-one;

6-(1-{[(1S)-2,2-difluorocyclopropyl]methyl}-1H-pyrazol-4-yl)-1,2-dimethyl-7-(trifluoromethyl)-1H,5H-imidazo[1,2-a]pyrimidin-5-one;

1-{[(1R)-2,2-difluorocyclopropyl]methyl}-2-methyl-7-(trifluoromethyl)-6-[1-(3,3,3-trifluoropropyl)-1H-pyrazol-4-yl]-1H,5H-imidazo[1,2-a]pyrimidin-5-one; or 1-{[(1S)-2,2-difluorocyclopropyl]methyl}-2-methyl-7-(trifluoromethyl)-6-[1-(3,3,3-trifluoropropyl)-1H-pyrazol-4-yl]-1H,5H-imidazo[1,2-a]pyrimidin-5-one.

21. The compound according to claim 1, or a tautomer thereof, or a pharmaceutically acceptable salt of said compound or said tautomer, wherein the compound is 2-methyl-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one;

2-(methoxymethyl)-7-(trifluoromethyl)-6-[1-(3,3,3-trifluoropropyl)-1H-pyrazol-4-yl]-5H-[1,3,4]thiadiazolo[3,2-a]pyrimidin-5-one;

2-cyclopropyl-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one;

2-cyclopropyl-7-(trifluoromethyl)-6-[1-(3,3,3-trifluoropropyl)-1H-pyrazol-4-yl]-5H-[1,3,4]thiadiazolo[3,2-a]pyrimidin-5-one;

7-ethyl-2-methyl-6-[1-(2,2,3,3,3-pentafluoropropyl)-1H-pyrazol-4-yl]-5H-[1,3,4]thiadiazolo[3,2-a]pyrimidin-5-one;

2-methyl-7-(trifluoromethyl)-6-[1-(3,3,3-trifluoropropyl)-1H-pyrazol-4-yl]-5H-[1,3,4]thiadiazolo[3,2-a]pyrimidin-5-one;

6-{1-[(2,2-difluorocyclopropyl)methyl]-1H-pyrazol-4-yl}-2-methyl-7-(trifluoromethyl)-5H-[1,3,4]thiadiazolo[3,2-a]pyrimidin-5-one;

6-{1-[(3,3-difluorocyclobutyl)methyl]-1H-pyrazol-4-yl}-2-methyl-7-(trifluoromethyl)-5H-[1,3,4]thiadiazolo[3,2-a]pyrimidin-5-one;

2-methyl-6-{1-[(oxetan-3-yl)methyl]-1H-pyrazol-4-yl}-7-(trifluoromethyl)-5H-[1,3,4]thiadiazolo[3,2-a]pyrimidin-5-one;

2-methyl-6-[1-(2,2,3,3,3-pentafluoropropyl)-1H-pyrazol-3-yl]-7-(trifluoromethyl)-5H-[1,3,4]thiadiazolo[3,2-a]pyrimidin-5-one;

2-methyl-6-[4-(2,2,2-trifluoroethoxy)phenyl]-7-(trifluoromethyl)-5H-[1,3,4]thiadiazolo[3,2-a]pyrimidin-5-one;

7-ethoxy-2-methyl-6-[1-(2,2,3,3,3-pentafluoropropyl)-1H-pyrazol-4-yl]-5H-[1,3,4]thiadiazolo[3,2-a]pyrimidin-5-one;

2-(methoxymethyl)-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one;

2-methoxy-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one;

2-(hydroxymethyl)-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one;

2-(hydroxymethyl)-7-(trifluoromethyl)-6-[1-(3,3,3-trifluoropropyl)-1H-pyrazol-4-yl]-5H-[1,3,4]thiadiazolo[3,2-a]pyrimidin-5-one;

2-(fluoromethyl)-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one;

2-[(dimethylamino)methyl]-6-[1-(2,2,3,3,3-pentafluoropropyl)-1H-pyrazol-4-yl]-7-(trifluoromethyl)-5H-[1,3,4]thiadiazolo[3,2-a]pyrimidin-5-one;

6-(1-{[(1R)-2,2-difluorocyclopropyl]methyl}-1H-pyrazol-4-yl)-2-methyl-7-(trifluoromethyl)-5H-[1,3,4]thiadiazolo[3,2-a]pyrimidin-5-one; or 6-(1-{[(1S)-2,2-difluorocyclopropyl]methyl}-1H-pyrazol-4-yl)-2-methyl-7-(trifluoromethyl)-5H-[1,3,4]thiadiazolo[3,2-a]pyrimidin-5-one.

22. The compound according to claim 1, or a pharmaceutically acceptable salt thereof, wherein the compound is

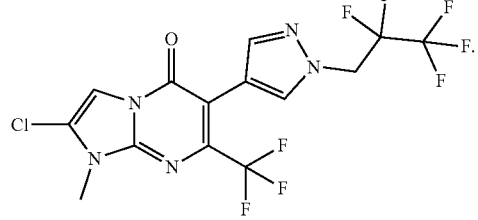

23. The compound according to claim 1, or a pharmaceutically acceptable salt thereof, wherein the compound is

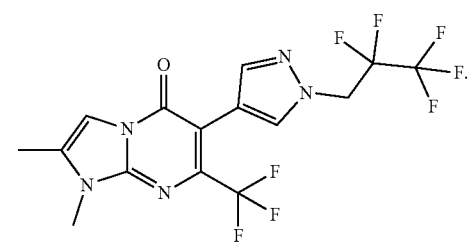 [SMILES: Cc1cn2c(=O)c(-c3cnn(CC(F)(F)C(F)(F)F)c3)c(C(F)(F)F)nc2n1C]

24. The compound according to claim 1, or a pharmaceutically acceptable salt thereof, wherein the compound is

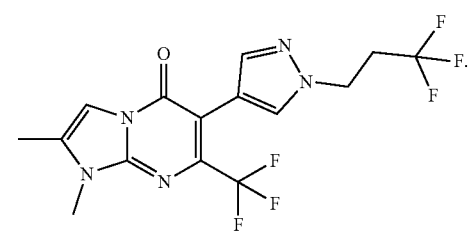 [SMILES: Cc1cn2c(=O)c(-c3cnn(CCC(F)(F)F)c3)c(C(F)(F)F)nc2n1C]

25. The compound according to claim 1, or a pharmaceutically acceptable salt thereof, wherein the compound is

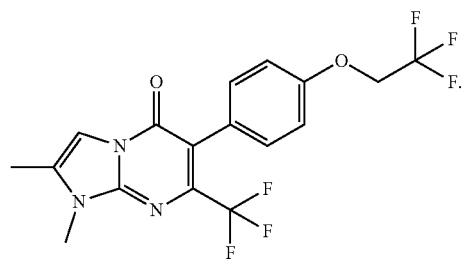 [SMILES: Cc1cn2c(=O)c(-c3ccc(OCC(F)(F)F)cc3)c(C(F)(F)F)nc2n1C]

26. The compound according to claim 1, or a pharmaceutically acceptable salt thereof, wherein the compound is

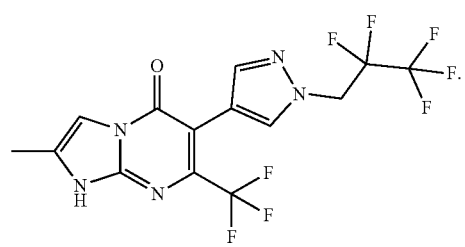 [SMILES: Cc1cn2c(=O)c(-c3cnn(CC(F)(F)C(F)(F)F)c3)c(C(F)(F)F)nc2[nH]1]

27. The compound according to claim 1, or a pharmaceutically acceptable salt thereof, wherein the compound is

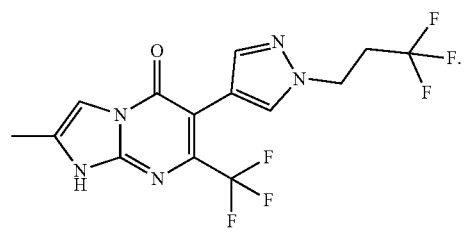 [SMILES: Cc1cn2c(=O)c(-c3cnn(CCC(F)(F)F)c3)c(C(F)(F)F)nc2[nH]1]

28. The compound according to claim 1, or a pharmaceutically acceptable salt thereof, wherein the compound is

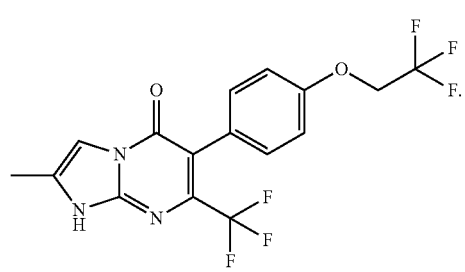 [SMILES: Cc1cn2c(=O)c(-c3ccc(OCC(F)(F)F)cc3)c(C(F)(F)F)nc2[nH]1]

29. The compound according to claim 1, or a pharmaceutically acceptable salt thereof, wherein the compound is

30. The compound according to claim 1, or a pharmaceutically acceptable salt thereof, wherein the compound is

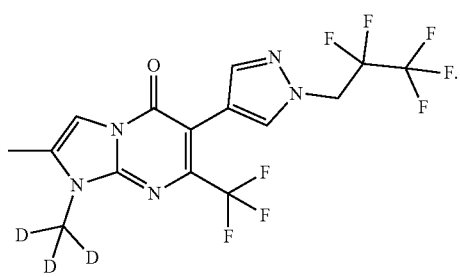 [SMILES: [2H]C([2H])([2H])n1c(C)cn2c(=O)c(-c3cnn(CC(F)(F)C(F)(F)F)c3)c(C(F)(F)F)nc12]

31. The compound according to claim 1, or a pharmaceutically acceptable salt thereof, wherein the compound is

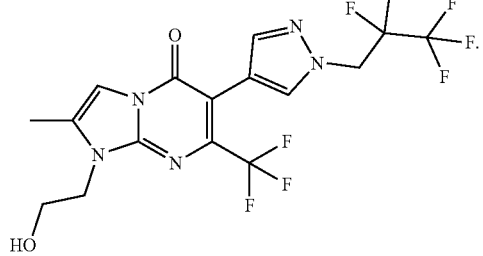

32. The compound according to claim 1, or a pharmaceutically acceptable salt thereof, wherein the compound is

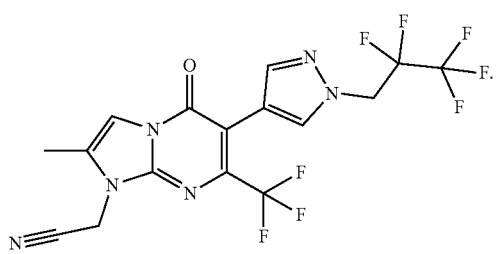 [SMILES: Cc1cn2c(=O)c(-c3cnn(CC(F)(F)C(F)(F)F)c3)c(C(F)(F)F)nc2n1CC#N]

33. The compound according to claim 1, or a pharmaceutically acceptable salt thereof, wherein the compound is

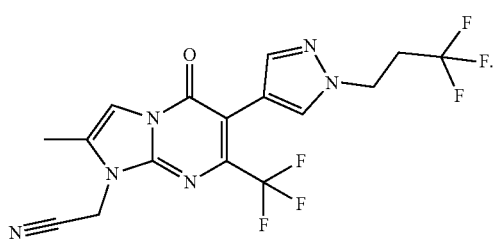 [SMILES: Cc1cn2c(=O)c(-c3cnn(CCC(F)(F)F)c3)c(C(F)(F)F)nc2n1CC#N]

34. The compound according to claim 1, or a pharmaceutically acceptable salt thereof, wherein the compound is

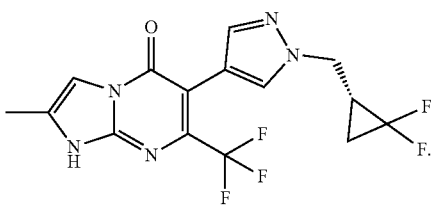 [SMILES: Cc1cn2c(=O)c(-c3cnn(C[C@H]4CC4(F)F)c3)c(C(F)(F)F)nc2[nH]1]

35. The compound according to claim 1, or a pharmaceutically acceptable salt thereof, wherein the compound is

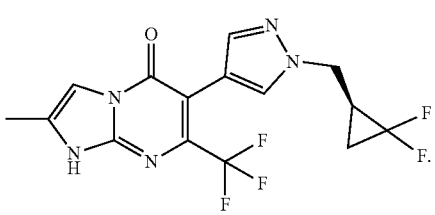 [SMILES: Cc1cn2c(=O)c(-c3cnn(C[C@@H]4CC4(F)F)c3)c(C(F)(F)F)nc2[nH]1]

36. The compound according to claim 1, or a pharmaceutically acceptable salt thereof, wherein the compound is

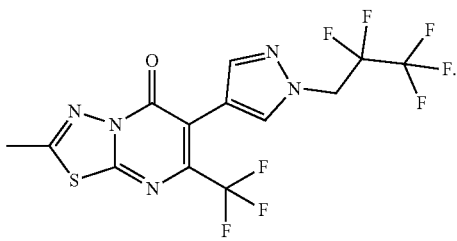 [SMILES: Cc1nn2c(=O)c(-c3cnn(CC(F)(F)C(F)(F)F)c3)c(C(F)(F)F)nc2s1]

37. The compound according to claim 1, or a pharmaceutically acceptable salt thereof, wherein the compound is

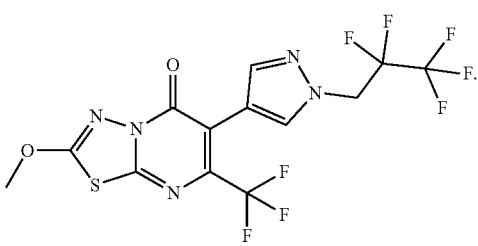 [SMILES: COc1nn2c(=O)c(-c3cnn(CC(F)(F)C(F)(F)F)c3)c(C(F)(F)F)nc2s1]

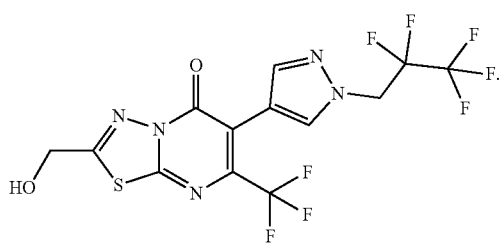 [SMILES: O=c1c(-c2cnn(CC(F)(F)C(F)(F)F)c2)c(C(F)(F)F)nc2sc(CO)nn12]

38. A pharmaceutical composition comprising the compound according to claim 1, or a tautomer thereof, or a pharmaceutically acceptable salt of said compound or said tautomer, and a pharmaceutically acceptable excipient.

\* \* \* \* \*